US012723260B2

(12) United States Patent
Yurchenco et al.

(10) Patent No.: US 12,723,260 B2
(45) Date of Patent: Sep. 1, 2026

(54) AAV-COMPATIBLE ALPHA-LAMININ-NIDOGEN CHIMERIC LINKER POLYMERIZATION PROTEIN

(71) Applicant: Rutgers, The State University of New Jersey, New Brunswick, NJ (US)

(72) Inventors: Peter D. Yurchenco, New Brunswick, NJ (US); Karen K. McKee, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1323 days.

(21) Appl. No.: 17/058,625

(22) PCT Filed: May 8, 2019

(86) PCT No.: PCT/US2019/031369
§ 371 (c)(1),
(2) Date: Nov. 24, 2020

(87) PCT Pub. No.: WO2019/217582
PCT Pub. Date: Nov. 14, 2019

(65) Prior Publication Data
US 2021/0207168 A1 Jul. 8, 2021

Related U.S. Application Data

(60) Provisional application No. 62/668,664, filed on May 8, 2018.

(51) Int. Cl.
*C12N 15/86* (2006.01)
*A61K 31/713* (2006.01)

(52) U.S. Cl.
CPC ............ *C12N 15/86* (2013.01); *A61K 31/713* (2013.01); *C12N 2750/14122* (2013.01); *C12N 2750/14143* (2013.01)

(58) Field of Classification Search
CPC .......... C12N 15/86; C12N 2750/14143; A61K 31/713; A61K 48/005
See application file for complete search history.

(56) References Cited

U.S. PATENT DOCUMENTS

2003/0108540 A1 6/2003 Kalluri
2008/0019946 A1 1/2008 Nenoi et al.
(Continued)

FOREIGN PATENT DOCUMENTS

AU 2012 228376 A1 9/2013
CN 107635575 A 1/2018
(Continued)

OTHER PUBLICATIONS

Hambrock et al., SC1/Hevin, An Extracellular Calcium-Modulated Protein That Binds Collagen, (2003, Glycobiology and extracellular matrices, 278, p. 11251-11358) (Year: 2003).*
(Continued)

*Primary Examiner* — Jennifer Dunston
*Assistant Examiner* — Keyur A Vyas
(74) *Attorney, Agent, or Firm* — Leason Ellis LLP

(57) ABSTRACT

The present invention relates to recombinant laminin adeno-associated viral vector (AAV) constructs and related methods for restoring laminin expression in deficient mammals, or in mammals with basement membrane instability.

18 Claims, 22 Drawing Sheets

Specification includes a Sequence Listing.

(56) References Cited

U.S. PATENT DOCUMENTS

| | | | | |
|---|---|---|---|---|
| 2013/0323302 | A1 | 12/2013 | Constable et al. | |
| 2015/0190481 | A1 | 7/2015 | Finn | |
| 2016/0304904 | A1 | 10/2016 | Xiao et al. | |
| 2018/0320200 | A1 * | 11/2018 | Hajitou | A61P 35/00 |

FOREIGN PATENT DOCUMENTS

| | | | | |
|---|---|---|---|---|
| JP | 2014513928 A | 6/2014 | | |
| WO | WO-2009081114 A1 * | 7/2009 | | C07K 14/4725 |
| WO | 2012/123430 A1 | 9/2012 | | |
| WO | WO 2019/217582 A1 | 11/2019 | | |

OTHER PUBLICATIONS

*Homo sapiens* laminin subunit alpha 1 (LAMA1), mRNA, NCBI Reference Sequence: NM_005559.4, https://www.ncbi.nlm.nih.gov/nuccore/NM_005559.4, accessed Jun. 11, 2024, pub. date 1990 (Year: 1990).*

*Homo sapiens* nidogen 1 (NID1) mRNA sequence, NCBI Reference Sequence: NM_002508.3, https://www.ncbi.nlm.nih.gov/nuccore/NM_002508.3; accessed Jun. 12, 2024, pub. date 1991 (Year: 1991).*

Hopf et al., Crystal structure and mutational analysis of a perlecan-binding fragment of nidogen-1, 2001, Nature Structural & Mol. Biol., 8, 634-640. (Year: 2001).*

McKee et al., Chimeric protein identification of dystrophic, Pierson and other laminin polymerization residues, available online Apr. 2018, Matrix Biology, 67, 32-46. (Year: 2018).*

Kang and Kramer,Nidogen Is Nonessential and Not Required for Normal Type IV Collagen Localization in Caenorhabditis elegans, 2000, Mol. Biol. Of the Cell, 11, p. 3911-3923. (Year: 2000).*

Second Office Action in corresponding Chinese Application No. 2019800290378, mailed Apr. 1, 2023.

Office Action in corresponding Chinese Application No. 201980029037.8, dated Sep. 12, 2023 (6 pages).

Singapore Search Report in corresponding Singapore Application No. 11202009914S, dated Jun. 30, 2022.

Singapore Written opinion in corresponding Singapore Application No. 11202009914S, dated Jun. 30, 2022.

International Preliminary Report on Patentability in corresponding International Application No. PCT/US2019/031369, mailed Nov. 10, 2020.

International Search Report and Written Opinion in corresponding International Application No. PCT/US2020/050530, mailed Nov. 23, 2020.

Karen K. Mckee et al, "Chimeric protein repair of laminin polymerization ameliorates muscular dystrophy phenotype", The Journal of Clinical Investigation, vol. 127, No. 3, Mar. 1, 2017 (Mar. 1, 2017), pp. 1075-1089.

Karen K. Mckee et al, Scaffold-forming and Adhesive Contributions of Synthetic Laminin-binding Proteins to Basement Membrane Assembly, Journal of Biological Chemistry, vol. 284, No. 13, Mar. 27, 2009 (Mar. 27, 2009), pp. 8984-8994.

Peter D. Yurchenco et al, "Laminin-deficient muscular dystrophy: Molecular pathogenesis and structural repair strategies", Matrix Biology, vol. 71-72, Oct. 1, 2018 (Oct. 1, 2018), pp. 174-187.

International Search Report and Written Opinion in corresponding International Application No. PCT/US2019/031369, mailed Oct. 24, 2019.

Chinese Office Action and Search Report in corresponding Chinese Application No. 2019800290378, issued Sep. 14, 2022 (English Translation).

Judith R. Reinhard et al., Linker proteins restore basement membrane and correct LAMA2-related muscular dystrophy in mice, Sci Transl Med., Jun. 6, 2017, pp. 1-13.

Supplemental Partial European Search Report in corresponding European Application No. EP 19799178, dated Mar. 22, 2022.

Judith R. Reinhard et al: "Linker proteins restore basement membrane and correct LAMA2-related muscular dystrophy in mice", Science Translational Medicine, vol. 9, No. 396, Jun. 28, 2017 (Jun. 28, 2017), p. eaa14649.

Dan Wang et al: "The potential of adeno-associated viral vectors for gene delivery to muscle tissue", Expert Opinion on Drug Delivery, vol. 11, No. 3, Mar. 1, 2014 (Mar. 1, 2014), pp. 345-364.

Wang Zejing et al: "Immunity and AAV-Mediated Gene Therapy for Muscular Dystrophies in Large Animal Models and Human Trials", Frontiers in Microbiology, vol. 2, Jan. 1, 2011 (Jan. 1, 2011), XP055891188.

Jerry R. Mendell et al: "Gene therapy for muscular dystrophy: Lessons learned and path forward", Neuroscience Letters, vol. 527, No. 2, Oct. 1, 2012 (Oct. 1, 2012), pp. 90-99.

Prabhpreet Sing Bassi: "Assessing the Therapeutic Potential of CRISPR/Cas9-Mediated Gene Modulation in Merosin-Deficient Congenital Muscular Dystrophy Type 1A", Nov. 1, 2017 (Nov. 1, 2017), pp. 1-76.

Reinhard J et al: "P.332 Effect of linker protein expression on LAMA2-related muscular dystrophy (MDC1A)", Neuromuscular Disorders, Elsevier Ltd, GB, vol. 29, Sep. 29, 2019 (Sep. 29, 2019), XP085845029.

Japanese First Office Action in corresponding Japanese Patent Application No. 2020-561690, May 20, 2022 (English translation).

Karen K. McKee, et al., "Chimeric protein repair of laminin polymerization ameliorates muscular dystrophy phenotype," The Journal of Clinical Investigation, 2017, vol. 127, No. 3, pp. 1075-1089.

Karen K. McKee, et al., "Chimeric protein identification of dystropic, Pierson and other laminin polymerization residues," Matrix Biol., Apr. 2018, vol. 67, pp. 32-46.

Seong Hoon Kang, et al., "Nidogen Is Nonessential and Not Required for Normal Type IV Collagen Localization in Caenorhabditis elegans," Molecular Biology of the Cell, Nov. 2000, vol. 11, pp. 3911-3923.

Israel Office Action in corresponding Israeli Application No. 278383, issued Sep. 14, 2022.

Korean Office Action in corresponding Korean Application No. 10-2020-7031675, dated Jan. 15, 2025, 9 pages.

Mckee, et al., "Chimeric protein repair of laminin polymerizationameliorates muscular dystrophy phenotype," The Journal of Clinical Investigation, Mar. 2017, vol. 127, No. 3, pp. 1075-1089.

Mckee, et al., "Chimeric protein identification of dystrophic, Pierson and other laminin polymerization residues," Matrix Biol., Apr. 2018, 67: 32-46. doi:10.1016, 24 pages.

* cited by examiner

| Score | Expect | Method | Identities | Positives | Gaps |
|---|---|---|---|---|---|
| 1855 bits(4806) | 0.0 | Compositional matrix adjust. | 875/1002(87%) | 935/1002(93%) | 0/1002(0%) |

```
Query  1    MRAWIFFLLCLAGRALARQRGLFPAILNLASNAHISTNATCGEKGPEMFCKLVEHVPGRP  60
            MRAWIFFLLCLAGRALA+QRGLFPAILNLA+NAHIS NATCGEKGPEMFCKLVEHVPGRP
Sbjct  1    MRAWIFFLLCLAGRALAQQRGLFPAILNLATNAHISANATCGEKGPEMFCKLVEHVPGRP  60

Query  61   VRNPQCRICDGNSANPRERHPISHAIDGTNNWWQSPSIQNGREYHWVTITLDLRQVFQVA  120
            VR+ QCR+CDGNS NPRERHPISHAIDGTNNWWQSPSIQNGREYHWVT+TLDLRQVFQVA
Sbjct  61   VRHAQCRVCDGNSTNPRERHPISHAIDGTNNWWQSPSIQNGREYHWVTVTLDLRQVFQVA  120

Query  121  YVIIKAANAPRPGNWILERSLDGTTFSPWQYYAVSDSECLSRYNITPRRGPPTYRADDEV  180
            Y+IIKAANAPRPGNWILERS+DG  F PWQYYAVSD+ECL+RY ITPRRGPPTYRAD+EV
Sbjct  121  YIIIKAANAPRPGNWILERSVDGVKFKPWQYYAVSDTECLTRYKITPRRGPPTYRADNEV  180

Query  181  ICTSYYSRLVPLEHGEIHTSLINGRPSADDLSPKLLEFTSARYIRLRLQRIRTLNADLMT  240
            ICTSYYS+LVPLEHGEIHTSLINGRPSADD SP+LLEFTSARYIRLRLQRIRTLNADLMT
Sbjct  181  ICTSYYSKLVPLEHGEIHTSLINGRPSADDPSPQLLEFTSARYIRLRLQRIRTLNADLMT  240

Query  241  LSHREPKELDPIVTRRYYYSIKDISVGGMCICYGHASSCPWDETTKKLQCQCEHNTCGES  300
            LSHR+ ++LDPIVTRRYYYSIKDISVGGMCICYGHASSCPWDE  K+LQCQCEHNTCGES
Sbjct  241  LSHRDLRDLDPIVTRRYYYSIKDISVGGMCICYGHASSCPWDEEAKQLQCQCEHNTCGES  300

Query  301  CNRCCPGYHQQPWRPGTVSSGNTCEACNCHNKAKDCYYDESVAKQKKSLNTAGQFRGGGV  360
            C+RCCPGYHQQPWRPGT+SSGN CE CNCHNKAKDCYYD SVAK+++SLNTAGQ+ GGGV
Sbjct  301  CDRCCPGYHQQPWRPGTISSGNECEECNCHNKAKDCYYDSSVAKERRSLNTAGQYSGGGV  360

Query  361  CINCLQNTMGINCETCIDGYYRPHKVSPYEDEPCRPCNCDPVGSLSSVCIKDDLHSDLHN  420
            C+NC QNT GINCETCID YYRPHKVSPY+D PCRPCNCDPVGSLSSVCIKDD H+DL N
Sbjct  361  CVNCSQNTTGINCETCIDQYYRPHKVSPYDDHPCRPCNCDPVGSLSSVCIKDDRHADLAN  420

Query  421  GKQPGQCPCKEGYTGEKCDRCQLGYKDYPTCVSCGCNPVGSASDEPCTGPCVCKENVEGK  480
            GK PGQCPC++GY G+KCDRCQ GY+ +P C+ C C  VGS +++PC  PC+CK+NVEGK
Sbjct  421  GKWPGQCPCRKGYAGDKCDRCQFGYRGFPNCIPCDCRTVGSLNEDPCIEPCLCKKNVEGK  480

Query  481  ACDRCKPGFYNLKEKNPRGCSECFCFGVSDVCPINYCETGLHNCDIPQRAQCIYTGGSSY  540
```

FIG. 9

```
              CDRCKPGFYNLKE+NP GCSECFCFGVS VCPINYCETGLHNCDIPQRAQCIY GGSSY
Sbjct  481   NCDRCKPGFYNLKERNPEGCSECFCFGVSGVCPINYCETGLHNCDIPQRAQCIYMGGSSY   540

Query  541   TCSCLPGFSGDGQACQDVDECQPSRCHPDAFCYNTPGSFTCQCKPGYQGDGFRCVPGEVE   600
             TCSCLPGFSGDG+AC+DVDECQ SRCHPDAFCYNTPGSFTCQCKPGYQGDGFRC+PGEV
Sbjct  541   TCSCLPGFSGDGRACRDVDECQHSRCHPDAFCYNTPGSFTCQCKPGYQGDGFRCMPGEVS   600

Query  601   KTRCQHEREHILGAAGATDPQRPIPPGLFVPECDAHGHYAPTQCHGSTGYCWCVDRDGRE   660
             KTRCQ EREHILGAAG  D QRP   G+FVP+CD +GHY PTQCH STGYCWCVDRDGRE
Sbjct  601   KTRCQLEREHILGAAGGADAQRPTLQGMFVPQCDEYGHYVPTQCHHSTGYCWCVDRDGRE   660

Query  661   VEGTRTRPGMTPPCLSTVAPPIHQGPAVPTAVIPLPPGTHLLFAQTGKIERLPLEGNTMR   720
             +EG+RT PGM PPCLSTVAPPIHQGP VPTAVIPLPPGTHLLFAQTGKIERLPLE NTM+
Sbjct  661   LEGSRTPPGMRPPCLSTVAPPIHQGPVVPTAVIPLPPGTHLLFAQTGKIERLPLERNTMK   720

Query  721   KTEAKAFLHVPAKVIIGLAFDCVDKMVYWTDITEPSIGRASLHGGEPTTIIRQDLGSPEG   780
             KTE KAFLH+PAKVIIGLAFDCVDK+VYWTDI+EPSIGRASLHGGEPTTIIRQDLGSPEG
Sbjct  721   KTERKAFLHIPAKVIIGLAFDCVDKVVYWTDISEPSIGRASLHGGEPTTIIRQDLGSPEG   780

Query  781   IAVDHLGRNIFWTDSNLDRIEVAKLDGTQRRVLFETDLVNPRGIVTDSVRGNLYWTDWNR   840
             IA+DHLGR IFWTDS LDRIEVAK+DGTQRRVLF+T LVNPRGIVTD VRGNLYWTDWNR
Sbjct  781   IALDHLGRTIFWTDSQLDRIEVAKMDGTQRRVLFDTGLVNPRGIVTDPVRGNLYWTDWNR   840

Query  841   DNPKIETSYMDGTNRRILVQDDLGLPNGLTFDAFSSQLCWVDAGTNRAECLNPSQPSRRK   900
             DNPKIETS+MDGTNRRIL QD+LGLPNGLTFDAFSSQLCWVDAGT+RAECLNP+QP RRK
Sbjct  841   DNPKIETSHMDGTNRRILAQDNLGLPNGLTFDAFSSQLCWVDAGTHRAECLNPAQPGRRK   900

Query  901   ALEGLQYPFAVTSYGKNLYFTDWKMNSVVALDLAISKETDAFQPHKQTRLYGITTALSQC   960
              LEGLQYPFAVTSYGKNLY+TDWK NSV+A+DLAISKE D F PHKQTRLYGIT ALSQC
Sbjct  901   VLEGLQYPFAVTSYGKNLYYTDWKTNSVIAMDLAISKEMDTFHPHKQTRLYGITIALSQC   960

Query  961   PQGHNYCSVNNGGCTHLCLATPGSRTCRCPDNTLGVDCIEQK                   1002
             PQGHNYCSVNNGGCTHLCL TPGSRTCRCPDNTLGVDCIE+K
Sbjct  961   PQGHNYCSVNNGGCTHLCLPTPGSRTCRCPDNTLGVDCIERK                   1002
```

FIG.9 continued

```
1     ATGAGGGCCT GGATCTTCTT TCTCCTTTGC CTGGCCGGGA GGGCTCTGGC ACGGCAGAGA GGCCTGTTTC CTGCCATTCT CAATCTTGCC AGCAATGCTC ACATCAGCAC
       M  R  A  W  I  F  F  L  L  C  L  A  G  R  A  L  A  R  Q  R  G  L  F  P  A  I  L  N  L  A  S  N  A  H  I  S  T
111   CAATGCCACC TGTGGCGAGA AGGGGCCGGA GATGTTCTGC AAACTTGTGG AGCATGTGCC AGGTCGGCCC GTCCGAAACC CACAGTGCCG GATCTGTGAT GGCAACAGCG
       N  A  T  C  G  E  K  G  P  E  M  F  C  K  L  V  E  H  V  P  G  R  P  V  R  N  P  Q  C  R  I  C  D  G  N  S  A
221   CAAACCCCAG AGAACGCCAT CCAATATCAC ATGCCATAGA TGGCACCAAT AACTGGTGGC AAAGTCCCAG CATTCAGAAT GGGAGAGAAT ATCACTGGGT CACAATCACT
       N  P  R  E  R  H  P  I  S  H  A  I  D  G  T  N  N  W  W  Q  S  P  S  I  Q  N  G  R  E  Y  H  W  V  T  I  T
331   CTGGACTTAA GACAGGTCTT TCAAGTTGCA TATGTCATCA TTAAAGCTGC CAATGCCCCT CGACCTGGAA ACTGGATTTT GGAGCGTTCT CTGGATGGCA CCACGTTCAG
       L  D  L  R  Q  V  F  Q  V  A  Y  V  I  I  K  A  A  N  A  P  R  P  G  N  W  I  L  E  R  S  L  D  G  T  T  F  S
441   CCCCTGGCAG TATTATGCAG TCAGCGACTC AGAGTGTTTG TCTCGTTACA ATATAACTCC AAGACGAGGG CCACCCACCT ACAGGGCTGA TGATGAAGTG ATCTGCACCT
       P  W  Q  Y  Y  A  V  S  D  S  E  C  L  S  R  Y  N  I  T  P  R  R  G  P  P  T  Y  R  A  D  D  E  V  I  C  T  S
551   CCTATTATTC CAGATTGGTG CCACTTGAGC ATGGAGAGAT TCATACATCA CTCATCAATG GCAGACCAAG CGCTGACGAT CTTTCACCCA AGTTGTTGGA ATTCACTTCT
       Y  Y  S  R  L  V  P  L  E  H  G  E  I  H  T  S  L  I  N  G  R  P  S  A  D  D  L  S  P  K  L  L  E  F  T  S
661   GCACGATATA TTCGCCTTCG CTTGCAACGC ATTAGAACGC TCAATGCAGA TCTCATGACC CTTAGCCACC GGGAACCTAA AGAACTGGAT CCTATTGTTA CCAGACGCTA
       A  R  Y  I  R  L  R  L  Q  R  I  R  T  L  N  A  D  L  M  T  L  S  H  R  E  P  K  E  L  D  P  I  V  T  R  R  Y
771   TTATTATTCA ATAAAGGACA TTTCTGTTGG AGGCATGTGT ATCTGCTATG GCCATGCTAG TAGCTGCCCA TGGGATGAAA CTACAAAGAA ACTGCAGTGT CAATGTGAGC
       Y  Y  S  I  K  D  I  S  V  G  G  M  C  I  C  Y  G  H  A  S  S  C  P  W  D  E  T  T  K  K  L  Q  C  Q  C  E  H
881   ATAATACTTG CGGGGAGAGC TGTAACAGGT GCTGTCCTGG GTACCATCAG CAGCCCTGGA GGCCGGGAAC CGTGTCCTCC GGCAATACAT GTGAAGCATG TAATTGTCAC
       N  T  C  G  E  S  C  N  R  C  C  P  G  Y  H  Q  Q  P  W  R  P  G  T  V  S  S  G  N  T  C  E  A  C  N  C  H
991   AATAAAGCCA AAGACTGTTA CTATGATGAA AGTGTTGCAA AGCAGAAGAA AAGTTTGAAT ACTGCTGGAC AGTTCAGAGG AGGAGGGGTT TGCATAAATT GCTTGCAGAA
       N  K  A  K  D  C  Y  Y  D  E  S  V  A  K  Q  K  K  S  L  N  T  A  G  Q  F  R  G  G  G  V  C  I  N  C  L  Q  N
1101  CACCATGGGA ATCAACTGTG AAACCTGTAT TGATGGATAT TATAGACCAC ACAAAGTGTC TCCTTATGAG GATGAGCCTT GCCGCCCCTG TAATTGTGAC CCTGTGGGGT
       T  M  G  I  N  C  E  T  C  I  D  G  Y  Y  R  P  H  K  V  S  P  Y  E  D  E  P  C  R  P  C  N  C  D  P  V  G  S
1211  CCCTCAGTTC TGTCTGTATT AAGGATGACC TCCATTCTGA CTTACACAAT GGGAAGCAGC CAGGTCAGTG CCCATGTAAG GAAGGTTATA CAGGAGAAAA ATGTGATCGC
       L  S  S  V  C  I  K  D  D  L  H  S  D  L  H  N  G  K  Q  P  G  Q  C  P  C  K  E  G  Y  T  G  E  K  C  D  R
1321  TGCCAACTTG GCTATAAGGA TTACCCGACC TGTGTCTCCT GTGGGTGCAA CCCAGTGGGC AGTGCCAGTG ATGAGCCCTG CACAGGGCCC TGTGTTTGTA AGGAAAACGT
       C  Q  L  G  Y  K  D  Y  P  T  C  V  S  C  G  C  N  P  V  G  S  A  S  D  E  P  C  T  G  P  C  V  C  K  E  N  V
1431  TGAGGGGAAG GCCTGTGATC GCTGCAAGCC AGGATTCTAT AACTTGAAGG AAAAAAACCC CCGGGGCTGC TCCGAGTGCT TCTGCTTTGG CGTTTCTGAT GTCTGCCCCA
       E  G  K  A  C  D  R  C  K  P  G  F  Y  N  L  K  E  K  N  P  R  G  C  S  E  C  F  C  F  G  V  S  D  V  C  P  I
```

FIG. 10

```
1541 TCAACTACTG TGAAACTGGC CTTCATAACT GCGACATACC CCAGCGGGCC CAGTGTATCT ACACAGGAGG CTCCTCCTAC ACCTGTTCCT GCTTGCCAGG CTTTTCTGGG
       N Y C  E T G  L H N C  D I P  Q R A  Q C I Y  T G G  S S Y  T C S C  L P G  F S G
1651 GATGGCCAAG CCTGCCAAGA TGTAGATGAA TGCCAGCCAA GCCGATGTCA CCCTGACGCC TTCTGCTACA ACACTCCAGG CTCTTTCACG TGCCAGTGCA AACCTGGTTA
     D G Q A  C Q D  V D E  C Q P S  R C H  P D A  F C Y N  T P G  S F T  C Q C K  P G Y
1761 TCAGGGAGAC GGCTTCCGTT GCGTGCCCGG AGAGGTGGAG AAAACCCGGT GCCAGCACGA GCGAGAACAC ATTCTCGGGG CAGCGGGGGC GACAGACCCA CAGCGACCCA
      Q G D  G F R C  V P G  E V E  K T R C  Q H E  R E H  I L G A  A G A  T D P  Q R P I
1871 TTCCTCCGGG GCTGTTCGTT CCTGAGTGCG ATGCGCACGG GCACTACGCG CCCACCCAGT GCCACGGCAG CACCGGCTAC TGCTGGTGCG TGGATCGCGA CGGCCGCGAG
       P P G  L F V  P E C D  A H G  H Y A  P T Q C  H G S  T G Y  C W C V  D R D  G R E
1981 GTGGAGGGCA CCAGGACCAG GCCCGGGATG ACGCCCCCGT GTCTGAGTAC AGTGGCTCCC CCGATTCACC AAGGACCTGC GGTGCCTACC GCCGTGATCC CCTTGCCTCC
     V E G T  R T R  P G M  T P P C  L S T  V A P  P I H Q  G P A  V P T  A V I P  L P P
2091 TGGGACCCAT TTACTCTTTG CCCAGACTGG GAAGATTGAG CGCCTGCCCC TGGAGGGAAA TACCATGAGG AAGACAGAAG CAAAGGCGTT CCTTCATGTC CCGGCTAAAG
      G T H  L L F A  Q T G  K I E  R L P L  E G N  T M R  K T E A  K A F  L H V  P A K V
2201 TCATCATTGG ACTGGCCTTT GACTGCGTGG ACAAGATGGT TTACTGGACG GACATCACTG AGCCTTCCAT TGGGAGAGCT AGTCTACATG GTGGAGAGCC AACCACCATC
       I I G  L A F  D C V D  K M V  Y W T  D I T E  P S I  G R A  S L H G  G E P  T T I
2311 ATTAGACAAG ATCTTGGAAG TCCAGAAGGT ATCGCTGTTG ATCACCTTGG CCGCAACATC TTCTGGACAG ACTCTAACCT GGATCGAATA GAAGTGGCGA AGCTGGACGG
     I R Q D  L G S  P E G  I A V D  H L G  R N I  F W T D  S N L  D R I  E V A K  L D G
2421 CACGCAGCGC CGGGTGCTCT TTGAGACTGA CTTGGTGAAT CCCAGAGGCA TTGTAACGGA TTCCGTGAGA GGGAACCTTT ACTGGACAGA CTGGAACAGA GATAACCCCA
      T Q R  R V L F  E T D  L V N  P R G I  V T D  S V R  G N L Y  W T D  W N R  D N P K
2531 AGATTGAAAC TTCCTACATG GACGGCACGA ACCGGAGGAT CCTTGTGCAG GATGACCTGG GCTTGCCCAA TGGACTGACC TTCGATGCGT TCTCATCTCA GCTCTGCTGG
       I E T  S Y M  D G T N  R R I  L V Q  D D L G  L P N  G L T  F D A F  S S Q  L C W
2641 GTGGATGCAG GCACCAATCG GGCGGAATGC CTGAACCCCA GTCAGCCCAG CAGACGCAAG GCTCTCGAAG GGCTCCAGTA TCCTTTTGCT GTGACGAGCT ACGGGAAGAA
     V D A G  T N R  A E C  L N P S  Q P S  R R K  A L E G  L Q Y  P F A  V T S Y  G K N
2751 TCTGTATTTC ACAGACTGGA AGATGAATTC CGTGGTTGCT CTCGATCTTG CAATTTCCAA GGAGACGGAT GCTTTCCAAC CCCACAAGCA GACCCGGCTG TATGGCATCA
      L Y F  T D W K  M N S  V V A  L D L A  I S K  E T D  A F Q P  H K Q  T R L  Y G I T
2861 CCACGGCCCT GTCTCAGTGT CCGCAAGGCC ATAACTACTG CTCAGTGAAC AATGGCGGCT GCACCCACCT ATGCTTGGCC ACCCCAGGGA GCAGGACCTG CCGTTGCCCT
       T A L  S Q C  P Q G H  N Y C  S V N  N G G C  T H L  C L A  T P G S  R T C  R C P
2971 GACAACACCT TGGGAGTTGA CTGTATCGAA CAGAAATGA
     D N T L  G V D  C I E  Q K .
```

FIG.10 continued

```
1     ATGAGGGCCT GGATCTTCTT TCTCCTTTGC CTGGCCGGGA GGGCTCTGGC ACGGCAGAGA GGCCTGTTTC CTGCCATTCT CAATCTTGCC AGCAATGCTC ACATCAGCAC
      M R A W I F F L L C L A G R A L A R Q R G L F P A I L N L A S N A H I S T
111   CAATGCCACC TGTGGCGAGA AGGGGCCGGA GATGTTCTGC AAACTTGTGG AGCATGTGCC AGGTCGGCCC GTCCGAAACC CACAGTGCCG GATCTGTGAT GGCAACAGCG
      N A T C G E K G P E M F C K L V E H V P G R P V R N P Q C R I C D G N S A
221   CAAACCCCAG AGAACGCCAT CCAATATCAC ATGCCATAGA TGGCACCAAT AACTGGTGGC AAAGTCCCAG CATTCAGAAT GGGAGAGAAT ATCACTGGGT CACAATCACT
      N P R E R H P I S H A I D G T N N W W Q S P S I Q N G R E Y H W V T I T
331   CTGGACTTAA GACAGGTCTT TCAAGTTGCA TATGTCATCA TTAAAGCTGC CAATGCCCCT CGACCTGGAA ACTGGATTTT GGAGCGTTCT CTGGATGGCA CCACGTTCAG
      L D L R Q V F Q V A Y V I I K A A N A P R P G N W I L E R S L D G T T F S
441   CCCCTGGCAG TATTATGCAG TCAGCGACTC AGAGTGTTTG TCTCGTTACA ATATAACTCC AAGACGAGGG CCACCCACCT ACAGGGCTGA TGATGAAGTG ATCTGCACCT
      P W Q Y Y A V S D S E C L S R Y N I T P R R G P P T Y R A D D E V I C T S
551   CCTATTATTC CAGATTGGTG CCACTTGAGC ATGGAGAGAT TCATACATCA CTCATCAATG GCAGACCAAG CGCTGACGAT CTTTCACCCA AGTTGTTGGA ATTCACTTCT
      Y Y S R L V P L E H G E I H T S L I N G R P S A D D L S P K L L E F T S
661   GCACGATATA TTCGCCTTCG CTTGCAACGC ATTAGAACGC TCAATGCAGA TCTCATGACC CTTAGCCACC GGGAACCTAA AGAACTGGAT CCTATTGTTA CCAGACGCTA
      A R Y I R L R L Q R I R T L N A D L M T L S H R E P K E L D P I V T R R Y
771   TTATTATTCA ATAAAGGACA TTTCTGTTGG AGGCATGTGT ATCTGCTATG GCCATGCTAG TAGCTGCCCA TGGGATGAAA CTACAAAGAA ACTGCAGTGT CAATGTGAGC
      Y Y S I K D I S V G G M C I C Y G H A S S C P W D E T T K K L Q C Q C E H
881   ATAATACTTG CGGGGAGAGC TGTAACAGGT GCTGTCCTGG GTACCATCAG CAGCCCTGGA GGCCGGGAAC CGTGTCCTCC GGCAATACAT GTGAAGCATG TAATTGTCAC
      N T C G E S C N R C C P G Y H Q Q P W R P G T V S S G N T C E A C N C H
991   AATAAAGCCA AAGACTGTTA CTATGATGAA AGTGTTGCAA AGCAGAAGAA AAGTTTGAAT ACTGCTGGAC AGTTCAGAGG AGGAGGGGTT TGCATAAATT GCTTGCAGAA
      N K A K D C Y Y D E S V A K Q K K S L N T A G Q F R G G G V C I N C L Q N
1101  CACCATGGGA ATCAACTGTG AAACCTGTAT TGATGGATAT TATAGACCAC ACAAAGTGTC TCCTTATGAG GATGAGCCTT GCCGCCCCTG TAATTGTGAC CCTGTGGGGT
      T M G I N C E T C I D G Y Y R P H K V S P Y E D E P C R P C N C D P V G S
1211  CCCTCAGTTC TGTCTGTATT AAGGATGACC TCCATTCTGA CTTACACAAT GGGAAGCAGC CAGGTCAGTG CCCATGTAAG GAAGGTTATA CAGGAGAAAA ATGTGATCGC
      L S S V C I K D D L H S D L H N G K Q P G Q C P C K E G Y T G E K C D R
1321  TGCCAACTTG GCTATAAGGA TTACCCGACC TGTGTCTCCT GTGGGTGCAA CCCAGTGGGC AGTGCCAGTG ATGAGCCCTG CACAGGGCCC TGTGTTTGTA AGGAAAACGT
      C Q L G Y K D Y P T C V S C G C N P V G S A S D E P C T G P C V C K E N V
```

FIG. 11

```
1431 TGAGGGGAAG GCCTGTGATC GCTGCAAGCC AGGATTCTAT AACTTGAAGG AAAAAAACCC CCGGGGCTGC TCCGAGTGCT TCTGCTTTGG CGTTTCTGAT GTCTGCCCCA
      E G K  A C D R  C K P  G F Y  N L K E  K N P  R G C  S E C F  C F G  V S D  V C P I
1541 TCAACTACTG TGAAACTGGC CTTCATAACT GCGACATACC CCAGCGGGCC CAGTGTATCT ACACAGGAGG CTCCTCCTAC ACCTGTTCCT GCTTGCCAGG CTTTTCTGGG
      N Y C  E T G  L H N C  D I P  Q R A  Q C I Y  T G G  S S Y  T C S C  L P G  F S G
1651 GATGGCCAAG CCTGCCAAGA TGTAGATGAA TGCCAGCCAA GCCGATGTCA CCCTGACGCC TTCTGCTACA ACACTCCAGG CTCTTTCACG TGCCAGTGCA AACCTGGTTA
     D G Q A  C Q D  V D E  C Q P S  R C H  P D A  F C Y N  T P G  S F T  C Q C K  P G Y
1761 TCAGGGAGAC GGCTTCCGTT GCGTGCCCGG AGAGGTGGAG AAAACCCGGT GCCAGCACGA GCGAGAACAC ATTCTCGGGG CAGCGGGGGC GACAGACCCA CAGCGACCCA
      Q G D  G F R C  V P G  E V E  K T R C  Q H E  R E H  I L G A  A G A  T D P  Q R P I
1871 TTCCTCCGGG GCTGTTCGTT CCTGAGTGCG ATGCGCACGG GCACTACGCG CCCACCCAGT GCCACGGCAG CACCGGCTAC TGCTGGTGCG TGGATCGCGA CGGCCGCGAG
      P P G  L F V  P E C D  A H G  H Y A  P T Q C  H G S  T G Y  C W C V  D R D  G R E
1981 GTGGAGGGCA CCAGGACCAG GCCCGGGATG ACGCCCCCGT GTCTGAGTAC AGTGGCTCCC CCGATTCACC AAGGACCTGC GGTGCCTACC GCCGTGATCC CCTTGCCTCC
     V E G T  R T R  P G M  T P P C  L S T  V A P  P I H Q  G P A  V P T  A V I P  L P P
2091 TGGGACCCAT TTACTCTTTG CCCAGACTGG GAAGATTGAG CGCCTGCCCC TGGAGGGAAA TACCATGAGG AAGACAGAAG CAAAGGCGTT CCTTCATGTC CCGGCTAAAG
      G T H  L L F A  Q T G  K I E  R L P L  E G N  T M R  K T E A  K A F  L H V  P A K V
2201 TCATCATTGG ACTGGCCTTT GACTGCGTGG ACAAGATGGT TTACTGGACG GACATCACTG AGCCTTCCAT TGGGAGAGCT AGTCTACATG GTGGAGAGCC AACCACCATC
      I I G  L A F  D C V D  K M V  Y W T  D I T E  P S I  G R A  S L H G  G E P  T T I
2311 ATTAGACAAG ATCTTGGAAG TCCAGAAGGT ATCGCTGTTG ATCACCTTGG CCGCAACATC TTCTGGACAG ACTCTAACCT GGATCGAATA GAAGTGGCGA AGCTGGACGG
     I R Q D  L G S  P E G  I A V D  H L G  R N I  F W T D  S N L  D R I  E V A K  L D G
2421 CACGCAGCGC CGGGTGCTCT TTGAGACTGA CTTGGTGAAT CCCAGAGGCA TTGTAACGGA TTCCGTGAGA GGGAACCTTT ACTGGACAGA CTGGAACAGA GATAACCCCA
      T Q R  R V L F  E T D  L V N  P R G I  V T D  S V R  G N L Y  W T D  W N R  D N P K
2531 AGATTGAAAC TTCCTACATG GACGGCACGA ACCGGAGGAT CCTTGTGCAG GATGACCTGG GCTTGCCCAA TGGACTGACC TTCGATGCGT TCTCATCTCA GCTCTGCTGG
      I E T  S Y M  D G T N  R R I  L V Q  D D L G  L P N  G L T  F D A F  S S Q  L C W
2641 GTGGATGCAG GCACCAATCG GGCGGAATGC CTGAACCCCA GTCAGCCCAG CAGACGCAAG GCTCTCGAAG GGCTCCAGTA TCCTTTTGCT GTGACGAGCT ACGGGAAGAA
      V D A G  T N R  A E C  L N P S  Q P S  R R K  A L E G  L Q Y  P F A  V T S Y  G K N
2751 TCTGTATTTC ACAGACTGGA AGATGAATTC CGTGGTTGCT CTCGATCTTG CAATTTCCAA GGAGACGGAT GCTTTCCAAC CCCACAAGCA GACCCGGCTG TATGGCATCA
      L Y F  T D W K  M N S  V V A  L D L A  I S K  E T D  A F Q P  H K Q  T R L  Y G I T
2861 CCACGGCCCT GTCTCAGTGT CCGCAAGGCC ATAACTACTG CTCAGTGAAC AATGGCGGCT GCACCCACCT ATGCTTGGCC ACCCCAGGGA GCAGGACCTG CCGTTGCCCT
      T A L  S Q C  P Q G H  N Y C  S V N  N G G C  T H L  C L A  T P G S  R T C  R C P
2971 GACAACACCT TGGGAGTTGA CTGTATCGAA CAGAAATGA
     D N T L  G V D  C I E  Q K
```

FIG.11 continued

ATGAGGGCCTGGATCTTCTTTCTCCTTTGCCTGGCCGGGAGGGCTCTGGCACAGCAGAGAGGCTTGTTCCCTG
CCATTCTCAACCTGGCCACCAATGCCCACATCAGCGCCAATGCTACCTGTGGAGAGAAGGGGCCTGAGATGTT
CTGCAAACTCGTGGAGCACGTGCCGGGCCGGCCTGTTCGACACGCCCAATGCCGGGTCTGTGACGGTAACAG
TACGAATCCTAGAGAGCGCCATCCGATATCACACGCAATCGATGGCACCAACAACTGGTGGCAGAGCCCCAG
TATTCAGAATGGGAGAGAGTATCACTGGGTCACTGTCACCCTGGACTTACGGCAGGTCTTTCAAGTTGCATAC
ATCATCATTAAAGCTGCCAATGCCCCTCGGCCTGGAAACTGGATTTTGGAGCGCTCCGTGGATGGCGTCAAGT
TCAAACCCTGGCAGTACTATGCCGTCAGCGATACAGAGTGTTTGACCCGCTACAAAATAACTCCACGGCGGGG
ACCTCCCACTTACAGAGCAGACAACGAAGTCATCTGCACCTCGTATTATTCAAAGCTGGTGCCACTTGAACATG
GAGAGATTCACACATCACTCATCAATGGCAGACCCAGCGCTGACGACCCCTCACCCCAGTTGCTGGAATTCAC
CTCAGCACGGTACATTCGCCTTCGTCTTCAGCGCATCAGAACACTCAACGCAGACCTCATGACCCTTAGCCATC
GGGACCTCAGAGACCTTGACCCCATTGTCACAAGACGTTATTACTATTCGATAAAAGACATTTCCGTTGGAGG
CATGTGCATTTGCTACGGCCATGCCAGCAGCTGCCCGTGGGATGAAGAAGCAAAGCAACTACAGTGTCAGTG
TGAACACAATACGTGTGGCGAGAGCTGCGACAGGTGCTGTCCTGGCTACCATCAGCAGCCCTGGAGGCCCGG
AACCATTTCCTCCGGCAACGAGTGTGAGGAATGCAACTGTCACAACAAAGCCAAAGATTGTTACTATGACAGC
AGTGTTGCAAAGGAGAGGAGAAGCCTGAACACTGCCGGGCAGTACAGTGGAGGAGGGGTTTGTGTCAACTG
CTCGCAGAATACCACAGGGATCAACTGTGAAACCTGTATCGACCAGTATTACAGACCTCACAAGGTATCTCCTT
ATGATGACCACCCTTGCCGTCCCTGTAACTGTGACCCTGTGGGGTCTCTGAGTTCTGTCTGTATCAAGGATGAC
CGCCATGCCGATTTAGCCAATGGAAAGTGGCCAGGTCAGTGTCCATGTAGGAAAGGTTATGCTGGAGATAAA
TGTGACCGCTGCCAGTTTGGCTACCGGGGTTTCCCAAATTGCATCCCCTGTGACTGCAGGACTGTCGGCAGCC
TGAATGAGGATCCATGCATAGAGCCGTGTCTTTGTAAGAAAAATGTTGAGGGTAAGAACTGTGATCGCTGCA
AGCCAGGATTCTACAACTTGAAGGAACGAAACCCCGAGGGCTGCTCCGAGTGCTTCTGCTTCGGTGTCTCTGG
TGTCTGTCCCATCAACTACTGTGAAACTGGTCTCCACAACTGTGATATCCCCCAGCGAGCCCAGTGCATCTATA
TGGGTGGTTCCTCCTACACCTGCTCCTGTCTGCCTGGCTTCTCTGGGGATGGCAGAGCCTGCCGAGACGTGGA
TGAATGCCAGCACAGCCGATGTCACCCCGATGCCTTCTGCTACAACACACCAGGCTCTTTCACATGTCAGTGCA
AGCCTGGCTATCAGGGGGATGGCTTCCGATGCATGCCCGGAGAGGTGAGCAAAACCCGGTGTCAACTGGAA
CGAGAGCACATCCTTGGAGCAGCCGGCGGGGCAGATGCACAGCGGCCCACCCTGCAGGGGATGTTTGTGCCT
CAGTGTGATGAATATGGACACTATGTACCCACCCAGTGTCACCACAGCACTGGCTACTGCTGGTGTGTGGACC
GAGATGGTCGGGAGCTGGAGGGTAGCCGTACCCCACCTGGGATGAGGCCCCCGTGTCTGAGTACAGTGGCT
CCTCCTATTCACCAGGGACCAGTAGTACCTACAGCTGTCATCCCCCTGCCTCCAGGGACACACTTACTCTTTGCT
CAGACTGGAAAGATTGAACGCCTGCCCCTGGAAAGAAACACCATGAAGAAGACAGAACGCAAGGCCTTTCTC
CATATCCCTGCAAAAGTCATCATTGGACTGGCCTTTGACTGCGTGGACAAGGTGGTTTACTGGACAGACATCA
GCGAGCCTTCCATTGGGAGAGCCAGCCTCCACGGTGGAGAGCCAACCACCATCATTCGACAAGATCTTGGAA
GCCCTGAAGGCATTGCCCTTGACCATCTTGGTCGAACCATCTTCTGGACGGACTCTCAGTTGGATCGAATAGA
AGTTGCAAAGATGGATGGCACCCAGCGCCGAGTGCTGTTTGACACGGGTTTGGTGAATCCCAGAGGCATTGT
GACAGACCCCGTAAGAGGGAACCTTTATTGGACAGATTGGAACAGAGATAATCCCAAAATTGAGACTTCTCAC
ATGGATGGCACCAACCGGAGGATTCTCGCACAGGACAACCTGGGCTTGCCCAATGGTCTGACCTTTGATGCAT
TCTCATCTCAGCTTTGCTGGGTGGATGCAGGCACCCATAGGGCAGAATGCCTGAACCCAGCTCAGCCTGGCAG
ACGCAAAGTTCTCGAAGGGCTCCAGTATCCTTTCGCTGTGACTAGCTATGGGAAGAATTTGTACTACACAGAC
TGGAAGACGAATTCAGTGATTGCCATGGACCTTGCTATATCCAAAGAGATGGATACCTTCCACCCACACAAGC
AGACCCGGCTATATGGCATCACCATCGCCCTGTCCCAGTGTCCCCAAGGCCACAATTACTGCTCAGTGAATAAT
GGTGGATGTACCCACCTCTGCTTGCCCACTCCAGGGAGCAGGACCTGCCGATGTCCTGACAACACCCTGGGAG
TTGACTGCATTGAACGGAAATGA

FIG. 12

MRAWIFFLLCLAGRALAQQRGLFPAILNLATNAHISANATCGEKGPEMFCKLVEHVPGRPVRHAQCRVCDGNSTN
PRERHPISHAIDGTNNWWQSPSIQNGREYHWVTVTLDLRQVFQVAYIIIKAANAPRPGNWILERSVDGVKFKPW
QYYAVSDTECLTRYKITPRRGPPTYRADNEVICTSYYSKLVPLEHGEIHTSLINGRPSADDPSPQLLEFTSARYIRLRLQ
RIRTLNADLMTLSHRDLRDLDPIVTRRYYYSIKDISVGGMCICYGHASSCPWDEEAKQLQCQCEHNTCGESCDRCC
PGYHQQPWRPGTISSGNECEECNCHNKAKDCYYDSSVAKERRSLNTAGQYSGGGVCVNCSQNTTGINCETCIDQ
YYRPHKVSPYDDHPCRPCNCDPVGSLSSVCIKDDRHADLANGKWPGQCPCRKGYAGDKCDRCQFGYRGFPNCIP
CDCRTVGSLNEDPCIEPCLCKKNVEGKNCDRCKPGFYNLKERNPEGCSECFCFGVSGVCPINYCETGLHNCDIPQRA
QCIYMGGSSYTCSCLPGFSGDGRACRDVDECQHSRCHPDAFCYNTPGSFTCQCKPGYQGDGFRCMPGEVSKTRC
QLEREHILGAAGGADAQRPTLQGMFVPQCDEYGHYVPTQCHHSTGYCWCVDRDGRELEGSRTPPGMRPPCLST
VAPPIHQGPVVPTAVIPLPPGTHLLFAQTGKIERLPLERNTMKKTERKAFLHIPAKVIIGLAFDCVDKVVYWTDISEPS
IGRASLHGGEPTTIIRQDLGSPEGIALDHLGRTIFWTDSQLDRIEVAKMDGTQRRVLFDTGLVNPRGIVTDPVRGNL
YWTDWNRDNPKIETSHMDGTNRRILAQDNLGLPNGLTFDAFSSQLCWVDAGTHRAECLNPAQPGRRKVLEGLQ
YPFAVTSYGKNLYYTDWKTNSVIAMDLAISKEMDTFHPHKQTRLYGITIALSQCPQGHNYCSVNNGGCTHLCLPTP
GSRTCRCPDNTLGVDCIERK

FIG.13

ATGAGGGCCTGGATCTTCTTTCTCCTTTGCCTGGCCGGGAGGGCTCTGGCACGGCAGAGAGGCCTGTTTCCTG
CCATTCTCAATCTTGCCAGCAATGCTCACATCAGCACCAATGCCACCTGTGGCGAGAAGGGGCCGGAGATGTT
CTGCAAACTTGTGGAGCATGTGCCAGGTCGGCCCGTCCGAAACCCACAGTGCCGGATCTGTGATGGCAACAG
CGCAAACCCCAGAGAACGCCATCCAATATCACATGCCATAGATGGCACCAATAACTGGTGGCAAAGTCCCAGC
ATTCAGAATGGGAGAGAATATCACTGGGTCACAATCACTCTGGACTTAAGACAGGTCTTTCAAGTTGCATATG
TCATCATTAAAGCTGCCAATGCCCCTCGACCTGGAAACTGGATTTTGGAGCGTTCTCTGGATGGCACCACGTTC
AGCCCCTGGCAGTATTATGCAGTCAGCGACTCAGAGTGTTTGTCTCGTTACAATATAACTCCAAGACGAGGGC
CACCCACCTACAGGGCTGATGATGAAGTGATCTGCACCTCCTATTATTCCAGATTGGTGCCACTTGAGCATGG
AGAGATTCATACATCACTCATCAATGGCAGACCAAGCGCTGACGATCTTTCACCCAAGTTGTTGGAATTCACTT
CTGCACGATATATTCGCCTTCGCTTGCAACGCATTAGAACGCTCAATGCAGATCTCATGACCCTTAGCCACCGG
GAACCTAAAGAACTGGATCCTATTGTTACCAGACGCTATTATTATTCAATAAAGGACATTTCTGTTGGAGGCAT
GTGTATCTGCTATGGCCATGCTAGTAGCTGCCCATGGGATGAAACTACAAAGAAACTGCAGTGTCAATGTGAG
CATAATACTTGCGGGGAGAGCTGTAACAGGTGCTGTCCTGGGTACCATCAGCAGCCCTGGAGGCCGGGAACC
GTGTCCTCCGGCAATACATGTGAAGCATGTAATTGTCACAATAAAGCCAAAGACTGTTACTATGATGAAAGTG
TTGCAAAGCAGAAGAAAAGTTTGAATACTGCTGGACAGTTCAGAGGAGGAGGGGTTTGCATAAATTGCTTGC
AGAACACCATGGGAATCAACTGTGAAACCTGTATTGATGGATATTATAGACCACACAAAGTGTCTCCTTATGA
GGATGAGCCTTGCCGCCCCTGTAATTGTGACCCTGTGGGGTCCCTCAGTTCTGTCTGTATTAAGGATGACCTCC
ATTCTGACTTACACAATGGGAAGCAGCCAGGTCAGTGCCCATGTAAGGAAGGTTATACAGGAGAAAAATGTG
ATCGCTGCCAACTTGGCTATAAGGATTACCCGACCTGTGTCTCCTGTGGGTGCAACCCAGTGGGCAGTGCCAG
TGATGAGCCCTGCACAGGGCCCTGTGTTTGTAAGGAAAACGTTGAGGGGAAGGCCTGTGATCGCTGCAAGCC
AGGATTCTATAACTTGAAGGAAAAAAACCCCCGGGGCTGCTCCGAGTGCTTCTGCTTTGGCGTTTCTGATGTC
TGCCCCATCAACTACTGTGAAACTGGCCTTCATAACTGCGACATACCCCAGCGGGCCCAGTGTATCTACACAG
GAGGCTCCTCCTACACCTGTTCCTGCTTGCCAGGCTTTTCTGGGGATGGCCAAGCCTGCCAAGATGTAGATGA
ATGCCAGCCAAGCCGATGTCACCCTGACGCCTTCTGCTACAACACTCCAGGCTCTTTCACGTGCCAGTGCAAAC
CTGGTTATCAGGGAGACGGCTTCCGTTGCGTGCCCGGAGAGGTGGAGAAAACCCGGTGCCAGCACGAGCGA
GAACACATTCTCGGGGCAGCGGGGGCGACAGACCCACAGCGACCCATTCCTCCGGGGCTGTTCGTTCCTGAG
TGCGATGCGCACGGGCACTACGCGCCCACCCAGTGCCACGGCAGCACCGGCTACTGCTGGTGCGTGGATCGC
GACGGCCGCGAGGTGGAGGGCACCAGGACCAGGCCCGGGATGACGCCCCCGTGTCTGAGTACAGTGGCTCC
CCCGATTCACCAAGGACCTGCGGTGCCTACCGCCGTGATCCCCTTGCCTCCTGGGACCCATTTACTCTTTGCCC
AGACTGGGAAGATTGAGCGCCTGCCCCTGGAGGGAAATACCATGAGGAAGACAGAAGCAAAGGCGTTCCTT
CATGTCCCGGCTAAAGTCATCATTGGACTGGCCTTTGACTGCGTGGACAAGATGGTTTACTGGACGGACATCA
CTGAGCCTTCCATTGGGAGAGCTAGTCTACATGGTGGAGAGCCAACCACCATCATTAGACAAGATCTTGGAAG
TCCAGAAGGTATCGCTGTTGATCACCTTGGCCGCAACATCTTCTGGACAGACTCTAACCTGGATCGAATAGAA
GTGGCGAAGCTGGACGGCACGCAGCGCCGGGTGCTCTTTGAGACTGACTTGGTGAATCCCAGAGGCATTGTA
ACGGATTCCGTGAGAGGGAACCTTTACTGGACAGACTGGAACAGAGATAACCCCAAGATTGAAACTTCCTAC
ATGGACGGCACGAACCGGAGGATCCTTGTGCAGGATGACCTGGGCTTGCCCAATGGACTGACCTTCGATGCG
TTCTCATCTCAGCTCTGCTGGGTGGATGCAGGCACCAATCGGGCGGAATGCCTGAACCCCAGTCAGCCCAGCA
GACGCAAGGCTCTCGAAGGGCTCCAGTATCCTTTTGCTGTGACGAGCTACGGGAAGAATCTGTATTTCACAGA
CTGGAAGATGAATTCCGTGGTTGCTCTCGATCTTGCAATTTCCAAGGAGACGGATGCTTTCCAACCCCACAAG
CAGACCCGGCTGTATGGCATCACCACGGCCCTGTCTCAGTGTCCGCAAGGCCATAACTACTGCTCAGTGAACA
ATGGCGGCTGCACCCACCTATGCTTGGCCACCCCAGGGAGCAGGACCTGCCGTTGCCCTGACAACACCTTGGG
AGTTGACTGTATCGAACAGAAATGA

FIG. 14

MRAWIFFLLCLAGRALARQRGLFPAILNLASNAHISTNATCGEKGPEMFCKLVEHVPGRPVRNPQCRICDGNSANP
RERHPISHAIDGTNNWWQSPSIQNGREYHWVTITLDLRQVFQVAYVIIKAANAPRPGNWILERSLDGTTFSPWQY
YAVSDSECLSRYNITPRRGPPTYRADDEVICTSYYSRLVPLEHGEIHTSLINGRPSADDLSPKLLEFTSARYIRLRLQRIR
TLNADLMTLSHREPKELDPIVTRRYYYSIKDISVGGMCICYGHASSCPWDETTKKLQCQCEHNTCGESCNRCCPGY
HQQPWRPGTVSSGNTCEACNCHNKAKDCYYDESVAKQKKSLNTAGQFRGGGVCINCLQNTMGINCETCIDGYY
RPHKVSPYEDEPCRPCNCDPVGSLSSVCIKDDLHSDLHNGKQPGQCPCKEGYTGEKCDRCQLGYKDYPTCVSCGC
NPVGSASDEPCTGPCVCKENVEGKACDRCKPGFYNLKEKNPRGCSECFCFGVSDVCPINYCETGLHNCDIPQRAQC
IYTGGSSYTCSCLPGFSGDGQACQDVDECQPSRCHPDAFCYNTPGSFTCQCKPGYQGDGFRCVPGEVEKTRCQHE
REHILGAAGATDPQRPIPPGLFVPECDAHGHYAPTQCHGSTGYCWCVDRDGREVEGTRTRPGMTPPCLSTVAPPI
HQGPAVPTAVIPLPPGTHLLFAQTGKIERLPLEGNTMRKTEAKAFLHVPAKVIIGLAFDCVDKMVYWTDITEPSIGR
ASLHGGEPTTIIRQDLGSPEGIAVDHLGRNIFWTDSNLDRIEVAKLDGTQRRVLFETDLVNPRGIVTDSVRGNLYWT
DWNRDNPKIETSYMDGTNRRILVQDDLGLPNGLTFDAFSSQLCWVDAGTNRAECLNPSQPSRRKALEGLQYPFA
VTSYGKNLYFTDWKMNSVVALDLAISKETDAFQPHKQTRLYGITTALSQCPQGHNYCSVNNGGCTHLCLATPGSR
TCRCPDNTLGVDCIEQK.

FIG. 15

AAV-COMPATIBLE ALPHA-LAMININ-NIDOGEN CHIMERIC LINKER POLYMERIZATION PROTEIN

STATEMENT OF GOVERNMENT SUPPORT

This invention was made with government support under grant number R01-DK36425 awarded by the National Institutes of Health. The government has certain rights in this invention.

SEQUENCE LISTING

The instant application contains a Sequence Listing which has been filed electronically in ASCII format and is hereby incorporated by reference in its entirety. Said ASCII copy, created on May 8, 2019 is named 10491_006542-WO0_V2_ST25.txt and is 170 KB (174,236 bytes) in size.

FIELD OF THE INVENTION

The present invention relates to recombinant laminin adeno-associated viral vector (AAV) constructs and related methods for restoring laminin expression in deficient mammals, or in mammals with basement membrane instability.

BACKGROUND

Laminins are essential components of basement membranes (BMs) and their assembly. These large glycoproteins are heterotrimers consisting of α-, β- and γ subunits joined in a long coiled-coil. The fundamental role of laminins is to create a primary scaffold that (1) attaches the extracellular matrix to the cell surface and cytoskeleton and (2) that serves as a platform to which other extracellular matrix components, such as the nidogens, collagens and perlecan/agrin heparin sulfate proteoglycans, become stably attached.

Many different types of diseases involve basement membranes and laminins. Metastasizing solid tumors must pass through basement membranes to reach the vascular system, and various microbes and viruses enter the cells through direct interaction with laminins. At least nine of the laminins are essential for life based on genetic evidence in mice. Mutations in the laminin N-terminal (LN) polymerization domain of several laminins are causative of muscle, nerve, and kidney diseases. See, Scheele et al., 2007 J Mol Med 85(8):825-36.

Laminin-211 (a heterotrimer consisting of α2, β1 and γ1 subunits, abbreviated as Lm211) is the major laminin of the basement membranes of skeletal muscle and peripheral nerve Schwann cell (SC) and is found also in brain capillaries. See, Aumailley et al., (2005) Matrix Biol 24(5):326-32.

During embryogenesis, the laminin α2 chain is expressed along developing muscles from embryonic day 11 of development. LN domain mutations within the LAMA2 gene coding for the laminin α2 chain can result in a complete or near-complete loss of laminin α2 protein subunit expression to cause laminin α2-deficient muscular dystrophy (LAMA2-MD). LAMA2-MD is an autosomal recessive disease that typically presents as a non-ambulatory congenital muscular dystrophy (CMD), also known as congenital muscular dystrophy type 1A (MDC1A), a particularly severe non-ambulatory congenital dystrophy that begins at birth or infancy and is often accompanied by involvement of peripheral nerve and brain.

A recent study of 249 LAMA2 MD patients in United Kingdom revealed that LAMA2 mutations were the most common (37.4%) followed by dystroglycanopathies and Ullrich-CMD. See, Sframeli, et al., (2017) Neuromuscul Disor 27(9): 793-803. There are also a small number of missense and inframe deletion mutations, mostly mapping to the laminin α2 short-arm polymerization domain (LN), that cause a milder ambulatory dystrophy. See, Allamand, et al., (1997) Hum Mol Genet 6(5):747-52; Gavassini, et al., (2011) Muscle Nerve 44(5):703-9; Bonnemann, et al., (2014) Neuromuscul Disord 24(4):289-311; Chan, et al., (2014) Neuromuscul Disord 24(8):677-83. The pathology in both consists of muscle degeneration, regeneration, chronic inflammation and fibrosis accompanied by white matter brain anomalies and reduced peripheral nerve conduction. See, Jimenez-Mallebrera, et al., (20025) Cell Mol Life Sci 62(7-8):809-23. Patients with null-expression mutations never ambulate, can have peripheral nerve conduction defects, seizures and moderate mental retardation, and often die of muscle wasting and respiratory failure at a young age. Patients with defective α2-laminin present later in life with a less severe ambulatory form of dystrophy, typically limb-girdle type, and also exhibit peripheral and central nervous system defects. See, Bonnemann, et al., (2014) Neuromuscul Disord 24(4):289-311. Treatment generally focuses on managing the individual signs and symptoms of the condition. There is currently no cure for either.

Another neuromuscular disease, Pierson syndrome, is associated with a deficiency of the laminin β2 chain, which is prominently expressed in the glomerular basement membrane at the neuromuscular junctions, as well as in the intraocular muscles, lens and retina. The laminin β2 chain deficiency is caused by missense and in-frame deletion mutations of the LAMB2 gene. Pierson syndrome is an autosomal recessive disease, a very rare condition that mainly affects the kidneys and eyes. Most affected children have early-onset, chronic renal failure, neurodevelopmental problems, distinct eye abnormalities that may include blindness, hypotonia, psychomotor delay, hemiparesis and abnormal movements. See, Schéele et al., (2007) J Mol Med 85:825-836. Affected infants may not survive past the first weeks or months of life. Those that survive past infancy typically have neurological disabilities and developmental delays. Most require a renal transplant for end-stage kidney disease within the first decade of life. The long-term outlook is poor.

There is an ongoing need for better treatments, especially for gene therapy to restore laminin polymerization expression and basement membrane assembly in patients, and in particular for treating diseases involving laminin α2 and laminin β2 deficiencies.

SUMMARY OF INVENTION

In certain embodiments, the present invention relates to a recombinant adeno-associated vector (rAAV) comprising a nucleic acid sequence comprising a transgene encoding alphaLNNdDeltaG2short (αLNNdΔG2'). In certain embodiments, the αLNNdΔG2' comprises SEQ ID NO: 1. In certain embodiments, the rAAV further comprises a CMV promoter comprising SEQ ID NO: 12. In certain embodiments, the rAAV is AAV8 or AAV-DJ. In certain embodiments, the rAAV further comprises inverted terminal repeats (ITRs). In certain embodiments, the ITRs are a 5' ITR comprising SEQ ID NO: 11 and a 3' ITR comprising SEQ ID NO: 16.

In certain embodiments, the present invention relates to a composition comprising any of the recombinant AAV's described herein. In certain embodiments, the composition further comprises a pharmaceutical carrier.

In certain embodiments, the present invention relates to a kit comprising a container housing comprising the composition described herein. In certain embodiments, the container is a syringe.

In certain embodiments, the present invention relates to a method of restoring laminin polymerization expression and basement membrane assembly in a subject, comprising administering to the subject an effective amount of any of the recombinant AAV vectors described herein.

In certain embodiments, the present invention relates to a method of treating laminin α-2 deficiency in a subject in need thereof, comprising administering to the subject an effective amount of any of the recombinant AAV vectors described herein.

In certain embodiments, the present invention relates to a method of alleviating in a subject at least one of the symptoms associated with laminin deficiencies selected from the group consisting of laminin-deficient muscular dystrophies and laminin α2-deficient muscular dystrophy, wherein the method comprises administering to the subject an effective amount of any of the recombinant AAV vectors described herein.

In certain embodiments, the present invention relates to a method of alleviating in a subject at least one of the symptoms associated with laminin α2-deficiencies selected from the group consisting of muscle degeneration, regeneration, chronic inflammation, fibrosis, white matter brain anomalies, reduced peripheral nerve conduction, seizures, moderate mental retardation, and respiratory failure, wherein the method comprises administering to the subject an effective amount of any of the recombinant AAV vectors described herein.

In certain aspects, embodiments of the invention relate to a method for treating laminin α2-deficient muscular dystrophy in a subject characterized by the defect or haploinsufficiency of an LAMA2 gene. The method may include administering to the subject an effective amount of a recombinant adeno-associated virus carrying a nucleic acid sequence (i.e., a transgene) encoding an alphaLNNdDeltaG2short (αLNNdΔG2'), under the control of a promoter sequence which expresses the αLNNdΔG2' product in the desired cells. In certain embodiments, the promoter sequence provides for expression of the αLNNdΔG2' product in basement membranes. In certain embodiments, expression of the transgene gene provides to the cells the product necessary to restore or maintain desired laminin polymerization expression and basement membrane assembly in the subject. In still another embodiment, the invention provides a composition for treatment of laminin α2-deficient muscular dystrophy. Such compositions may be formulated with a carrier and additional components suitable for injection.

Other aspects and advantages of the present invention are described further in the following detailed description of the preferred embodiments thereof.

BRIEF DESCRIPTION OF THE DRAWINGS

FIG. 3A shows the domain structure and functional activities of αLNNd and mag. Regions derived from laminin-α1 are in green; regions derived from nidogen-1 are in orange. Mag is a miniaturized version of agrin with N-terminal regions (blue) and C-terminal parts (red). FIG. 3B shows rotary shadowed EM images of αLNNd and mag, and complexes with laminins. FIG. 3C shows that in the ambulatory form of LAMA2 MD and its dy2J/dy2J mouse model, a truncated version of Lm-211 ("dy2J-Lm-211") is expressed. αLNNd binds to the nidogen-binding site and creates an artificial short arm with a functional LN domain. Co-expression of αLNNd and mag provide the necessary domains for polymerization and αDG anchorage. FIG. 3D shows shortened versions of polymerization linker proteins lacking G2 domain±2 EGF-like repeats, i.e., αLNNd, αLNNdΔG2, and αLNNdΔG2. FIG. 3E shows linker-laminin complex formation of αLNNdΔG2 with Lmα1ΔLN-L4b.

FIGS. 5A and 5B show, respectively, αLNNdΔG2'-AAV and mag5myc-AAV infection of 293 cells expressing Lm411. Complex with Lm411 is shown by immunoprecipitation of N-terminal FLAG-tagged Lm411 from medium followed by cutting the membrane with immunoblotting of the upper segment for Lmα4 and the lower segment for αLNNdΔG2' in FIG. 5A or mag and αLNNdΔG2' in FIG. 5B. FIGS. 5C and 5D show a substantial increase of Lm411 assembly resulted from AAV-generated αLNNdΔG2'. FIG. 5E shows the detection in sarcolemma of antibody stained αLNNdΔG2' (red) and laminins (green) from the i.m. injection of AAV-αLNNdΔG2' into a 1 week old dy3K/dy3K, mag Tg mouse.

FIG. 9 is a comparison of the mouse and human amino acid sequences for the αLNNdΔG2' protein using a protein BLAST alignment. Query=the human αLNNdΔG2' amino acid sequence (SEQ ID NO: 22). Subject—the mouse αLNNdΔG2' amino acid sequence (SEQ ID NO: 21).

FIG. 10 provides the nucleotide and amino acid sequences of the open reading frame of the mouse αLNNdΔG2' (short-noG2) as inserted in an AAV, SEQ ID NO; 1 (nucleotide sequence) and SEQ ID NO: 21 (amino acid sequence). The signal peptide is encoded by nucleotides 1 to 51. Lma1 LN is encoded by nucleotides 52 to 804. LEa1 is encoded by nucleotides 805 to 975. LEa2 is encoded by nucleotides 976 to 1185. LEa3 is encoded by nucleotides 1186 to 1356. Lea4 is encoded by nucleotides 1357 to 1503. Lma1 LF segment is encoded by nucleotides 1504 to 1536. Nd egf-4 is encoded by nucleotides 1537 to 1668. Nd egf-5 is encoded by nucleotides 1669 to 1809. NdTY is encoded by nucleotides 1810 to 2091. Nd G3 is encoded by nucleotides 2092 to 2835. Nd egf-6 is encoded by nucleotides 2836 to 3006.

FIG. 11 provides the nucleotide and amino acid sequences of the open reading frame of the human αLNNdΔG2' (short-noG2) as inserted in an AAV, SEQ ID NO; 24 (nucleotide sequence) and SEQ ID NO: 22 (amino acid sequence). The signal peptide is encoded by nucleotides 1 to 51. Lma1 LN is encoded by nucleotides 52 to 804. LEa1 is encoded by nucleotides 805 to 975. LEa2 is encoded by nucleotides 976 to 1185. LEa3 is encoded by nucleotides 1186 to 1356. LEa 4 is encoded by nucleotides 1357 to 1503. LF fragment is encoded by nucleotides 1504 to 1536. Nd egf-4 is encoded by nucleotides 1537 to 1668. Nd egf-5 is encoded by nucleotides 1669 to 1809. NdTY is encoded by nucleotides 1810 to 2091. Nd G3 is encoded by nucleotides 2092 to 2835. Nd egf-6 is encoded by nucleotides 2836 to 3006.

FIG. 12 provides the nucleotide sequence of the open reading frame of the mouse αLNNdΔG2' (short-noG2) as inserted in an AAV (SEQ ID NO: 1).

FIG. 13 provides the amino acid sequence of the mouse αLNNdΔG2' (short-noG2) (SEQ ID NO: 21).

FIG. 14 provides the nucleotide sequence of the open reading frame of the human αLNNdΔG2' (short-noG2) as inserted in an AAV (SEQ ID NO: 24).

FIG. 15 provides the amino acid sequence of the human αLNNdΔG2' (short-noG2) (SEQ ID NO: 22).

DETAILED DESCRIPTION

The heterotrimeric laminins are a defining component of all basement membranes and self-assemble into a cell-associated network. In mammals, all laminins are heterotrimers composed of one of five α chains, one of three β chains and one of three γ chains. Despite a total of at least 45 potential αβγ chain combinations, only 15 different laminin isoforms were reported as of 2010. Based on in vitro studies, there are at least 16 allowed laminin isoforms (Table 1 below).

TABLE 1

Mammalian laminins.[1 2]

| Name | Abbreviated Name | Chain composition |
|---|---|---|
| Laminin-111 | Lm111 | α1β1γ1 |
| Laminin-121 | Lm121 | α1β2γ1 |
| Laminin-211 | Lm211 | α2β1γ1 |
| Laminin-213 | Lm213 | α2β1γ3 |
| Laminin-221 | Lm221 | α2β2γ1 |
| Laminin-311[3] | Lm311 | α3β1γ1 |
| Laminin-312[4] | Lm312 | α3β1γ2 |
| Laminin-321 | Lm321 | α3β2γ1 |
| Laminin-332 | Lm332 | α3β3γ2 |
| Laminin-411 | Lm411 | α4β1γ1 |
| Laminin-421 | Lm421 | α4β2γ1 |
| Laminin-422[5] | Lm422 | α4β2γ2 |
| Laminin-423 | Lm423 | α4β2γ3 |
| Laminin-511 | Lm511 | α5β1γ1 |
| Laminin-521 | Lm521 | α5β2γ1 |
| Laminin-523 | Lm523 | α5β2γ3 |

[1]Table based on P.R. Macdonald et al., 2010, J. Struct. Biol. 170: 398-405.

[2] Note:

Little is known of the subunit partners or tissue distribution of the laminin β4 subunit.

[3] The laminin α3 subunit can exist as shorter (A) and longer (B) splice variants sharing the same coiled-coil and LG domains. The B variant additionally possesses a short arm with an LN polymerization domain. The α3B variant is thought to assemble with the same β- and γ- subunits as α3A.

[4]While it is uncertain if Lm212 exists in vivo, its assembly has been detected in vitro.

[5]While it is uncertain if Lm422 exists in vivo, its assembly has been detected in vitro.

Laminins are essential central organizers of basement membranes, a likely consequence of the unique ability of laminins to bind to cells, to self, and to other basement membrane components. Basement membranes, which are required for the emergence of tissues and differentiated cells, are important in embryo development, tissue homeostasis and human disease.

The three short arms of the cross-shaped laminin molecule form the network nodes, with a strict requirement for one α, one β and one γ arm. The homologous short arms are composed of a distal laminin N-terminal (LN) domain that is followed by tandem repeats of laminin-type epidermal growth factor-like (LE) domains, interspersed with globular domains of unknown structure. The LN domains are essential for laminin polymerization and BM assembly. Laminin polymerization is also important for myelination. Laminins containing the α3A, α4, and β2 subunits do not have a full complement of LN domains and therefore cannot polymerize (reviewed in Hohenester and Yurchenco. 2012. *Cell Adh. Migr.* 2013. 7(1):56-63).

Figure 1:
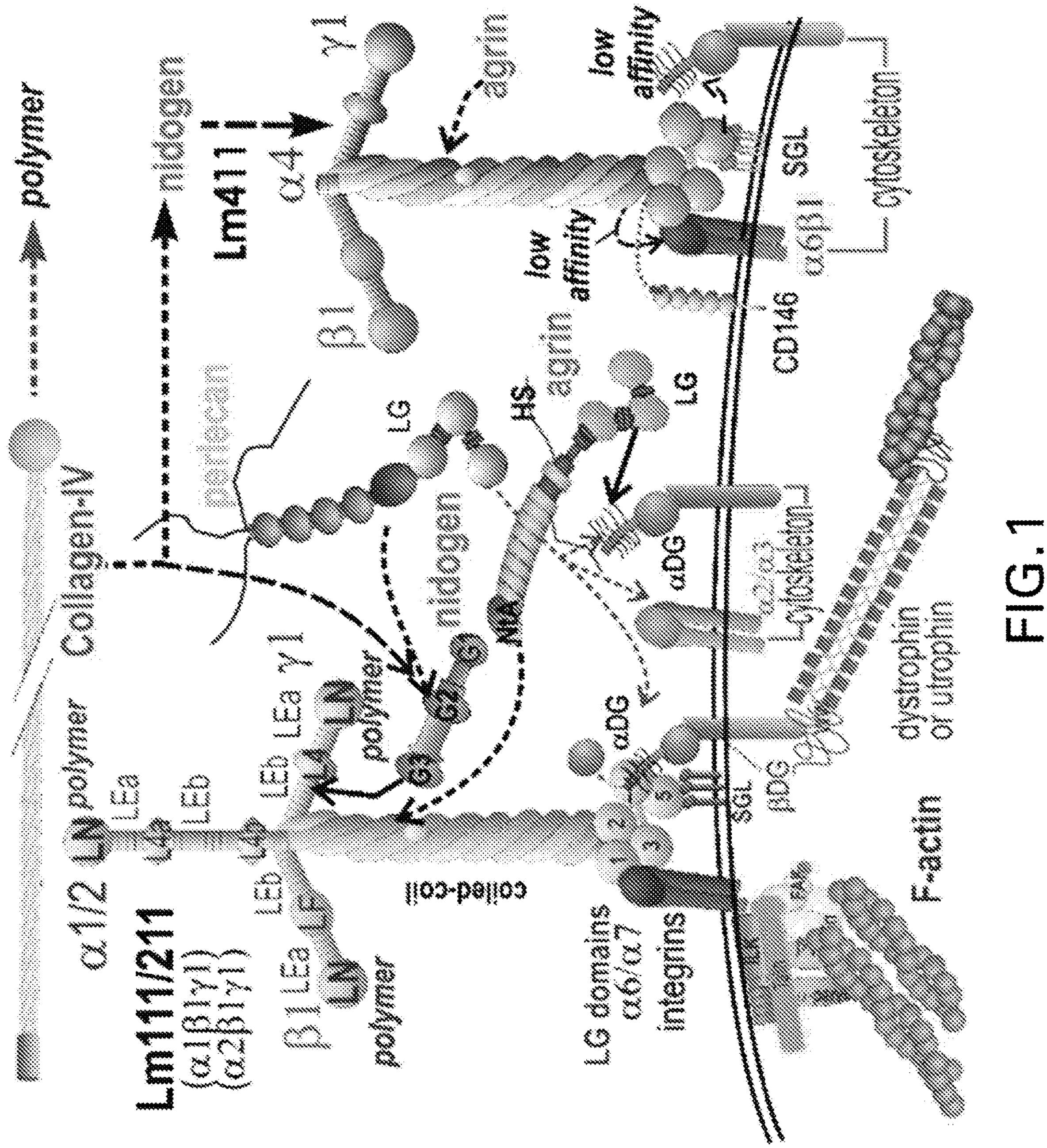
FIG. 1 illustrates the neuromuscular laminin interactions with core basement membrane (BM) components. Relevant laminin and other protein domains are labeled. Dashed and dotted lines indicate domain binding interactions. Abbreviations: laminin (Lm); laminin 111 (Lm111); laminin 411 (Lm411); sulfated glycolipids (SGL); α-dystroglycan (αDG); nidogen (Nd); Lmα2 short-arm polymerization domain (LN).

The long arm of the cross (75-80 nm length) is an α-helical coiled coil formed from all three chains, whereas the three short arms (35-50 nm) are composed of one chain each. At the distal end of the long arm, the α chain adds five laminin G-like (LG) domains that contain the major cell-adhesive sites of laminin. This globular domain at the end of the long arm binds to cellular receptors, including integrins, α-dystroglycan, heparan sulfates and sulfated glycolipids. Collateral anchorage of the laminin network is provided by the proteoglycans perlecan and agrin. A second network is then formed by type IV collagen, which interacts with the laminin network through the heparan sulfate chains of perlecan and agrin and additional linkage by nidogen. See generally, Hohenester et al. (2013) Cell Ahd Migr. 7(1):56-63. This maturation of basement membranes becomes essential at later stages of embryo development. In FIG. 1, Lm111, a prototypical laminin (Lm) expressed in embryogenesis, binds to cell surface sulfated glycolipids (SGL), integrins, α-dystroglycan (αDG), nidogen (Nd), agrin, and polymerizes via its LN domains. Collagen-IV and perlecan bind to nidogen. Integrin and αDG attach through adaptor proteins to the cytoskeleton. Lm411, a Lm isoform that does not polymerize, exhibits very weak integrin and αDG binding.

Figure 2:
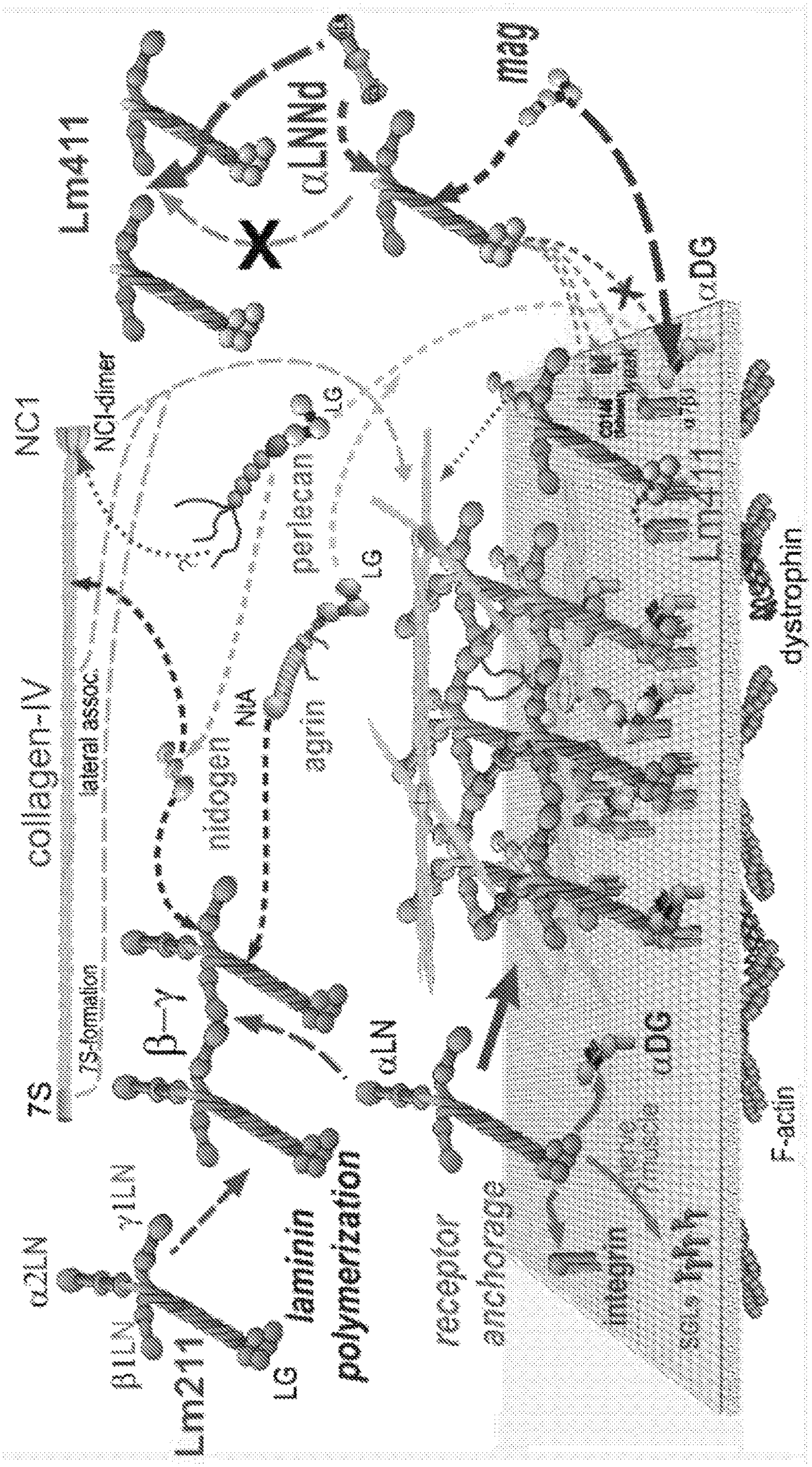
FIG. 2 illustrates a model of Lm211 and Lm411 mediated BM assembly in muscle and peripheral nerve. Abbreviations: laminin 211 (Lm211); laminin 411 (Lm411); sulfated glycolipids (SGL); α-dystroglycan (αDG); nidogen (Nd); Lmα2 short-arm polymerization domain (LN); N-terminal domain of agrin that binds to laminin coiled-coils (agrin-NtA); laminin G-like domain (LG).

Lm211 and Lm411 mediate BM assembly in muscle and peripheral nerve. The laminin forms the initial nascent scaffolding by binding to sulfated glycolipids (SGL) such as sulfatides, binding to integrin α7β1 and α-dystroglycan (αDG), and polymerizing via LN interactions, illustrated in FIG. 2. Nidogen (mostly nidogen-1) binds to laminin and to collagen-IV, acting as a bridge, with the collagen polymerizing to form a second network. All components become directly or indirectly tethered to cell receptors through laminin but can separately interact with other integrins. Lm411 is a non-polymerizing laminin that co-assembles with Lm211 in nerves. αLNNd binds to Lm411 and imparts polymerization activity. Miniagrin (mag, mA) binds to Lm411 and imparts αDG binding. (See McKee et al. 2017. J. Clin. Invest. 127: 1075-1089 and Reinhard et al. 2017, Sci. Transl. Med. 28:9 (396), pii: eaal4649. doi: 10.1126/scitranslmed.aal4649).

Schwann cell (SC) BMs share the overall architectural organization with muscle BMs; however, they differ in several respects: (i) β1-integrins are the major mediators of myelination whereas in muscle αDG is the paramount receptor; (ii) several SC integrins are available to interact with BM (but only α7β1 in muscle), allowing integrin ligation of other BM components; (iii) Lmα4, absent in myofibers, is a normal SC subunit that contributes to myelination; (iv) SCs express sulfatides and CD146 that may enable α4-laminin adhesion; and (v) Dy2J amyelination is most evident in the sciatic nerve and roots, suggesting a special importance of laminin polymerization. Alpha 2-laminin is also found in capillaries forming the blood-brain barrier. Loss of the laminin subunit makes the barrier leaky to water, likely explaining the brain white matter changes detected by MRI in nearly all LAMA2-MD patients.

Laminin a 2-deficient muscular dystrophy (LAMA2-MD) is an autosomal recessive disease caused by mutations within the LAMA2 gene that typically presents as a non-ambulatory congenital muscular dystrophy (CMD). The dystrophy is often accompanied by involvement of peripheral nerve and brain. The great majority of LAMA2 mutations result in a complete or near-complete loss of protein subunit expression, in particular Lm211, to cause a particularly severe non-ambulatory congenital dystrophy. There are also a small number of missense and in-frame deletion mutations, mostly mapping to the Lm α short-arm polymerization domain (LN), that cause a milder ambulatory dystrophy. In LAMA2-MD, there is increased transcription and protein accumulation of Lm411, with minor increases in Lm511. Lm411 is unusual in that it binds weakly to muscle αDG and integrins and lacks the ability to polymerize. Lm411 is inadequate for BM assembly such that high Lm411 concentrations are required for cell surface accumulation relative to other laminins, which explains its limited ability to rescue LAMA2 mutations. These compositional changes underlie the structural attenuations of the BM seen in the absence of laminin-α2. See review, Yurehenco et al. 2017, Matrix Biology, pii: S0945-053X(17)30333-5. doi: 10.1016/j.matbio.2017.11.009.

Several mouse models for the laminin α2 chain deficiency are available, and they also display muscular dystrophy and peripheral and central nervous system myelination defects. BMs are disrupted, and the expression of LM α2-chain receptors and some BM associated proteins are altered in the LM α2-chain deficient muscles, and both structural and signaling defects may be detrimental for normal muscle function. Furthermore, critical roles for laminin α2 chain inducing Schwann cell proliferation and oligodendrocyte spreading, as well as myelination in the peripheral nervous system and central nervous system, respectively, have been demonstrated. See, Schéele et al., (2007) J Mol Med 85:825-836. Laminin α2 is greatly reduced in dyW ($dy^W/dy^W$) mice while completely absent in dy3K ($dy^{3K}/dy^{3K}$) Lama2-knockout mice. These two models represent the majority of LAMA2-MD patients that either express very low or no laminin α2 subunit at all. The dy3K mice, the most severely affected of the mice, are extremely weak, small, and very short-lived. A third model is the dy2J ($dy^{2J}/dy^{2J}$ genotype) mouse in which laminin α2 is slightly decreased while laminin α4 is modestly increased. Lm211 in dy2J mice is unable to polymerize because of the loss of the LN-domain. Dy2J mice are characterized by progressive weakness and paralysis beginning at about 3½ weeks of age with the hindlimbs affected first and later the axial and forelimb musculature, Schwann cells fail to sort and ensheathe axons resulting in amyelination. These mice, however, can survive many months.

There are challenges for development of a treatment for LAMA2-MD. A direct approach of restoring laminin expression by germ-line transgenesis of Lama1 (Lmα1) has been effective in its ability to restore normal function in mice; however, the 9.3 kb DNA construct is too large for available delivery systems. Drug therapies show improvements, but importantly do not correct the underlying structural defect. EHS-derived Lm111, delivered to inflamed muscle parentally, has been found beneficial in dyW mice, but this approach has not been shown to be effective with recombinant laminin, which would be needed for treatment. While exon-skipping to correct out-of-frame mutations has been used to treat dystrophin-deficiency, it is problematic for laminin-deficiency in that exon borders do not match protein domain borders and skipping of nearly all LAMA2 exons will likely result in cysteine mispairing and domain misfolding. AAV-delivered CRISPR/Cas9 has been used to repair splice defects, which are found in approximately 20% of LAMA2-MD subjects. Transgenic minagrin (mag) expression was shown to partially ameliorate the muscle pathophysiology of mouse models of laminin-α2-deficient muscular dystrophy, even when expressed after birth. Similar benefits were observed when a mag gene was introduced into perinatal dyW (dyW/dyW) mice by AAV. See, Qiao, et al., Proc Natl Acad Sci USA (2005) 102(34):11999-2004. Micro-dystrophin AAV delivery to treat Duchenne muscular dystrophy in humans has been demonstrated. See, Mendell, Neurosci Lett (2012). The present invention provides a repair of basement membranes with potential to improve all LAMA2-MDs.

Recombinant laminins and chimeric linker proteins can repair basement membrane defects in models of LAMA2-MD. Recent advances in understanding the requirements for BM assembly have shown that laminin-binding proteins may provide an alternative arm for polymerization in a laminin that lacked an LN domain. αLNNd, βLNNd and γLNNd linker proteins can enable polymerization in laminins that lacked the corresponding αLN, βLN and γLN domains. See, McKee et al., Matrix Biol (2018) www.//doi.org/10.1016/j.matbio.2018.01.012, Chimeric protein identification of dystrophic, Pierson and other laminin polymerization residues. αLNNd consists of three globular domains with intervening rods resulting from the fusion of the Lma1 LN-Lea domains with the nidogen-1 G2-G3 domains, shown in FIG. 3A and FIG. 4. The LN globular domain is a polymerization domain. G2 binds to collagen-IV and perlecan while G3 binds to the Lmγ1-LEb3 domain, creating an artificial arm that is attached to a locus near the short arm cross intersection. When bound to non-polymerizing laminin lacking the α-LN domain, α LNNd enables polymerization and collagen-TV recruitment to BMs, with no adverse effect on WT laminin. See, McKee, et al., J Biol Chem, (2009) 284(13):8984-8994.

Transgenic expression of αLNNd has been shown to ameliorate the dy2J muscular dystrophy and that, in combination with minagrin, a protein that enhanced receptor binding, also ameliorated the more severe dyW dystrophy. See, McKee et al., J Clin Invest (2017) 127(3) 1075-1089; Reinhard, et al., Sci Transl Med (2017) 9(396). Of additional note, it may be possible to treat patients with Pierson syndrome resulting from failures of laminin self-assembly by using βLNNd instead of αLNNd proteins to restore polymerization to glomerular Lm521 bearing β2LN mutations.

Adeno-associated virus (AAV) is one of the most promising of the gene delivery systems in which high expression can be achieved in muscle, peripheral nerve and other tissue. Potential risks include host cellular immune responses to transgene products and AAV capsid with subsequent loss of protein. However, this problem has been reduced by avoiding the creation of transgene neoantigens. The domains of αLNNd, βLNNd and γLNNd linker proteins are normally expressed as parts of larger basement membrane proteins, even in the dystrophic state, and are unlikely to be immunogenic. In order to take advantage of recent improvements in AAV delivery in which the CMV promoter has been enhanced, and with the largest insert capacity, the preferred AAV system for the present invention is the AAV-DJ system that employs an enhanced CMV promoter with a mixed serotype capsid and allows up to a 3.1 kB insert (Cell Biolabs, Inc., San Diego, CA) (see FIGS. 6-8).

Figure 3A:
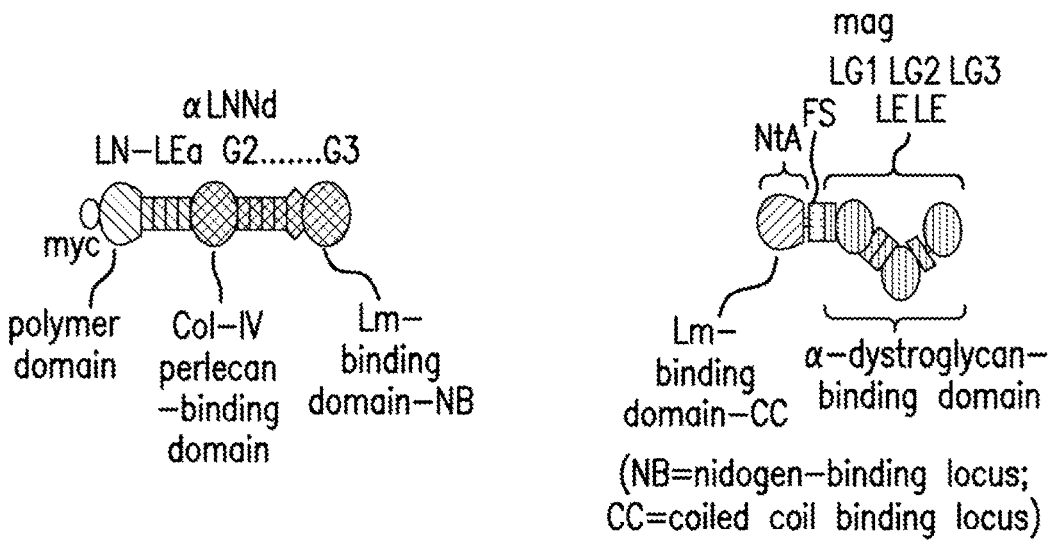
FIGS. 3A-E are illustrations, EM images and SDS-PAGE images showing linker protein repair of laminin function.
Figure 4:
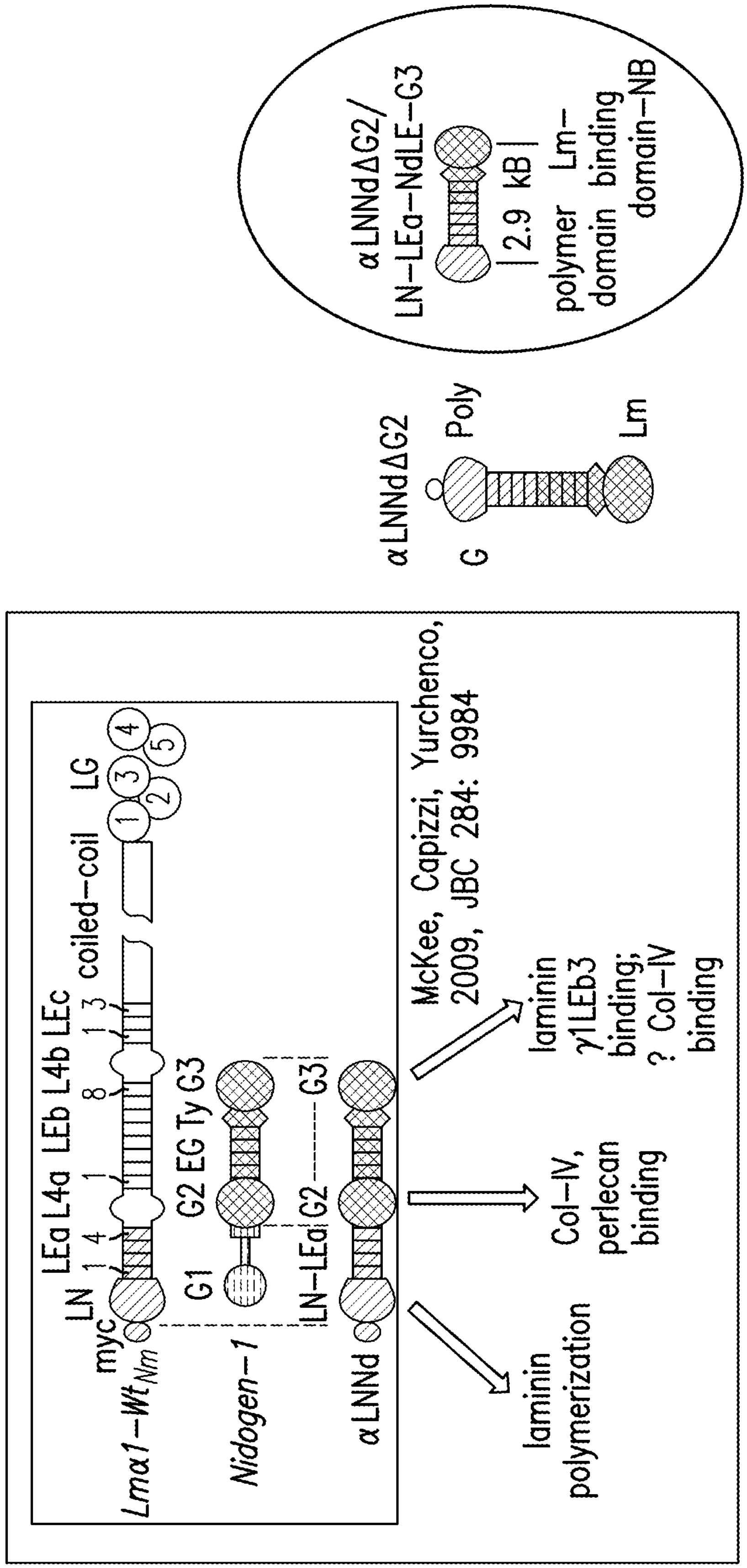
FIG. 4 shows shortened versions of αLNNd polymerization linker proteins lacking G2 domain±2 EGF-like repeats, i.e., αLNNd (alphaLNNd where alpha refers to laminin-alpha1, LN refers to the LN domain, and Nd refers to nidogen), αLNNdΔG2 (alphaLNNdDeltaG2), and αLNNdΔG2' (alphaLNNdDeltaG2short).

A problem for AAV somatic gene expression of αLNNd is that while αLNNd is small enough to be expressed by AAV, the promoter would have to be very small and would be unlikely to provide good expression. A potential solution to this problem would be to reduce the size of the αLNNd DNA, which is 4.17 kB, so it could fit into AAV, but the concern was that reducing the size could affect the function of the protein for basement membrane assembly and myelination. Since the N- and C-terminal domains are essential, the focus was on reducing the size of the internal domains. The first modified protein that was made and designated αLNNdΔG2 is shown in FIGS. 3A and 4. Removal of G2 gave most of the needed reduction, but at the expense of losing direct coupling of the polymerizing laminin to collagen-IV and perlecan. Experiments conducted with Schwann cells, myotubes, and dorsal root ganglia revealed that G2 and its flanking LE/EGF-like domains to 3 kB were expendable so long as some nidogen-1 was present in the test system. Other experiments with transgenesis showed that substantial nidogen-1 remains in the basement membrane, indicating that size reduction of the αLNNd linker protein could be pursued. The present invention provides a new αLNNd linker protein designated αLNNdΔG2' in which the internal G2 and two EGF-like spacer domains have been removed, reducing the size of the nucleotide sequence to about 2.9-3.0 kB, making it small enough to be expressed by AAV yet retaining the function of the protein for basement membrane assembly and myelination.

The present invention relates to using AAV-DJ-αLNNdΔG2' constructs to restore laminin polymerization and basement membrane assembly in muscle, peripheral nerve and other tissue and ameliorate LAMA2-MD. It is expected that such methods and AAV-DJ-αLNNdΔG2' constructs can be effective treatments for the human disease. For ease of reference, the vector constructs described herein are referred to as various AAV-DJ-αLNNdΔG2' constructs, which indicate AAV-DJ constructs comprising nucleic acid sequences that encode mouse alphaLNNdDeltaG2short protein, among other elements. The human alphaLLNdDeltaG2short protein has an 87% identity with mouse alphaLLNdDeltaG2short protein, as shown in FIG. 9. It is expected that codon-optimized human constructs will function in the same desired manner to restore laminin polymerization and basement membrane assembly in muscle, peripheral nerve and other tissue and ameliorate LAMA2-MD. It is believed that patients with Pierson syndrome can be treated using the same AAV-DJ constructs by replacing the alpha1 segment with a beta1 segment from βLNNd protein in order to restore polymerization to glomerular Lm521 bearing β2LN mutations.

AAV-Compatible Laminin-Linker Protein alphaLNNdDeltaG2short Abbreviations

AAV: adeno-associated virus
rAAV recombinant adeno-associated virus or viral vector
BM: basement membrane
αLNNd alpha laminin N-terminal domain linking protein
αLNNdΔG2' alpha laminin N-terminal domain delta G2 short linking protein, alphaLNNdDeltaG2short
α-DG α-dystroglycan
βLNNdΔG2' beta laminin N-terminal domain delta G2 short linking protein, betaLNNdDeltaG2short
ECM extracellular matrix
γLNNdΔG2' gamma laminin N-terminal domain delta G2 short linking protein, gammaLNNdDeltaG2short
LE domain laminin-type epidermal growth factor-like domain
LG domain laminin G-like domain
LM or Lm laminin
LN domain laminin N-terminal domain Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., (catalytic activity)/(mg protein), or (immunological activity)/(mg protein), concentration in a biological compartment, or the like. "Activity" may refer to modulation of components of the innate or the adaptive immune systems.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human, including a human patient.

"alphaLNNd" (αLNNd) is a linker protein consisting of three globular domains with intervening rods resulting from the fusion of the Lma1 LN-LEa domains with the nidogen-1 G2-G3 domains. The LN globular domain is a polymerization domain. G2 binds to collagen-IV and perlecan while G3 binds to the Lma1-LEb3 domain, creating an artificial arm that is attached to a locus near the short arm cross intersection. When bound to non-polymerizing laminin lacking the αLN domain, αLNNd enables polymerization and collagen-IV recruitment to BMs, with no adverse effect on WT laminin.

"Treat" or "treating" means to administer a therapeutic agent, such as a composition containing any of the rAAV constructs of the present invention, internally or externally to a subject or patient having one or more disease symptoms, or being suspected of having a disease or being at elevated at risk of acquiring a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the subject Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom (s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

"Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses transfection of any of the rAAV constructs or related methods of the present invention as applied to a human or animal subject, a cell, tissue, physiological compartment, or physiological fluid.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

Recombinant AAVs

In some aspects, the invention provides isolated AAVs. As used herein with respect to AAVs, the term "isolated" refers to an AAV that has been isolated from its natural environment (e.g., from a host cell, tissue, or subject) or artificially produced. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities. Thus, a rAAV having a capsid appropriate for the tissue being targeted can be selected.

For targeting the desired tissue in the context of treating laminin alpha-2 deficiency, a preferred rAAV is a combination of AAV-DJ capsid and AAV-2 Rep gene backbone, resulting in the various rAAV's described herein (See the sequence listing).

Methods for obtaining recombinant AAVs having a desired capsid protein have been described (See, for example, US 2003/0138772, the contents of which are incorporated herein by reference in their entirety). A number of different AAV capsid proteins have been described, for example, those disclosed in G. Gao, et al., J. Virol, 78(12): 6381-6388 (June 2004); G. Gao, et at, Proc Natl Acad Sci USA, 100(10):6081-6086 (May 13, 2003); US 2003-0138772, US 2007/0036760, US 2009/0197338 the contents of which relating to AAVs capsid proteins and associated nucleotide and amino acid sequences are incorporated herein by reference. For the desired packaging of the presently described constructs and methods, the AAV-DJ vector and capsid is preferred (SEQ ID NO: 17). Typically, the methods involve culturing a host cell which contains a nucleic acid sequence encoding an AAV capsid protein or fragment thereof; a functional rep gene; a recombinant AAV vector composed of AAV inverted terminal repeats (ITRs) and a transgene; and sufficient helper functions to permit packaging of the recombinant AAV vector into the AAV capsid proteins.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component (s) may be under the control of a constitutive promoter. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters.

The recombinant AAV vector, rep sequences, cap sequences, and helper functions for producing the rAAV may be delivered to the packaging host cell using any appropriate genetic element (vector). The selected genetic element may be delivered by any suitable method, including those described herein. See, e.g., K. Fisher et at, J. Virol., 70:520-532 (1993) and U.S. Pat. No. 5,478,745.

In some embodiments, recombinant AAVs may be produced using the triple transfection method (e.g., as described in detail in U.S. Pat. No. 6,001,650, the contents of which relating to the triple transfection method are incorporated herein by reference). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present invention include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

With respect to transfected host cells, the term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

With respect to cells, the term "isolated" refers to a cell that has been isolated from its natural environment (e.g., from a tissue or subject). The term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

The term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "operatively linked," "under control," or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA) from a transcribed gene.

Recombinant AAV Vectors

"Recombinant AAV (rAAV) vectors" described herein are typically composed of, at a minimum, a transgene (e.g., encoding αLNNdΔG2') and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product of interest (e.g., αLNNdΔG2'). The nucleic acid coding sequence is operatively linked to regulatory components in a manner which permits transgene transcription, translation, and/or expression in a cell of a target tissue.

The AAV sequences of the vector may comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are typically about 145 bp in length. Preferably, substantially the entire sequences encoding the ITRs are used in the molecule, although some degree of minor modification of these sequences is permissible. (See, e.g., texts such as Sambrook et at, "Molecular Cloning. A Laboratory Manual", 2d ed., Cold Spring harbor Laboratory, New York (1989); and K. Fisher et al., J. Virol., 70:520 532 (1996)). An example of such a molecule is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In addition to the elements identified above for recombinant AAV vectors, the vector may also include conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA).

For nucleic acids encoding proteins, a polyadenylation sequence generally is inserted following the transgene sequences and before the 3' AAV ITR sequence. An rAAV construct useful in the present invention may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available (see, e.g., Sambrook et at, and references cited therein at, for example, pages 3.18 3.26 and 16.17 16.27 and Ausubel et al., Current Protocols in Molecular Biology, John Wiley & Sons, New York, 1989). In some circumstances, a Foot and Mouth Disease Virus 2A sequence may be included in a polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931.; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors may optionally include 5' leader or signal sequences.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the 13-actin promoter, the phosphoglycerol kinase (PGK) promoter, and the EF1a promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100: 2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter, or fragment thereof, for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. IDSA, 88:5611-5 (1991)), and the neuron-specific vgf gene promoter (Piccioli et al., Neuron, 15:373-84 (1995)). In some embodiments, the tissue-specific promoter is a promoter of a gene selected from: neuronal nuclei (NeuN), glial fibrillary acidic protein (GFAP), adenomatous polyposis coli (APC), and ionized calcium-binding adapter molecule 1 (Iba-1). In some embodiments, the promoter is a CMV promoter.

Transgene Coding Sequences

The composition of the transgene sequence of a rAAV vector will depend upon the use to which the resulting vector will be put. For example, one type of transgene sequence includes a reporter sequence, which upon expression produces a detectable signal. In another example, the transgene encodes a therapeutic αLNNdΔG2' protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

In some aspects, the invention provides rAAV vectors for use in methods of preventing or treating a LAMA2 gene defect (e.g., heritable gene defects, somatic gene alterations) in a mammal, such as for example, a gene defect that results in a laminin alpha-2 polypeptide deficiency in a subject, and particularly for treating or reducing the severity or extent of deficiency in a subject manifesting a laminin alpha-2 deficiency. In some embodiments, methods involve administration of a rAAV vector that encodes one or more therapeutic peptides, polypeptides, shRNAs, microRNAs, antisense nucleotides, etc. in a pharmaceutically-acceptable carrier to the subject in an amount and for a period of time sufficient to treat the LAMA2 disorder in the subject having or suspected of having such a disorder.

Recombinant AAV Administration rAAVS are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected tissue (e.g., intracerebral administration, intrathecal administration), intravenous, oral, inhalation (including intranasal and intratracheal delivery), intraocular, intravenous, intramuscular, subcutaneous, intradermal, intratumoral, and other parental routes of administration. Routes of administration may be combined, if desired.

Delivery of certain rAAVs to a subject may be, for example, by administration into the bloodstream of the subject. Administration into the bloodstream may be by injection into a vein, an artery, or any other vascular conduit. Moreover, in certain instances, it may be desirable to deliver the rAAVs to brain tissue, meninges, neuronal cells, glial cells, astrocytes, oligodendrocytes, cerebrospinal fluid (CSF), interstitial spaces and the like. In some embodiments, recombinant AAVs may be delivered directly to the spinal cord or brain with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000). In certain circumstances it will be desirable to deliver the rAAV-based therapeutic constructs in suitably formulated pharmaceutical compositions disclosed herein either subcutaneously, intrapancreatically, intranasally, parenterally, intravenously, intramuscularly, intracerebrally, intrathecally, intracerebrally, orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs.

Recombinant AAV Compositions

The rAAVs may be delivered to a subject in compositions according to any appropriate methods known in the art. The rAAV, preferably suspended in a physiologically compatible carrier (e.g., in a composition), may be administered to a subject, e.g., a human, mouse, rat, cat, dog, sheep, rabbit, horse, cow, goat, pig, guinea pig, hamster, chicken, turkey, or a non-human primate (e.g., Macaque). In certain embodiments, compositions may comprise a rAAV alone, or in combination with one or more other viruses (e.g., a second rAAV encoding having one or more different transgenes).

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The dose of rAAV virions required to achieve a desired effect or "therapeutic effect," e.g., the units of dose in vector genomes/per kilogram of body weight (vg/kg), will vary based on several factors including, but not limited to: the route of rAAV administration, the level of gene or RNA expression required to achieve a therapeutic effect, the specific disease or disorder being treated, and the stability of the gene or RNA product. One of skill in the art can readily determine a rAAV virion dose range to treat a subject having a particular disease or disorder based on the aforementioned factors, as well as other factors that are well known in the art. An effective amount of the rAAV is generally in the range of from about 10 μl to about 100 ml of solution containing from about $10^9$ to $10^{16}$ genome copies per subject. Other volumes of solution may be used. The volume used will typically depend, among other things, on the size of the subject, the dose of the rAAV, and the route of administration. For example, for intrathecal or intracerebral administration a volume in range of 1 μl to 10 μl or 10 μl to 100 μl may be used. For intravenous administration a volume in range of 10 μl to 100 μl, 100 μl to 1 ml, 1 ml to 10 ml, or more may be used. In some cases, a dosage between about $10^{10}$ to $10^{12}$ rAAV genome copies per subject is appropriate. In certain embodiments, $10^{12}$ rAAV genome copies per subject is effective to target CNS tissues. In some embodiments the rAAV is administered at a dose of $10^{10}$, $10^{11}$, $10^{12}$, $10^{13}$, $10^{14}$, or $10^{15}$ genome copies per subject. In some embodiments the rAAV is administered at a dose of $10^{10}$, $10^{11}$, $10^{12}$, $10^{13}$, or $10^{14}$ genome copies per kg.

In some embodiments, rAAV compositions are formulated to reduce aggregation of AAV particles in the composition, particularly where high rAAV concentrations are present (e.g., about $10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005)12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active ingredient or more, although the percentage of the active ingredient(s) may, of course, be varied and may conveniently be between about 1 or 2% and about 70% or 80% or more of the weight or volume of the total formulation. Naturally, the amount of active ingredient in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present invention into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

General Methods Relating to Delivery of rAAV Compositions

The present invention provides stable pharmaceutical compositions comprising rAAV virions. The compositions remain stable and active even when subjected to freeze/thaw cycling and when stored in containers made of various materials, including glass.

Recombinant AAV virions containing a heterologous nucleotide sequence of interest can be used for gene delivery, such as in gene therapy applications, for the production of transgenic animals, in nucleic acid vaccination, ribozyme and antisense therapy, as well as for the delivery of genes in vitro, to a variety of cell types.

Generally, rAAV virions are introduced into the cells of a subject using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with the cells e.g., in appropriate media, and screening for those cells harboring the DNA of interest using conventional techniques such as Southern blots and/or PCR, or by using selectable markers. Transduced cells can then be formulated into pharmaceutical compositions, described more fully below, and the composition introduced into the subject by various routes, such as by intramuscular, intravenous, intra-arterial, subcutaneous and intraperitoneal injection, or by injection into smooth muscle, using e.g., a catheter, or directly into an organ.

For in vivo delivery, the rAAV virions will be formulated into a pharmaceutical composition and will generally be administered parenterally, e.g., by intramuscular injection directly into skeletal muscle, intra-articularly, intravenously or directly into an organ.

Appropriate doses will depend on the subject being treated (e.g., human or nonhuman primate or other mammal), age and general condition of the subject to be treated, the severity of the condition being treated, the mode of administration of the rAAV virions, among other factors. An appropriate effective amount can be readily determined by one of skill in the art.

Thus, a "therapeutically effective amount" will fall in a relatively broad range that can be determined through clinical trials. For example, for in vivo injection, i.e., injection directly to the subject, a therapeutically effective dose will be on the order of from about $10^5$ to $10^{16}$ of the rAAV virions, more preferably $10^8$ to $10^{14}$ rAAV virions. For in vitro transduction, an effective amount of rAAV virions to be delivered to cells will be on the order of $10^5$ to $10^{13}$, preferably $10^8$ to $10^{13}$ of the rAAV virions. If the composition comprises transduced cells to be delivered back to the subject, the amount of transduced cells in the pharmaceutical compositions will be from about $10^4$ to $10^{10}$ cells, more preferably $10^5$ to $10^8$ cells. The dose, of course, depends on the efficiency of transduction, promoter strength, the stability of the message and the protein encoded thereby, etc. Effective dosages can be readily established by one of ordinary skill in the art through routine trials establishing dose response curves.

Dosage treatment may be a single dose schedule or a multiple dose schedule to ultimately deliver the amount specified above. Moreover, the subject may be administered as many doses as appropriate. Thus, the subject may be given, e.g., $10^5$ to $10^{16}$ rAAV virions in a single dose, or two, four, five, six or more doses that collectively result in delivery of, e.g., $10^5$ to $10^{16}$ rAAV virions. One of skill in the art can readily determine an appropriate number of doses to administer.

Pharmaceutical compositions will thus comprise sufficient genetic material to produce a therapeutically effective amount of the protein of interest, i.e., an amount sufficient to reduce or ameliorate symptoms of the disease state in question or an amount sufficient to confer the desired benefit. Thus, rAAV virions will be present in the subject compositions in an amount sufficient to provide a therapeutic effect when given in one or more doses. The rAAV virions can be provided as lyophilized preparations and diluted in the virion-stabilizing compositions for immediate or future use. Alternatively, the rAAV virions may be provided immediately after production and stored for future use.

The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

As used herein, "polymerase chain reaction" or "PCR" refers to a procedure or technique in which specific nucleic acid sequences, RNA and/or DNA, are amplified as described in, e.g., U.S. Pat. No. 4,683,195. Generally, sequence information from the ends of the region of interest or beyond is used to design oligonucleotide primers. These primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

Nucleic Acids

The invention also comprises certain constructs and nucleic acids encoding the αLNNdΔG2'protein described herein. Certain constructs and sequences, including selected sequences listed in the sequence listing including SEQ ID NO: 1 and SEQ ID NO: 24 may be useful in embodiments of the present invention.

Preferably, the nucleic acids hybridize under low, moderate or high stringency conditions, and encode an αLNNdΔG2'protein that maintains biological function. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook, et al., supra). The conditions of temperature and ionic strength determine the "stringency" of the hybridization. Typical low stringency hybridization conditions include 55° C., 5×SSC, 0.1% SDS and no formamide; or 30% formamide, 5×SSC, 0.5% SDS at 42° C. Typical moderate stringency hybridization conditions are 40% formamide, with 5× or 6×SSC and 0.1% SDS at 42° C. High stringency hybridization conditions are 50% formamide, 5× or 6×SSC at 42° C. or, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, e.g., oligonucleotides, the position of mismatches becomes more important, and the length of the oligonucleotide determines its specificity (see Sambrook, et al., supra, 11.7-11.8).

The αLNNdΔG2' mouse polypeptide comprises the amino acid sequence of SEQ ID NO: 21. The αLNNdΔG2' human polypeptide comprises the amino acid sequence of SEQ ID NO: 22 and has an 87% identity with the mouse polypeptide as shown in FIG. 9. αLNNdΔG2'polypeptides comprising amino acid sequences that are at least about 90% identical and most preferably at least about 95% identical (e.g., 95%, 96%, 97%, 98%, 99%, 100%) to the αLNNdΔG2' amino acid sequences provided herein (e.g., SEQ ID NOs: 21-22) are contemplated with respect to restoring laminin polymerization function, when the comparison is performed by a BLAST algorithm wherein the parameters of the algorithm are selected to give the largest match between the respective sequences over the entire length of the respective reference sequences. Polypeptides comprising amino acid sequences that are at least about 90% similar and most preferably at least about 95% similar (e.g., 95%, 96%, 97%, 98%, 99%, 100%) to any of the reference αLNNdΔG2' amino acid sequences when the comparison is performed with a BLAST algorithm wherein the parameters of the algorithm are selected to give the largest match between the respective sequences over the entire length of the respective reference sequences, are also included in constructs and methods of the present invention.

Sequence identity refers to the degree to which the amino acids of two polypeptides are the same at equivalent positions when the two sequences are optimally aligned. Sequence similarity includes identical residues and nonidentical, biochemically related amino acids. Biochemically related amino acids that share similar properties and may be interchangeable are discussed above.

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, DC; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, DC; Altschul, S. F., (1991) J. Mol. Biol. 219:555-565; States, D J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

This invention also provides expression vectors comprising various nucleic acids, wherein the nucleic acid is operably linked to control sequences that are recognized by a host cell when the host cell is transfected with the vector. Also provided are the virions comprising recombinant AAV-DJ and certain AAV-2 sequences, as well as nucleic acid sequences for expressing αLNNdΔG2' under the direction of a CMV promoter and a CMV enhancer. Alternative promoters may be used provided that they are small in size and have high activity with good expression. Within these constructs, the rAAV2 sequences correspond to the 5' and 3' ITR sequences, e.g., SEQ ID NOS: 11 and 16 and others as described in the sequence listing). These sequences were packaged with the AAV-DJ capsid to form the virions that are therapeutic to laminin alpha-2 deficiency in the present invention.

Pharmaceutical Compositions and Administration

To prepare pharmaceutical or sterile compositions of the compositions of the present invention, the AAV-DJ vectors or related compositions may be admixed with a pharmaceutically acceptable carrier or excipient. See, e.g., *Remington's Pharmaceutical Sciences and U.S. Pharmacopeia: National Formulary*, Mack Publishing Company, Easton, PA (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, NY; Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY).

Toxicity and therapeutic efficacy of the therapeutic compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, therapeutic compositions exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In an embodiment of the invention, a composition of the invention is administered to a subject in accordance with the Physicians' Desk Reference 2003 (Thomson Healthcare; 57th edition (Nov. 1, 2002)).

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the composition or therapeutic can be administered by an invasive route such as by injection (see above). In further embodiments of the invention, the composition, therapeutic, or pharmaceutical composition thereof, is administered intravenously, subcutaneously, intramuscularly, intraarterially, intra-articularly (e.g., in arthritis joints), intratumorally, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector.

The pharmaceutical compositions of the invention may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

Alternately, one may administer the AAV-DJ vector or related compound in a local rather than systemic manner, for example, via injection of directly into the desired target site, often in a depot or sustained release formulation. Furthermore, one may administer the composition in a targeted drug delivery system, for example, in a liposome coated with a tissue-specific antibody, targeting, for example, the brain. The liposomes will be targeted to and taken up selectively by the desired tissue.

The administration regimen depends on several factors, including the serum or tissue turnover rate of the therapeutic composition, the level of symptoms, and the accessibility of the target cells in the biological matrix. Preferably, the administration regimen delivers sufficient therapeutic composition to effect improvement in the target disease state, while simultaneously minimizing undesired side effects. Accordingly, the amount of biologic delivered depends in part on the particular therapeutic composition and the severity of the condition being treated.

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent.

As used herein, “inhibit” or “treat” or “treatment” includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms “therapeutically effective amount”, “therapeutically effective dose” and “effective amount” refer to an amount of a rAAV-DJ-αLNNdΔG2' based compound of the invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Kits

The present invention also provides kits comprising the components of the combinations of the invention in kit form. A kit of the present invention includes one or more components including, but not limited to, rAAV-DJ-αLNNdΔG2' based compound, as discussed herein, in association with one or more additional components including, but not limited to a pharmaceutically acceptable carrier and/or a chemotherapeutic agent, as discussed herein. The rAAV-DJ-αLNNdΔG2' based compound or composition and/or the therapeutic agent can be formulated as a pure composition or in combination with a pharmaceutically acceptable carrier, in a pharmaceutical composition.

In one embodiment, a kit includes an rAAV-DJ-αLNNdΔG2' based compound/composition of the invention or a pharmaceutical composition thereof in one container (e.g., in a sterile glass or plastic vial) and a pharmaceutical composition thereof and/or a chemotherapeutic agent in another container (e.g., in a sterile glass or plastic vial).

In another embodiment of the invention, the kit comprises a combination of the invention, including an rAAV-DJ-αLNNdΔG2' based compound, along with a pharmaceutically acceptable carrier, optionally in combination with one or more chemotherapeutic agent component formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, NY; Sambrook and Russell (2001) *Molecular Cloning*, $3^{rd}$ ed., Cold Spring Harbor Laboratory Press, Cold Spring Harbor, NY; Wu (1993) *Recombinant DNA*, Vol. 217, Academic Press, San Diego, CA). Standard methods also appear in Ausbel, et al. (2001) *Current Protocols in Molecular Biology*, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology,* Vol. 3, John Wiley and Sons, Inc., NY, NY, pp. 16.0.5-16.22.17; Sigma-Aldrich, Co. (2001) *Products for Life Science Research*, St. Louis, MO; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, NY; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

EXAMPLES

Example 1

AlphaLNNdDeltaG2short (αLNNdΔG2') Construct Development

Removal of the G2 nidogen-1 domain in αLNNd pcDNA3.1 Zeo was accomplished with overlapping PCR. In the first round of PCR, a 1.2 Kb-5' (F1noG2 1F 5'-ctgggtcactgtcaccctgg-3' (SEQ ID NO: 2) and noG2 2R 5'-atggattctgaagacagacaccagagacac-3' (SEQ ID NO: 3)) and 1.8 Kb-3' (no G2 2F5'-ctggtgtctgtcttcagaatccatgctac-3' (SEQ ID NO: 4) and F1 no G21R 5'-gaaggcacagtcgaggctgatcag-3' (SEQ ID NO: 5)) product was generated on either side of the G2 nidogen-1 domain of αLNNd. They were sewn together with a second round of PCR (F1noG2 Fand F1 no G2 1R) into a 3 Kb product which was then digested with EcoRI to 2.4 Kb and ligated into the 5.85 Kb EcoRI αLNNd pcDNA 3.1 zeo vector (generating an 8.25 Kb noG2 αLNNd pcDNA3.1 zeo plasmid). A further 2 EGF (270 bp) deletion of noG2 αLNND was performed with overlapping PCR primers (Bam shnoG2 1F 5'-cggcagcctgaatgaggatccatgcataga-3' (SEQ ID NO: 6) and shnoG2 2R 5'-cacagtagttgatgggacagacacc-3' (SEQ ID NO: 7)) and 3' (shnoG2 2F 5'-gtctctggtgtctgtcccatcaacta-3' (SEQ ID NO: 8) and sse shnoG2 1R 5'-gaggcacaaacatcccctgcagggtgggcc-3' (SEQ ID NO: 9) to generate 160 bp and 357 bp products, respectively. After a second round of PCR, a 485 bp BamHI-SbfI digested insert was ligated into a likewise digested noG2 αLNNd pcDNA3.1 zeo vector (7.5 Kb). To remove the N-terminal Myc tag on the short no G2 αLNNd open reading frame (ORF), a 1.5 Kb BamHI insert was moved from the F3-8 mck-pA construct to the MCS-AAV vector (4.6 Kb Cell Biolabs, VPK-410-DJ) generating a 6.1 Kb AAV-5'F1 no tag-10 plasmid. The short noG2 αLNND pcDNA3.1 zeo plasmid was digested with FseI and XhoI to generate a 2.8 Kb insert which was ligated into the similarly digested AAV-5'F1 no tag-10 vector (4.9 Kb). The final vector size was 7.7 Kb with an ORF for alphaLNNdDeltaG2short (αLNNdΔG2') of 3009 bp (SEQ ID NO: 1).

Example 2

Generation of AAV Virus

Figure 6:
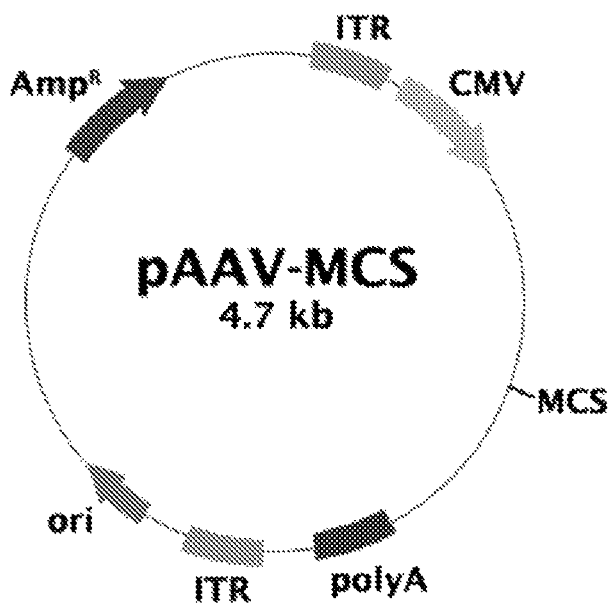
FIG. 6 is a map of the pAAV-MCS expression vector.
Figure 7:
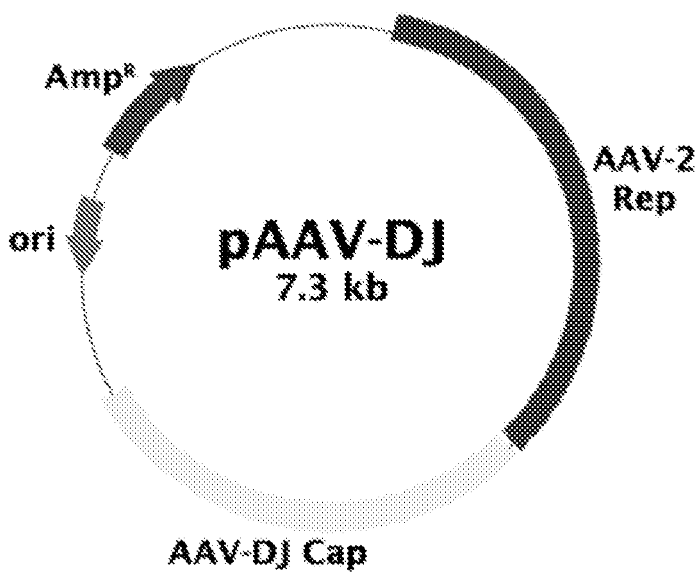
FIG. 7 is a map of the pAAV-DJ Vector.
Figure 8:
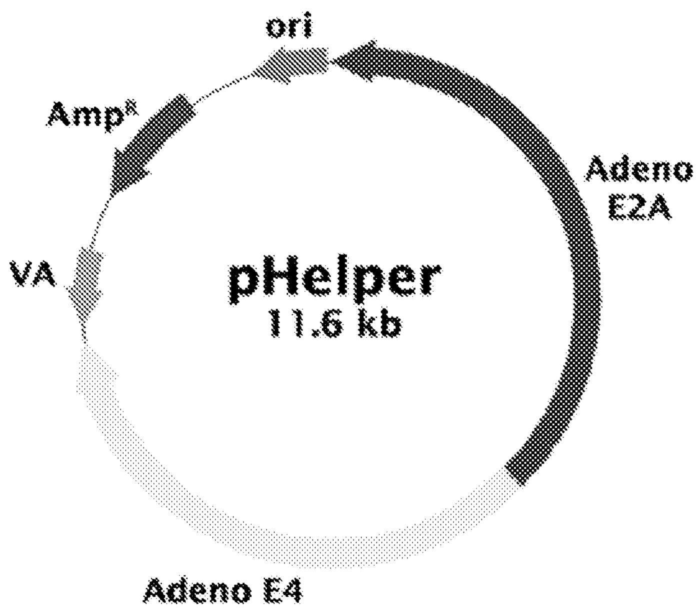
FIG. 8 is a map of the pHelper vector.

The αLNNdΔG2'-MCS plasmid was triple transfected along with AAV-DJ pHelper pHelper plasmids (SEQ ID NOS: 1, 17, 20, respectively; FIGS. 6-8) (Cell Biolabs, Inc., San Diego, CA) into adherent HEK293 in a 1:1:1 ratio using a common method of calcium phosphate transient transfection. Briefly, 12.5 ug each/150 mm dish (10-150 mm dishes per prep) were added to the 75% confluent HEK293 cells overnight according to manufacturer's instructions (Sigma-Aldrich Corp., St. Louis, MO, catalog #CAPHOS). Virus was harvested from the cultures 96 hours later with an AAVpro purification kit (Takara Bio USA, Inc., Mountain View, CA, catalog #6666). Alternative methods of purification are available including freeze-thaw or Triton-100 lysis of cells followed by PEG8000 and/or cesium chloride centrifugation. Viral titer was determined with real time PCR (AAVpro titration kit, Takara Bio USA, Inc., Mountain View, CA, catalog #6233).

Example 3

Expression and Analysis of AAV-Generated αLNNdΔG2' Protein

Figure 5A:
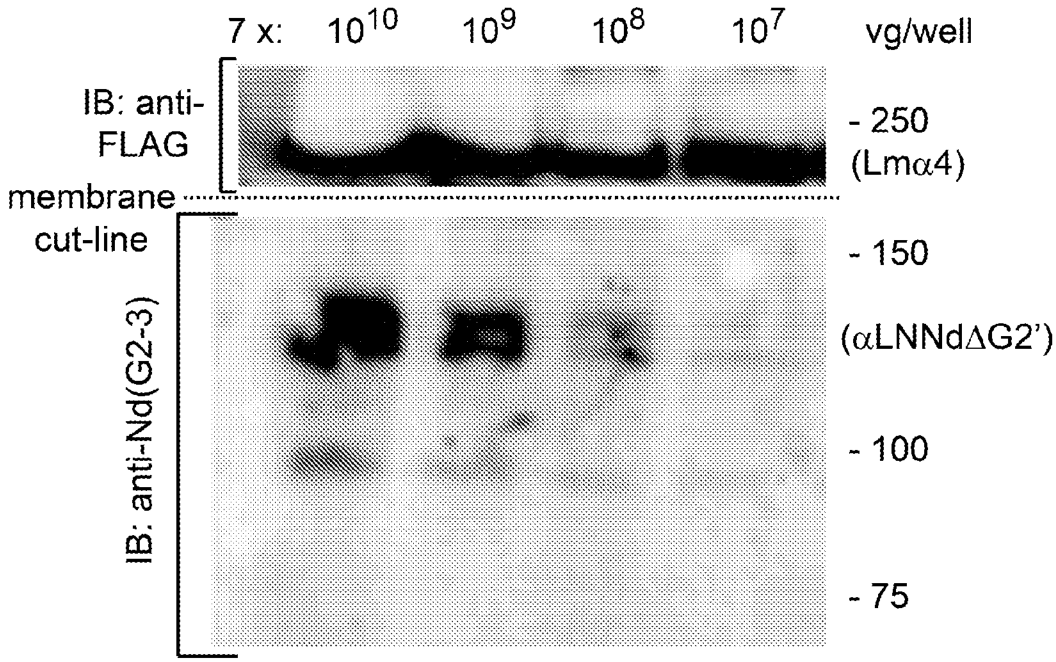
FIGS. 5A-E are SDS-PAGE, immunofluorescent images, and a graph showing AAV expression of αLNNdΔG2' and mag bound to Lm411 and assembly of αLNNdΔG'-Lm411 on Schwann cells.
Figure 5B:
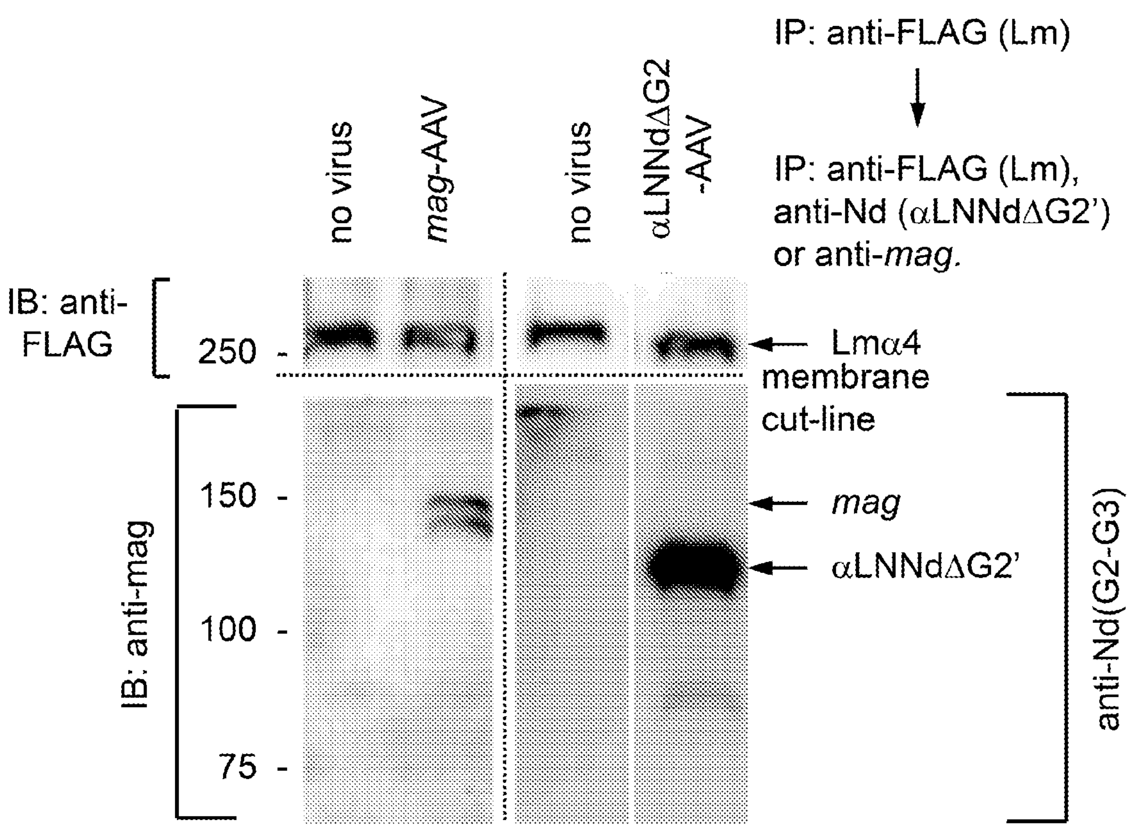
Figure 5C:
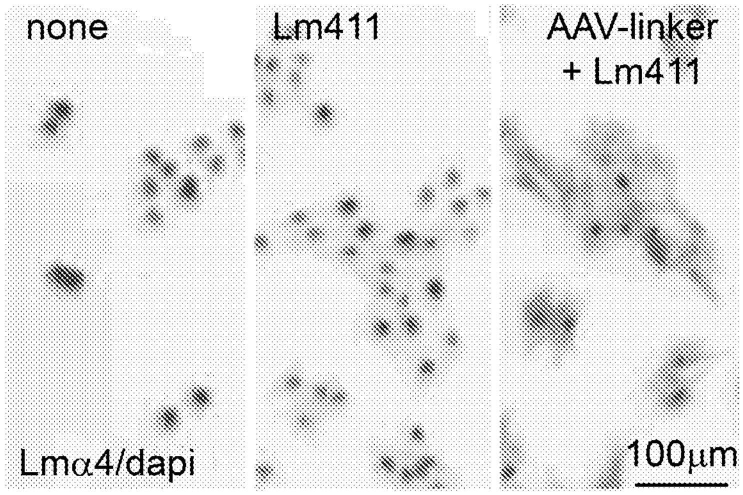
Figure 5D:
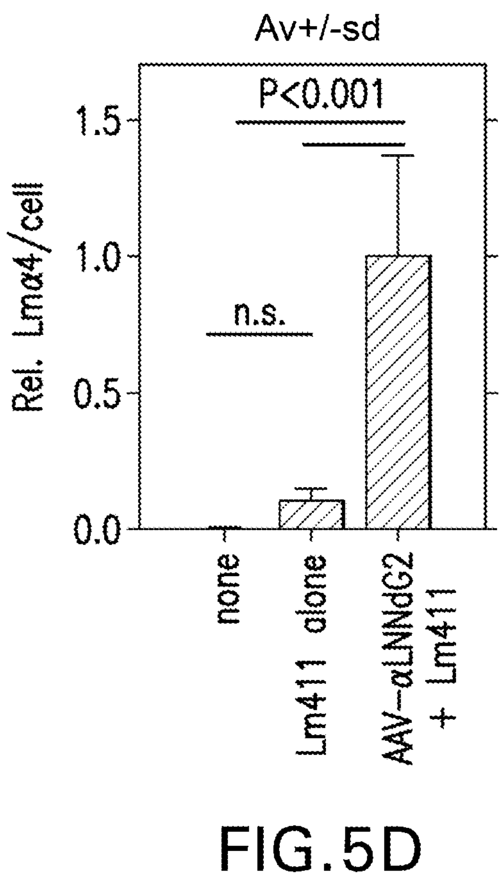

Stably transfected 411 HEK293 cells were infected with approximately 6×10 vg/6-wells dish. Four days later, the conditioned media was evaluated by immunoprecipitation with a-flag agarose beads for 1 hour at room temperature, followed by western blot analysis. Western blots were cut and stained with anti-flag (top) or anti-G2-G2 nidogen (bottom) at 1 μg/ml. Results are shown in FIG. 5A. Additionally, the conditioned AAV 411 HEK293 media was added to high passage rat Schwann cells for 1 hr and analyzed by immunofluorescence for 411 laminin assembly using 1 ug/ml chicken anti-α4 and 1:100 anti-chicken Alexa Fluor 647 (Life Technologies, Carlsbad, CA, catalog #A-21449). A substantial increase of Lm411 assembly resulted from the AAV-generated αLNNdΔG2' protein, shown in FIGS. 5C and 5D.

Figure 5E:
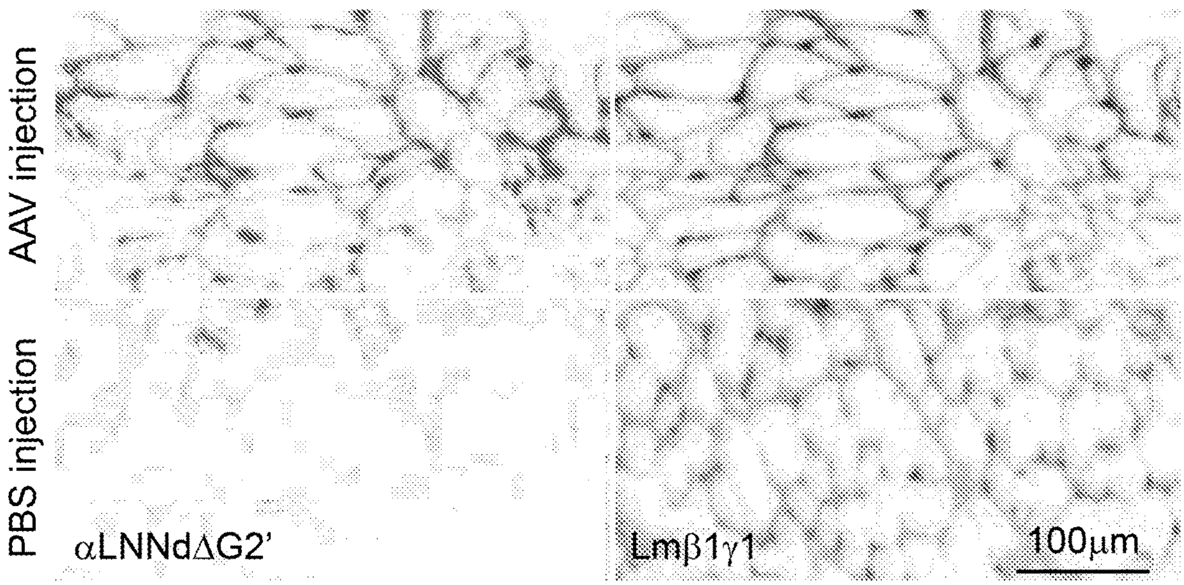

AAVαLNNdΔG2' (virus, $10^{10}$ vg in ~25 μl) or PBS buffer was injected i.m. into a 1-week old dy3K/dy3K mag mouse. Two week later, the quadriceps were harvested, sectioned, and stained with antibody to detect αLNNdΔG2' (red) and laminins (green), shown in FIG. 5E. The ∞1LN epitope of αLNNdΔG2' was detected in the quadriceps muscle tissue, indicating the linker was incorporated into the muscle sarcolemma.

Example 4

Restoring Laminin α2 to Symptomatic Mice

Figure 3B:
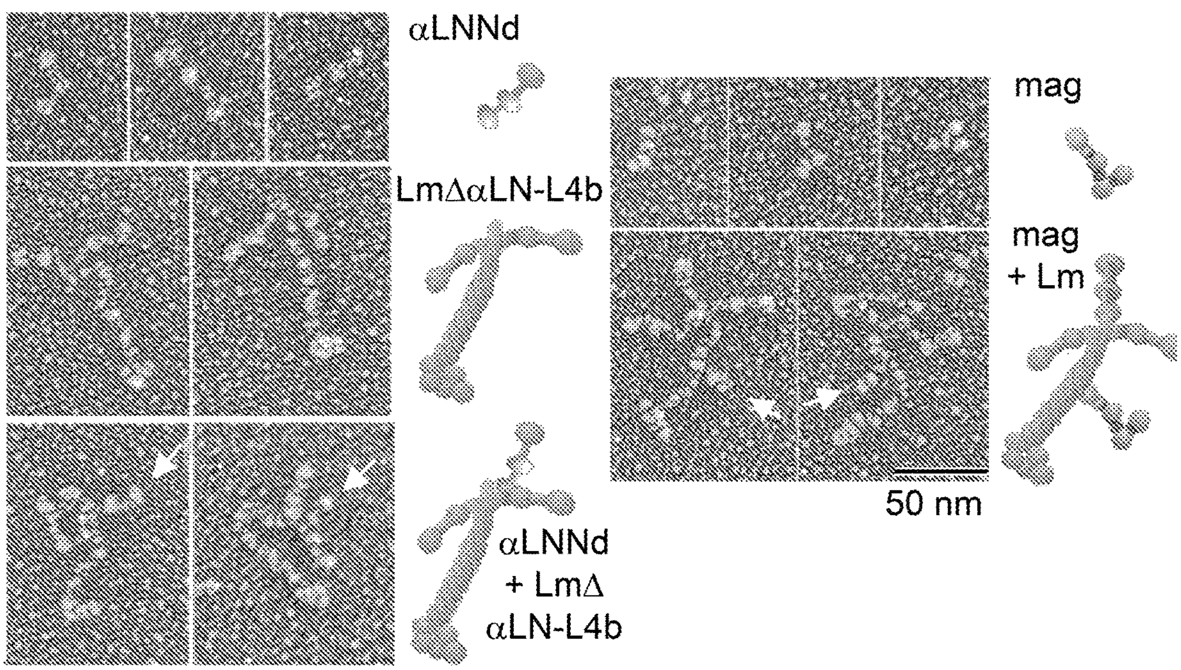
Figure 3C:
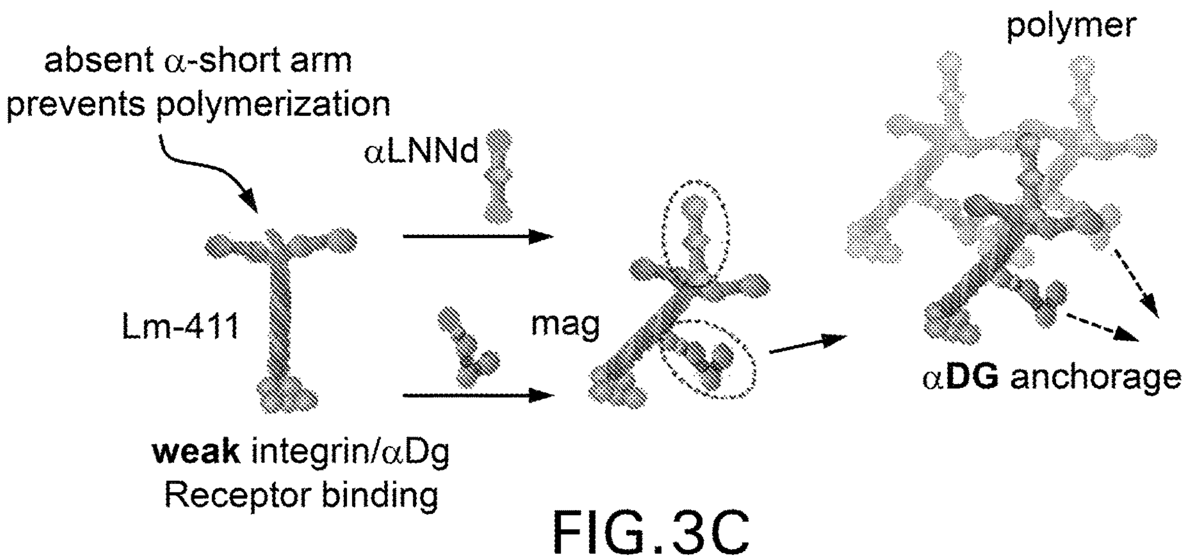
Figure 3D:
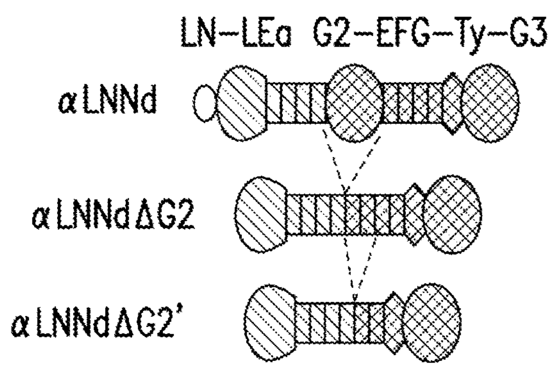
Figure 3E:
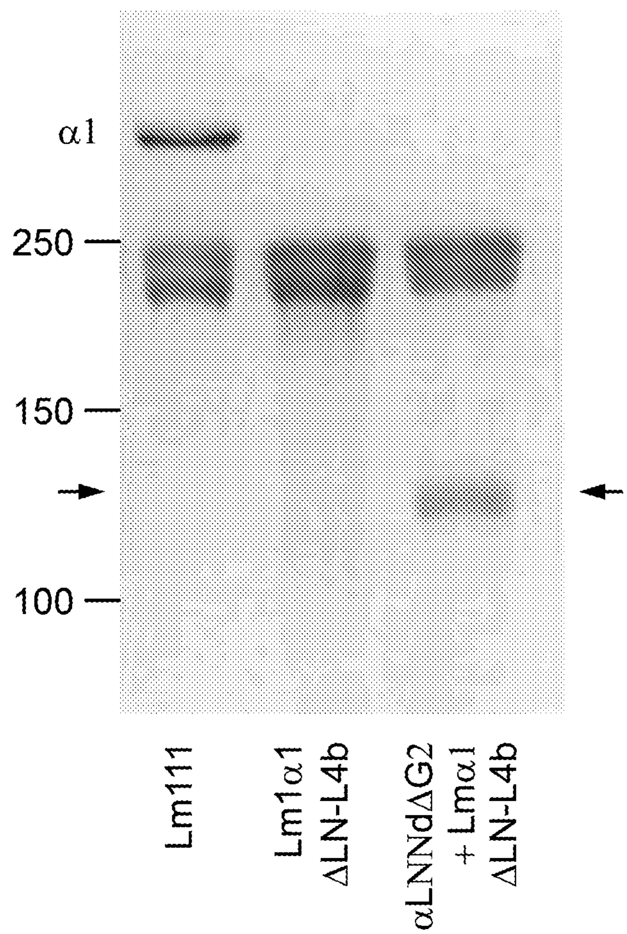

Injection of AAV-DJ-αLNNdΔG2' constructs in dy3K/dy3K mice expressing a mag transgene, a miniaturized version of agrin FIG. 3B (SEQ ID NO: 23) and injection of AAV-DJ-αLNNdΔG2' construct in dy3K/dy3K mice expressing the αLNNd transgene are done to evaluate one virus infection at a time in conjunction with stable and already characterized expression of the paired linker protein and to validate each linker protein separately, minimizing variability. The initial analysis is on muscle to determine which muscles are populated with αLNNdΔG2' and mag following the extent of nerve expression, and the persistence of expression following injection, using immunofluorescence microscopy with specific linker and laminin antibodies described in McKee, et al., (2017) J Clin Invest 127(3): 1075-1089; Reinhard, et al., (2017) Sci Transl Med 9(396).

Following assessment of the initial analysis, dy3K/dy3K mice are co-infected with both virus preparations. Injections will be given post-natal day 1 or 2, given the perinatal time course of myelination (SC proliferation commencing before birth by radial sorting occurring substantially in the first post-natal week). Phenotype and histology analyses to be done include (1) measurements of measure survival, body weights, muscle weights, time on vertical grids, grip strength and overall behavior at different ages; (2) examination of diaphragm, intercostal muscles and phrenic nerve; (3) skeletal muscle analysis by H&E and Sirius Red (collagen)-stained histology of forelimb extensor carpi radialis and diaphragm/intercostal muscles at different ages with morphometric quantitation of fiber size, number, regeneration (fraction of myofibers with central nuclei), inflammation and fibrosis; (4) peripheral nerve analysis by examining immunostained nerve and roots to estimate the extent of linker-protein expression and to detect relative changes in laminin subunits; examine methylene-blue stained semi-thin sections using electron microscopy to quantitatively evaluate the extent of axonal sorting, myelination, myelin thickness, and fraction of naked axons; determine SC proliferation from EdU/dapi ratios, and using qRT-PCR to evaluate maturation of myelination (e.g., Oct6, Sox2, cJun).

Results of the analysis are used to optimize delivery and evaluate variants of the αLNNdΔG2' and mag linker proteins that may further improve functions.

Example 5

Expression of αLNNdΔG2' with AAV with a Variant Serotype Capsid

The αLNNdΔG2' DNA is inserted into an AAV vector with coding for a different capsid serotype or composite serotype for the purpose of altering tissue specificity, e.g. only skeletal muscle plus heart or predominantly liver. Note: αLNNdΔG2' is a soluble secreted protein in which the site of synthesis need not be the target cell type.

Example 6

AAV Capsid Sequence Modified to Reduce Ubiquitination

AAV-DJ, like other AAV, contain several phosphorylation and ubiquitination sites on the capsid. Point mutations on the rep/cap plasmid at K137R, S503A, and T251A were found to substantially increase protein expression in vitro and in vivo (described in Mao, Wang, Yan, Li, Wang and Li, 2016, “Single point mutation in adeno-associated viral vectors –DJ capsid leads to improvement for gene delivery in vivo. BMC Biotechnology 16: 1-8). The AAV plasmid can readily be modified to introduce this improvement.

Example 7

Expression of αLNNdΔG2' with AAV Using a Specialized Promoter

The αLNNdΔG2' DNA is inserted into an AAV vector with a different promoter/enhancer with the effect of (a) changing specificity and/or (b) increasing the allowable open reading frame of the insert. An example, used to drive expression of micro-dystrophin in skeletal muscle and heart, is the 436 bp CK8e promoter/enhancer that has been modified from the muscle creatine kinase gene basal promoter and upstream enhancer. The CK8e promoter/enhancer is described in J. N. Ramos et al., 2019, Molecular Therapy, 27: 623-635.

Example 8

Expression of Lmα1LNNdΔG2' with Alternative Signal Sequence

The protein αLNNdΔG2' and related proteins have been expressed in vitro and in mice using the BM-40 signal sequence, which has the nucleotide sequence in SEQ ID NO: 25 and has been given the letter code A in Table 2 below. An alternative is to express the protein with the endogenous α1 subunit signal peptide, which has the nucleotide sequence in SEQ ID NO: 27 and has been given the letter code A' in Table 2.

Table 2 provides a list of all of the variant protein sequences with assigned letter codes that can be used with either the BM-40 signal peptide or the laminin endogenous signal peptide that normally precedes the laminin N-terminal subunit. These domains can be used to create linker proteins that enable laminin polymerization. Mouse domains of the laminin-binding linker protein and internally reduced-sized linker proteins that can enable polymerization have been assigned letter codes A, A' to P for both nucleotide and amino acid sequences (SEQ ID NOS: 25-58). Alternative N-terminal domains, mouse and human, have been assigned letter codes Q to Z and a to b for both nucleotide and amino acid sequences (SEQ ID NOS: 59-106). Additional C-terminal domains, mouse and human non-neural agrin dystroglycan-binding domains that can be fused C-terminal (5' to) to the nidogen laminin-binding G3 domain of polymerization linker proteins, have been assigned letter codes c to j for both nucleotide and amino acid sequences (SEQ ID NOS: 107-138).

Table 3 provides the mouse and human nucleotide and amino acid sequences for each of the variant protein sequences listed in Table 2 and provides the SEQ ID NO assigned to these sequences in the Sequence Listing.

TABLE 2

Domain Single Letter Codes

| Letter Code | Gene | Protein | Domain | DNA size, bp[6] |
|---|---|---|---|---|
| A | LAMA1 | Laminin-α1 | BM-40 signal peptide | 51 |
| A' | LAMA1 | Laminin-α1 | endogenous signal peptide | 72 |
| B | LAMA1 | Laminin-α1 | LN | 753 |
| C | LAMA1 | Laminin-α1 | LEa-1 | 171 |
| D | LAMA1 | Laminin-α1 | LEa-2 | 210 |
| E | LAMA1 | Laminin-α1 | LEa-3 | 177 |
| F | LAMA1 | Laminin-α1 | LEa-4 | 168 |
| G | LAMA1 | Laminin-α1 | LF fragment | 33 |
| H | NID1 | Nidogen-1 | G2 | 843 |
| I | NID1 | Nidogen-1 | EGF-like-2 | 126 |
| J | NID1 | Nidogen-1 | EGF-like-3 | 126 |
| K | NID1 | Nidogen-1 | spacer betw. EGF-like 3 & 4 | 18 |
| L | NID1 | Nidogen-1 | EGF-like-4 | 132 |
| M | NID1 | Nidogen-1 | EGF-like-5 | 141 |
| N | NID1 | Nidogen-1 | G3-TY | 282 |
| O | NID1 | Nidogen-1 | G3-Propeller | 744 |
| P | NID1 | Nidogen-1 | G3-EGF-like-6 | 171 |
| Q | LAMB1 | Laminin-β1 | signal peptide | 63 |
| R | LAMB1 | Laminin-β1 | LN | 744 |
| S | LAMB1 | Laminin-β1 | LEa-1 | 192 |
| T | LAMB1 | Laminin-β1 | LEa-2 | 189 |

TABLE 2-continued

Domain Single Letter Codes

| Letter Code | Gene | Protein | Domain | DNA size, bp[6] |
|---|---|---|---|---|
| U | LAMB1 | Laminin-β1 | LEa-3 | 180 |
| V | LAMB1 | Laminin-β1 | LEa-4 | 156 |
| W | LAMC1 | Laminin-γ1 | signal peptide | 99 |
| X | LAMC1 | Laminin-γ1 | LN | 768 |
| Y | LAMC1 | Laminin-γ1 | LEa-1 | 168 |
| Z | LAMC1 | Laminin-γ1 | LEa-2 | 168 |
| a | LAMC1 | Laminin-γ1 | LEa-3 | 168 |
| b | LAMC1 | Laminin-γ1 | LEa-4 | 168 |
| c | AGRN | non-neural agrin | LG spacer-1 | 27 |
| d | AGRN | non-neural agrin | EGF-like 2 | 114 |
| e | AGRN | non-neural agrin | EGF-like 3 | 117 |
| f | AGRN | non-neural agrin | LG spacer-2 | 27 |
| g | AGRN | non-neural agrin | LG2 | 537 |
| h | AGRN | non-neural agrin | EGF-like 4 | 120 |
| i | AGRN | non-neural agrin | LG spacer-2 | 30 |
| j | AGRN | non-neural agrin | LG3 | 537 |

[6]Mouse bp number shown. Human bp same or similar.

TABLE 3

Domain Sequences

| SEQ ID NO | Domain Letter Code | Domain Name | Sequence |
|---|---|---|---|
| 25 | A | Mouse BM-40 (Sparc) signal sequence [DNA, 51 bp) | ATGAGGGCCTGGATCTTCTTTCTCCTTTGCCTGGCC<br>GGGAGGGCTCTGGCA |
| 26 | A | Mouse BM-40 (Sparc) signal peptide | MRAWIFFLLCLAGRALA |
| 27 | A' | Mouse Lm α1 endogenous signal sequence [DNA, 72 bp] | ATGCGCGGCAGCGGCACGGGAGCCGCGCTCCTGG<br>TGCTCCTGGCCTCGGTGCTCTGGGTCACCGTGCGG<br>AGC |
| 28 | A' | Mouse laminin α1 endogenous signal peptide | MRGSGTGAALLVLLASVLWVTVRS |
| 29 | A' | Laminin (Lm) α1 signal peptide [DNA, 51 bp] | ATGAGGGCCTGGATCTTCTTTCTCCTTTGCCTGGCC<br>GGGAGGGCTCTGGCA |
| 30 | A' | Human laminin α1 signal peptide | MRAWIFFLLCLAGRALA |
| 31 | B | Mouse Lm α1 LN domain [DNA, 753 bp] | CAGCAGAGAGGCTTGTTCCCTGCCATTCTCAACCT<br>GGCCACCAATGCCCACATCAGCGCCAATGCTACCT<br>GTGGAGAGAAGGGGCCTGAGATGTTCTGCAAACT<br>CGTGGAGCACGTGCCGGGCCGGCCTGTTCGACAC<br>GCCCAATGCCGGGTCTGTGACGGTAACAGTACGA<br>ATCCTAGAGAGCGCCATCCGATATCACACGCAATC<br>GATGGCACCAACAACTGGTGGCAGAGCCCCAGTA<br>TTCAGAATGGGAGAGAGTATCACTGGGTCACTGTC<br>ACCCTGGACTTACGGCAGGTCTTTCAAGTTGCATA<br>CATCATCATTAAAGCTGCCAATGCCCCTCGGCCTG<br>GAAACTGGATTTTGGAGCGCTCCGTGGATGGCGTC<br>AAGTTCAAACCCTGGCAGTACTATGCCGTCAGCGA<br>TACAGAGTGTTTGACCCGCTACAAAATAACTCCAC<br>GGCGGGGACCTCCCACTTACAGAGCAGACAACGA<br>AGTCATCTGCACCTCGTATTATTCAAAGCTGGTGC<br>CACTTGAACATGGAGAGATTCACACATCACTCATC<br>AATGGCAGACCCAGCGCTGACGACCCCTCACCCC<br>AGTTGCTGGAATTCACCTCAGCACGGTACATTCGC<br>CTTCGTCTTCAGCGCATCAGAACACTCAACGCAGA<br>CCTCATGACCCTTAGCCATCGGGACCTCAGAGACC<br>TTGACCCCATTGTCACAAGACGTTATTACTATTCG<br>ATAAAAGACATTTCCGTTGGAGGC |
| 32 | B | Mouse Lm α1 LN [polymerization domain] | QQRGLFPAILNLATNAHISANATCGEKGPEMFCKLV<br>EHVPGRPVRHAQCRVCDGNSTNPRERHPISHAIDGT<br>NNWWQSPSIQNGREYHWVTVTLDLRQVFQVAYIIIK<br>AANAPRPGNWILERSVDGVKFKPWQYYAVSDTECL<br>TRYKITPRRGPPTYRADNEVICTSYYSKLVPLEHGEI |

TABLE 3-continued

| SEQ ID NO | Domain Letter Code | Domain Name | Sequence |
|---|---|---|---|
| Domain Sequences | | | |
| | | | HTSLINGRPSADDPSPQLLEFTSARYIRLRLQRIRTLN ADLMTLSHRDLRDLDPIVTRRYYYSIKDISVGG |
| 33 | B | Human Lmα1 LN [DNA, 753 bp] | CGGCAGAGAGGCCTGTTTCCTGCCATTCTCAATCT TGCCAGCAATGCTCACATCAGCACCAATGCCACCT GTGGCGAGAAGGGGCCGGAGATGTTCTGCAAACT TGTGGAGCATGTGCCAGGTCGGCCCGTCCGAAAC CCACAGTGCCGGATCTGTGATGGCAACAGCGCAA ACCCCAGAGAACGCCATCCAATATCACATGCCAT AGATGGCACCAATAACTGGTGGCAAAGTCCCAGC ATTCAGAATGGGAGAGAATATCACTGGGTCACAA TCACTCTGGACTTAAGACAGGTCTTTCAAGTTGCA TATGTCATCATTAAAGCTGCCAATGCCCCTCGACC TGGAAACTGGATTTTGGAGCGTTCTCTGGATGGCA CCACGTTCAGCCCCTGGCAGTATTATGCAGTCAGC GACTCAGAGTGTTTGTCTCGTTACAATATAACTCC AAGACGAGGGCCACCCACCTACAGGGCTGATGAT GAAGTGATCTGCACCTCCTATTATTCCAGATTGGT GCCACTTGAGCATGGAGAGATTCATACATCACTCA TCAATGGCAGACCAAGCGCTGACGATCTTTCACCC AAGTTGTTGGAATTCACTTCTGCACGATATATTCG CCTTCGCTTGCAACGCATTAGAACGCTCAATGCAG ATCTCATGACCCTTAGCCACCGGGAACCTAAAGA ACTGGATCCTATTGTTACCAGACGCTATTATTATT CAATAAAGGACATTTCTGTTGGAGGC |
| 34 | B | Human Lmα1 LN | RQRGLFPAILNLASNAHISTNATCGEKGPEMFCKLVE HVPGRPVRNPQCRICDGNSANPRERHPISHAIDGTNN WWQSPSIQNGREYHWVTITLDLRQVFQVAYVIIKAA NAPRPGNWILERSLDGTTFSPWQYYAVSDSECLSRY NITPRRGPPTYRADDEVICTSYYSRLVPLEHGEIHTSL INGRPSADDLSPKLLEFTSARYIRLRLQRIRTLNADL MTLSHREPKELDPIVTRRYYYSIKDISVGG |
| 35 | C | Mouse Lm α1 LEa-1 domain [DNA, 171 bp] | ATGTGCATTTGCTACGGCCATGCCAGCAGCTGCCC GTGGGATGAAGAAGCAAAGCAACTACAGTGTCAG TGTGAACACAATACGTGTGGCGAGAGCTGCGACA GGTGCTGTCCTGGCTACCATCAGCAGCCCTGGAGG CCCGGAACCATTTCCTCCGGCAACGAGTGTGAG |
| 36 | C | Mouse Lm α1 LEa-1 [required for LN folding; spacer domain] | MCICYGHASSCPWDEEAKQLQCQCEHNTCGESCDR CCPGYHQQPWRPGTISSGNECE |
| 37 | C | Human Lmα1 LEa-1 [DNA, 171 bp] | ATGTGTATCTGCTATGGCCATGCTAGTAGCTGCCC ATGGGATGAAACTACAAAGAAACTGCAGTGTCAA TGTGAGCATAATACTTGCGGGGAGAGCTGTAACA GGTGCTGTCCTGGGTACCATCAGCAGCCCTGGAGG CCGGGAACCGTGTCCTCCGGCAATACATGTGAA |
| 38 | C | Human Lmα1 LEa-1 | MCICYGHASSCPWDETTKKLQCQCEHNTCGESCNR CCPGYHQQPWRPGTVSSGNTCE |
| 39 | D | Mouse Lm α1 LEa-2 domain [DNA, 210 bp] | GAATGCAACTGTCACAACAAAGCCAAAGATTGTT ACTATGACAGCAGTGTTGCAAAGGAGAGGAGAAG CCTGAACACTGCCGGGCAGTACAGTGGAGGAGGG GTTTGTGTCAACTGCTCGCAGAATACCACAGGGAT CAACTGTGAAACCTGTATCGACCAGTATTACAGAC CTCACAAGGTATCTCCTTATGATGACCACCCTTGC CGT |
| 40 | D | Mouse Lm α1 LEa-2 [required for LN folding; spacer domain] | ECNCHNKAKDCYYDSSVAKERRSLNTAGQYSGGGV CVNCSQNTTGINCETCIDQYYRPHKVSPYDDHPCR |
| 41 | D | Human Lmα1 LEa-2 [DNA, 210 bp] | GCATGTAATTGTCACAATAAAGCCAAAGACTGTTA CTATGATGAAAGTGTTGCAAAGCAGAAGAAAAGT TTGAATACTGCTGGACAGTTCAGAGGAGGAGGGG TTTGCATAAATTGCTTGCAGAACACCATGGGAATC AACTGTGAAACCTGTATTGATGGATATTATAGACC ACACAAAGTGTCTCCTTATGAGGATGAGCCTTGCC GC |

TABLE 3-continued

| Domain Sequences | | | |
|---|---|---|---|
| SEQ ID NO | Domain Letter Code | Domain Name | Sequence |
| 42 | D | Human Lmα1 LEa-2 | ACNCHNKAKDCYYDESVAKQKKSLNTAGQFRGGG<br>VCINCLQNTMGINCETCIDGYYRPHKVSPYEDEPCR |
| 43 | E | Mouse Lm α1 LEa-3 domain [DNA, 171 bp] | CCCTGTAACTGTGACCCTGTGGGGTCTCTGAGTTC<br>TGTCTGTATCAAGGATGACCGCCATGCCGATTTAG<br>CCAATGGAAAGTGGCCAGGTCAGTGTCCATGTAG<br>GAAAGGTTATGCTGGAGATAAATGTGACCGCTGC<br>CAGTTTGGCTACCGGGGTTTCCCAAATTGCATC |
| 44 | E | Mouse Lm α1 LEa-3 [domain acting as spacer] | PCNCDPVGSLSSVCIKDDRHADLANGKWPGQCPCR<br>KGYAGDKCDRCQFGYRGFPNCI |
| 45 | E | Human Lmα1 LEa-3 [DNA, 171 bp] | CCCTGTAATTGTGACCCTGTGGGGTCCCTCAGTTC<br>TGTCTGTATTAAGGATGACCTCCATTCTGACTTAC<br>ACAATGGGAAGCAGCCAGGTCAGTGCCCATGTAA<br>GGAAGGTTATACAGGAGAAAAATGTGATCGCTGC<br>CAACTTGGCTATAAGGATTACCCGACCTGTGTC |
| 46 | E | Human Lmα1 LEa-3 | PCNCDPVGSLSSVCIKDDLHSDLHNGKQPGQCPCKE<br>GYTGEKCDRCQLGYKDYPTCV |
| 47 | F | Mouse Lm α1 LEa-4 domain [DNA, 147 bp] | CCCTGTGACTGCAGGACTGTCGGCAGCCTGAATGA<br>GGATCCATGCATAGAGCCGTGTCTTTGTAAGAAAA<br>ATGTTGAGGGTAAGAACTGTGATCGCTGCAAGCC<br>AGGATTCTACAACTTGAAGGAACGAAACCCCGAG<br>GGCTGCTCC |
| 48 | F | Mouse Lm α1 LEa-4 [spacer domain] | PCDCRTVGSLNEDPCIEPCLCKKNVEGKNCDRCKPG<br>FYNLKERNPEGCS |
| 49 | F | Human Lmα1 LEa-4 [DNA, 147 bp] | TCCTGTGGGTGCAACCCAGTGGGCAGTGCCAGTG<br>ATGAGCCCTGCACAGGGCCCTGTGTTTGTAAGGAA<br>AACGTTGAGGGGAAGGCCTGTGATCGCTGCAAGC<br>CAGGATTCTATAACTTGAAGGAAAAAAACCCCCG<br>GGGCTGCTCC |
| 50 | F | Human Lmα1 LEa-4 | SCGCNPVGSASDEPCTGPCVCKENVEGKACDRCKPG<br>FYNLKEKNPRGCS |
| 51 | G | Mouse Lm α1 LF domain LE-type fragment with 3 cys [DNA, 33 bp] | GAGTGCTTCTGCTTCGGTGTCTCTGGTGTCTGT |
| 52 | G | Mouse Lm α1 LF fragment (with 3 cys) [spacer segment] | ECFCFGVSGVC |
| 53 | G | Human Lmα1 LF fragment (with 3 cys)[DNA, 33 bp] | GAGTGCTTCTGCTTTGGCGTTTCTGATGTCTGC |
| 54 | G | Human Lmα1 LF fragment (with 3 cys) | CFCFGVSDVC |
| 55 | H | Mouse Nidogen-1 G2 domain [DNA, 843 bp] | CAGCAGACTTGTGCCAACAATAGACACCAGTGCT<br>CCGTGCATGCAGAGTGCAGAGACTATGCTACTGG<br>CTTCTGCTGCAGGTGTGTGGCCAACTACACAGGCA<br>ATGGCAGACAGTGCGTGGCAGAAGGCTCTCCACA<br>ACGGGTCAATGGCAAGGTGAAGGGAAGGATCTTC<br>GTGGGGAGCAGCCAGGTCCCCGTGGTGTTTGAGA<br>ACACTGACCTGCACTCCTATGTGGTGATGAACCAC<br>GGGCGCTCTTACACAGCCATCAGCACCATCCCTGA<br>AACCGTCGGCTACTCTCTGCTCCCCCTGGCACCCA<br>TTGGAGGCATCATCGGATGGATGTTTGCAGTGGAG<br>CAGGATGGGTTCAAGAATGGGTTTAGCATCACTG<br>GGGGCGAGTTTACCCGGCAAGCTGAGGTGACCTT<br>CCTGGGGCACCCAGGCAAGCTGGTCCTGAAGCAG<br>CAGTTCAGCGGTATTGATGAACATGGACACCTGAC<br>CATCAGCACGGAGCTGGAGGGCCGCGTGCCGCAG<br>ATCCCCTATGGAGCCTCGGTGCACATTGAGCCCTA<br>CACCGAACTGTACCACTACTCCAGCTCAGTGATCA |

TABLE 3-continued

| SEQ ID NO | Domain Letter Code | Domain Name | Sequence |
|---|---|---|---|
| | | | CTTCCTCCTCCACCCGGGAGTACACGGTGATGGAG CCTGATCAGGACGGCGCTGCACCCTCACACACCCA TATTTACCAGTGGCGTCAGACCATCACCTTCCAGG AGTGTGCCCACGATGACGCCAGGCCAGCCCTGCC CAGCACCCAGCAGCTCTCTGTGGACAGCGTGTTTG TCCTGTACAACAAGGAGGAGAGGATCTTGCGCTA TGCCCTCAGCAACTCCATCGGGCCTGTGAGGGATG GCTCCCCTGATGCC |
| 56 | H | Mouse Nidogen-1 G2 domain [direct collagen-IV, perlecan binding] | QQTCANNRHQCSVHAECRDYATGFCCRCVANYTG NGRQCVAEGSPQRVNGKVKGRIFVGSSQVPVVFENT DLHSYVVMNHGRSYTAISTIPETVGYSLLPLAPIGGII GWMFAVEQDGFKNGFSITGGEFTRQAEVTFLGHPG KLVLKQQFSGIDEHGHLTISTELEGRVPQIPYGASVHI EPYTELYHYSSSVITSSSTREYTVMEPDQDGAAPSHT HIYQWRQTITFQECAHDDARPALPSTQQLSVDSVFV LYNKEERILRYALSNSIGPVRDGSPDA |
| 57 | H | Human Nidogen-1 G2 domain (direct collagen-IV, perlecan binding)[DNA, 843 bp] | CGCCAGACGTGTGCTAACAACAGACACCAGTGCT CGGTGCACGCAGAGTGCAGGGACTACGCCACGGG CTTCTGCTGCAGCTGTGTCGCTGGCTATACGGGCA ATGGCAGGCAATGTGTTGCAGAAGGTTCCCCCCA GCGAGTCAATGGCAAGGTGAAAGGAAGGATCTTT GTGGGGAGCAGCCAGGTCCCCATTGTCTTTGAGAA CACTGACCTCCACTCTTACGTAGTAATGAACCACG GGCGCTCCTACACAGCCATCAGCACCATTCCCGAG ACCGTTGGATATTCTCTGCTTCCACTGGCCCCAGT TGGAGGCATCATTGGATGGATGTTTGCAGTGGAGC AGGACGGATTCAAGAATGGGTTCAGCATCACCGG GGGTGAGTTCACTCGCCAGGCTGAGGTGACCTTCG TGGGGCACCCGGGCAATCTGGTCATTAAGCAGCG GTTCAGCGGCATCGATGAGCATGGGCACCTGACC ATCGACACGGAGCTGGAGGGCCGCGTGCCGCAGA TTCCGTTCGGCTCCTCCGTGCACATTGAGCCCTAC ACGGAGCTGTACCACTACTCCACCTCAGTGATCAC TTCCTCCTCCACCCGGGAGTACACGGTGACTGAGC CCGAGCGAGATGGGGCATCTCCTTCACGCATCTAC ACTTACCAGTGGCGCCAGACCATCACCTTCCAGGA ATGCGTCCACGATGACTCCCGGCCAGCCCTGCCCA GCACCCAGCAGCTCTCGGTGGACAGCGTGTTCGTC CTGTACAACCAGGAGGAGAAGATCTTGCGCTATG CTCTCAGCAACTCCATTGGGCCTGTGAGGGAAGGC TCCCCTGATGCT |
| 58 | H | Human Nidogen-1 G2 domain (direct collagen-IV, perlecan binding) | RQTCANNRHQCSVHAECRDYATGFCCSCVAGYTGN GRQCVAEGSPQRVNGKVKGRIFVGSSQVPIVFENTD LHSYVVMNHGRSYTAISTIPETVGYSLLPLAPVGGIIG WMFAVEQDGFKNGFSITGGEFTRQAEVTFVGHPGN LVIKQRFSGIDEHGHLTIDTELEGRVPQIPFGSSVHIEP YTELYHYSTSVITSSSTREYTVTEPERDGASPSRIYTY QWRQTITFQECVHDDSRPALPSTQQLSVDSVFVLYN QEEKILRYALSNSIGPVREGSPDA |
| 59 | I | Mouse Nidogen-1 EGF-like 2 domain [126 bp] | CTTCAGAATCCATGCTACATTGGCACCCATGGGTG TGACAGCAATGCTGCCTGTCGCCCTGGCCCTGGAA CACAGTTCACCTGCGAATGCTCCATCGGCTTCCGA GGAGACGGGCAGACTTGCTAT |
| 60 | I | Mouse Nidogen-1 EGF-like 2 [spacer] | LQNPCYIGTHGCDSNAACRPGPGTQFTCECSIGFRGD GQTCY |
| 61 | I | Human Nidogen-1 EGF-like 2 domain [DNA, 126 bp] | CTTCAGAATCCCTGCTACATCGGCACTCATGGGTG TGACACCAACGCGGCCTGTCGCCCTGGTCCCAGGA CACAGTTCACCTGCGAGTGCTCCATCGGCTTCCGA GGAGACGGGCGAACCTGCTAT |
| 62 | I | Human Nidogen-1 EGF-like 2 domain | LQNPCYIGTHGCDTNAACRPGPRTQFTCECSIGFRGD GRTCY |
| 63 | J | Mouse Niogen-1 EGF-like 3 domain [126 bp]: | GATATTGATGAGTGTTCAGAGCAGCCTTCCCGCTG TGGGAACCATGCGGTCTGCAACAACCTCCCAGGA ACCTTCCGCTGCGAGTGTGTAGAGGGCTACCACTT CTCAGACAGGGGAACATGCGTG |

TABLE 3-continued

| SEQ ID NO | Domain Letter Code | Domain Name | Sequence |
|---|---|---|---|
| | | Domain Sequences | |
| 64 | J | Mouse Nidogen-1 EGF-like 3 | DIDECSEQPSRCGNHAVCNNLPGTFRCECVEGYHES DRGTCV |
| 65 | J | Human Nidogen-1 EGF-like 3 domain [DNA, 126 bp] | CTTCAGAATCCCTGCTACATCGGCACTCATGGGTG TGACACCAACGCGGCCTGTCGCCCTGGTCCCAGGA CACAGTTCACCTGCGAGTGCTCCATCGGCTTCCGA GGAGACGGGCGAACCTGCTAT |
| 66 | J | Human Nidogen-1 EGF-like 3 domain | LQNPCYIGTHGCDTNAACRPGPRTQFTCECSIGFRGD GRTCY |
| 67 | K | Mouse Nidogen-1 spacer segment between EGF-3 and -4 [DNA, 18 bp] | GCTGCCGAGGACCAACGT |
| 68 | K | Mouse Nidogen-1 spacer segment between EGF-3 and -4 | AAEDQR |
| 69 | K | Human Nidogen-1 spacer segment between EGF-3 and -4 [DNA, 18 bp] | GCTGTCGTGGACCAGCGC |
| 70 | K | Human Nidogen-1 spacer segment between EGF-3 and -4 | AVVDQR |
| 71 | L | Mouse Nidogen-1 EGF-like 4 domain [132 bp] | CCCATCAACTACTGTGAAACTGGTCTCCACAACTG TGATATCCCCCAGCGAGCCCAGTGCATCTATATGG GTGGTTCCTCCTACACCTGCTCCTGTCTGCCTGGCT TCTCTGGGGATGGCAGAGCCTGCCGA |
| 72 | L | Mouse Nidogen-1 EGF-like 4 | PINYCETGLHNCDIPQRAQCIYMGGSSYTCSCLPGFS GDGRACR |
| 73 | L | Human Nidogen-1 EGF-like 4 domain [DNA, 132 bp] | CCCATCAACTACTGTGAAACTGGCCTTCATAACTG CGACATACCCCAGCGGGCCCAGTGTATCTACACA GGAGGCTCCTCCTACACCTGTTCCTGCTTGCCAGG CTTTTCTGGGGATGGCCAAGCCTGCCAA |
| 74 | L | Human Nidogen-1 EGF-like 4 domain | PINYCETGLHNCDIPQRAQCIYTGGSSYTCSCLPGFSG DGQACQ |
| 75 | M | Mouse Nidogen-1 EGF-like 5 domain [DNA, 141 bp] | GACGTGGATGAATGCCAGCACAGCCGATGTCACC CCGATGCCTTCTGCTACAACACACCAGGCTCTTTC ACATGTCAGTGCAAGCCTGGCTATCAGGGGGATG GCTTCCGATGCATGCCCGGAGAGGTGAGCAAAAC CCGG |
| 76 | M | Mouse Nidogen-1 EGF-like 5 [spacer] | DVDECQHSRCHPDAFCYNTPGSFTCQCKPGYQGDG FRCMPGEVSKTR |
| 77 | M | Human Nidogen-1 EGF-like 5 domain [DNA, 141 bp] | GATGTAGATGAATGCCAGCCAAGCCGATGTCACC CTGACGCCTTCTGCTACAACACTCCAGGCTCTTTC ACGTGCCAGTGCAAACCTGGTTATCAGGGAGACG GCTTCCGTTGCGTGCCCGGAGAGGTGGAGAAAAC CCGG |
| 78 | M | Human Nidogen-1 EGF-like 5 domain | DVDECQPSRCHPDAFCYNTPGSFTCQCKPGYQGDGF RCVPGEVEKTR |
| 79 | N | Mouse Nidogen-1 G3 TY (thyroglobulin-like) domain [DNA, 282 bp] | TGTCAACTGGAACGAGAGCACATCCTTGGAGCAG CCGGCGGGGCAGATGCACAGCGGCCCACCCTGCA GGGGATGTTTGTGCCTCAGTGTGATGAATATGGAC ACTATGTACCCACCCAGTGTCACCACAGCACTGGC TACTGCTGGTGTGTGGACCGAGATGGTCGGGAGCT GGAGGGTAGCCGTACCCCACCTGGGATGAGGCCC CCGTGTCTGAGTACAGTGGCTCCTCCTATTCACCA GGGACCAGTAGTACCTACAGCTGTCATCCCCCTGC CTCCA |

TABLE 3-continued

Domain Sequences

| SEQ ID NO | Domain Letter Code | Domain Name | Sequence |
|---|---|---|---|
| 80 | N | Mouse Nidogen "G3" TY (thyroglobulin-like) domain | CQLEREHILGAAGGADAQRPTLQGMFVPQCDEYGH<br>YVPTQCHHSTGYCWCVDRDGRELEGSRTPPGMRPP<br>CLSTVAPPIHQGPVVPTAVIPLPP |
| 81 | N | Human Nidogen-1 G3 TY (thyroglobulin-like) domain [DNA, 282 bp] | TGCCAGCACGAGCGAGAACACATTCTCGGGGCAG<br>CGGGGGCGACAGACCCACAGCGACCCATTCCTCC<br>GGGGCTGTTCGTTCCTGAGTGCGATGCGCACGGGC<br>ACTACGCGCCCACCCAGTGCCACGGCAGCACCGG<br>CTACTGCTGGTGCGTGGATCGCGACGGCCGCGAG<br>GTGGAGGGCACCAGGACCAGGCCCGGGATGACGC<br>CCCCGTGTCTGAGTACAGTGGCTCCCCCGATTCAC<br>CAAGGACCTGCGGTGCCTACCGCCGTGATCCCCTT<br>GCCTCCT |
| 82 | N | Human Nidogen-1 G3 TY (thyroglobulin-like) domain | CQHEREHILGAAGATDPQRPIPPGLFVPECDAHGHY<br>APTQCHGSTGYCWCVDRDGREVEGTRTRPGMTPPC<br>LSTVAPPIHQGPAVPTAVIPLPP |
| 83 | O | Mouse Nidogen-1 G3 β-Propeller domain [DNA, 744 bp] | GGGACACACTTACTCTTTGCTCAGACTGGAAAGAT<br>TGAACGCCTGCCCCTGGAAAGAAACACCATGAAG<br>AAGACAGAACGCAAGGCCTTTCTCCATATCCCTGC<br>AAAAGTCATCATTGGACTGGCCTTTGACTGCGTGG<br>ACAAGGTGGTTTACTGGACAGACATCAGCGAGCC<br>TTCCATTGGGAGAGCCAGCCTCCACGGTGGAGAG<br>CCAACCACCATCATTCGACAAGATCTTGGAAGCCC<br>TGAAGGCATTGCCCTTGACCATCTTGGTCGAACCA<br>TCTTCTGGACGGACTCTCAGTTGGATCGAATAGAA<br>GTTGCAAAGATGGATGGCACCCAGCGCCGAGTGC<br>TGTTTGACACGGGTTTGGTGAATCCCAGAGGCATT<br>GTGACAGACCCCGTAAGAGGGAACCTTTATTGGA<br>CAGATTGGAACAGAGATAATCCCAAAATTGAGAC<br>TTCTCACATGGATGGCACCAACCGGAGGATTCTCG<br>CACAGGACAACCTGGGCTTGCCCAATGGTCTGACC<br>TTTGATGCATTCTCATCTCAGCTTTGCTGGGTGGAT<br>GCAGGCACCCATAGGGCAGAATGCCTGAACCCAG<br>CTCAGCCTGGCAGACGCAAAGTTCTCGAAGGGCT<br>CCAGTATCCTTTCGCTGTGACTAGCTATGGGAAGA<br>ATTTGTACTACACAGACTGGAAGACGAATTCAGTG<br>ATTGCCATGGACCTTGCTATATCCAAAGAGATGGA<br>TACCTTCCACCCACAC |
| 84 | O | Mouse Nidogen "G3" β-Propeller [laminin-binding domain] | GTHLLFAQTGKIERLPLERNTMKKTERKAFLHIPAKV<br>IIGLAFDCVDKVVYWTDISEPSIGRASLHGGEPTTIIR<br>QDLGSPEGIALDHLGRTIFWTDSQLDRIEVAKMDGT<br>QRRVLFDTGLVNPRGIVTDPVRGNLYWTDWNRDNP<br>KIETSHMDGTNRRILAQDNLGLPNGLTFDAFSSQLC<br>WVDAGTHRAECLNPAQPGRRKVLEGLQYPFAVTSY<br>GKNLYYTDWKTNSVIAMDLAISKEMDTFHPH |
| 85 | O | Human Nidogen-1 G3 β-Propeller domain [DNA, 744 bp] | GGGACCCATTTACTCTTTGCCCAGACTGGGAAGAT<br>TGAGCGCCTGCCCCTGGAGGGAAATACCATGAGG<br>AAGACAGAAGCAAAGGCGTTCCTTCATGTCCCGG<br>CTAAAGTCATCATTGGACTGGCCTTTGACTGCGTG<br>GACAAGATGGTTTACTGGACGGACATCACTGAGC<br>CTTCCATTGGGAGAGCTAGTCTACATGGTGGAGAG<br>CCAACCACCATCATTAGACAAGATCTTGGAAGTCC<br>AGAAGGTATCGCTGTTGATCACCTTGGCCGCAACA<br>TCTTCTGGACAGACTCTAACCTGGATCGAATAGAA<br>GTGGCGAAGCTGGACGGCACGCAGCGCCGGGTGC<br>TCTTTGAGACTGACTTGGTGAATCCCAGAGGCATT<br>GTAACGGATTCCGTGAGAGGGAACCTTTACTGGA<br>CAGACTGGAACAGAGATAACCCCAAGATTGAAAC<br>TTCCTACATGGACGGCACGAACCGGAGGATCCTTG<br>TGCAGGATGACCTGGGCTTGCCCAATGGACTGACC<br>TTCGATGCGTTCTCATCTCAGCTCTGCTGGGTGGA<br>TGCAGGCACCAATCGGGCGGAATGCCTGAACCCC<br>AGTCAGCCCAGCAGACGCAAGGCTCTCGAAGGGC<br>TCCAGTATCCTTTTGCTGTGACGAGCTACGGGAAG<br>AATCTGTATTTCACAGACTGGAAGATGAATTCCGT<br>GGTTGCTCTCGATCTTGCAATTTCCAAGGAGACGG<br>ATGCTTTCCAACCCCAC |

TABLE 3-continued

Domain Sequences

| SEQ ID NO | Domain Letter Code | Domain Name | Sequence |
|---|---|---|---|
| 86 | O | Human Nidogen-1 G3 β-Propeller domain | GTHLLFAQTGKIERLPLEGNTMRKTEAKAFLHVPAK VIIGLAFDCVDKMVYWTDITEPSIGRASLHGGEPTTII RQDLGSPEGIAVDHLGRNIFWTDSNLDRIEVAKLDG TQRRVLFETDLVNPRGIVTDSVRGNLYWTDWNRDN PKIETSYMDGTNRRILVQDDLGLPNGLTFDAFSSQLC WVDAGTNRAECLNPSQPSRRKALEGLQYPFAVTSY GKNLYFTDWKMNSVVALDLAISKETDAFQPH |
| 87 | P | Mouse Nidogen-1 G3 EGF-like 6 domain [DNA, 171 bp] | AAGCAGACCCGGCTATATGGCATCACCATCGCCCT GTCCCAGTGTCCCCAAGGCCACAATTACTGCTCAG TGAATAATGGTGGATGTACCCACCTCTGCTTGCCC ACTCCAGGGAGCAGGACCTGCCGATGTCCTGACA ACACCCTGGGAGTTGACTGCATTGAACGGAAA |
| 88 | P | Mouse Nidogen "G3" EGF-like 6 [contacts laminin LE surface] | KQTRLYGITIALSQCPQGHNYCSVNNGGCTHLCLPTP GSRTCRCPDNTLGVDCIERK* |
| 89 | P | Human Nidogen-1 G3 EGF-like 6 domain [DNA, 162 bp] | AAGCAGACCCGGCTGTATGGCATCACCACGGCCC TGTCTCAGTGTCCGCAAGGCCATAACTACTGCTCA GTGAACAATGGCGGCTGCACCCACCTATGCTTGGC CACCCCAGGGAGCAGGACCTGCCGTTGCCCTGAC AACACCTTGGGAGTTGACTGTATC |
| 90 | P | Human Nidogen-1 G3 EGF-like 6 domain | KQTRLYGITTALSQCPQGHNYCSVNNGGCTHLCLAT PGSRTCRCPDNTLGVDCI |
| 91 | Q | Mouse Laminin β1 signal peptide [63 bp]: | ATGGGGCTGCTCCAGGTGTTCGCCTTTGGTGTCCT AGCCCTATGGGGCACCCGAGTGTGCGCT |
| 92 | Q | Mouse Laminin β1 signal peptide | MGLLQVFAFGVLALWGTRVCA |
| 93 | Q | Human Laminin β1 signal [63 bp] | ATGGGGCTTCTCCAGTTGCTAGCTTTCAGTTTCTTA GCCCTGTGCAGAGCCCGAGTGCGCGCT |
| 94 | Q | Human Laminin β1 signal peptide | MGLLQLLAFSFLALCRARVRA |
| 95 | R | Mouse Laminin β1 LN domain [744 bp] | CAGGAACCGGAGTTCAGCTATGGCTGCGCAGAAG GCAGCTGCTACCCTGCCACTGGCGACCTTCTCATC GGCCGAGCGCAAAAGCTCTCCGTGACTTCGACAT GTGGACTGCACAAACCAGAGCCCTACTGTATTGTT AGCCACCTGCAGGAGGACAAGAAATGCTTCATAT GTGACTCCCGAGACCCTTATCACGAGACCCTCAAC CCCGACAGCCATCTCATTGAGAACGTGGTCACCAC ATTTGCTCCAAACCGCCTTAAGATCTGGTGGCAAT CGGAAAATGGTGTGGAGAACGTGACCATCCAACT GGACCTGGAAGCAGAATTCCATTTCACTCATCTCA TCATGACCTTCAAGACATTCCGCCCAGCCGCCATG CTGATCGAGCGGTCTTCTGACTTTGGGAAGACTTG GGGCGTGTACAGATACTTCGCCTACGACTGTGAGA GCTCGTTCCCAGGCATTTCAACTGGACCCATGAAG AAAGTGGATGACATCATCTGTGACTCTCGATATTC TGACATTGAGCCCTCGACAGAAGGAGAGGTAATA TTTCGTGCTTTAGATCCTGCTTTCAAAATTGAAGA CCCTTATAGTCCAAGGATACAGAATCTATTAAAAA TCACCAACTTGAGAATCAAGTTTGTGAAACTGCAC ACCTTGGGGGATAACCTTTTGGACTCCAGAATGGA AATCCGAGAGAAGTACTATTACGCTGTTTATGATA TGGTGGTTCGAGGG |
| 96 | R | Mouse Laminin β1 LN | QEPEFSYGCAEGSCYPATGDLLIGRAQKLSVTSTCGL HKPEPYCIVSHLQEDKKCFICDSRDPYHETLNPDSHLI ENVVTTFAPNRLKIWWQSENGVENVTIQLDLEAEFH FTHLIMTFKTFRPAAMLIERSSDFGKTWGVYRYFAY DCESSFPGISTGPMKKVDDIICDSRYSDIEPSTEGEVIF RALDPAFKIEDPYSPRIQNLLKITNLRIKFVKLHTLGD NLLDSRMEIREKYYYAVYDMVVRG |
| 97 | R | Human Laminin β1 LN domain [DNA, 744 bp] | CAGGAACCCGAGTTCAGCTACGGCTGCGCAGAAG GCAGCTGCTATCCCGCCACGGGCGACCTTCTCATC GGCCGAGCACAGAAGCTTTCGGTGACCTCGACGT |

TABLE 3-continued

| SEQ ID NO | Domain Letter Code | Domain Name | Sequence |
|---|---|---|---|
| | | | GCGGGCTGCACAAGCCCGAACCCTACTGTATCGTC AGCCACTTGCAGGAGGACAAAAAATGCTTCATAT GCAATTCCCAAGATCCTTATCATGAGACCCTGAAT CCTGACAGCCATCTCATTGAAAATGTGGTCACTAC ATTTGCTCCAAACCGCCTTAAGATTTGGTGGCAAT CTGAAAATGGTGTGGAAAATGTAACTATCCAACT GGATTTGGAAGCAGAATTCCATTTTACTCATCTCA TAATGACTTTCAAGACATTCCGTCCAGCTGCTATG CTGATAGAACGATCGTCCGACTTTGGGAAAACCTG GGGTGTGTATAGATACTTCGCCTATGACTGTGAGG CCTCGTTTCCAGGCATTTCAACTGGCCCCATGAAA AAAGTCGATGACATAATTTGTGATTCTCGATATTC TGACATTGAACCCTCAACTGAAGGAGAGGTGATA TTTCGTGCTTTAGATCCTGCTTTCAAAATAGAAGA TCCTTATAGCCCAAGGATACAGAATTTATTAAAAA TTACCAACTTGAGAATCAAGTTTGTGAAACTGCAT ACTTTGGGAGATAACCTTCTGGATTCCAGGATGGA AATCAGAGAAAAGTATTATTATGCAGTTTATGATA TGGTGGTTCGAGGA |
| 98 | R | Human Laminin β1 LN | QEPEFSYGCAEGSCYPATGDLLIGRAQKLSVTSTCGL HKPEPYCIVSHLQEDKKCFICNSQDPYHETLNPDSHL IENVVTTFAPNRLKIWWQSENGVENVTIQLDLEAEF HFTHLIMTFKTFRPAAMLIERSSDFGKTWGVYRYFA YDCEASFPGISTGPMKKVDDIICDSRYSDIEPSTEGEV IFRALDPAFKIEDPYSPRIQNLLKITNLRIKFVKLHTLG DNLLDSRMEIREKYYYAVYDMVVRG |
| 99 | S | Mouse Laminin β1 LEa-1 domain [DNA, 192 bp] | AACTGCTTCTGCTATGGCCACGCCAGTGAATGCGC CCCTGTGGATGGAGTCAATGAAGAAGTGGAAGGA ATGGTTCACGGGCACTGCATGTGCAGACACAACA CCAAAGGCCTGAACTGTGAGCTGTGCATGGATTTC TACCACGATTTGCCGTGGAGACCTGCTGAAGGCCG GAACAGCAACGCCTGCAAA |
| 100 | S | Mouse Laminin β1 LEa-1 | NCFCYGHASECAPVDGVNEEVEGMVHGHCMCRHN TKGLNCELCMDFYHDLPWRPAEGRNSNACK |
| 101 | S | Human Laminin β1 LEa-1 [DNA, 192 bp] | AATTGCTTCTGCTATGGTCATGCCAGCGAATGTGC CCCTGTGGATGGATTCAATGAAGAAGTGGAAGGA ATGGTTCACGGACACTGCATGTGCAGGCATAACA CCAAGGGCTTAAACTGTGAACTCTGCATGGATTTC TACCATGATTTACCTTGGAGACCTGCTGAAGGCCG AAACAGCAACGCCTGTAAA |
| 102 | S | Human Laminin β1 LEa-1 | NCFCYGHASECAPVDGFNEEVEGMVHGHCMCRHN TKGLNCELCMDFYHDLPWRPAEGRNSNACK |
| 103 | T | Mouse Laminin β1 LEa-2 domain [DNA, 189 bp] | AAATGTAACTGCAATGAACATTCCAGCTCGTGTCA CTTTGACATGGCAGTCTTCCTGGCTACTGGCAACG TCAGCGGGGGAGTGTGTGATAACTGTCAGCACAA CACCATGGGGCGCAACTGTGAACAGTGCAAACCG TTCTACTTCCAGCACCCTGAGAGGGACATCCGGGA CCCCAATCTCTGTGAA |
| 104 | T | Mouse Laminin β1 LEa-2 | KCNCNEHSSSCHFDMAVFLATGNVSGGVCDNCQHN TMGRNCEQCKPFYFQHPERDIRDPNLCE |
| 105 | T | Human Laminin β1 LEa-2 [DNA, 189 bp] | AAATGTAACTGCAATGAACATTCCATCTCTTGTCA CTTTGACATGGCTGTTTACCTGGCCACGGGGAACG TCAGCGGAGGCGTGTGTGATGACTGTCAGCACAA CACCATGGGGCGCAACTGTGAGCAGTGCAAGCCG TTTTACTACCAGCACCCAGAGAGGGACATCCGAG ATCCTAATTTCTGTGAA |
| 106 | T | Human Laminin β1 LEa- | KCNCNEHSISCHFDMAVYLATGNVSGGVCDDCQHN TMGRNCEQCKPFYYQHPERDIRDPNFCE |
| 107 | U | Mouse Laminin β1 LEa-3 domain [DNA, 180 bp] | CCATGTACCTGTGACCCAGCTGGTTCTGAGAATGG CGGGATCTGTGATGGGTACACTGATTTTTCTGTGG GTCTCATTGCTGGTCAGTGTCGGTGCAAATTGCAC GTGGAGGGAGAGCGCTGTGATGTTTGTAAAGAAG GCTTCTACGACTTAAGTGCTGAAGACCCGTATGGT TGTAAA |

TABLE 3-continued

Domain Sequences

| SEQ ID NO | Domain Letter Code | Domain Name | Sequence |
|---|---|---|---|
| 108 | U | Mouse Laminin β1 LEa-3 | PCTCDPAGSENGGICDGYTDFSVGLIAGQCRCKLHV EGERCDVCKEGFYDLSAEDPYGCK |
| 109 | U | Human Laminin β1 LEa-3 [DNA, 180 bp] | CGATGTACGTGTGACCCAGCTGGCTCTCAAAATGA GGGAATTTGTGACAGCTATACTGATTTTTCTACTG GTCTCATTGCTGGCCAGTGTCGGTGTAAATTAAAT GTGGAAGGAGAACATTGTGATGTTTGCAAAGAAG GCTTCTATGATTTAAGCAGTGAAGATCCATTTGGT TGTAAA |
| 110 | U | Human Laminin β1 LEa-3 | RCTCDPAGSQNEGICDSYTDFSTGLIAGQCRCKLNVE GEHCDVCKEGFYDLSSEDPFGCK |
| 111 | V | Mouse Laminin β1 LEa-4 domain [DNA, 156 bp] | TCATGTGCTTGCAATCCTCTGGGAACAATTCCTGG TGGGAATCCTTGTGATTCTGAGACTGGCTACTGCT ACTGTAAGCGCCTGGTGACAGGACAGCGCTGTGA CCAGTGCCTGCCGCAGCACTGGGGTTTAAGCAATG ATTTGGATGGGTGTCGA |
| 112 | V | Mouse Laminin β1 LEa-4 | SCACNPLGTIPGGNPCDSETGYCYCKRLVTGQRCDQ CLPQHWGLSNDLDGCR |
| 113 | V | Human Laminin β1 LEa-4 [DNA, 156 bp] | TCTTGTGCTTGCAATCCTCTGGGAACAATTCCTGG AGGGAATCCTTGTGATTCCGAGACAGGTCACTGCT ACTGCAAGCGTCTGGTGACAGGACAGCATTGTGA CCAGTGCCTGCCAGAGCACTGGGGCTTAAGCAAT GATTTGGATGGATGTCGA |
| 114 | V | Human Laminin β1 LEa-4 | SCACNPLGTIPGGNPCDSETGHCYCKRLVTGQHCDQ CLPEHWGLSNDLDGCR |
| 115 | W | Mouse Laminin γ1 signal peptide [DNA, 99 bp] | ATGACGGGCGGCGGGCGGGCCGCGCTGGCCCTGC AGCCCCGGGGGCGGCTGTGGCCGCTGTTGGCTGTG CTGGCGGCTGTGGCGGGCTGTGTCCGGGCG |
| 116 | W | Mouse Laminin γ1 signal peptide | MTGGGRAALALQPRGRLWPLLAVLAAVAGCVRA |
| 117 | W | Human Laminin γ1 signal peptide [DNA, 99 bp] | ATGAGAGGGAGCCATCGGGCCGCGCCGGCCCTGC GGCCCCGGGGGCGGCTCTGGCCCGTGCTGGCCGT GCTGGCGGCGGCCGCCGCGGCGGGCTGTGCC |
| 118 | W | HUMAN Laminin γlsignal peptide: | MRGSHRAAPALRPRGRLWPVLAVLAAAAAAGCA |
| 119 | X | Mouse Laminin γ1 LN domain [DNA, 768 bp] (note: E/GAG (2) in human γ1 vs D/GAC (1) D or E in mouse γI, but E in crystal structure of mouse LN-LEa) | GCCATGGACTACAAGGACGACGATGACAAGGAGT GCGCGGATGAGGGCGGGCGGCCGCAGCGCTGCAT GCCGGAGTTTGTTAATGCCGCCTTCAATGTGACCG TGGTGGCTACCAACACGTGTGGGACTCCGCCCGA GGAGTACTGCGTGCAGACTGGGGTGACCGGAGTC ACTAAGTCCTGTCACCTGTGCGACGCCGGCCAGCA GCACCTGCAACACGGGGCAGCCTTCCTGACCGACT ACAACAACCAGGCCGACACCACCTGGTGGCAAAG CCAGACTATGCTGGCCGGGGTGCAGTACCCCAACT CCATCAACCTCACGCTGCACCTGGGAAAGGCTTTT GACATCACTTACGTGCGCCTCAAGTTCCACACCAG CCGTCCAGAGAGCTTCGCCATCTATAAGCGCACTC GGGAAGACGGGCCCTGGATTCCTTATCAGTACTAC AGTGGGTCCTGTGAGAACACGTACTCAAAGGCTA ACCGTGGCTTCATCAGGACCGGAGGGGACGAGCA GCAGGCCTTGTGTACTGATGAATTCAGTGACATTT CCCCCCTCACCGGTGGCAACGTGGCCTTTTCAACC CTGGAAGGACGGCCGAGTGCCTACAACTTTGACA ACAGCCCTGTGCTCCAGGAATGGGTAACTGCCACT GACATCAGAGTGACGCTCAATCGCCTGAACACCTT TGGAGATGAAGTGTTTAACGAGCCCAAAGTTCTC AAGTCTTACTATTACGCAATCTCAGACTTTGCTGT GGGCGGC |
| 120 | X | Mouse Laminin γ1 LN domain | AMDECADEGGRPQRCMPEFVNAAFNVTVVATNTC GTPPEEYCVQTGVTGVTKSCHLCDAGQQHLQHGAA FLTDYNNQADTTWWQSQTMLAGVQYPNSINLTLHL GKAFDITYVRLKFHTSRPESFAIYKRTREDGPWIPYQ |

TABLE 3-continued

| Domain Sequences | | | |
|---|---|---|---|
| SEQ ID NO | Domain Letter Code | Domain Name | Sequence |
| | | | YYSGSCENTYSKANRGFIRTGGDEQQALCTDEFSDIS PLTGGNVAFSTLEGRPSAYNFDNSPVLQEWVTATDI RVTLNRLNTFGDEVFNEPKVLKSYYYAISDFAVGG |
| 121 | X | Human Laminin γ1 LN domain [DNA, 753 bp] | CAGGCAGCCATGGACGAGTGCACGGACGAGGGCG GGCGGCCGCAACGCTGCATGCCCGAGTTCGTCAA CGCCGCTTTCAACGTGACTGTGGTGGCCACCAACA CGTGTGGGACTCCGCCCGAGGAATACTGTGTGCA GACCGGGGTGACCGGGGTCACCAAGTCCTGTCAC CTGTGCGACGCCGGGCAGCCCCACCTGCAGCACG GGGCAGCCTTCCTGACCGACTACAACAACCAGGC CGACACCACCTGGTGGCAAAGCCAGACCATGCTG GCCGGGGTGCAGTACCCCAGCTCCATCAACCTCAC GCTGCACCTGGGAAAAGCTTTTGACATCACCTATG TGCGTCTCAAGTTCCACACCAGCCGCCCGGAGAGC TTTGCCATTTACAAGCGCACATGGGAAGACGGGC CCTGGATTCCTTACCAGTACTACAGTGGTTCCTGC GAGAACACCTACTCCAAGGCAAACCGCGGCTTCA TCAGGACAGGAGGGGACGAGCAGCAGGCCTTGTG TACTGATGAATTCAGTGACATTTCTCCCCTCACTG GGGGCAACGTGGCCTTTTCTACCCTGGAAGGAAG GCCCAGCGCCTATAACTTTGACAATAGCCCTGTGC TGCAGGAATGGGTAACTGCCACTGACATCAGTGT AACTCTTAATCGCCTGAACACTTTTGGAGATGAAG TGTTTAACGATCCCAAAGTTCTCAAGTCCTATTAT TATGCCATCTCTGATTTTGCTGTAGGTGGC |
| 122 | X | Human Laminin γ1 LN domain | QAAMDECTDEGGRPQRCMPEFVNAAFNVTVVATNT CGTPPEEYCVQTGVTGVTKSCHLCDAGQPHLQHGA AFLTDYNNQADTTWWQSQTMLAGVQYPSSINLTLH LGKAFDITYVRLKFHTSRPESFAIYKRTWEDGPWIPY QYYSGSCENTYSKANRGFIRTGGDEQQALCTDEFSDI SPLTGGNVAFSTLEGRPSAYNFDNSPVLQEWVTATD ISVTLNRLNTFGDEVENDPKVLKSYYYAISDFAVGG |
| 123 | Y | Mouse Laminin γ1 LEa-1 domain [DNA, 68 bp] (note: TGC for cys (Durkin, et al., Biochemistry 27 (14), 5198-5204 (1988); but earlier publications suggested TCC for serine (see, e.g., Sasaki and Yamada , J. Biol. Chem. 262 (35), 17111-17117 (1987) | AGGTGTAAATGTAACGGACATGCCAGCGAGTGTG TAAAGAACGAGTTTGACAAACTCATGTGCAACTG CAAACATAACACATACGGAGTTGACTGTGAAAAG TGCCTGCCTTTCTTCAATGACCGGCCGTGGAGGAG GGCGACTGCTGAGAGCGCCAGCGAGTGCCTT |
| 124 | Y | Mouse Laminin γ1 LEa-1 | RCKCNGHASECVKNEFDKLMCNCKHNTYGVDCEK CLPFFNDRPWRRATAESASECL |
| 125 | Y | Human Laminin γ1 LEa-1 [DNA, 168 bp] | AGATGTAAATGTAATGGACACGCAAGCGAGTGTA TGAAGAACGAATTTGATAAGCTGGTGTGTAATTGC AAACATAACACATATGGAGTAGACTGTGAAAAGT GTCTTCCTTTCTTCAATGACCGGCCGTGGAGGAGG GCAACTGCGGAAAGTGCCAGTGAATGCCTG |
| 126 | Y | Human Laminin 1 LEa-1 | RCKCNGHASECMKNEFDKLVCNCKHNTYGVDCEK CLPFFNDRPWRRATAESASECL |
| 127 | Z | Mouse Laminin γ1 LEa-2 domain [DNA, 168 bp] | CCTTGTGACTGCAATGGCCGATCCCAAGAGTGCTA CTTTGATCCTGAACTATACCGTTCCACTGGACATG GTGGCCACTGTACCAACTGCCGGGATAACACAGA TGGTGCCAAGTGCGAGAGGTGCCGGGAGAATTTC TTCCGCCTGGGGAACACTGAAGCCTGCTCT |
| 128 | Z | Mouse Laminin γ1 LEa-2 | PCDCNGRSQECYFDPELYRSTGHGGHCTNCRDNTD GAKCERCRENFFRLGNTEACS |
| 129 | Z | Human Laminin γ1 LEa-2 [DNA, 168 bp] | CCCTGTGATTGCAATGGTCGATCCCAGGAATGCTA CTTCGACCCTGAACTCTATCGTTCCACTGGCCATG GGGGCCACTGTACCAACTGCCAGGATAACACAGA |

TABLE 3-continued

| Domain Sequences | | | |
|---|---|---|---|
| SEQ ID NO | Domain Letter Code | Domain Name | Sequence |
| | | | TGGCGCCCACTGTGAGAGGTGCCGAGAGAACTTC TTCCGCCTTGGCAACAATGAAGCCTGCTCT |
| 130 | Z | Human Laminin γ1 LEa-2 | PCDCNGRSQECYFDPELYRSTGHGGHCTNCQDNTD GAHCERCRENFFRLGNNEACS |
| 131 | a | Mouse Laminin γ1 LEa-3 domain [DNA, 141 bp] | CCGTGCCACTGCAGCCCTGTTGGTTCTCTCAGCAC ACAGTGTGACAGTTACGGCAGATGCAGCTGTAAG CCAGGAGTGATGGGTGACAAGTGTGACCGTTGTC AGCCTGGGTTCCATTCCCTCACTGAGGCAGGATGC AGG |
| 132 | a | Mouse Laminin γ1 LEa-3 | PCHCSPVGSLSTQCDSYGRCSCKPGVMGDKCDRCQP GFHSLTEAGCR |
| 133 | a | Human Laminin γ1 LEa-3 [DNA, 141 bp] | TCATGCCACTGTAGTCCTGTGGGCTCTCTAAGCAC ACAGTGTGATAGTTACGGCAGATGCAGCTGTAAG CCAGGAGTGATGGGGGACAAATGTGACCGTTGCC AGCCTGGATTCCATTCTCTCACTGAAGCAGGATGC AGG |
| 134 | a | Human Laminin γ1 LEa-3 | SCHCSPVGSLSTQCDSYGRCSCKPGVMGDKCDRCQP GFHSLTEAGCR |
| 135 | b | Mouse Laminin γ1 LEa-4 [DNA, 150 bp] | CCATGCTCCTGCGATCTTCGGGGCAGCACAGACGA GTGTAATGTTGAAACAGGAAGATGCGTTTGCAAA GACAATGTTGAAGGCTTCAACTGTGAGAGATGCA AACCTGGATTTTTTAATCTGGAGTCATCTAATCCT AAGGGCTGCACA |
| 136 | b | Mouse Laminin γ1 LEa-4 | PCSCDLRGSTDECNVETGRCVCKDNVEGFNCERCKP GFFNLESSNPKGCT |
| 137 | b | Human Laminin γ1 LEa-4 [DNA, 150 bp] | CCATGCTCTTGTGATCCCTCTGGCAGCATAGATGA ATGTAATGTTGAAACAGGAAGATGTGTTTGCAAA GACAATGTCGAAGGCTTCAATTGTGAAAGATGCA AACCTGGATTTTTTAATCTGGAATCATCTAATCCT CGGGGTTGCACA |
| 138 | b | Human Laminin γ1 LEa-4 | PCSCDPSGSIDECNVETGRCVCKDNVEGFNCERCKP GFFNLESSNPRGCT |
| 139 | C | Mouse agrin LG1 domain [DNA, 531 bp] | CCCTCTGTGCCAGCTTTTAAGGGCCACTCCTTCTTG GCCTTCCCCACCCTCCGAGCCTACCACACGCTGCG TCTGGCACTAGAATTCCGGGCGCTGGAGACAGAG GGACTGCTGCTCTACAATGGCAATGCACGTGGCA AAGATTTCCTGGCTCTGGCTCTGTTGGATGGTCAT GTACAGTTCAGGTTCGACACGGGCTCAGGGCCGG CGGTGCTAACAAGCTTAGTGCCAGTGGAACCGGG ACGGTGGCACCGCCTCGAGTTGTCACGGCATTGGC GGCAGGGCACACTTTCTGTGGATGGCGAGGCTCCT GTTGTAGGTGAAAGTCCGAGTGGCACTGATGGCCT CAACTTGGACACGAAGCTCTATGTGGGTGGTCTCC CAGAAGAACAAGTTGCCACGGTGCTTGATCGGAC CTCTGTGGGCATCGGCCTGAAAGGATGCATTCGTA TGTTGGACATCAACAACCAGCAGCTGGAGCTGAG CGATTGGCAGAGGGCTGTGGTTCAAAGCTCTGGTG TGGGGGAATGC |
| 140 | C | Mouse agrin LG1 domain | PSVPAFKGHSFLAFPTLRAYHTLRLALEFRALETEGL LLYNGNARGKDFLALALLDGHVQFRFDTGSGPAVL TSLVPVEPGRWHRLELSRHWRQGTLSVDGEAPVVG ESPSGTDGLNLDTKLYVGGLPEEQVATVLDRTSVGI GLKGCIRMLDINNQQLELSDWQRAVVQSSGVGEC |
| 141 | c | Human Agrin LG1 [DNA, 531 bp] | GCCCCTGTGCCGGCCTTCGAGGGCCGCTCCTTCCT GGCCTTCCCCACTCTCCGCGCCTACCACACGCTGC GCCTGGCACTGGAATTCCGGGCGCTGGAGCCTCA GGGGCTGCTGCTGTACAATGGCAACGCCCGGGGC AAGGACTTCCTGGCATTGGCGCTGCTAGATGGCCG CGTGCAGCTCAGGTTTGACACAGGTTCGGGGCCG GCGGTGCTGACCAGTGCCGTGCCGGTAGAGCCGG GCCAGTGGCACCGCCTGGAGCTGTCCCGGCACTG GCGCCGGGGCACCCTCTCGGTGGATGGTGAGACC |

TABLE 3-continued

Domain Sequences

| SEQ ID NO | Domain Letter Code | Domain Name | Sequence |
|---|---|---|---|
| | | | CCTGTTCTGGGCGAGAGTCCCAGTGGCACCGACG GCCTCAACCTGGACACAGACCTCTTTGTGGGCGGC GTACCCGAGGACCAGGCTGCCGTGGCGCTGGAGC GGACCTTCGTGGGCGCCGGCCTGAGGGGGTGCAT CCGTTTGCTGGACGTCAACAACCAGCGCCTGGAGC TTGGCATTGGGCCGGGGGCTGCCACCCGAGGCTCT GGCGTGGGCGAGTGC |
| 142 | C | Human Agrin LG1 | APVPAFEGRSFLAFPTLRAYHTLRLALEFRALEPQGL LLYNGNARGKDFLALALLDGRVQLRFDTGSGPAVL TSAVPVEPGQWHRLELSRHWRRGTLSVDGETPVLG ESPSGTDGLNLDTDLFVGGVPEDQAAVALERTFVGA GLRGCIRLLDVNNQRLELGIGPGAATRGSGVGEC |
| 143 | d | Mouse agrin EGF-like domain 2 [DNA, 114 bp] | GGAGACCATCCCTGCTCACCTAACCCCTGCCATGG CGGGGCCCTCTGCCAGGCCCTGGAGGCTGGCGTGT TCCTCTGTCAGTGCCCACCTGGCCGCTTTGGCCCA ACTTGTGCA |
| 144 | d | Mouse agrin EGF-like domain 2 | GDHPCSPNPCHGGALCQALEAGVFLCQCPPGRFGPT CA |
| 145 | d | Human agrin EGF-like domain 2 [DNA, 114 bp] | GGGGACCACCCCTGCCTGCCCAACCCCTGCCATGG CGGGGCCCCATGCCAGAACCTGGAGGCTGGAAGG TTCCATTGCCAGTGCCCGCCCGGCCGCGTCGGACC AACCTGTGCC |
| 146 | d | Human Agrin EGF-like 2 | GDHPCLPNPCHGGAPCQNLEAGRFHCQCPPGRVGPT CA |
| 147 | e | Mouse agrin EGF-like domain 3 [DNA, 117 bp] | GATGAAAAGAACCCCTGCCAACCGAACCCCTGCC ACGGGTCAGCCCCCTGCCATGTGCTTTCCAGGGGT GGGGCCAAGTGTGCGTGCCCCCTGGGACGCAGTG GTTCCTTCTGTGAG |
| 148 | e | Mouse agrin EGF-like domain 3 | DEKNPCQPNPCHGSAPCHVLSRGGAKCACPLGRSGS FCE |
| 149 | e | Human Agrin EGF-like 3 [DNA, 117 bp] | GATGAGAAGAGCCCCTGCCAGCCCAACCCCTGCC ATGGGGCGGCGCCCTGCCGTGTGCTGCCCGAGGG TGGTGCTCAGTGCGAGTGCCCCCTGGGGCGTGAG GGCACCTTCTGCCAG |
| 150 | e | Human Agrin EGF-like 3 | DEKSPCQPNPCHGAAPCRVLPEGGAQCECPLGREGT FCQ |
| 151 | f | Mouse agrin LG Spacer-1 [DNA, 27 bp] | ACAGTCCTGGAGAATGCTGGCTCCCGG |
| 152 | f | Mouse agrin spacer domain-1 | TVLENAGSR |
| 153 | f | Human spacer [DNA, 27 bp] | ACAGCCTCGGGGCAGGACGGCTCTGGG |
| 154 | f | Human spacer | TASGQDGSG |
| 155 | g | Mouse agrin LG2 domain [DNA, 537 bp] | CCCTTCCTGGCTGACTTTAATGGCTTCTCCTACCTG GAACTGAAAGGCTTGCACACCTTCGAGAGAGACC TAGGGGAGAAGATGGCGCTGGAGATGGTGTTCTT GGCTCGTGGGCCCAGTGGCTTACTCCTCTACAATG GGCAGAAGACGGATGGCAAGGGGGACTTTGTATC CCTGGCCCTGCATAACCGGCACCTAGAGTTCCGCT ATGACCTTGGCAAGGGGGCTGCAATCATCAGGAG CAAAGAGCCCATAGCCCTGGGCACCTGGGTTAGG GTATTCCTGGAACGAAATGGCCGCAAGGGTGCCC TTCAAGTGGGTGATGGGCCCCGTGTGCTAGGGGA ATCTCCGGTCCCGCACACCATGCTCAACCTCAAGG AGCCCCTCTATGTGGGGGGAGCTCCTGACTTCAGC AAGCTGGCTCGGGGCGCTGCAGTGGCCTCCGGCTT TGATGGTGCCATCCAGCTGGTGTCTCTAAGAGGCC ATCAGCTGCTGACTCAGGAGCATGTGTTGCGGGCA GTAGATGTAGCGCCTTTT |

TABLE 3-continued

| Domain Sequences | | | |
|---|---|---|---|
| SEQ ID NO | Domain Letter Code | Domain Name | Sequence |
| 156 | g | Mouse agrin LG2 domain | PFLADENGFSYLELKGLHTFERDLGEKMALEMVFLA RGPSGLLLYNGQKTDGKGDFVSLALHNRHLEFRYD LGKGAAIIRSKEPIALGTWVRVFLERNGRKGALQVG DGPRVLGESPVPHTMLNLKEPLYVGGAPDFSKLARG AAVASGFDGAIQLVSLRGHQLLTQEHVLRAVDVAPF |
| 157 | g | Human Agrin G2 [DNA, 537 bp] | CCCTTCCTGGCTGACTTCAACGGCTTCTCCCACCT GGAGCTGAGAGGCCTGCACACCTTTGCACGGGAC CTGGGGGAGAAGATGGCGCTGGAGGTCGTGTTCC TGGCACGAGGCCCCAGCGGCCTCCTGCTCTACAAC GGGCAGAAGACGGACGGCAAGGGGGACTTCGTGT CGCTGGCACTGCGGGACCGCCGCCTGGAGTTCCGC TACGACCTGGGCAAGGGGGCAGCGGTCATCAGGA GCAGGGAGCCAGTCACCCTGGGAGCCTGGACCAG GGTCTCACTGGAGCGAAACGGCCGCAAGGGTGCC CTGCGTGTGGGCGACGGCCCCCGTGTGTTGGGGG AGTCCCCGGTTCCGCACACCGTCCTCAACCTGAAG GAGCCGCTCTACGTAGGGGGCGCTCCCGACTTCAG CAAGCTGGCCCGTGCTGCTGCCGTGTCCTCTGGCT TCGACGGTGCCATCCAGCTGGTCTCCCTCGGAGGC CGCCAGCTGCTGACCCCGGAGCACGTGCTGCGGC AGGTGGACGTCACGTCCTTT |
| 158 | g | Human Agrin LG2 | PFLADENGFSHLELRGLHTFARDLGEKMALEVVFLA RGPSGLLLYNGQKTDGKGDFVSLALRDRRLEFRYDL GKGAAVIRSREPVTLGAWTRVSLERNGRKGALRVG DGPRVLGESPVPHTVLNLKEPLYVGGAPDFSKLARA AAVSSGFDGAIQLVSLGGRQLLTPEHVLRQVDVTSF |
| 159 | h | Mouse agrin EGF-like domain 4 [DNA, 120 bp] | GCAGGCCACCCTTGTACCCAGGCCGTGGACAACC CCTGCCTTAATGGGGGCTCCTGTATCCCGAGGGAA GCCACTTATGAGTGCCTGTGTCCTGGGGGCTTCTC TGGGCTGCACTGCGAG |
| 160 | h | Mouse agrin EGF-like domain 4 | AGHPCTQAVDNPCLNGGSCIPREATYECLCPGGFSG LHCE |
| 161 | h | Human Agrin Egf-like 4 [DNA, 120 bp] | GCAGGTCACCCCTGCACCCGGGCCTCAGGCCACCC CTGCCTCAATGGGGCCTCCTGCGTCCCGAGGGAGG CTGCCTATGTGTGCCTGTGTCCCGGGGGATTCTCA GGACCGCACTGCGAG |
| 162 | h | Human Agrin EGF-like 4 | AGHPCTRASGHPCLNGASCVPREAAYVCLCPGGFSG PHCE |
| 163 | i | Mouse agrin LG Spacer-2 [DNA, 30 bp] | AAGGGGATAGTTGAGAAGTCAGTGGGGGAC |
| 164 | i | Mouse agrin LG Spacer-2 | KGIVEKSVGD |
| 165 | i | Human Spacer [30 bp] | AAGGGGCTGGTGGAGAAGTCAGCGGGGGAC |
| 166 | i | Human Spacer | KGLVEKSAGD |
| 167 | | Mouse agrin LG3 domain [DNA, 537 bp] | CTAGAAACACTGGCCTTTGATGGGCGGACCTACAT CGAGTACCTCAATGCTGTGACTGAGAGTGAGAAA GCGCTGCAGAGCAACCACTTTGAGCTGAGCTTACG CACTGAGGCCACGCAGGGGCTGGTGCTGTGGATT GGAAAGGTTGGAGAACGTGCAGACTACATGGCTC TGGCCATTGTGGATGGGCACCTACAACTGAGCTAT GACCTAGGCTCCCAGCCAGTTGTGCTGCGCTCCAC TGTGAAGGTCAACACCAACCGCTGGCTTCGAGTCA GGGCTCACAGGGAGCACAGGGAAGGTTCCCTTCA GGTGGGCAATGAAGCCCCTGTGACTGGCTCTTCCC CGCTGGGTGCCACACAATTGGACACAGATGGAGC CCTGTGGCTTGGAGGCCTACAGAAGCTTCCTGTGG GGCAGGCTCTCCCCAAGGCCTATGGCACGGGTTTT GTGGGCTGTCTGCGGGACGTGGTAGTGGGCCATC GCCAGCTGCATCTGCTGGAGGACGCTGTCACCAA ACCAGAGCTAAGACCCTGC |
| 168 | j | Mouse agrin LG3 domain | LETLAFDGRTYIEYLNAVTESEKALQSNHFELSLRTE ATQGLVLWIGKVGERADYMALAIVDGHLQLSYDLG |

TABLE 3-continued

| Domain Sequences | | | |
|---|---|---|---|
| SEQ ID NO | Domain Letter Code | Domain Name | Sequence |
| | | | SQPVVLRSTVKVNTNRWLRVRAHREHREGSLQVGN EAPVTGSSPLGATQLDTDGALWLGGLQKLPVGQAL PKAYGTGFVGCLRDVVVGHRQLHLLEDAVTKPELR PC |
| 169 | j | Human Agrin LG3 [DNA, 537 bp] | GTGGATACCTTGGCCTTTGACGGGCGGACCTTTGT CGAGTACCTCAACGCTGTGACCGAGAGCGAGAAG GCACTGCAGAGCAACCACTTTGAACTGAGCCTGC GCACTGAGGCCACGCAGGGGCTGGTGCTCTGGAG TGGCAAGGCCACGGAGCGGGCAGACTATGTGGCA CTGGCCATTGTGGACGGGCACCTGCAACTGAGCTA CAACCTGGGCTCCCAGCCCGTGGTGCTGCGTTCCA CCGTGCCCGTCAACACCAACCGCTGGTTGCGGGTC GTGGCACATAGGGAGCAGAGGGAAGGTTCCCTGC AGGTGGGCAATGAGGCCCCTGTGACCGGCTCCTCC CCGCTGGGCGCCACGCAGCTGGACACTGATGGAG CCCTGTGGCTTGGGGGCCTGCCGGAGCTGCCCGTG GGCCCAGCACTGCCCAAGGCCTACGGCACAGGCT TTGTGGGCTGCTTGCGGGACGTGGTGGTGGGCCGG CACCCGCTGCACCTGCTGGAGGACGCCGTCACCA AGCCAGAGCTGCGGCCCTGC |
| 170 | j | Human Agrin LG3 | VDTLAFDGRTFVEYLNAVTESEKALQSNHFELSLRT EATQGLVLWSGKATERADYVALAIVDGHLQLSYNL GSQPVVLRSTVPVNTNRWLRVVAHREQREGSLQVG NEAPVTGSSPLGATQLDTDGALWLGGLPELPVGPAL PKAYGTGFVGCLRDVVVGRHPLHLLEDAVTKPELRP C |

Example 9

Simplification and Modification of LmαLNNdΔG2' for Functional Enhancement

The current evaluated AAV-DJ constructs allow for inclusion of 3.1 kB DNA representing the open reading frame. Other constructs, existing or planned, can allow for larger inclusions. Basing allowed protein size on the AAV-DJ limit, it is noted that the nidogen G3 domain of LmαLNNdΔG2' can be reduced in size to that of the propeller domain (~270 residues, 810 bp), retaining laminin-binding as described in J. Takagi et al., 2003, Nature 424: 963-974. The reduction of 393 bp allows for domain rearrangement so that the G2 type IV collagen and perlecan-binding domain can be included. New arrangements allow for laminin polymerization to be coupled to collagen/perlecan binding. Examples are (a) αLNNdG2Propeller (3.08 kB) and (b) αLNNdG2Propeller-2 (3.02 kB). The domain composition for each of these is shown in Table 4 below using the letter domain coding provided in Table 2. The nucleotide and protein sequences for the domains used in the domain composition are provided in Table 3 and in the Sequence Listing. Another arrangement allows for laminin polymerization to be coupled to dystroglycan binding, an example of which is αLNNdPropellerAgrinLG (3.6 kB). The domain composition for αLNNdPropellerAgrinLG is shown in Table 4 below using the letter domain coding provided in Table 2. The nucleotide and protein sequences for the domains used in the domain composition are provided in Table 3 and in the Sequence Listing.

TABLE 4

| Laminin Linker Proteins With Domain Composition By Letter Code[7] | | | | |
|---|---|---|---|---|
| Chimeric Protein | Domain Sequence Using Table 2 Letter Codes | Purpose | DNA size kB | Comments |
| αLNNdΔG2' | ABCDEFGLMNOP (or A'BCDEFGLMNOP) | AAV expressed linker protein (Lmα1 and nidogen-1 chimera) to ameliorate LAMA2 MD by enabling polymerization | 3.02 | binds to laminins with defective or absent α2 LN domain near short arm junction providing missing polymerization arm |
| αLNNdG2Propeller | ABCDEH(J, K or M)O | AAV expressed linker protein to ameliorate LAMA2 MD by enabling polymerization and direct collagen-IV/perlecan binding | 3.08 | alternative form that reduces size of nidogen G3 allowing insertion of G2 domain |
| αLNNdG2Propeller-2 | ABCDHIJO | AAV expressed linker protein to ameliorate LAMA2 MD by enabling | 3.02 | alternative form that reduces size of nidogen G3 allowing insertion of |

TABLE 4-continued

| Laminin Linker Proteins With Domain Composition By Letter Code[7] | | | | |
|---|---|---|---|---|
| Chimeric Protein | Domain Sequence Using Table 2 Letter Codes | Purpose | DNA size kB | Comments |
| | | polymerization and direct collagen-IV/perlecan binding | | G2 domain |
| αLNNdPropellerAgrinLG | ABCDEOPcdefg | linker protein to ameliorate LAMA2 MD by enabling polymerization and dystroglycan binding | 3.60 | alternative form for polymerization and DG binding (used with CKe8 promoter) |
| βLNNdΔG2' | QRSTUVLMNOP | AAV expressed linker protein to ameliorate Pierson syndrome by enabling polymerization | 2.99 | binds to laminins with defective or absent β2 LN domain near short arm junction providing missing polymerization arm |
| βLNNdG2Propeller | QRSTUH(J, K or M)O | AAV expressed linker protein to ameliorate Pierson syndrome by enabling polymerization and direct collagen-IV/perlecan binding | 3.08 | " |
| γLNNdΔG2' | WXYZabLMNOP | AAV expressed linker protein to ameliorate γ subunit LN deficiencies | 3.01 | binds to laminins with defective or absent γl or γ3 LN domain near short arm junction providing missing polymerization arm |
| γLNNdG2Propeller | WXYZaH(J, K or M)O | AAV expressed linker protein to ameliorate γ subunit LN deficiencies by enabling polymerization with direct collagen-IV/perlecan binding | 3.08 | |

[7]DNA open reading frame insert consists of the DNA domain segments ligated in the designated sequence

Example 10

Repair of Other Laminins with Polymerization Defects

Pierson syndrome is a congenital nephrotic syndrome with ocular abnormalities, leading to early end-stage renal disease, blindness and death. The causes are null, in-frame deleting or missense mutations in the LAMB2 gene that codes for the laminin β2 subunit. These mutations prevent subunit expression or alter the subunit properties. Several of the missense mutations are clustered in the β2 LN-domain (see Maatejas et al., 2010, Hum Mutat. 38: 992-1002 and K. K. McKee, M. Aleksandrova and P. D. Yurchenco, 2018, Matrix Biology 67: 32-46.). The LN domain mediates polymerization of the laminin. The possible effects of these mutations are failure-to-fold the domain that can be low/non-secretors and failure to polymerize mutations. Two highly conserved mutations in Pierson syndrome (S80R and H147R) were evaluated after placing them into the β1 subunit (S68R and H135R). Both mutations greatly reduced polymerization, and it was found that βLNNd (β1 LN-LEa domains swapped for α1 LN-LEa in fusion with nidogen G3) was able to rescue recombinant laminin unable to polymerize because the laminin lacked the βLN domain (described in K. K. McKee, M. Aleksandrova and P. D. Yurchenco, 2018, Matrix Biology 67: 32-46.) Since βLNNd can repair the Pierson defects in vitro, it follows that the shorter βLNNdΔG2 can be used to treat the disease. Similarly, other diseases due to laminin LN mutations affecting polymerization are expected to be treatable by expression of related laminin linker proteins in which their corresponding LN-LEa segments have replaced the α1LN-LEa segment in the fusion protein. These proteins (βLNNdΔG2', βLNNdG2Propeller, LNNdΔG2' and γLNNdG2Propeller) are described by domain composition in Tables 2 and 4 with sequences for the domains used in the domain composition provided in Table 3 and in the Sequence Listing.

Example 11

Direct Addition of Dystroglycan-Binding Activity to αLNNdΔG2

Employment of the nidogen propeller domain instead of the full G3 domain complex creates room (in the context of allowed AAV insert size) for addition of a dystroglycan-binding domain. The protein is designated αLNNdΔG2PropellerAgrinLG. The domain composition is shown in Tables 2 and 4 with sequences for the domains used in the domain composition provided in Table 3 and in the Sequence Listing. The size increase here prevents use in the standard AAV-DJ virus and requires a virus that allows a larger insert such as one containing the smaller CK8e promoter.

Example 12

Delivery of Protein by Parenteral Injection

The LmαLNNdΔG2' protein and any of its alternative forms can be injected parenterally (intra-peritoneal, intra-vascular, intra-muscular routes) to deliver the protein to its intended tissue targets as an alternative to virally-delivered somatic gene therapy.

Codon Optimization of Constructs

To optimize expression of the test constructs described herein not just as a means of reducing viral titers during the manufacturing process, but also to address safety concerns associated with large concentrations of the virus, the αLNNdΔG2' transgene will be evaluated using a codon optimization process using freely available software, www.idtdna.com/CodonOpt. In addition, consensus Kozak sequences will be introduced into constructs as needed. Thus, any of the constructs or elements described herein may be codon optimized in this manner. Each of the modified constructs will be tested in parallel with the parental constructs in mice. Briefly, the constructs will be systemically administered through the temporal vein into mouse pups. The animals will then be euthanized either two or three weeks later and levels of protein from each of the constructs determined by Q-PCR and western blotting. Constructs delivering the most rapid and high levels of expression will be considered for eventual use in non-human primate studies and eventually in clinical trials for human patients.

REFERENCES

1. Donnelly, M. L. et al. (2001). The 'cleavage' activities of foot-and-mouth disease virus 2A site directed mutants and naturally occurring '2A-like' sequences. *J. Gen. Virol.* 82, 1027-1041.
2. Foust, K. D., Nurre, E., Montgomery, C. L., Hernandez, A., Chan, C. M. and Kaspar, B. K. (2009). Intravascular AAV9 preferentially targets neonatal neurons and adult astrocytes. *Nat. Biotech.* 27, 59-65.
3. Grieger J C, Samulski R J (2005) Adeno-associated virus as a gene therapy vector: vector development, production and clinical applications. *Adv Biochem Eng Biotechnol.* 99, 119-145.
4. Grieger J C, Samulski R J (2012) Adeno-associated virus vectorology, manufacturing, and clinical applications. Methods Enzymol. 507, 229-254.
5. Kariya S, Re D B, Jacquier A, Nelson K, Przedborski S, Monani U R (2012) Mutant superoxide dismutase 1 (SOD1), a cause of amyotrophic lateral sclerosis, disrupts the recruitment of SMN, the spinal muscular atrophy protein to nuclear Cajal bodies. *Hum Mot Genet.* 21, 3421-3434.
6. Foust K D, Wang X, McGovern V L, Braun L, Bevan A K, Haidet A M, Le T T, Morales P R, Rich M M, Burghes A H, Kaspar B K (2010) Rescue of the spinal muscular atrophy phenotype in a mouse model by early postnatal delivery of SMN. *Nat. Biotech.* 28, 271-274.
7. Fleming J O, Ting J Y, Stohlman S A, Weiner L P (1983) Improvements in obtaining and characterizing mouse cerebrospinal fluid. Application to mouse hepatitis virus-induced encephalomyelitis. *J Neuroimmunol.* 4, 129-140.
8. Gao, G. P., and Sena-Esteves, M. (2012). Introducing Genes into Mammalian Cells: Viral Vectors. In Molecular Cloning, Vol 2: A Laboratory Manual (M. R. Green and J. Sambrook eds.) pp. 1209-1313. Cold Spring Harbor Laboratory Press, New York.
9. Rapti K, Louis-Jeune V, Kohlbrenner E, Ishikawa K, Ladage D, Zolotukhin S, Hajjar R J, Weber (2012) Neutralizing antibodies against AAV serotypes 1, 2, 6, and 9 in sea of commonly used animal models. Mol. Ther. 20, 73-83.
10. Goulder P J, Addo M M, Altfeld M A, Rosenberg E S, Tang Y, Govender U, Mngqundaniso N, Annamalai K, Vogel T U, Hammond M, Bunce M, Coovadia H M, Walker B D (2001) Rapid definition of five novel HLA-A*3002-restricted human immunodeficiency virus-specific cytotoxic T-lymphocyte epitopes by elispot and intracellular cytokine staining assays. J. Virol. 75, 1339-1347.
11. Aumailley, M., L. Bruckner-Tuderman, W. G. Carter, R. Deutzmann, D. Edgar, P. Ekblom, J. Engel, E. Engvall, E. Hohenester, J. C. Jones, H. K. Kleinman, M. P. Marinkovich, G. R. Martin, U. Mayer, G. Meneguzzi, J. H. Miner, K. Miyazaki, M.
12. Patarroyo, M. Paulsson, V. Quaranta, J. R. Sanes, T. Sasaki, K. Sekiguchi, L. M. Sorokin, J. F. Talts, K. Tryggvason, J. Uitto, I. Virtanen, K. von der Mark, U. M. Wewer, Y. Yamada, and P. D. Yurchenco, A simplified laminin nomenclature. *Matrix Biol,* 2005. 24(5): p. 326-32.
13. Jimenez-Mallebrera, C., S. C. Brown, C. A. Sewry, and F. Muntoni, Congenital musculardystrophy: molecular and cellular aspects. *Cell Mol Life Sci,* 2005. 62(7-8): p. 809-23.
14. Sframeli, M., A. Sarkozy, M. Bertoli, G. Astrea, J. Hudson, M. Scoto, R. Mein, M. Yau, R. Phadke, L. Feng, C. Sewry, A. N. S. Fen, C. Longman, G. McCullagh, V. Straub, S. Robb, A. Manzur, K. Bushby, and F. Muntoni, Congenital muscular dystrophies in the UK population: Clinical and molecular spectrum of a large cohort diagnosed over a 12-year period. *Neuromuscul Disord,* 2017. 27(9): p. 793-803.
15. Allamand, V., Y. Sunada, M. A. Salih, V. Straub, C. O. Ozo, M. H. Al-Turaiki, M. Akbar, T. Kolo, H. Colognato, X. Zhang, L. M. Sorokin, P. D. Yurchenco, K. Tryggvason, and K. P. Campbell, Mild congenital muscular dystrophy in two patients with an internally deleted laminin alpha2-chain. *Hum Mot Genet,* 1997. 6(5): p. 747-52.
16. Gavassini, B. F., N. Carboni, J. E. Nielsen, E. R. Danielsen, C. Thomsen, K. Svenstrup, L. Bello, M. A. Maioli, G. Marrosu, A. F. Ticca, M. Mura, M. G. Marrosu, G. Soraru, C. Angelini, J. Vissing, and E. Pegoraro, Clinical and molecular characterization of limb girdle muscular dystrophy due to LAMA2 mutations. *Muscle Nerve,* 2011. 44(5): p. 703-9.
17. Bonnemann, C. G., C. H. Wang, S. Quijano-Roy, N. Deconinck, E. Bertini, A. Ferreiro, F. Muntoni, C. Sewry, C. Beroud, K. D. Mathews, S. A. Moore, J. Bellini, A. Rutkowski, and K. N. North, Diagnostic approach to the congenital muscular dystrophies. *Neuromuscul Disord,* 2014.24(4): p. 289-311.
18. Chan, S. H., A. R. Foley, R. Phadke, A. A. Mathew, M. Pitt, C. Sewry, and F. Muntoni, Limb girdle muscular dystrophy due to LAMA2 mutations: diagnostic difficulties due to associated peripheral neuropathy. *Neuromuscul Disord,* 2014. 24(8): p. 677-83.
19. McKee, K. K., D. Harrison, S. Capizzi, and P. D. Yurchenco, Role of laminin terminal globular domains in basement membrane assembly. *J Biol Chem,* 2007. 282 (29): p. 21437-47.
20. McKee, K. K., D. H. Yang, R. Patel, Z. L. Chen, S. Strickland, J. Takagi, K. Sekiguchi, and P. D. Yurchenco, Schwann Cell Myelination Requires Integration of Laminin Activities. *J Cell Sci,* 2012. 125(19): p. 4609-4619. PMC3500866
21. McKee, K. K., S. Capizzi, and P. D. Yurchenco, Scaffold-forming and adhesive contributions of synthetic laminin-binding proteins to basement membrane assembly. *J Biol Chem,* 2009. 284(13): p. 8984-8994. PMC2659255
22. Smirnov, S. P., P. Barzaghi, K. K. McKee, M. A. Ruegg, and P. D. Yurchenco, Conjugation of LG domains of agrins and perlecan to polymerizing laminin-2 promotes acetylcholine receptor clustering. *J Biol Chem,* 2005. 280(50): p. 41449-57.

23. Chang, C., H. L. Goel, H. Gao, B. Pursell, L. D. Shultz, D. L. Greiner, S. Ingerpuu, M. Patarroyo, S. Cao, E. Lim, J. Mao, K. K. McKee, P. D. Yurchenco, and A. M. Mercurio, Alaminin 511 matrix is regulated by TAZ and functions as the ligand for the alpha6Bbeta1 integrin to sustain breast cancer stem cells. *Genes Dev,* 2015. 29(1): p. 1-6. PMC4281560
24. Colombelli, C., M. Palmisano, Y. Eshed-Eisenbach, D. Zambroni, E. Pavoni, C. Ferri, S. Saccucci, S. Nicole, R. Soininen, K. K. McKee, P. D. Yurchenco, E. Peles, L. Wrabetz, and M. L. Feltri, Perlecan is recruited by dystroglycan to nodes of Ranvier and binds the clustering molecule gliomedin. *J Cell Biol,* 2015. 208(3): p. 313-29. PMC4315246
25. Yazlovitskaya, E. M., H. Y. Tseng, O. Viquez, T. Tu, G. Mernaugh, K. K. McKee, K. Riggins, V. Quaranta, A. Pathak, B. D. Carter, P. Yurchenco, A. Sonnenberg, R. T. Bottcher, A. Pozzi, and R. Zent, Integrin alpha3beta1 regulates kidney collecting duct development via TRAF6-dependent K63-linked polyubiquitination of Akt. *Mol Biol Cell,* 2015. 26(10): p. 1857-74. PMC4436831
26. Reuten, R., T. R. Patel, M. McDougall, N. Rama, D. Nikodemus, B. Gibert, J. G. Delcros, C. Prein, M. Meier, S. Metzger, Z. Zhou, J. Kaltenberg, K. K. McKee, T. Bald, T. Tuting, P. Zigrino, V. Djonov, W. Bloch, H. Clausen-Schaumann, E. Poschl, P. D. Yurchenco, M. Ehrbar, P. Mehlen, J. Stetefeld, and M. Koch, Structural decoding of netrin-4 reveals a regulatory function towards mature basement membranes. *Nat Commun,* 2016. 7: p. 13515. PMC514367

Many modifications and variations of this invention can be made without departing from its spirit and scope, as will be apparent to those skilled in the art. The invention is defined by the terms of the appended claims, along with the full scope of equivalents to which such claims are entitled. The specific embodiments described herein, including the following examples, are offered by way of example only, and do not by their details limit the scope of the invention.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

The invention claimed is:

1. A recombinant adeno-associated vector (rAAV) comprising a nucleic acid sequence comprising a transgene encoding alphaLNNdDeltaG2short, wherein the alphaLNNdDeltaG2short comprises SEQ ID NO: 1 or SEQ ID NO: 24.

2. The recombinant AAV of claim 1, wherein the AAV is AAV8 or AAV-DJ.

3. The recombinant AAV of claim 1, further comprising a CMV promoter.

4. The recombinant AAV of claim 3, wherein the CMV promoter comprises SEQ ID NO: 12.

5. The recombinant AAV of claim 1, wherein the recombinant vector further comprises inverted terminal repeats (ITRs).

6. The recombinant AAV of claim 5, wherein the inverted terminal repeat (ITR) is a 5' ITR comprising SEQ ID NO: 11.

7. The recombinant AAV of claim 5, wherein the inverted terminal repeat (ITR) is a 3' ITR comprising SEQ ID NO: 16.

8. A pharmaceutical composition comprising the recombinant AAV of claim 1 and a pharmaceutical carrier.

9. A kit comprising a container housing comprising the pharmaceutical composition of claim 8.

10. A method of restoring laminin polymerization expression and basement membrane assembly in a subject, comprising administering to the subject an effective amount of the recombinant AAV vector of claim 1.

11. A method of treating laminin $\alpha$-2 deficiency syndrome in a subject in need thereof, wherein the method comprises administering to the subject an effective amount of the recombinant AAV vector of claim 1.

12. The method of claim 11, wherein the AAV is AAV8 or AAV-DJ.

13. The method of claim 11, wherein the recombinant AAV further comprises a CMV promoter.

14. The method of claim 13, wherein the CMV promoter comprises SEQ ID NO: 12.

15. The method of claim 11, wherein the recombinant vector further comprises inverted terminal repeats (ITRs).

16. The method of claim 15, wherein the inverted terminal repeat (ITR) is a 5' ITR comprising SEQ ID NO: 11.

17. The method of claim 15, wherein the inverted terminal repeat (ITR) is a 3' ITR comprising SEQ ID NO: 16.

18. The method of claim 11, wherein the recombinant AAV is comprised within a pharmaceutical composition further comprising a pharmaceutical carrier.

* * * * *

SEQUENCE LISTING

```
<160> NUMBER OF SEQ ID NOS: 170

<210> SEQ ID NO 1
<211> LENGTH: 3009
<212> TYPE: DNA
<213> ORGANISM: Artificial Sequence
<220> FEATURE:
<223> OTHER INFORMATION: alphaLNNdDeltaG2 open reading frame no tag used
      in the AAV construct

<400> SEQUENCE: 1

atgagggcct ggatcttctt tctcctttgc ctggccggga gggctctggc acagcagaga     60

ggcttgttcc ctgccattct caacctggcc accaatgccc acatcagcgc caatgctacc    120

tgtggagaga aggggcctga gatgttctgc aaactcgtgg agcacgtgcc gggccggcct    180

gttcgacacg cccaatgccg ggtctgtgac ggtaacagta cgaatcctag agagcgccat    240

ccgatatcac acgcaatcga tggcaccaac aactggtggc agagccccag tattcagaat    300

gggagagagt atcactgggt cactgtcacc ctggacttac ggcaggtctt tcaagttgca    360

tacatcatca ttaaagctgc caatgcccct cggcctggaa actggatttt ggagcgctcc    420

gtggatggcg tcaagttcaa accctggcag tactatgccg tcagcgatac agagtgtttg    480

acccgctaca aataactcc acggcgggga cctcccactt acagagcaga caacgaagtc    540

atctgcacct cgtattattc aaagctggtg ccacttgaac atggagagat tcacacatca    600
```

-continued

```
ctcatcaatg gcagacccag cgctgacgac ccctcacccc agttgctgga attcacctca    660
gcacggtaca ttcgccttcg tcttcagcgc atcagaacac tcaacgcaga cctcatgacc    720
cttagccatc gggacctcag agaccttgac cccattgtca caagacgtta ttactattcg    780
ataaaagaca tttccgttgg aggcatgtgc atttgctacg gccatgccag cagctgcccg    840
tgggatgaag aagcaaagca actacagtgt cagtgtgaac acaatacgtg tggcgagagc    900
tgcgacaggt gctgtcctgg ctaccatcag cagccctgga ggcccggaac catttcctcc    960
ggcaacgagt gtgaggaatg caactgtcac aacaaagcca aagattgtta ctatgacagc   1020
agtgttgcaa aggagaggag aagcctgaac actgccgggc agtacagtgg aggaggggtt   1080
tgtgtcaact gctcgcagaa taccacaggg atcaactgtg aaacctgtat cgaccagtat   1140
tacagacctc acaaggtatc tccttatgat gaccacccct gccgtccctg taactgtgac   1200
cctgtggggt ctctgagttc tgtctgtatc aaggatgacc gccatgccga tttagccaat   1260
ggaaagtggc caggtcagtg tccatgtagg aaaggttatg ctggagataa atgtgaccgc   1320
tgccagtttg gctaccgggg tttcccaaat tgcatcccct gtgactgcag gactgtcggc   1380
agcctgaatg aggatccatg catagagccg tgtctttgta agaaaaatgt tgagggtaag   1440
aactgtgatc gctgcaagcc aggattctac aacttgaagg aacgaaaccc cgagggctgc   1500
tccgagtgct tctgcttcgg tgtctctggt gtctgtccca tcaactactg tgaaactggt   1560
ctccacaact gtgatatccc ccagcgagcc cagtgcatct atatgggtgg ttcctcctac   1620
acctgctcct gtctgcctgg cttctctggg gatggcagag cctgccgaga cgtggatgaa   1680
tgccagcaca gccgatgtca ccccgatgcc ttctgctaca acacaccagg ctctttcaca   1740
tgtcagtgca agcctggcta tcagggggat ggcttccgat gcatgcccgg agaggtgagc   1800
aaaacccggt gtcaactgga acgagagcac atccttggag cagccggcgg ggcagatgca   1860
cagcggccca ccctgcaggg gatgtttgtg cctcagtgtg atgaatatgg acactatgta   1920
cccacccagt gtcaccacag cactggctac tgctggtgtg tggaccgaga tggtcgggag   1980
ctggagggta gccgtacccc acctgggatg aggcccccgt gtctgagtac agtggctcct   2040
cctattcacc agggaccagt agtacctaca gctgtcatcc ccctgcctcc agggacacac   2100
ttactctttg ctcagactgg aaagattgaa cgcctgcccc tggaaagaaa caccatgaag   2160
aagacagaac gcaaggcctt tctccatatc cctgcaaaag tcatcattgg actggccttt   2220
gactgcgtgg acaaggtggt ttactggaca gacatcagcg agccttccat tgggagagcc   2280
agcctccacg gtggagagcc aaccaccatc attcgacaag atcttggaag ccctgaaggc   2340
attgcccttg accatcttgg tcgaaccatc ttctggacgg actctcagtt ggatcgaata   2400
gaagttgcaa agatggatgg cacccagcgc cgagtgctgt ttgacacggg tttggtgaat   2460
cccagaggca ttgtgacaga ccccgtaaga gggaaccttt attggacaga ttggaacaga   2520
gataatccca aaattgagac ttctcacatg gatggcacca accggaggat tctcgcacag   2580
gacaacctgg gcttgcccaa tggtctgacc tttgatgcat tctcatctca gctttgctgg   2640
gtggatgcag gcacccatag ggcagaatgc ctgaacccag ctcagcctgg cagacgcaaa   2700
gttctcgaag ggctccagta tcctttcgct gtgactagct atgggaagaa tttgtactac   2760
acagactgga agacgaattc agtgattgcc atggaccttg ctatatccaa agagatggat   2820
accttccacc cacacaagca gacccggcta tatggcatca ccatcgccct gtcccagtgt   2880
ccccaaggcc acaattactg ctcagtgaat aatggtggat gtacccacct ctgcttgccc   2940
```

-continued

```
actccaggga gcaggacctg ccgatgtcct gacaacaccc tgggagttga ctgcattgaa   3000

cggaaatga                                                            3009


<210> SEQ ID NO 2
<211> LENGTH: 20
<212> TYPE: DNA
<213> ORGANISM: Artificial Sequence
<220> FEATURE:
<223> OTHER INFORMATION: F1noG2 1F

<400> SEQUENCE: 2

ctgggtcact gtcaccctgg                                                 20


<210> SEQ ID NO 3
<211> LENGTH: 30
<212> TYPE: DNA
<213> ORGANISM: Artificial Sequence
<220> FEATURE:
<223> OTHER INFORMATION: noG2 2R

<400> SEQUENCE: 3

atggattctg aagacagaca ccagagacac                                      30


<210> SEQ ID NO 4
<211> LENGTH: 29
<212> TYPE: DNA
<213> ORGANISM: Artificial Sequence
<220> FEATURE:
<223> OTHER INFORMATION: no G2 2F

<400> SEQUENCE: 4

ctggtgtctg tcttcagaat ccatgctac                                       29


<210> SEQ ID NO 5
<211> LENGTH: 24
<212> TYPE: DNA
<213> ORGANISM: Artificial Sequence
<220> FEATURE:
<223> OTHER INFORMATION: F1 no G2 1R

<400> SEQUENCE: 5

gaaggcacag tcgaggctga tcag                                            24


<210> SEQ ID NO 6
<211> LENGTH: 30
<212> TYPE: DNA
<213> ORGANISM: Artificial Sequence
<220> FEATURE:
<223> OTHER INFORMATION: Bam shnoG2 1F

<400> SEQUENCE: 6

cggcagcctg aatgaggatc catgcataga                                      30


<210> SEQ ID NO 7
<211> LENGTH: 25
<212> TYPE: DNA
<213> ORGANISM: Artificial Sequence
<220> FEATURE:
<223> OTHER INFORMATION: shnoG2 2R

<400> SEQUENCE: 7

cacagtagtt gatgggacag acacc                                           25


<210> SEQ ID NO 8
<211> LENGTH: 26
```

-continued

<212> TYPE: DNA
<213> ORGANISM: Artificial Sequence
<220> FEATURE:
<223> OTHER INFORMATION: shnoG2 2F

<400> SEQUENCE: 8
gtctctggtg tctgtcccat caacta 26

<210> SEQ ID NO 9
<211> LENGTH: 30
<212> TYPE: DNA
<213> ORGANISM: Artificial Sequencce
<220> FEATURE:
<223> OTHER INFORMATION: sse shnoG2 1R

<400> SEQUENCE: 9
gaggcacaaa catcccctgc agggtgggcc 30

<210> SEQ ID NO 10
<211> LENGTH: 4639
<212> TYPE: DNA
<213> ORGANISM: Artificial Sequence
<220> FEATURE:
<223> OTHER INFORMATION: pAAV-MCS Expression Vector

<400> SEQUENCE: 10
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtggagct agttattaat agtaatcaat tacggggtca 180
ttagttcata gcccatatat ggagttccgc gttacataac ttacggtaaa tggcccgcct 240
ggctgaccgc ccaacgaccc ccgcccattg acgtcaataa tgacgtatgt tcccatagta 300
acgtcaatag ggactttcca ttgacgtcaa tgggtggagt atttacggta aactgcccac 360
ttggcagtac atcaagtgta tcatatgcca agtacgcccc ctattgacgt caatgacggt 420
aaatggcccg cctggcatta tgcccagtac atgaccttat gggactttcc tacttggcag 480
tacatctacg tattagtcat cgctattacc atggtgatgc ggttttggca gtacatcaat 540
gggcgtggat agcggtttga ctcacgggga tttccaagtc tccaccccat tgacgtcaat 600
gggagtttgt tttgcaccaa aatcaacggg actttccaaa atgtcgtaac aactccgccc 660
cattgacgca aatgggcggt aggcgtgtac ggtgggaggt ctatataagc agagctcgtt 720
tagtgaaccg tcagatcgcc tggagacgcc atccacgctg ttttgacctc catagaagac 780
accgggaccg atccagcctc cgcggattcg aatcccggcc gggaacggtg cattggaacg 840
cggattcccc gtgccaagag tgacgtaagt accgcctata gagtctatag gcccacaaaa 900
aatgctttct tcttttaata tacttttttg tttatcttat ttctaatact ttccctaatc 960
tctttctttc agggcaataa tgatacaatg tatcatgcct ctttgcacca ttctaaagaa 1020
taacagtgat aatttctggg ttaaggcaat agcaatattt ctgcatataa atatttctgc 1080
atataaattg taactgatgt aagaggtttc atattgctaa tagcagctac aatccagcta 1140
ccattctgct tttattttat ggttgggata aggctggatt attctgagtc caagctaggc 1200
ccttttgcta atcatgttca tacctcttat cttcctccca cagctcctgg gcaacgtgct 1260
ggtctgtgtg ctggcccatc actttggcaa agaattggga ttcgaacatc gattgaattc 1320
cccggggatc ctctagagtc gacctgcaga agcttgcctc gagcagcgct gctcgagaga 1380
tctacgggtg gcatccctgt gacccctccc cagtgcctct cctggccctg gaagttgcca 1440

-continued

```
ctccagtgcc caccagcctt gtcctaataa aattaagttg catcattttg tctgactagg   1500
tgtccttcta taatattatg gggtggaggg gggtggtatg gagcaagggg caagttggga   1560
agacaacctg tagggcctgc ggggtctatt gggaaccaag ctggagtgca gtggcacaat   1620
cttggctcac tgcaatctcc gcctcctggg ttcaagcgat tctcctgcct cagcctcccg   1680
agttgttggg attccaggca tgcatgacca ggctcagcta atttttgttt ttttggtaga   1740
gacggggttt caccatattg gccaggctgg tctccaactc ctaatctcag gtgatctacc   1800
caccttggcc tcccaaattg ctgggattac aggcgtgaac cactgctccc ttccctgtcc   1860
ttctgatttt gtaggtaacc acgtgcggac cgagcggccg caggaacccc tagtgatgga   1920
gttggccact ccctctctgc gcgctcgctc gctcactgag gccgggcgac caaaggtcgc   1980
ccgacgcccg ggctttgccc gggcggcctc agtgagcgag cgagcgcgca gctgcctgca   2040
ggggcgcctg atgcggtatt ttctccttac gcatctgtgc ggtatttcac accgcatacg   2100
tcaaagcaac catagtacgc gccctgtagc ggcgcattaa gcgcggcggg tgtggtggtt   2160
acgcgcagcg tgaccgctac acttgccagc gccctagcgc ccgctccttt cgctttcttc   2220
ccttcctttc tcgccacgtt cgccggcttt ccccgtcaag ctctaaatcg ggggctccct   2280
ttagggttcc gatttagtgc tttacggcac ctcgacccca aaaaacttga tttgggtgat   2340
ggttcacgta gtgggccatc gccctgatag acggtttttc gccctttgac gttggagtcc   2400
acgttcttta atagtggact cttgttccaa actggaacaa cactcaaccc tatctcgggc   2460
tattcttttg atttataagg gattttgccg atttcggcct attggttaaa aaatgagctg   2520
atttaacaaa aatttaacgc gaattttaac aaaatattaa cgtttacaat tttatggtgc   2580
actctcagta caatctgctc tgatgccgca tagttaagcc agccccgaca cccgccaaca   2640
cccgctgacg cgccctgacg ggcttgtctg ctcccggcat ccgcttacag acaagctgtg   2700
accgtctccg ggagctgcat gtgtcagagg ttttcaccgt catcaccgaa acgcgcgaga   2760
cgaaagggcc tcgtgatacg cctattttta taggttaatg tcatgataat aatggtttct   2820
tagacgtcag gtggcacttt tcggggaaat gtgcgcggaa cccctatttg tttatttttc   2880
taaatacatt caaatatgta tccgctcatg agacaataac cctgataaat gcttcaataa   2940
tattgaaaaa ggaagagtat gagtattcaa catttccgtg tcgcccttat tccctttttt   3000
gcggcatttt gccttcctgt ttttgctcac ccagaaacgc tggtgaaagt aaaagatgct   3060
gaagatcagt tgggtgcacg agtgggttac atcgaactgg atctcaacag cggtaagatc   3120
cttgagagtt ttcgccccga agaacgtttt ccaatgatga gcacttttaa agttctgcta   3180
tgtggcgcgg tattatcccg tattgacgcc gggcaagagc aactcggtcg ccgcatacac   3240
tattctcaga atgacttggt tgagtactca ccagtcacag aaaagcatct tacggatggc   3300
atgacagtaa gagaattatg cagtgctgcc ataaccatga gtgataacac tgcggccaac   3360
ttacttctga caacgatcgg aggaccgaag gagctaaccg cttttttgca caacatgggg   3420
gatcatgtaa ctcgccttga tcgttgggaa ccggagctga atgaagccat accaaacgac   3480
gagcgtgaca ccacgatgcc tgtagcaatg gcaacaacgt tgcgcaaact attaactggc   3540
gaactactta ctctagcttc ccggcaacaa ttaatagact ggatggaggc ggataaagtt   3600
gcaggaccac ttctgcgctc ggcccttccg gctggctggt ttattgctga taaatctgga   3660
gccggtgagc gtgggtctcg cggtatcatt gcagcactgg ggccagatgg taagccctcc   3720
cgtatcgtag ttatctacac gacggggagt caggcaacta tggatgaacg aaatagacag   3780
atcgctgaga taggtgcctc actgattaag cattggtaac tgtcagacca agtttactca   3840
```

-continued

```
tatatacttt agattgattt aaaacttcat ttttaattta aaaggatcta ggtgaagatc   3900

ctttttgata atctcatgac caaaatccct taacgtgagt tttcgttcca ctgagcgtca   3960

gaccccgtag aaaagatcaa aggatcttct tgagatcctt tttttctgcg cgtaatctgc   4020

tgcttgcaaa caaaaaaacc accgctacca gcggtggttt gtttgccgga tcaagagcta   4080

ccaactcttt ttccgaaggt aactggcttc agcagagcgc agataccaaa tactgtcctt   4140

ctagtgtagc cgtagttagg ccaccacttc aagaactctg tagcaccgcc tacatacctc   4200

gctctgctaa tcctgttacc agtggctgct gccagtggcg ataagtcgtg tcttaccggg   4260

ttggactcaa gacgatagtt accggataag gcgcagcggt cgggctgaac ggggggttcg   4320

tgcacacagc ccagcttgga gcgaacgacc tacaccgaac tgagatacct acagcgtgag   4380

ctatgagaaa gcgccacgct tcccgaaggg agaaaggcgg acaggtatcc ggtaagcggc   4440

agggtcggaa caggagagcg cacgagggag cttccagggg gaaacgcctg gtatctttat   4500

agtcctgtcg ggtttcgcca cctctgactt gagcgtcgat ttttgtgatg ctcgtcaggg   4560

gggcggagcc tatggaaaaa cgccagcaac gcggcctttt tacggttcct ggccttttgc   4620

tggccttttg ctcacatgt                                                4639
```

<210> SEQ ID NO 11
<211> LENGTH: 130
<212> TYPE: DNA
<213> ORGANISM: Artificial Sequence
<220> FEATURE:
<223> OTHER INFORMATION: 5' ITR

<400> SEQUENCE: 11

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct                                                           130
```

<210> SEQ ID NO 12
<211> LENGTH: 663
<212> TYPE: DNA
<213> ORGANISM: Artificial Sequence
<220> FEATURE:
<223> OTHER INFORMATION: CMV Promoter

<400> SEQUENCE: 12

```
acgcgtggag ctagttatta atagtaatca attacggggt cattagttca tagcccatat     60

atggagttcc gcgttacata acttacggta aatggcccgc ctggctgacc gcccaacgac    120

ccccgcccat tgacgtcaat aatgacgtat gttcccatag taacgtcaat agggactttc    180

cattgacgtc aatgggtgga gtatttacgg taaactgccc acttggcagt acatcaagtg    240

tatcatatgc caagtacgcc ccctattgac gtcaatgacg gtaaatggcc cgcctggcat    300

tatgcccagt acatgacctt atgggacttt cctacttggc agtacatcta cgtattagtc    360

atcgctatta ccatggtgat gcggttttgg cagtacatca atgggcgtgg atagcggttt    420

gactcacggg gatttccaag tctccacccc attgacgtca atgggagttt gttttgcacc    480

aaaatcaacg ggactttcca aaatgtcgta acaactccgc cccattgacg caaatgggcg    540

gtaggcgtgt acggtgggag gtctatataa gcagagctcg tttagtgaac cgtcagatcg    600

cctggagacg ccatccacgc tgttttgacc tccatagaag acaccgggac cgatccagcc    660

tcc                                                                  663
```

-continued

<210> SEQ ID NO 13
<211> LENGTH: 493
<212> TYPE: DNA
<213> ORGANISM: Artificial Sequence
<220> FEATURE:
<223> OTHER INFORMATION: Human beta globin Intron

<400> SEQUENCE: 13
cgaatcccgg ccgggaacgg tgcattggaa cgcggattcc ccgtgccaag agtgacgtaa 60
gtaccgccta tagagtctat aggcccacaa aaaatgcttt cttcttttaa tatacttttt 120
tgtttatctt atttctaata ctttccctaa tctctttctt tcagggcaat aatgatacaa 180
tgtatcatgc ctctttgcac cattctaaag aataacagtg ataatttctg ggttaaggca 240
atagcaatat ttctgcatat aaatatttct gcatataaat tgtaactgat gtaagaggtt 300
tcatattgct aatagcagct acaatccagc taccattctg cttttatttt atggttggga 360
taaggctgga ttattctgag tccaagctag gcccttttgc taatcatgtt catacctctt 420
atcttcctcc cacagctcct gggcaacgtg ctggtctgtg tgctggccca tcactttggc 480
aaagaattgg gat 493

<210> SEQ ID NO 14
<211> LENGTH: 76
<212> TYPE: DNA
<213> ORGANISM: Artificial Sequence
<220> FEATURE:
<223> OTHER INFORMATION: MCS

<400> SEQUENCE: 14
atcgattgaa ttccccgggg atcctctaga gtcgacctgc agaagcttgc ctcgagcagc 60
gctgctcgag agatct 76

<210> SEQ ID NO 15
<211> LENGTH: 479
<212> TYPE: DNA
<213> ORGANISM: Artificial Sequence
<220> FEATURE:
<223> OTHER INFORMATION: PolyA

<400> SEQUENCE: 15
acgggtggca tccctgtgac ccctccccag tgcctctcct ggccctggaa gttgccactc 60
cagtgcccac cagccttgtc ctaataaaat taagttgcat cattttgtct gactaggtgt 120
ccttctataa tattatgggg tggagggggg tggtatggag caaggggcaa gttgggaaga 180
caacctgtag ggcctgcggg gtctattggg aaccaagctg gagtgcagtg gcacaatctt 240
ggctcactgc aatctccgcc tcctgggttc aagcgattct cctgcctcag cctcccgagt 300
tgttgggatt ccaggcatgc atgaccaggc tcagctaatt tttgtttttt tggtagagac 360
ggggtttcac catattggcc aggctggtct ccaactccta atctcaggtg atctacccac 420
cttggcctcc caaattgctg ggattacagg cgtgaaccac tgctcccttc cctgtcctt 479

<210> SEQ ID NO 16
<211> LENGTH: 141
<212> TYPE: DNA
<213> ORGANISM: Artificial Sequence
<220> FEATURE:
<223> OTHER INFORMATION: 3' ITR

<400> SEQUENCE: 16
aggaacccct agtgatggag ttggccactc cctctctgcg cgctcgctcg ctcactgagg 60

```
ccgggcgacc aaaggtcgcc cgacgcccgg gctttgcccg ggcggcctca gtgagcgagc    120

gagcgcgcag ctgcctgcag g                                              141


<210> SEQ ID NO 17
<211> LENGTH: 7333
<212> TYPE: DNA
<213> ORGANISM: Artificial Sequence
<220> FEATURE:
<223> OTHER INFORMATION: pAAV-DJ Vector

<400> SEQUENCE: 17

ccgccatgcc ggggttttac gagattgtga ttaaggtccc cagcgacctt gacgagcatc     60

tgcccggcat ttctgacagc tttgtgaact gggtggccga gaaggaatgg gagttgccgc    120

cagattctga catggatctg aatctgattg agcaggcacc cctgaccgtg gccgagaagc    180

tgcagcgcga ctttctgacg gaatggcgcc gtgtgagtaa ggccccggag gcccttttct    240

ttgtgcaatt tgagaaggga gagagctact tccacatgca cgtgctcgtg gaaaccaccg    300

gggtgaaatc catggttttg ggacgtttcc tgagtcagat tcgcgaaaaa ctgattcaga    360

gaatttaccg cgggatcgag ccgactttgc caaactggtt cgcggtcaca aagaccagaa    420

atggcgccgg aggcgggaac aaggtggtgg atgagtgcta catccccaat tacttgctcc    480

ccaaaaccca gcctgagctc cagtgggcgt ggactaatat ggaacagtat ttaagcgcct    540

gtttgaatct cacggagcgt aaacggttgg tggcgcagca tctgacgcac gtgtcgcaga    600

cgcaggagca gaacaaagag aatcagaatc ccaattctga tgcgccggtg atcagatcaa    660

aaacttcagc caggtacatg gagctggtcg ggtggctcgt ggacaagggg attacctcgg    720

agaagcagtg gatccaggag gaccaggcct catacatctc cttcaatgcg gcctccaact    780

cgcggtccca aatcaaggct gccttggaca atgcgggaaa gattatgagc ctgactaaaa    840

ccgcccccga ctacctggtg ggccagcagc ccgtggagga catttccagc aatcggattt    900

ataaaatttt ggaactaaac gggtacgatc cccaatatgc ggcttccgtc tttctgggat    960

gggccacgaa aaagttcggc aagaggaaca ccatctggct gtttgggcct gcaactaccg   1020

ggaagaccaa catcgcggag gccatagccc acactgtgcc cttctacggg tgcgtaaact   1080

ggaccaatga gaactttccc ttcaacgact gtgtcgacaa gatggtgatc tggtgggagg   1140

aggggaagat gaccgccaag gtcgtggagt cggccaaagc cattctcgga ggaagcaagg   1200

tgcgcgtgga ccagaaatgc aagtcctcgg cccagataga cccgactccc gtgatcgtca   1260

cctccaacac caacatgtgc gccgtgattg acgggaactc aacgaccttc gaacaccagc   1320

agccgttgca agaccggatg ttcaaatttg aactcacccg ccgtctggat catgactttg   1380

ggaaggtcac caagcaggaa gtcaaagact ttttccggtg ggcaaaggat cacgtggttg   1440

aggtggagca tgaattctac gtcaaaaagg gtggagccaa gaaaagaccc gcccccagtg   1500

acgcagatat aagtgagccc aaacgggtgc gcgagtcagt tgcgcagcca tcgacgtcag   1560

acgcggaagc ttcgatcaac tacgcagaca ggtaccaaaa caaatgttct cgtcacgtgg   1620

gcatgaatct gatgctgttt ccctgcagac aatgcgagag aatgaatcag aattcaaata   1680

tctgcttcac tcacggacag aaagactgtt tagagtgctt tcccgtgtca gaatctcaac   1740

ccgtttctgt cgtcaaaaag gcgtatcaga aactgtgcta cattcatcat atcatgggaa   1800

aggtgccaga cgcttgcact gcctgcgatc tggtcaatgt ggatttggat gactgcatct   1860

ttgaacaata aatgatttaa atcaggtatg gctgccgatg gttatcttcc agattggctc   1920
```

-continued

```
gaggacactc tctctgaagg aataagacag tggtggaagc tcaaacctgg cccaccacca   1980
ccaaagcccg cagagcggca taaggacgac agcaggggtc ttgtgcttcc tgggtacaag   2040
tacctcggac ccttcaacgg actcgacaag ggagagccgg tcaacgaggc agacgccgcg   2100
gccctcgagc acgacaaagc ctacgaccgg cagctcgaca gcggagacaa cccgtacctc   2160
aagtacaacc acgccgacgc cgagttccag gagcggctca aagaagatac gtcttttggg   2220
ggcaacctcg ggcgagcagt cttccaggcc aaaaagaggc ttcttgaacc tcttggtctg   2280
gttgaggaag cggctaagac ggctcctgga aagaagaggc ctgtagagca ctctcctgtg   2340
gagccagact cctcctcggg aaccggaaag gcgggccagc agcctgcaag aaaaagattg   2400
aattttggtc agactggaga cgcagactca gtcccagacc ctcaaccaat cggagaacct   2460
cccgcagccc cctcaggtgt gggatctctt acaatggctg caggcggtgg cgcaccaatg   2520
gcagacaata acgagggcgc cgacggagtg ggtaattcct cgggaaattg gcattgcgat   2580
tccacatgga tgggcgacag agtcatcacc accagcaccc gaacctgggc cctgcccacc   2640
tacaacaacc acctctacaa gcaaatctcc aacagcacat ctggaggatc ttcaaatgac   2700
aacgcctact tcggctacag caccccctgg gggtattttg actttaacag attccactgc   2760
cacttttcac cacgtgactg gcagcgactc atcaacaaca actggggatt ccggcccaag   2820
agactcagct tcaagctctt caacatccag gtcaaggagg tcacgcagaa tgaaggcacc   2880
aagaccatcg ccaataacct caccagcacc atccaggtgt ttacggactc ggagtaccag   2940
ctgccgtacg ttctcggctc tgcccaccag ggctgcctgc ctccgttccc ggcggacgtg   3000
ttcatgattc cccagtacgg ctacctaaca ctcaacaacg gtagtcaggc cgtgggacgc   3060
tcctccttct actgcctgga atactttcct tcgcagatgc tgagaaccgg caacaacttc   3120
cagtttactt acaccttcga ggacgtgcct ttccacagca gctacgccca cagccagagc   3180
ttggaccggc tgatgaatcc tctgattgac cagtacctgt actacttgtc tcggactcaa   3240
acaacaggag gcacgacaaa tacgcagact ctgggcttca gccaaggtgg gcctaataca   3300
atggccaatc aggcaaagaa ctggctgcca ggaccctgtt accgccagca gcgagtatca   3360
aagacatctg cggataacaa caacagtgaa tactcgtgga ctggagctac caagtaccac   3420
ctcaatggca gagactctct ggtgaatccg ggcccggcca tggcaagcca caaggacgat   3480
gaagaaaagt tttttcctca gagcggggtt ctcatctttg ggaagcaagg ctcagagaaa   3540
acaaatgtgg acattgaaaa ggtcatgatt acagacgaag aggaaatcag gacaaccaat   3600
cccgtggcta cggagcagta tggttctgta tctaccaacc tccagagagg caacagacaa   3660
gcagctaccg cagatgtcaa cacacaaggc gttcttccag gcatggtctg gcaggacaga   3720
gatgtgtacc ttcaggggcc catctgggca aagattccac acacggacgg acattttcac   3780
ccctctcccc tcatgggtgg attcggactt aaacaccctc cgcctcagat cctgatcaag   3840
aacacgcctg tacctgcgga tcctccgacc accttcaacc agtcaaagct gaactctttc   3900
atcacccagt attctactgg ccaagtcagc gtggagatcg agtgggagct gcagaaggaa   3960
aacagcaagc gctggaaccc cgagatccag tacacctcca actactacaa atctacaagt   4020
gtggactttg ctgttaatac agaaggcgtg tactctgaac cccgccccat tggcacccgt   4080
tacctcaccc gtaatctgta attgcctgtt aatcaataaa ccggttgatt cgtttcagtt   4140
gaactttggt ctctgcgaag ggcgaattcg tttaaacctg caggactaga ggtcctgtat   4200
tagaggtcac gtgagtgttt tgcgacattt tgcgacacca tgtggtcacg ctgggtattt   4260
aagcccgagt gagcacgcag ggtctccatt ttgaagcggg aggtttgaac gcgcagccgc   4320
```

-continued caagccgaat tctgcagata tccatcacac tggcggccgc tcgactagag cggccgccac 4380
cgcggtggag ctccagcttt tgttcccttt agtgagggtt aattgcgcgc ttggcgtaat 4440
catggtcata gctgtttcct gtgtgaaatt gttatccgct cacaattcca cacaacatac 4500
gagccggaag cataaagtgt aaagcctggg gtgcctaatg agtgagctaa ctcacattaa 4560
ttgcgttgcg ctcactgccc gctttccagt cgggaaacct gtcgtgccag ctgcattaat 4620
gaatcggcca acgcgcgggg agaggcggtt tgcgtattgg gcgctcttcc gcttcctcgc 4680
tcactgactc gctgcgctcg gtcgttcggc tgcggcgagc ggtatcagct cactcaaagg 4740
cggtaatacg gttatccaca gaatcagggg ataacgcagg aaagaacatg tgagcaaaag 4800
gccagcaaaa ggccaggaac cgtaaaaagg ccgcgttgct ggcgtttttc cataggctcc 4860
gcccccctga cgagcatcac aaaaatcgac gctcaagtca gaggtggcga aacccgacag 4920
gactataaag ataccaggcg tttccccctg gaagctccct cgtgcgctct cctgttccga 4980
ccctgccgct taccggatac ctgtccgcct ttctcccttc gggaagcgtg gcgctttctc 5040
atagctcacg ctgtaggtat ctcagttcgg tgtaggtcgt tcgctccaag ctgggctgtg 5100
tgcacgaacc ccccgttcag cccgaccgct gcgccttatc cggtaactat cgtcttgagt 5160
ccaacccggt aagacacgac ttatcgccac tggcagcagc cactggtaac aggattagca 5220
gagcgaggta tgtaggcggt gctacagagt tcttgaagtg gtggcctaac tacggctaca 5280
ctagaagaac agtatttggt atctgcgctc tgctgaagcc agttaccttc ggaaaaagag 5340
ttggtagctc ttgatccggc aaacaaacca ccgctggtag cggtggtttt tttgtttgca 5400
agcagcagat tacgcgcaga aaaaaaggat ctcaagaaga tcctttgatc ttttctacgg 5460
ggtctgacgc tcagtggaac gaaaactcac gttaagggat tttggtcatg agattatcaa 5520
aaaggatctt cacctagatc cttttaaatt aaaaatgaag ttttaaatca atctaaagta 5580
tatatgagta aacttggtct gacagttacc aatgcttaat cagtgaggca cctatctcag 5640
cgatctgtct atttcgttca tccatagttg cctgactccc cgtcgtgtag ataactacga 5700
tacgggaggg cttaccatct ggccccagtg ctgcaatgat accgcgagac ccacgctcac 5760
cggctccaga tttatcagca ataaaccagc cagccggaag ggccgagcgc agaagtggtc 5820
ctgcaacttt atccgcctcc atccagtcta ttaattgttg ccgggaagct agagtaagta 5880
gttcgccagt taatagtttg cgcaacgttg ttgccattgc tacaggcatc gtggtgtcac 5940
gctcgtcgtt tggtatggct tcattcagct ccggttccca acgatcaagg cgagttacat 6000
gatcccccat gttgtgcaaa aaagcggtta gctccttcgg tcctccgatc gttgtcagaa 6060
gtaagttggc cgcagtgtta tcactcatgg ttatggcagc actgcataat tctcttactg 6120
tcatgccatc cgtaagatgc ttttctgtga ctggtgagta ctcaaccaag tcattctgag 6180
aatagtgtat gcggcgaccg agttgctctt gcccggcgtc aatacgggat aataccgcgc 6240
cacatagcag aactttaaaa gtgctcatca ttggaaaacg ttcttcgggg cgaaaactct 6300
caaggatctt accgctgttg agatccagtt cgatgtaacc cactcgtgca cccaactgat 6360
cttcagcatc ttttactttc accagcgttt ctgggtgagc aaaaacagga aggcaaaatg 6420
ccgcaaaaaa gggaataagg gcgacacgga aatgttgaat actcatactc ttcctttttc 6480
aatattattg aagcatttat cagggttatt gtctcatgag cggatacata tttgaatgta 6540
tttagaaaaa taaacaaata ggggttccgc gcacatttcc ccgaaaagtg ccacctaaat 6600
tgtaagcgtt aatattttgt taaaattcgc gttaaatttt tgttaaatca gctcattttt 6660

-continued

```
taaccaatag gccgaaatcg gcaaaatccc ttataaatca aaagaataga ccgagatagg   6720

gttgagtgtt gttccagttt ggaacaagag tccactatta aagaacgtgg actccaacgt   6780

caaagggcga aaaaccgtct atcagggcga tggcccacta cgtgaaccat caccctaatc   6840

aagttttttg gggtcgaggt gccgtaaagc actaaatcgg aaccctaaag ggagcccccg   6900

atttagagct tgacggggaa agccggcgaa cgtggcgaga aaggaaggga agaaagcgaa   6960

aggagcgggc gctagggcgc tggcaagtgt agcggtcacg ctgcgcgtaa ccaccacacc   7020

cgccgcgctt aatgcgccgc tacagggcgc gtcccattcg ccattcaggc tgcgcaactg   7080

ttgggaaggg cgatcggtgc gggcctcttc gctattacgc cagctggcga aagggggatg   7140

tgctgcaagg cgattaagtt gggtaacgcc agggttttcc cagtcacgac gttgtaaaac   7200

gacggccagt gagcgcgcgt aatacgactc actatagggc gaattgggta ccgggccccc   7260

cctcgatcga ggtcgacggt atcgggggag ctcgcagggt ctccattttg aagcgggagg   7320

tttgaacgcg cag                                                      7333
```

```
<210> SEQ ID NO 18
<211> LENGTH: 1866
<212> TYPE: DNA
<213> ORGANISM: Artificial Sequence
<220> FEATURE:
<223> OTHER INFORMATION: AAV-2 Rep gene

<400> SEQUENCE: 18

atgccggggt tttacgagat tgtgattaag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggccct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccgcggga tcgagccgac tttgccaaac tggttcgcgg tcacaaagac cagaaatggc    420

gccggaggcg ggaacaaggt ggtggatgag tgctacatcc ccaattactt gctccccaaa    480

acccagcctg agctccagtg ggcgtggact aatatggaac agtatttaag cgcctgtttg    540

aatctcacgg agcgtaaacg gttggtggcg cagcatctga cgcacgtgtc gcagacgcag    600

gagcagaaca aagagaatca gaatcccaat tctgatgcgc cggtgatcag atcaaaaact    660

tcagccaggt acatggagct ggtcgggtgg ctcgtggaca aggggattac ctcggagaag    720

cagtggatcc aggaggacca ggcctcatac atctccttca atgcggcctc caactcgcgg    780

tcccaaatca aggctgcctt ggacaatgcg ggaaagatta tgagcctgac taaaaccgcc    840

cccgactacc tggtgggcca gcagcccgtg gaggacattt ccagcaatcg gatttataaa    900

attttggaac taaacgggta cgatccccaa tatgcggctt ccgtctttct gggatgggcc    960

acgaaaaagt tcggcaagag gaacaccatc tggctgtttg ggcctgcaac taccgggaag   1020

accaacatcg cggaggccat agcccacact gtgcccttct acgggtgcgt aaactggacc   1080

aatgagaact ttcccttcaa cgactgtgtc gacaagatgg tgatctggtg ggaggagggg   1140

aagatgaccg ccaaggtcgt ggagtcggcc aaagccattc tcggaggaag caaggtgcgc   1200

gtggaccaga aatgcaagtc ctcggcccag atagacccga ctcccgtgat cgtcacctcc   1260

aacaccaaca tgtgcgccgt gattgacggg aactcaacga ccttcgaaca ccagcagccg   1320

ttgcaagacc ggatgttcaa atttgaactc acccgccgtc tggatcatga ctttgggaag   1380
```

```
gtcaccaagc aggaagtcaa agactttttc cggtgggcaa aggatcacgt ggttgaggtg   1440

gagcatgaat tctacgtcaa aaagggtgga gccaagaaaa gacccgcccc cagtgacgca   1500

gatataagtg agcccaaacg ggtgcgcgag tcagttgcgc agccatcgac gtcagacgcg   1560

gaagcttcga tcaactacgc agacaggtac caaaacaaat gttctcgtca cgtgggcatg   1620

aatctgatgc tgtttccctg cagacaatgc gagagaatga atcagaattc aaatatctgc   1680

ttcactcacg gacagaaaga ctgtttagag tgctttcccg tgtcagaatc tcaacccgtt   1740

tctgtcgtca aaaaggcgta tcagaaactg tgctacattc atcatatcat gggaaaggtg   1800

ccagacgctt gcactgcctg cgatctggtc aatgtggatt tggatgactg catctttgaa   1860

caataa                                                              1866
```

```
<210> SEQ ID NO 19
<211> LENGTH: 2214
<212> TYPE: DNA
<213> ORGANISM: Artificial Sequence
<220> FEATURE:
<223> OTHER INFORMATION: AAV-DJ Cap gene

<400> SEQUENCE: 19

atggctgccg atggttatct tccagattgg ctcgaggaca ctctctctga aggaataaga     60

cagtggtgga agctcaaacc tggcccacca ccaccaaagc ccgcagagcg gcataaggac    120

gacagcaggg gtcttgtgct tcctgggtac aagtacctcg gacccttcaa cggactcgac    180

aagggagagc cggtcaacga ggcagacgcc gcggccctcg agcacgacaa agcctacgac    240

cggcagctcg acagcggaga caacccgtac ctcaagtaca accacgccga cgccgagttc    300

caggagcggc tcaaagaaga tacgtctttt gggggcaacc tcgggcgagc agtcttccag    360

gccaaaaaga ggcttcttga acctcttggt ctggttgagg aagcggctaa gacggctcct    420

ggaaagaaga ggcctgtaga gcactctcct gtggagccag actcctcctc gggaaccgga    480

aaggcgggcc agcagcctgc aagaaaaaga ttgaattttg gtcagactgg agacgcagac    540

tcagtcccag accctcaacc aatcggagaa cctcccgcag ccccctcagg tgtgggatct    600

cttacaatgg ctgcaggcgg tggcgcacca atggcagaca ataacgaggg cgccgacgga    660

gtgggtaatt cctcgggaaa ttggcattgc gattccacat ggatgggcga cagagtcatc    720

accaccagca cccgaacctg ggccctgccc acctacaaca accacctcta caagcaaatc    780

tccaacagca catctggagg atcttcaaat gacaacgcct acttcggcta cagcaccccc    840

tgggggtatt ttgactttaa cagattccac tgccactttt caccacgtga ctggcagcga    900

ctcatcaaca acaactgggg attccggccc aagagactca gcttcaagct cttcaacatc    960

caggtcaagg aggtcacgca gaatgaaggc accaagacca tcgccaataa cctcaccagc   1020

accatccagg tgtttacgga ctcggagtac cagctgccgt acgttctcgg ctctgcccac   1080

cagggctgcc tgcctccgtt cccggcggac gtgttcatga ttccccagta cggctaccta   1140

acactcaaca acggtagtca ggccgtggga cgctcctcct tctactgcct ggaatacttt   1200

ccttcgcaga tgctgagaac cggcaacaac ttccagttta cttacacctt cgaggacgtg   1260

cctttccaca gcagctacgc ccacagccag agcttggacc ggctgatgaa tcctctgatt   1320

gaccagtacc tgtactactt gtctcggact caaacaacag gaggcacgac aaatacgcag   1380

actctgggct tcagccaagg tgggcctaat acaatggcca atcaggcaaa gaactggctg   1440

ccaggaccct gttaccgcca gcagcgagta tcaaagacat ctgcggataa caacaacagt   1500
```

```
gaatactcgt ggactggagc taccaagtac cacctcaatg gcagagactc tctggtgaat   1560

ccgggcccgg ccatggcaag ccacaaggac gatgaagaaa agtttttttcc tcagagcggg   1620

gttctcatct ttgggaagca aggctcagag aaaacaaatg tggacattga aaaggtcatg   1680

attacagacg aagaggaaat caggacaacc aatcccgtgg ctacggagca gtatggttct   1740

gtatctacca acctccagag aggcaacaga caagcagcta ccgcagatgt caacacacaa   1800

ggcgttcttc caggcatggt ctggcaggac agagatgtgt accttcaggg gcccatctgg   1860

gcaaagattc cacacacgga cggacatttt cacccctctc ccctcatggg tggattcgga   1920

cttaaacacc ctccgcctca gatcctgatc aagaacacgc ctgtacctgc ggatcctccg   1980

accaccttca accagtcaaa gctgaactct ttcatcaccc agtattctac tggccaagtc   2040

agcgtggaga tcgagtggga gctgcagaag gaaaacagca agcgctggaa ccccgagatc   2100

cagtacacct ccaactacta caaatctaca agtgtggact ttgctgttaa tacagaaggc   2160

gtgtactctg aaccccgccc cattggcacc cgttacctca cccgtaatct gtaa         2214
```

<210> SEQ ID NO 20
<211> LENGTH: 11635
<212> TYPE: DNA
<213> ORGANISM: Artificial Sequence
<220> FEATURE:
<223> OTHER INFORMATION: pHelper Vector

<400> SEQUENCE: 20

```
ggtacccaac tccatgctta acagtcccca ggtacagccc accctgcgtc gcaaccagga     60

acagctctac agcttcctgg agcgccactc gccctacttc cgcagccaca gtgcgcagat    120

taggagcgcc acttcttttt gtcacttgaa aaacatgtaa aaataatgta ctaggagaca    180

ctttcaataa aggcaaatgt ttttatttgt acactctcgg gtgattattt accccccacc    240

cttgccgtct gcgccgttta aaaatcaaag gggttctgcc gcgcatcgct atgcgccact    300

ggcagggaca cgttgcgata ctggtgttta gtgctccact taaactcagg cacaaccatc    360

cgcggcagct cggtgaagtt ttcactccac aggctgcgca ccatcaccaa cgcgtttagc    420

aggtcgggcg ccgatatctt gaagtcgcag ttggggcctc cgccctgcgc gcgcgagttg    480

cgatacacag ggttgcagca ctggaacact atcagcgccg ggtggtgcac gctggccagc    540

acgctcttgt cggagatcag atccgcgtcc aggtcctccg cgttgctcag ggcgaacgga    600

gtcaactttg gtagctgcct tcccaaaaag ggtgcatgcc caggctttga gttgcactcg    660

caccgtagtg gcatcagaag gtgaccgtgc ccggtctggg cgttaggata cagcgcctgc    720

atgaaagcct tgatctgctt aaaagccacc tgagcctttg cgccttcaga gaagaacatg    780

ccgcaagact tgccggaaaa ctgattggcc ggacaggccg cgtcatgcac gcagcacctt    840

gcgtcggtgt tggagatctg caccacattt cggccccacc ggttcttcac gatcttggcc    900

ttgctagact gctccttcag cgcgcgctgc ccgttttcgc tcgtcacatc catttcaatc    960

acgtgctcct tatttatcat aatgctcccg tgtagacact taagctcgcc ttcgatctca   1020

gcgcagcggt gcagccacaa cgcgcagccc gtgggctcgt ggtgcttgta ggttacctct   1080

gcaaacgact gcaggtacgc ctgcaggaat cgccccatca tcgtcacaaa ggtcttgttg   1140

ctggtgaagg tcagctgcaa cccgcggtgc tcctcgttta gccaggtctt gcatacggcc   1200

gccagagctt ccacttggtc aggcagtagc ttgaagtttg cctttagatc gttatccacg   1260

tggtacttgt ccatcaacgc gcgcgcagcc tccatgccct tctcccacgc agacacgatc   1320

ggcaggctca gcgggtttat caccgtgctt tcactttccg cttcactgga ctcttccttt   1380
```

-continued tcctcttgcg tccgcatacc ccgcgccact gggtcgtctt cattcagccg ccgcaccgtg 1440
cgcttacctc ccttgccgtg cttgattagc accggtgggt tgctgaaacc caccatttgt 1500
agcgccacat cttctctttc ttcctcgctg tccacgatca cctctgggga tggcgggcgc 1560
tcgggcttgg gagaggggcg cttctttttc tttttggacg caatggccaa atccgccgtc 1620
gaggtcgatg gccgcgggct gggtgtgcgc ggcaccagcg catcttgtga cgagtcttct 1680
tcgtcctcgg actcgagacg ccgcctcagc cgctttttg ggggcgcgcg gggaggcggc 1740
ggcgacggcg acggggacga cacgtcctcc atggttggtg gacgtcgcgc cgcaccgcgt 1800
ccgcgctcgg gggtggtttc gcgctgctcc tcttcccgac tggccatttc cttctcctat 1860
aggcagaaaa agatcatgga gtcagtcgag aaggaggaca gcctaaccgc cccctttgag 1920
ttcgccacca ccgcctccac cgatgccgcc aacgcgccta ccaccttccc cgtcgaggca 1980
cccccgcttg aggaggagga agtgattatc gagcaggacc caggttttgt aagcgaagac 2040
gacgaggatc gctcagtacc aacagaggat aaaaagcaag accaggacga cgcagaggca 2100
aacgaggaac aagtcgggcg gggggaccaa aggcatggcg actacctaga tgtgggagac 2160
gacgtgctgt tgaagcatct gcagcgccag tgcgccatta tctgcgacgc gttgcaagag 2220
cgcagcgatg tgcccctcgc catagcggat gtcagccttg cctacgaacg ccacctgttc 2280
tcaccgcgcg taccccccaa acgccaagaa aacggcacat gcgagcccaa cccgcgcctc 2340
aacttctacc ccgtatttgc cgtgccagag gtgcttgcca cctatcacat ctttttccaa 2400
aactgcaaga tacccctatc ctgccgtgcc aaccgcagcc gagcggacaa gcagctggcc 2460
ttgcggcagg gcgctgtcat acctgatatc gcctcgctcg acgaagtgcc aaaaatcttt 2520
gagggtcttg gacgcgacga gaaacgcgcg gcaaacgctc tgcaacaaga aaacagcgaa 2580
aatgaaagtc actgtggagt gctggtggaa cttgagggtg acaacgcgcg cctagccgtg 2640
ctgaaacgca gcatcgaggt cacccacttt gcctacccgg cacttaacct accccccaag 2700
gttatgagca cagtcatgag cgagctgatc gtgcgccgtg cacgacccct ggagagggat 2760
gcaaacttgc aagaacaaac cgaggagggc ctacccgcag ttggcgatga gcagctggcg 2820
cgctggcttg agacgcgcga gcctgccgac ttggaggagc gacgcaagct aatgatggcc 2880
gcagtgcttg ttaccgtgga gcttgagtgc atgcagcggt tctttgctga cccggagatg 2940
cagcgcaagc tagaggaaac gttgcactac acctttcgcc agggctacgt gcgccaggcc 3000
tgcaaaattt ccaacgtgga gctctgcaac ctggtctcct accttggaat tttgcacgaa 3060
aaccgcctcg ggcaaaacgt gcttcattcc acgctcaagg gcgaggcgcg ccgcgactac 3120
gtccgcgact gcgtttactt atttctgtgc tacacctggc aaacggccat gggcgtgtgg 3180
cagcaatgcc tggaggagcg caacctaaag gagctgcaga agctgctaaa gcaaaacttg 3240
aaggacctat ggacggcctt caacgagcgc tccgtggccg cgcacctggc ggacattatc 3300
ttccccgaac gcctgcttaa aaccctgcaa cagggtctgc cagacttcac cagtcaaagc 3360
atgttgcaaa actttaggaa ctttatccta gagcgttcag gaattctgcc cgccacctgc 3420
tgtgcgcttc ctagcgactt tgtgcccatt aagtaccgtg aatgccctcc gccgctttgg 3480
ggtcactgct accttctgca gctagccaac taccttgcct accactccga catcatggaa 3540
gacgtgagcg gtgacggcct actggagtgt cactgtcgct gcaacctatg caccccgcac 3600
cgctccctgg tctgcaattc gcaactgctt agcgaaagtc aaattatcgg tacctttgag 3660
ctgcagggtc cctcgcctga cgaaaagtcc gcggctccgg ggttgaaact cactccgggg 3720

-continued

```
ctgtggacgt cggcttacct tcgcaaattt gtacctgagg actaccacgc ccacgagatt   3780
aggttctacg aagaccaatc ccgcccgcca aatgcggagc ttaccgcctg cgtcattacc   3840
cagggccaca tccttggcca attgcaagcc atcaacaaag cccgccaaga gtttctgcta   3900
cgaaagggac ggggggttta cctggacccc cagtccggcg aggagctcaa cccaatcccc   3960
ccgccgccgc agccctatca gcagccgcgg gcccttgctt cccaggatgg cacccaaaaa   4020
gaagctgcag ctgccgccgc cgccacccac ggacgaggag gaatactggg acagtcaggc   4080
agaggaggtt ttggacgagg aggaggagat gatggaagac tgggacagcc tagacgaagc   4140
ttccgaggcc gaagaggtgt cagacgaaac accgtcaccc tcggtcgcat tcccctcgcc   4200
ggcgccccag aaattggcaa ccgttcccag catcgctaca acctccgctc ctcaggcgcc   4260
gccggcactg cctgttcgcc gacccaaccg tagatgggac accactggaa ccagggccgg   4320
taagtctaag cagccgccgc cgttagccca agagcaacaa cagcgccaag gctaccgctc   4380
gtggcgcggg cacaagaacg ccatagttgc ttgcttgcaa gactgtgggg gcaacatctc   4440
cttcgcccgc cgctttcttc tctaccatca cggcgtggcc ttcccccgta acatcctgca   4500
ttactaccgt catctctaca gcccctactg caccggcggc agcggcagcg gcagcaacag   4560
cagcggtcac acagaagcaa aggcgaccgg atagcaagac tctgacaaag cccaagaaat   4620
ccacagcggc ggcagcagca ggaggaggag cgctgcgtct ggcgcccaac gaacccgtat   4680
cgacccgcga gcttagaaat aggatttttc ccactctgta tgctatattt caacaaagca   4740
ggggccaaga acaagagctg aaaataaaaa acaggtctct gcgctccctc acccgcagct   4800
gcctgtatca caaaagcgaa gatcagcttc ggcgcacgct ggaagacgcg gaggctctct   4860
tcagcaaata ctgcgcgctg actcttaagg actagtttcg cgccctttct caaatttaag   4920
cgcgaaaact acgtcatctc cagcggccac acccggcgcc agcacctgtc gtcagcgcca   4980
ttatgagcaa ggaaattccc acgccctaca tgtggagtta ccagccacaa atgggacttg   5040
cggctggagc tgcccaagac tactcaaccc gaataaacta catgagcgcg ggaccccaca   5100
tgatatcccg ggtcaacgga atccgcgccc accgaaaccg aattctcctc gaacaggcgg   5160
ctattaccac cacacctcgt aataacctta atccccgtag ttggcccgct gccctggtgt   5220
accaggaaag tcccgctccc accactgtgg tacttcccag agacgcccag gccgaagttc   5280
agatgactaa ctcaggggcg cagcttgcgg gcggctttcg tcacagggtg cggtcgcccg   5340
ggcgttttag ggcggagtaa cttgcatgta ttgggaattg tagttttttt aaaatgggaa   5400
gtgacgtatc gtgggaaaac ggaagtgaag atttgaggaa gttgtgggtt ttttggcttt   5460
cgtttctggg cgtaggttcg cgtgcggttt tctgggtgtt ttttgtggac tttaaccgtt   5520
acgtcatttt ttagtcctat atatactcgc tctgtacttg gcccttttta cactgtgact   5580
gattgagctg gtgccgtgtc gagtggtgtt ttttaatagg tttttttact ggtaaggctg   5640
actgttatgg ctgccgctgt ggaagcgctg tatgttgttc tggagcggga gggtgctatt   5700
ttgcctaggc aggagggttt ttcaggtgtt tatgtgtttt tctctcctat taattttgtt   5760
atacctccta tgggggctgt aatgttgtct ctacgcctgc gggtatgtat tcccccgggc   5820
tatttcggtc gctttttagc actgaccgat gttaaccaac ctgatgtgtt taccgagtct   5880
tacattatga ctccggacat gaccgaggaa ctgtcggtgg tgctttttaa tcacggtgac   5940
cagttttttt acggtcacgc cggcatggcc gtagtccgtc ttatgcttat aagggttgtt   6000
tttcctgttg taagacaggc ttctaatgtt taaatgtttt tttttttgtt attttatttt   6060
gtgtttaatg caggaacccg cagacatgtt tgagagaaaa atggtgtctt tttctgtggt   6120
```

-continued

```
ggttccggaa cttacctgcc tttatctgca tgagcatgac tacgatgtgc ttgctttttt   6180
gcgcgaggct ttgcctgatt ttttgagcag caccttgcat tttatatcgc cgcccatgca   6240
acaagcttac ataggggcta cgctggttag catagctccg agtatgcgtg tcataatcag   6300
tgtgggttct tttgtcatgg ttcctggcgg ggaagtggcc gcgctggtcc gtgcagacct   6360
gcacgattat gttcagctgg ccctgcgaag ggacctacgg gatcgcggta tttttgttaa   6420
tgttccgctt ttgaatctta tacaggtctg tgaggaacct gaatttttgc aatcatgatt   6480
cgctgcttga ggctgaaggt ggagggcgct ctggagcaga tttttacaat ggccggactt   6540
aatattcggg atttgcttag agacatattg ataaggtggc gagatgaaaa ttatttgggc   6600
atggttgaag gtgctggaat gtttatagag gagattcacc ctgaagggtt tagcctttac   6660
gtccacttgg acgtgagggc agtttgcctt ttggaagcca ttgtgcaaca tcttacaaat   6720
gccattatct gttctttggc tgtagagttt gaccacgcca ccggagggga gcgcgttcac   6780
ttaatagatc ttcattttga ggttttggat aatcttttgg aataaaaaaa aaaaaacatg   6840
gttcttccag ctcttcccgc tcctcccgtg tgtgactcgc agaacgaatg tgtaggttgg   6900
ctgggtgtgg cttattctgc ggtggtggat gttatcaggg cagcggcgca tgaaggagtt   6960
tacatagaac ccgaagccag gggcgcctg gatgctttga gagagtggat atactacaac   7020
tactacacag agcgagctaa gcgacgagac cggagacgca gatctgtttg tcacgcccgc   7080
acctggtttt gcttcaggaa atatgactac gtccggcgtt ccatttggca tgacactacg   7140
accaacacga tctcggttgt ctcggcgcac tccgtacagt agggatcgcc tacctccttt   7200
tgagacagag acccgcgcta ccatactgga ggatcatccg ctgctgcccg aatgtaacac   7260
tttgacaatg cacaacgtga gttacgtgcg aggtcttccc tgcagtgtgg gatttacgct   7320
gattcaggaa tgggttgttc cctgggatat ggttctgacg cgggaggagc ttgtaatcct   7380
gaggaagtgt atgcacgtgt gcctgtgttg tgccaacatt gatatcatga cgagcatgat   7440
gatccatggt tacgagtcct gggctctcca ctgtcattgt tccagtcccg gttccctgca   7500
gtgcatagcc ggcgggcagg ttttggccag ctggtttagg atggtggtgg atggcgccat   7560
gtttaatcag aggtttatat ggtaccggga ggtggtgaat tacaacatgc caaaagaggt   7620
aatgtttatg tccagcgtgt ttatgagggg tcgccactta atctacctgc gcttgtggta   7680
tgatggccac gtgggttctg tggtccccgc catgagcttt ggatacagcg ccttgcactg   7740
tgggattttg aacaatattg tggtgctgtg ctgcagttac tgtgctgatt taagtgagat   7800
cagggtgcgc tgctgtgccc ggaggacaag gcgtctcatg ctgcgggcgg tgcgaatcat   7860
cgctgaggag accactgcca tgttgtattc ctgcaggacg gagcggcggc ggcagcagtt   7920
tattcgcgcg ctgctgcagc accaccgccc tatcctgatg cacgattatg actctacccc   7980
catgtaggcg tggacttccc cttcgccgcc cgttgagcaa ccgcaagttg gacagcagcc   8040
tgtggctcag cagctggaca gcgacatgaa cttaagcgag ctgcccgggg agtttattaa   8100
tatcactgat gagcgtttgg ctcgacagga aaccgtgtgg aatataacac ctaagaatat   8160
gtctgttacc catgatatga tgctttttaa ggccagccgg ggagaaagga ctgtgtactc   8220
tgtgtgttgg gagggaggtg gcaggttgaa tactagggtt ctgtgagttt gattaaggta   8280
cggtgatcaa tataagctat gtggtggtgg ggctatacta ctgaatgaaa aatgacttga   8340
aattttctgc aattgaaaaa taaacacgtt gaaacataac atgcaacagg ttcacgattc   8400
tttattcctg ggcaatgtag gagaaggtgt aagagttggt agcaaaagtt tcagtggtgt   8460
```

-continued

```
atttttccact ttcccaggac catgtaaaag acatagagta agtgcttacc tcgctagttt   8520
ctgtggattc actagaatcg atgtaggatg ttgcccctcc tgacgcggta ggagaagggg   8580
agggtgccct gcatgtctgc cgctgctctt gctcttgccg ctgctgagga ggggggcgca   8640
tctgccgcag caccggatgc atctgggaaa agcaaaaaag ggctcgtcc ctgtttccgg   8700
aggaatttgc aagcggggtc ttgcatgacg gggaggcaaa cccccgttcg ccgcagtccg   8760
gccggcccga gactcgaacc gggggtcctg cgactcaacc cttggaaaat aaccctccgg   8820
ctacagggag cgagccactt aatgctttcg ctttccagcc taaccgctta cgccgcgcgc   8880
ggccagtggc caaaaaagct agcgcagcag ccgccgcgcc tggaaggaag ccaaaaggag   8940
cgctcccccg ttgtctgacg tcgcacacct gggttcgaca cgcgggcggt aaccgcatgg   9000
atcacggcgg acggccggat ccggggttcg aaccccggtc gtccgccatg ataccttgc   9060
gaatttatcc accagaccac ggaagagtgc ccgcttacag gctctccttt tgcacggtct   9120
agagcgtcaa cgactgcgca cgcctcaccg gccagagcgt cccgaccatg gagcactttt   9180
tgccgctgcg caacatctgg aaccgcgtcc gcgactttcc gcgcgcctcc accaccgccg   9240
ccggcatcac ctggatgtcc aggtacatct acggattacg tcgacgttta aaccatatga   9300
tcagctcact caaaggcggt aatacggtta tccacagaat caggggataa cgcaggaaag   9360
aacatgtgag caaaaggcca gcaaaaggcc aggaaccgta aaaaggccgc gttgctggcg   9420
tttttccata ggctccgccc ccctgacgag catcacaaaa atcgacgctc aagtcagagg   9480
tggcgaaacc cgacaggact ataaagatac caggcgtttc cccctggaag ctccctcgtg   9540
cgctctcctg ttccgaccct gccgcttacc ggatacctgt ccgcctttct cccttcggga   9600
agcgtggcgc tttctcatag ctcacgctgt aggtatctca gttcggtgta ggtcgttcgc   9660
tccaagctgg gctgtgtgca cgaacccccc gttcagcccg accgctgcgc cttatccggt   9720
aactatcgtc ttgagtccaa cccggtaaga cacgacttat cgccactggc agcagccact   9780
ggtaacagga ttagcagagc gaggtatgta ggcggtgcta cagagttctt gaagtggtgg   9840
cctaactacg gctacactag aagaacagta tttggtatct gcgctctgct gaagccagtt   9900
accttcggaa aaagagttgg tagctcttga tccggcaaac aaaccaccgc tggtagcggt   9960
ggtttttttg tttgcaagca gcagattacg cgcagaaaaa aaggatctca agaagatcct  10020
ttgatctttt ctacggggtc tgacgctcag tggaacgaaa actcacgtta agggattttg  10080
gtcatgagat tatcaaaaag gatcttcacc tagatccttt taaattaaaa atgaagtttt  10140
aaatcaatct aaagtatata tgagtaaact tggtctgaca gttaccaatg cttaatcagt  10200
gaggcaccta tctcagcgat ctgtctattt cgttcatcca tagttgcctg actccccgtc  10260
gtgtagataa ctacgatacg ggagggctta ccatctggcc ccagtgctgc aatgataccg  10320
cgagacccac gctcaccggc tccagattta tcagcaataa accagccagc cggaagggcc  10380
gagcgcagaa gtggtcctgc aactttatcc gcctccatcc agtctattaa ttgttgccgg  10440
gaagctagag taagtagttc gccagttaat agtttgcgca acgttgttgc cattgctaca  10500
ggcatcgtgg tgtcacgctc gtcgtttggt atggcttcat tcagctccgg ttcccaacga  10560
tcaaggcgag ttacatgatc ccccatgttg tgcaaaaaag cggttagctc cttcggtcct  10620
ccgatcgttg tcagaagtaa gttggccgca gtgttatcac tcatggttat ggcagcactg  10680
cataattctc ttactgtcat gccatccgta agatgctttt ctgtgactgg tgagtactca  10740
accaagtcat tctgagaata gtgtatgcgg cgaccgagtt gctcttgccc ggcgtcaata  10800
cgggataata ccgcgccaca tagcagaact ttaaaagtgc tcatcattgg aaaacgttct  10860
```

-continued

```
tcggggcgaa aactctcaag gatcttaccg ctgttgagat ccagttcgat gtaacccact  10920

cgtgcaccca actgatcttc agcatctttt actttcacca gcgtttctgg gtgagcaaaa  10980

acaggaaggc aaaatgccgc aaaaaaggga ataagggcga cacggaaatg ttgaatactc  11040

atactcttcc tttttcaata ttattgaagc atttatcagg gttattgtct catgagcgga  11100

tacatatttg aatgtattta gaaaaataaa caaatagggg ttccgcgcac atttccccga  11160

aaagtgccac ctaaattgta agcgttaata ttttgttaaa attcgcgtta aatttttgtt  11220

aaatcagctc attttttaac caataggccg aaatcggcaa aatcccttat aaatcaaaag  11280

aatagaccga gatagggttg agtgttgttc cagtttggaa caagagtcca ctattaaaga  11340

acgtggactc caacgtcaaa gggcgaaaaa ccgtctatca gggcgatggc ccactacgtg  11400

aaccatcacc ctaatcaagt tttttggggt cgaggtgccg taaagcacta aatcggaacc  11460

ctaaagggag cccccgattt agagcttgac ggggaaagcc ggcgaacgtg gcgagaaagg  11520

aagggaagaa agcgaaagga gcgggcgcta gggcgctggc aagtgtagcg gtcacgctgc  11580

gcgtaaccac cacacccgcc gcgcttaatg cgccgctaca gggcgcgatg gatcc       11635
```

```
<210> SEQ ID NO 21
<211> LENGTH: 1002
<212> TYPE: PRT
<213> ORGANISM: Artificial Sequence
<220> FEATURE:
<223> OTHER INFORMATION: Mouse alphaLNNdDeltaG2

<400> SEQUENCE: 21

Met Arg Ala Trp Ile Phe Phe Leu Leu Cys Leu Ala Gly Arg Ala Leu
1               5                   10                  15

Ala Gln Gln Arg Gly Leu Phe Pro Ala Ile Leu Asn Leu Ala Thr Asn
            20                  25                  30

Ala His Ile Ser Ala Asn Ala Thr Cys Gly Glu Lys Gly Pro Glu Met
        35                  40                  45

Phe Cys Lys Leu Val Glu His Val Pro Gly Arg Pro Val Arg His Ala
    50                  55                  60

Gln Cys Arg Val Cys Asp Gly Asn Ser Thr Asn Pro Arg Glu Arg His
65                  70                  75                  80

Pro Ile Ser His Ala Ile Asp Gly Thr Asn Asn Trp Trp Gln Ser Pro
                85                  90                  95

Ser Ile Gln Asn Gly Arg Glu Tyr His Trp Val Thr Val Thr Leu Asp
            100                 105                 110

Leu Arg Gln Val Phe Gln Val Ala Tyr Ile Ile Ile Lys Ala Ala Asn
        115                 120                 125

Ala Pro Arg Pro Gly Asn Trp Ile Leu Glu Arg Ser Val Asp Gly Val
    130                 135                 140

Lys Phe Lys Pro Trp Gln Tyr Tyr Ala Val Ser Asp Thr Glu Cys Leu
145                 150                 155                 160

Thr Arg Tyr Lys Ile Thr Pro Arg Arg Gly Pro Pro Thr Tyr Arg Ala
                165                 170                 175

Asp Asn Glu Val Ile Cys Thr Ser Tyr Tyr Ser Lys Leu Val Pro Leu
            180                 185                 190

Glu His Gly Glu Ile His Thr Ser Leu Ile Asn Gly Arg Pro Ser Ala
        195                 200                 205

Asp Asp Pro Ser Pro Gln Leu Leu Glu Phe Thr Ser Ala Arg Tyr Ile
    210                 215                 220
```

-continued

```
Arg Leu Arg Leu Gln Arg Ile Arg Thr Leu Asn Ala Asp Leu Met Thr
225                 230                 235                 240

Leu Ser His Arg Asp Leu Arg Asp Leu Asp Pro Ile Val Thr Arg Arg
                245                 250                 255

Tyr Tyr Tyr Ser Ile Lys Asp Ile Ser Val Gly Gly Met Cys Ile Cys
            260                 265                 270

Tyr Gly His Ala Ser Ser Cys Pro Trp Asp Glu Glu Ala Lys Gln Leu
        275                 280                 285

Gln Cys Gln Cys Glu His Asn Thr Cys Gly Glu Ser Cys Asp Arg Cys
    290                 295                 300

Cys Pro Gly Tyr His Gln Gln Pro Trp Arg Pro Gly Thr Ile Ser Ser
305                 310                 315                 320

Gly Asn Glu Cys Glu Glu Cys Asn Cys His Asn Lys Ala Lys Asp Cys
                325                 330                 335

Tyr Tyr Asp Ser Ser Val Ala Lys Glu Arg Arg Ser Leu Asn Thr Ala
            340                 345                 350

Gly Gln Tyr Ser Gly Gly Gly Val Cys Val Asn Cys Ser Gln Asn Thr
        355                 360                 365

Thr Gly Ile Asn Cys Glu Thr Cys Ile Asp Gln Tyr Tyr Arg Pro His
    370                 375                 380

Lys Val Ser Pro Tyr Asp Asp His Pro Cys Arg Pro Cys Asn Cys Asp
385                 390                 395                 400

Pro Val Gly Ser Leu Ser Ser Val Cys Ile Lys Asp Asp Arg His Ala
                405                 410                 415

Asp Leu Ala Asn Gly Lys Trp Pro Gly Gln Cys Pro Cys Arg Lys Gly
            420                 425                 430

Tyr Ala Gly Asp Lys Cys Asp Arg Cys Gln Phe Gly Tyr Arg Gly Phe
        435                 440                 445

Pro Asn Cys Ile Pro Cys Asp Cys Arg Thr Val Gly Ser Leu Asn Glu
    450                 455                 460

Asp Pro Cys Ile Glu Pro Cys Leu Cys Lys Lys Asn Val Glu Gly Lys
465                 470                 475                 480

Asn Cys Asp Arg Cys Lys Pro Gly Phe Tyr Asn Leu Lys Glu Arg Asn
                485                 490                 495

Pro Glu Gly Cys Ser Glu Cys Phe Cys Phe Gly Val Ser Gly Val Cys
            500                 505                 510

Pro Ile Asn Tyr Cys Glu Thr Gly Leu His Asn Cys Asp Ile Pro Gln
        515                 520                 525

Arg Ala Gln Cys Ile Tyr Met Gly Gly Ser Ser Tyr Thr Cys Ser Cys
    530                 535                 540

Leu Pro Gly Phe Ser Gly Asp Gly Arg Ala Cys Arg Asp Val Asp Glu
545                 550                 555                 560

Cys Gln His Ser Arg Cys His Pro Asp Ala Phe Cys Tyr Asn Thr Pro
                565                 570                 575

Gly Ser Phe Thr Cys Gln Cys Lys Pro Gly Tyr Gln Gly Asp Gly Phe
            580                 585                 590

Arg Cys Met Pro Gly Glu Val Ser Lys Thr Arg Cys Gln Leu Glu Arg
        595                 600                 605

Glu His Ile Leu Gly Ala Ala Gly Gly Ala Asp Ala Gln Arg Pro Thr
    610                 615                 620

Leu Gln Gly Met Phe Val Pro Gln Cys Asp Glu Tyr Gly His Tyr Val
625                 630                 635                 640

Pro Thr Gln Cys His His Ser Thr Gly Tyr Cys Trp Cys Val Asp Arg
```

```
                645                 650                 655

Asp Gly Arg Glu Leu Glu Gly Ser Arg Thr Pro Pro Gly Met Arg Pro
            660                 665                 670

Pro Cys Leu Ser Thr Val Ala Pro Pro Ile His Gln Gly Pro Val Val
        675                 680                 685

Pro Thr Ala Val Ile Pro Leu Pro Pro Gly Thr His Leu Leu Phe Ala
    690                 695                 700

Gln Thr Gly Lys Ile Glu Arg Leu Pro Leu Glu Arg Asn Thr Met Lys
705                 710                 715                 720

Lys Thr Glu Arg Lys Ala Phe Leu His Ile Pro Ala Lys Val Ile Ile
                725                 730                 735

Gly Leu Ala Phe Asp Cys Val Asp Lys Val Val Tyr Trp Thr Asp Ile
            740                 745                 750

Ser Glu Pro Ser Ile Gly Arg Ala Ser Leu His Gly Gly Glu Pro Thr
        755                 760                 765

Thr Ile Ile Arg Gln Asp Leu Gly Ser Pro Glu Gly Ile Ala Leu Asp
    770                 775                 780

His Leu Gly Arg Thr Ile Phe Trp Thr Asp Ser Gln Leu Asp Arg Ile
785                 790                 795                 800

Glu Val Ala Lys Met Asp Gly Thr Gln Arg Arg Val Leu Phe Asp Thr
                805                 810                 815

Gly Leu Val Asn Pro Arg Gly Ile Val Thr Asp Pro Val Arg Gly Asn
            820                 825                 830

Leu Tyr Trp Thr Asp Trp Asn Arg Asp Asn Pro Lys Ile Glu Thr Ser
        835                 840                 845

His Met Asp Gly Thr Asn Arg Arg Ile Leu Ala Gln Asp Asn Leu Gly
    850                 855                 860

Leu Pro Asn Gly Leu Thr Phe Asp Ala Phe Ser Ser Gln Leu Cys Trp
865                 870                 875                 880

Val Asp Ala Gly Thr His Arg Ala Glu Cys Leu Asn Pro Ala Gln Pro
                885                 890                 895

Gly Arg Arg Lys Val Leu Glu Gly Leu Gln Tyr Pro Phe Ala Val Thr
            900                 905                 910

Ser Tyr Gly Lys Asn Leu Tyr Tyr Thr Asp Trp Lys Thr Asn Ser Val
        915                 920                 925

Ile Ala Met Asp Leu Ala Ile Ser Lys Glu Met Asp Thr Phe His Pro
    930                 935                 940

His Lys Gln Thr Arg Leu Tyr Gly Ile Thr Ile Ala Leu Ser Gln Cys
945                 950                 955                 960

Pro Gln Gly His Asn Tyr Cys Ser Val Asn Asn Gly Gly Cys Thr His
                965                 970                 975

Leu Cys Leu Pro Thr Pro Gly Ser Arg Thr Cys Arg Cys Pro Asp Asn
            980                 985                 990

Thr Leu Gly Val Asp Cys Ile Glu  Arg Lys
        995                 1000
```

<210> SEQ ID NO 22
<211> LENGTH: 1002
<212> TYPE: PRT
<213> ORGANISM: Artificial Sequence
<220> FEATURE:
<223> OTHER INFORMATION: Human shNoG2 amino acid sequence; Human alphaLNNDdDeltaG2

<400> SEQUENCE: 22

-continued

```
Met Arg Ala Trp Ile Phe Phe Leu Leu Cys Leu Ala Gly Arg Ala Leu
1               5                   10                  15

Ala Arg Gln Arg Gly Leu Phe Pro Ala Ile Leu Asn Leu Ala Ser Asn
            20                  25                  30

Ala His Ile Ser Thr Asn Ala Thr Cys Gly Glu Lys Gly Pro Glu Met
        35                  40                  45

Phe Cys Lys Leu Val Glu His Val Pro Gly Arg Pro Val Arg Asn Pro
    50                  55                  60

Gln Cys Arg Ile Cys Asp Gly Asn Ser Ala Asn Pro Arg Glu Arg His
65                  70                  75                  80

Pro Ile Ser His Ala Ile Asp Gly Thr Asn Asn Trp Trp Gln Ser Pro
                85                  90                  95

Ser Ile Gln Asn Gly Arg Glu Tyr His Trp Val Thr Ile Thr Leu Asp
            100                 105                 110

Leu Arg Gln Val Phe Gln Val Ala Tyr Val Ile Ile Lys Ala Ala Asn
        115                 120                 125

Ala Pro Arg Pro Gly Asn Trp Ile Leu Glu Arg Ser Leu Asp Gly Thr
    130                 135                 140

Thr Phe Ser Pro Trp Gln Tyr Tyr Ala Val Ser Asp Ser Glu Cys Leu
145                 150                 155                 160

Ser Arg Tyr Asn Ile Thr Pro Arg Arg Gly Pro Pro Thr Tyr Arg Ala
                165                 170                 175

Asp Asp Glu Val Ile Cys Thr Ser Tyr Tyr Ser Arg Leu Val Pro Leu
            180                 185                 190

Glu His Gly Glu Ile His Thr Ser Leu Ile Asn Gly Arg Pro Ser Ala
        195                 200                 205

Asp Asp Leu Ser Pro Lys Leu Leu Glu Phe Thr Ser Ala Arg Tyr Ile
    210                 215                 220

Arg Leu Arg Leu Gln Arg Ile Arg Thr Leu Asn Ala Asp Leu Met Thr
225                 230                 235                 240

Leu Ser His Arg Glu Pro Lys Glu Leu Asp Pro Ile Val Thr Arg Arg
                245                 250                 255

Tyr Tyr Tyr Ser Ile Lys Asp Ile Ser Val Gly Gly Met Cys Ile Cys
            260                 265                 270

Tyr Gly His Ala Ser Ser Cys Pro Trp Asp Glu Thr Thr Lys Lys Leu
        275                 280                 285

Gln Cys Gln Cys Glu His Asn Thr Cys Gly Glu Ser Cys Asn Arg Cys
    290                 295                 300

Cys Pro Gly Tyr His Gln Gln Pro Trp Arg Pro Gly Thr Val Ser Ser
305                 310                 315                 320

Gly Asn Thr Cys Glu Ala Cys Asn Cys His Asn Lys Ala Lys Asp Cys
                325                 330                 335

Tyr Tyr Asp Glu Ser Val Ala Lys Gln Lys Lys Ser Leu Asn Thr Ala
            340                 345                 350

Gly Gln Phe Arg Gly Gly Gly Val Cys Ile Asn Cys Leu Gln Asn Thr
        355                 360                 365

Met Gly Ile Asn Cys Glu Thr Cys Ile Asp Gly Tyr Tyr Arg Pro His
    370                 375                 380

Lys Val Ser Pro Tyr Glu Asp Glu Pro Cys Arg Pro Cys Asn Cys Asp
385                 390                 395                 400

Pro Val Gly Ser Leu Ser Ser Val Cys Ile Lys Asp Asp Leu His Ser
                405                 410                 415

Asp Leu His Asn Gly Lys Gln Pro Gly Gln Cys Pro Cys Lys Glu Gly
```

-continued

```
            420                 425                 430

Tyr Thr Gly Glu Lys Cys Asp Arg Cys Gln Leu Gly Tyr Lys Asp Tyr
        435                 440                 445

Pro Thr Cys Val Ser Cys Gly Cys Asn Pro Val Gly Ser Ala Ser Asp
    450                 455                 460

Glu Pro Cys Thr Gly Pro Cys Val Cys Lys Glu Asn Val Glu Gly Lys
465                 470                 475                 480

Ala Cys Asp Arg Cys Lys Pro Gly Phe Tyr Asn Leu Lys Glu Lys Asn
                485                 490                 495

Pro Arg Gly Cys Ser Glu Cys Phe Cys Phe Gly Val Ser Asp Val Cys
            500                 505                 510

Pro Ile Asn Tyr Cys Glu Thr Gly Leu His Asn Cys Asp Ile Pro Gln
        515                 520                 525

Arg Ala Gln Cys Ile Tyr Thr Gly Gly Ser Ser Tyr Thr Cys Ser Cys
    530                 535                 540

Leu Pro Gly Phe Ser Gly Asp Gly Gln Ala Cys Gln Asp Val Asp Glu
545                 550                 555                 560

Cys Gln Pro Ser Arg Cys His Pro Asp Ala Phe Cys Tyr Asn Thr Pro
                565                 570                 575

Gly Ser Phe Thr Cys Gln Cys Lys Pro Gly Tyr Gln Gly Asp Gly Phe
            580                 585                 590

Arg Cys Val Pro Gly Glu Val Glu Lys Thr Arg Cys Gln His Glu Arg
        595                 600                 605

Glu His Ile Leu Gly Ala Ala Gly Ala Thr Asp Pro Gln Arg Pro Ile
    610                 615                 620

Pro Pro Gly Leu Phe Val Pro Glu Cys Asp Ala His Gly His Tyr Ala
625                 630                 635                 640

Pro Thr Gln Cys His Gly Ser Thr Gly Tyr Cys Trp Cys Val Asp Arg
                645                 650                 655

Asp Gly Arg Glu Val Glu Gly Thr Arg Thr Arg Pro Gly Met Thr Pro
            660                 665                 670

Pro Cys Leu Ser Thr Val Ala Pro Pro Ile His Gln Gly Pro Ala Val
        675                 680                 685

Pro Thr Ala Val Ile Pro Leu Pro Pro Gly Thr His Leu Leu Phe Ala
    690                 695                 700

Gln Thr Gly Lys Ile Glu Arg Leu Pro Leu Glu Gly Asn Thr Met Arg
705                 710                 715                 720

Lys Thr Glu Ala Lys Ala Phe Leu His Val Pro Ala Lys Val Ile Ile
                725                 730                 735

Gly Leu Ala Phe Asp Cys Val Asp Lys Met Val Tyr Trp Thr Asp Ile
            740                 745                 750

Thr Glu Pro Ser Ile Gly Arg Ala Ser Leu His Gly Gly Glu Pro Thr
        755                 760                 765

Thr Ile Ile Arg Gln Asp Leu Gly Ser Pro Glu Gly Ile Ala Val Asp
    770                 775                 780

His Leu Gly Arg Asn Ile Phe Trp Thr Asp Ser Asn Leu Asp Arg Ile
785                 790                 795                 800

Glu Val Ala Lys Leu Asp Gly Thr Gln Arg Arg Val Leu Phe Glu Thr
                805                 810                 815

Asp Leu Val Asn Pro Arg Gly Ile Val Thr Asp Ser Val Arg Gly Asn
            820                 825                 830

Leu Tyr Trp Thr Asp Trp Asn Arg Asp Asn Pro Lys Ile Glu Thr Ser
        835                 840                 845
```

```
Tyr Met Asp Gly Thr Asn Arg Arg Ile Leu Val Gln Asp Asp Leu Gly
    850                 855                 860

Leu Pro Asn Gly Leu Thr Phe Asp Ala Phe Ser Ser Gln Leu Cys Trp
865                 870                 875                 880

Val Asp Ala Gly Thr Asn Arg Ala Glu Cys Leu Asn Pro Ser Gln Pro
                885                 890                 895

Ser Arg Arg Lys Ala Leu Glu Gly Leu Gln Tyr Pro Phe Ala Val Thr
            900                 905                 910

Ser Tyr Gly Lys Asn Leu Tyr Phe Thr Asp Trp Lys Met Asn Ser Val
        915                 920                 925

Val Ala Leu Asp Leu Ala Ile Ser Lys Glu Thr Asp Ala Phe Gln Pro
    930                 935                 940

His Lys Gln Thr Arg Leu Tyr Gly Ile Thr Thr Ala Leu Ser Gln Cys
945                 950                 955                 960

Pro Gln Gly His Asn Tyr Cys Ser Val Asn Asn Gly Gly Cys Thr His
                965                 970                 975

Leu Cys Leu Ala Thr Pro Gly Ser Arg Thr Cys Arg Cys Pro Asp Asn
            980                 985                 990

Thr Leu Gly Val Asp Cys Ile Glu  Gln Lys
        995                 1000
```

```
<210> SEQ ID NO 23
<211> LENGTH: 969
<212> TYPE: PRT
<213> ORGANISM: Artificial Sequence
<220> FEATURE:
<223> OTHER INFORMATION: mouse miniagrin sequence for AAV

<400> SEQUENCE: 23

Met Val Arg Pro Arg Leu Ser Phe Pro Ala Pro Leu Leu Pro Leu Leu
1               5                   10                  15

Leu Leu Leu Ala Ala Ala Ala Pro Ala Val Pro Gly Ala Ser Gly Thr
            20                  25                  30

Cys Pro Glu Arg Ala Leu Glu Arg Arg Glu Glu Glu Ala Asn Val Val
        35                  40                  45

Leu Thr Gly Thr Val Glu Glu Ile Leu Asn Val Asp Pro Val Gln His
    50                  55                  60

Thr Tyr Ser Cys Lys Val Arg Val Trp Arg Tyr Leu Lys Gly Lys Asp
65                  70                  75                  80

Val Val Ala Gln Glu Ser Leu Leu Asp Gly Gly Asn Lys Val Val Ile
                85                  90                  95

Gly Gly Phe Gly Asp Pro Leu Ile Cys Asp Asn Gln Val Ser Thr Gly
            100                 105                 110

Asp Thr Arg Ile Phe Phe Val Asn Pro Ala Pro Pro Tyr Leu Trp Pro
        115                 120                 125

Ala His Lys Asn Glu Leu Met Leu Asn Ser Ser Leu Met Arg Ile Thr
    130                 135                 140

Leu Arg Asn Leu Glu Glu Val Glu Phe Cys Val Glu Asp Lys Pro Gly
145                 150                 155                 160

Ile His Phe Thr Ala Ala Pro Ser Met Pro Pro Asp Val Cys Arg Gly
                165                 170                 175

Met Leu Cys Gly Phe Gly Ala Val Cys Glu Pro Ser Val Glu Asp Pro
            180                 185                 190

Gly Arg Ala Ser Cys Val Cys Lys Lys Asn Val Cys Pro Ala Met Val
        195                 200                 205
```

-continued

```
Ala Pro Val Cys Gly Ser Asp Ala Ser Thr Tyr Ser Asn Glu Cys Glu
    210                 215                 220

Leu Gln Arg Ala Gln Cys Asn Gln Gln Arg Arg Ile Arg Leu Leu Arg
225                 230                 235                 240

Gln Gly Pro Cys Pro Pro Lys Ser Cys Asp Ser Gln Pro Cys Leu His
                245                 250                 255

Gly Gly Thr Cys Gln Asp Leu Asp Ser Gly Lys Gly Phe Ser Cys Ser
            260                 265                 270

Cys Thr Ala Gly Arg Ala Gly Thr Val Cys Glu Lys Val Gln Leu Pro
        275                 280                 285

Ser Val Pro Ala Phe Lys Gly His Ser Phe Leu Ala Phe Pro Thr Leu
    290                 295                 300

Arg Ala Tyr His Thr Leu Arg Leu Ala Leu Glu Phe Arg Ala Leu Glu
305                 310                 315                 320

Thr Glu Gly Leu Leu Leu Tyr Asn Gly Asn Ala Arg Gly Lys Asp Phe
                325                 330                 335

Leu Ala Leu Ala Leu Leu Asp Gly His Val Gln Phe Arg Phe Asp Thr
            340                 345                 350

Gly Ser Gly Pro Ala Val Leu Thr Ser Leu Val Pro Val Glu Pro Gly
        355                 360                 365

Arg Trp His Arg Leu Glu Leu Ser Arg His Trp Arg Gln Gly Thr Leu
    370                 375                 380

Ser Val Asp Gly Glu Ala Pro Val Val Gly Glu Ser Pro Ser Gly Thr
385                 390                 395                 400

Asp Gly Leu Asn Leu Asp Thr Lys Leu Tyr Val Gly Gly Leu Pro Glu
                405                 410                 415

Glu Gln Val Ala Thr Val Leu Asp Arg Thr Ser Val Gly Ile Gly Leu
            420                 425                 430

Lys Gly Cys Ile Arg Met Leu Asp Ile Asn Asn Gln Gln Leu Glu Leu
        435                 440                 445

Ser Asp Trp Gln Arg Ala Val Val Gln Ser Ser Gly Val Gly Glu Cys
    450                 455                 460

Gly Asp His Pro Cys Ser Pro Asn Pro Cys His Gly Gly Ala Leu Cys
465                 470                 475                 480

Gln Ala Leu Glu Ala Gly Val Phe Leu Cys Gln Cys Pro Pro Gly Arg
                485                 490                 495

Phe Gly Pro Thr Cys Ala Asp Glu Lys Asn Pro Cys Gln Pro Asn Pro
            500                 505                 510

Cys His Gly Ser Ala Pro Cys His Val Leu Ser Arg Gly Gly Ala Lys
        515                 520                 525

Cys Ala Cys Pro Leu Gly Arg Ser Gly Ser Phe Cys Glu Thr Val Leu
    530                 535                 540

Glu Asn Ala Gly Ser Arg Pro Phe Leu Ala Asp Phe Asn Gly Phe Ser
545                 550                 555                 560

Tyr Leu Glu Leu Lys Gly Leu His Thr Phe Glu Arg Asp Leu Gly Glu
                565                 570                 575

Lys Met Ala Leu Glu Met Val Phe Leu Ala Arg Gly Pro Ser Gly Leu
            580                 585                 590

Leu Leu Tyr Asn Gly Gln Lys Thr Asp Gly Lys Gly Asp Phe Val Ser
        595                 600                 605

Leu Ala Leu His Asn Arg His Leu Glu Phe Arg Tyr Asp Leu Gly Lys
    610                 615                 620
```

-continued

```
Gly Ala Ala Ile Ile Arg Ser Lys Glu Pro Ile Ala Leu Gly Thr Trp
625                 630                 635                 640

Val Arg Val Phe Leu Glu Arg Asn Gly Arg Lys Gly Ala Leu Gln Val
                645                 650                 655

Gly Asp Gly Pro Arg Val Leu Gly Glu Ser Pro Val Pro His Thr Met
            660                 665                 670

Leu Asn Leu Lys Glu Pro Leu Tyr Val Gly Gly Ala Pro Asp Phe Ser
        675                 680                 685

Lys Leu Ala Arg Gly Ala Ala Val Ala Ser Gly Phe Asp Gly Ala Ile
    690                 695                 700

Gln Leu Val Ser Leu Arg Gly His Gln Leu Leu Thr Gln Glu His Val
705                 710                 715                 720

Leu Arg Ala Val Asp Val Ala Pro Phe Ala Gly His Pro Cys Thr Gln
                725                 730                 735

Ala Val Asp Asn Pro Cys Leu Asn Gly Gly Ser Cys Ile Pro Arg Glu
            740                 745                 750

Ala Thr Tyr Glu Cys Leu Cys Pro Gly Gly Phe Ser Gly Leu His Cys
        755                 760                 765

Glu Lys Gly Ile Val Glu Lys Ser Val Gly Asp Leu Glu Thr Leu Ala
    770                 775                 780

Phe Asp Gly Arg Thr Tyr Ile Glu Tyr Leu Asn Ala Val Thr Glu Ser
785                 790                 795                 800

Glu Lys Ala Leu Gln Ser Asn His Phe Glu Leu Ser Leu Arg Thr Glu
                805                 810                 815

Ala Thr Gln Gly Leu Val Leu Trp Ile Gly Lys Val Gly Glu Arg Ala
            820                 825                 830

Asp Tyr Met Ala Leu Ala Ile Val Asp Gly His Leu Gln Leu Ser Tyr
        835                 840                 845

Asp Leu Gly Ser Gln Pro Val Val Leu Arg Ser Thr Val Lys Val Asn
    850                 855                 860

Thr Asn Arg Trp Leu Arg Val Arg Ala His Arg Glu His Arg Glu Gly
865                 870                 875                 880

Ser Leu Gln Val Gly Asn Glu Ala Pro Val Thr Gly Ser Ser Pro Leu
                885                 890                 895

Gly Ala Thr Gln Leu Asp Thr Asp Gly Ala Leu Trp Leu Gly Gly Leu
            900                 905                 910

Gln Lys Leu Pro Val Gly Gln Ala Leu Pro Lys Ala Tyr Gly Thr Gly
        915                 920                 925

Phe Val Gly Cys Leu Arg Asp Val Val Val Gly His Arg Gln Leu His
    930                 935                 940

Leu Leu Glu Asp Ala Val Thr Lys Pro Glu Leu Arg Pro Cys Pro Thr
945                 950                 955                 960

Leu Ile Asp Gly Ser Gly Lys Ala Met
                965
```

<210> SEQ ID NO 24
<211> LENGTH: 3009
<212> TYPE: DNA
<213> ORGANISM: Artificial Sequence
<220> FEATURE:
<223> OTHER INFORMATION: Human shNoG2 nucleotide sequence

<400> SEQUENCE: 24

```
atgagggcct ggatcttctt tctcctttgc ctggccggga gggctctggc acggcagaga      60

ggcctgtttc ctgccattct caatcttgcc agcaatgctc acatcagcac caatgccacc     120
```

-continued

```
tgtggcgaga aggggccgga gatgttctgc aaacttgtgg agcatgtgcc aggtcggccc    180
gtccgaaacc cacagtgccg gatctgtgat ggcaacagcg caaaccccag agaacgccat    240
ccaatatcac atgccataga tggcaccaat aactggtggc aaagtcccag cattcagaat    300
gggagagaat atcactgggt cacaatcact ctggacttaa gacaggtctt tcaagttgca    360
tatgtcatca ttaaagctgc caatgcccct cgacctggaa actggatttt ggagcgttct    420
ctggatggca ccacgttcag cccctggcag tattatgcag tcagcgactc agagtgtttg    480
tctcgttaca atataactcc aagacgaggg ccacccacct acagggctga tgatgaagtg    540
atctgcacct cctattattc cagattggtg ccacttgagc atggagagat tcatacatca    600
ctcatcaatg gcagaccaag cgctgacgat ctttcaccca agttgttgga attcacttct    660
gcacgatata ttcgccttcg cttgcaacgc attagaacgc tcaatgcaga tctcatgacc    720
cttagccacc gggaacctaa agaactggat cctattgtta ccagacgcta ttattattca    780
ataaaggaca tttctgttgg aggcatgtgt atctgctatg gccatgctag tagctgccca    840
tgggatgaaa ctacaaagaa actgcagtgt caatgtgagc ataatacttg cggggagagc    900
tgtaacaggt gctgtcctgg gtaccatcag cagccctgga ggccgggaac cgtgtcctcc    960
ggcaatacat gtgaagcatg taattgtcac aataaagcca aagactgtta ctatgatgaa   1020
agtgttgcaa agcagaagaa aagtttgaat actgctggac agttcagagg aggaggggtt   1080
tgcataaatt gcttgcagaa caccatggga atcaactgtg aaacctgtat tgatggatat   1140
tatagaccac acaaagtgtc tccttatgag gatgagcctt gccgcccctg taattgtgac   1200
cctgtggggt ccctcagttc tgtctgtatt aaggatgacc tccattctga cttacacaat   1260
gggaagcagc caggtcagtg cccatgtaag gaaggttata caggagaaaa atgtgatcgc   1320
tgccaacttg gctataagga ttacccgacc tgtgtctcct gtgggtgcaa cccagtgggc   1380
agtgccagtg atgagccctg cacagggccc tgtgtttgta aggaaaacgt tgaggggaag   1440
gcctgtgatc gctgcaagcc aggattctat aacttgaagg aaaaaaaccc ccggggctgc   1500
tccgagtgct tctgctttgg cgtttctgat gtctgcccca tcaactactg tgaaactggc   1560
cttcataact gcgacatacc ccagcgggcc cagtgtatct acacaggagg ctcctcctac   1620
acctgttcct gcttgccagg cttttctggg gatggccaag cctgccaaga tgtagatgaa   1680
tgccagccaa gccgatgtca ccctgacgcc ttctgctaca acactccagg ctctttcacg   1740
tgccagtgca aacctggtta tcagggagac ggcttccgtt gcgtgcccgg agaggtggag   1800
aaaacccggt gccagcacga gcgagaacac attctcgggg cagcgggggc gacagaccca   1860
cagcgaccca ttcctccggg gctgttcgtt cctgagtgcg atgcgcacgg gcactacgcg   1920
cccacccagt gccacggcag caccggctac tgctggtgcg tggatcgcga cggccgcgag   1980
gtggagggca ccaggaccag gcccgggatg acgcccccgt gtctgagtac agtggctccc   2040
ccgattcacc aaggacctgc ggtgcctacc gccgtgatcc ccttgcctcc tgggacccat   2100
ttactctttg cccagactgg gaagattgag cgcctgcccc tggagggaaa taccatgagg   2160
aagacagaag caaaggcgtt ccttcatgtc ccggctaaag tcatcattgg actggccttt   2220
gactgcgtgg acaagatggt ttactggacg gacatcactg agccttccat tgggagagct   2280
agtctacatg gtggagagcc aaccaccatc attagacaag atcttggaag tccagaaggt   2340
atcgctgttg atcaccttgg ccgcaacatc ttctggacag actctaacct ggatcgaata   2400
gaagtggcga agctggacgg cacgcagcgc cgggtgctct ttgagactga cttggtgaat   2460
```

-continued

```
cccagaggca ttgtaacgga ttccgtgaga gggaaccttt actggacaga ctggaacaga   2520

gataacccca agattgaaac ttcctacatg gacggcacga accggaggat ccttgtgcag   2580

gatgacctgg gcttgcccaa tggactgacc ttcgatgcgt tctcatctca gctctgctgg   2640

gtggatgcag gcaccaatcg ggcggaatgc ctgaacccca gtcagcccag cagacgcaag   2700

gctctcgaag ggctccagta tccttttgct gtgacgagct acgggaagaa tctgtatttc   2760

acagactgga agatgaattc cgtggttgct ctcgatcttg caatttccaa ggagacggat   2820

gctttccaac cccacaagca gacccggctg tatggcatca ccacggccct gtctcagtgt   2880

ccgcaaggcc ataactactg ctcagtgaac aatggcggct gcacccacct atgcttggcc   2940

accccaggga gcaggacctg ccgttgccct gacaacacct tgggagttga ctgtatcgaa   3000

cagaaatga                                                           3009


<210> SEQ ID NO 25
<211> LENGTH: 51
<212> TYPE: DNA
<213> ORGANISM: Artificial Sequence
<220> FEATURE:
<223> OTHER INFORMATION: Mouse BM-40 (Sparc) signal sequence [DNA, 51
      bp)

<400> SEQUENCE: 25

atgagggcct ggatcttctt tctcctttgc ctggccggga gggctctggc a              51


<210> SEQ ID NO 26
<211> LENGTH: 17
<212> TYPE: PRT
<213> ORGANISM: Artificial Sequence
<220> FEATURE:
<223> OTHER INFORMATION: Mouse BM-40 (Sparc) signal peptide

<400> SEQUENCE: 26

Met Arg Ala Trp Ile Phe Phe Leu Leu Cys Leu Ala Gly Arg Ala Leu
1               5                   10                  15

Ala


<210> SEQ ID NO 27
<211> LENGTH: 72
<212> TYPE: DNA
<213> ORGANISM: Artificial Sequence
<220> FEATURE:
<223> OTHER INFORMATION: Mouse Lm 1 endogenous signal sequence [DNA, 72
      bp]

<400> SEQUENCE: 27

atgcgcggca gcggcacggg agccgcgctc ctggtgctcc tggcctcggt gctctgggtc     60

accgtgcgga gc                                                         72


<210> SEQ ID NO 28
<211> LENGTH: 24
<212> TYPE: PRT
<213> ORGANISM: Artificial Sequence
<220> FEATURE:
<223> OTHER INFORMATION: Mouse laminin 1 endogenous signal peptide

<400> SEQUENCE: 28

Met Arg Gly Ser Gly Thr Gly Ala Ala Leu Leu Val Leu Leu Ala Ser
1               5                   10                  15

Val Leu Trp Val Thr Val Arg Ser
            20
```

<210> SEQ ID NO 29
<211> LENGTH: 51
<212> TYPE: DNA
<213> ORGANISM: Artificial Sequence
<220> FEATURE:
<223> OTHER INFORMATION: Laminin (Lm) 1 signal peptide [DNA, 51 bp]

<400> SEQUENCE: 29
atgagggcct ggatcttctt tctcctttgc ctggccggga gggctctggc a 51

<210> SEQ ID NO 30
<211> LENGTH: 17
<212> TYPE: PRT
<213> ORGANISM: Artificial Sequence
<220> FEATURE:
<223> OTHER INFORMATION: Human laminin 1 signal peptide

<400> SEQUENCE: 30

Met Arg Ala Trp Ile Phe Phe Leu Leu Cys Leu Ala Gly Arg Ala Leu
1 5 10 15

Ala

<210> SEQ ID NO 31
<211> LENGTH: 753
<212> TYPE: DNA
<213> ORGANISM: Artificial Sequence
<220> FEATURE:
<223> OTHER INFORMATION: Mouse Lm 1 LN domain [DNA, 753 bp]

<400> SEQUENCE: 31
cagcagagag gcttgttccc tgccattctc aacctggcca ccaatgccca catcagcgcc 60
aatgctacct gtggagagaa ggggcctgag atgttctgca aactcgtgga gcacgtgccg 120
ggccggcctg ttcgacacgc ccaatgccgg gtctgtgacg gtaacagtac gaatcctaga 180
gagcgccatc cgatatcaca cgcaatcgat ggcaccaaca actggtggca gagccccagt 240
attcagaatg ggagagagta tcactgggtc actgtcaccc tggacttacg gcaggtcttt 300
caagttgcat acatcatcat taaagctgcc aatgcccctc ggcctggaaa ctggattttg 360
gagcgctccg tggatggcgt caagttcaaa ccctggcagt actatgccgt cagcgataca 420
gagtgtttga cccgctacaa aataactcca cggcggggac ctcccactta cagagcagac 480
aacgaagtca tctgcacctc gtattattca aagctggtgc cacttgaaca tggagagatt 540
cacacatcac tcatcaatgg cagacccagc gctgacgacc cctcacccca gttgctggaa 600
ttcacctcag cacggtacat tcgccttcgt cttcagcgca tcagaacact caacgcagac 660
ctcatgaccc ttagccatcg ggacctcaga gaccttgacc ccattgtcac aagacgttat 720
tactattcga taaaagacat ttccgttgga ggc 753

<210> SEQ ID NO 32
<211> LENGTH: 251
<212> TYPE: PRT
<213> ORGANISM: Artificial Sequence
<220> FEATURE:
<223> OTHER INFORMATION: Mouse Lm 1 LN [polymerization domain]

<400> SEQUENCE: 32

Gln Gln Arg Gly Leu Phe Pro Ala Ile Leu Asn Leu Ala Thr Asn Ala
1 5 10 15

His Ile Ser Ala Asn Ala Thr Cys Gly Glu Lys Gly Pro Glu Met Phe
20 25 30

```
Cys Lys Leu Val Glu His Val Pro Gly Arg Pro Val Arg His Ala Gln
        35                  40                  45

Cys Arg Val Cys Asp Gly Asn Ser Thr Asn Pro Arg Glu Arg His Pro
    50                  55                  60

Ile Ser His Ala Ile Asp Gly Thr Asn Asn Trp Trp Gln Ser Pro Ser
65                  70                  75                  80

Ile Gln Asn Gly Arg Glu Tyr His Trp Val Thr Val Thr Leu Asp Leu
                85                  90                  95

Arg Gln Val Phe Gln Val Ala Tyr Ile Ile Ile Lys Ala Ala Asn Ala
            100                 105                 110

Pro Arg Pro Gly Asn Trp Ile Leu Glu Arg Ser Val Asp Gly Val Lys
        115                 120                 125

Phe Lys Pro Trp Gln Tyr Tyr Ala Val Ser Asp Thr Glu Cys Leu Thr
    130                 135                 140

Arg Tyr Lys Ile Thr Pro Arg Arg Gly Pro Pro Thr Tyr Arg Ala Asp
145                 150                 155                 160

Asn Glu Val Ile Cys Thr Ser Tyr Tyr Ser Lys Leu Val Pro Leu Glu
                165                 170                 175

His Gly Glu Ile His Thr Ser Leu Ile Asn Gly Arg Pro Ser Ala Asp
            180                 185                 190

Asp Pro Ser Pro Gln Leu Leu Glu Phe Thr Ser Ala Arg Tyr Ile Arg
        195                 200                 205

Leu Arg Leu Gln Arg Ile Arg Thr Leu Asn Ala Asp Leu Met Thr Leu
    210                 215                 220

Ser His Arg Asp Leu Arg Asp Leu Asp Pro Ile Val Thr Arg Arg Tyr
225                 230                 235                 240

Tyr Tyr Ser Ile Lys Asp Ile Ser Val Gly Gly
                245                 250
```

<210> SEQ ID NO 33
<211> LENGTH: 1020
<212> TYPE: DNA
<213> ORGANISM: Artificial Sequence
<220> FEATURE:
<223> OTHER INFORMATION: Human Lm 1 LN [DNA, 753 bp]

<400> SEQUENCE: 33

```
cggcagagag gcctgtttcc tgccattctc aatcttgcca gcaatgctca catcagcacc     60

aatgccacct gtggcgagaa ggggccggag atgttctgca aacttgtgga gcatgtgcca    120

ggtcggcccg tccgaaaccc acagtgccgg atctgtgatg gcaacagcgc aaaccccaga    180

gaacgccatc caatatcaca tgccatagat ggcaccaata actggtggca aagtcccagc    240

attcagaatg ggagagaata tcactggcgg cagagaggcc tgtttcctgc cattctcaat    300

cttgccagca atgctcacat cagcaccaat gccacctgtg gcgagaaggg gccggagatg    360

ttctgcaaac ttgtggagca tgtgccaggt cggcccgtcc gaaacccaca gtgccggatc    420

tgtgatggca acagcgcaaa ccccagagaa cgccatccaa tatcacatgc catagatggc    480

accaataact ggtggcaaag tcccagcatt cagaatggga gagaatatca ctgggtcaca    540

atcactctgg acttaagaca ggtctttcaa gttgcatatg tcatcattaa agctgccaat    600

gcccctcgac ctggaaactg gattttggag cgttctctgg atggcaccac gttcagcccc    660

tggcagtatt atgcagtcag cgactcagag tgtttgtctc gttacaatat aactccaaga    720

cgagggccac ccacctacag ggctgatgat gaagtgatct gcacctccta ttattccaga    780

ttggtgccac ttgagcatgg agagattcat acatcactca tcaatggcag accaagcgct    840
```

gacgatcttt cacccaagtt gttggaattc acttctgcac gatatattcg ccttcgcttg 900
caacgcatta gaacgctcaa tgcagatctc atgaccctta gccaccggga acctaaagaa 960
ctggatccta ttgttaccag acgctattat tattcaataa aggacatttc tgttggaggc 1020

<210> SEQ ID NO 34
<211> LENGTH: 251
<212> TYPE: PRT
<213> ORGANISM: Artificial Sequence
<220> FEATURE:
<223> OTHER INFORMATION: Human Lm 1 LN

<400> SEQUENCE: 34

Arg Gln Arg Gly Leu Phe Pro Ala Ile Leu Asn Leu Ala Ser Asn Ala
1 5 10 15

His Ile Ser Thr Asn Ala Thr Cys Gly Glu Lys Gly Pro Glu Met Phe
20 25 30

Cys Lys Leu Val Glu His Val Pro Gly Arg Pro Val Arg Asn Pro Gln
35 40 45

Cys Arg Ile Cys Asp Gly Asn Ser Ala Asn Pro Arg Glu Arg His Pro
50 55 60

Ile Ser His Ala Ile Asp Gly Thr Asn Asn Trp Trp Gln Ser Pro Ser
65 70 75 80

Ile Gln Asn Gly Arg Glu Tyr His Trp Val Thr Ile Thr Leu Asp Leu
85 90 95

Arg Gln Val Phe Gln Val Ala Tyr Val Ile Ile Lys Ala Ala Asn Ala
100 105 110

Pro Arg Pro Gly Asn Trp Ile Leu Glu Arg Ser Leu Asp Gly Thr Thr
115 120 125

Phe Ser Pro Trp Gln Tyr Tyr Ala Val Ser Asp Ser Glu Cys Leu Ser
130 135 140

Arg Tyr Asn Ile Thr Pro Arg Arg Gly Pro Pro Thr Tyr Arg Ala Asp
145 150 155 160

Asp Glu Val Ile Cys Thr Ser Tyr Tyr Ser Arg Leu Val Pro Leu Glu
165 170 175

His Gly Glu Ile His Thr Ser Leu Ile Asn Gly Arg Pro Ser Ala Asp
180 185 190

Asp Leu Ser Pro Lys Leu Leu Glu Phe Thr Ser Ala Arg Tyr Ile Arg
195 200 205

Leu Arg Leu Gln Arg Ile Arg Thr Leu Asn Ala Asp Leu Met Thr Leu
210 215 220

Ser His Arg Glu Pro Lys Glu Leu Asp Pro Ile Val Thr Arg Arg Tyr
225 230 235 240

Tyr Tyr Ser Ile Lys Asp Ile Ser Val Gly Gly
245 250

<210> SEQ ID NO 35
<211> LENGTH: 171
<212> TYPE: DNA
<213> ORGANISM: Artificial Sequence
<220> FEATURE:
<223> OTHER INFORMATION: Mouse Lm 1 LEa-1 domain [DNA, 171 bp]

<400> SEQUENCE: 35
atgtgcattt gctacggcca tgccagcagc tgcccgtggg atgaagaagc aaagcaacta 60
cagtgtcagt gtgaacacaa tacgtgtggc gagagctgcg acaggtgctg tcctggctac 120
catcagcagc cctggaggcc cggaaccatt tcctccggca acgagtgtga g 171

<210> SEQ ID NO 36
<211> LENGTH: 57
<212> TYPE: PRT
<213> ORGANISM: Artificial Sequence
<220> FEATURE:
<223> OTHER INFORMATION: Mouse Lm 1 LEa-1 [required for LN folding; spacer domain]

<400> SEQUENCE: 36

Met Cys Ile Cys Tyr Gly His Ala Ser Ser Cys Pro Trp Asp Glu Glu
1 5 10 15

Ala Lys Gln Leu Gln Cys Gln Cys Glu His Asn Thr Cys Gly Glu Ser
20 25 30

Cys Asp Arg Cys Cys Pro Gly Tyr His Gln Gln Pro Trp Arg Pro Gly
35 40 45

Thr Ile Ser Ser Gly Asn Glu Cys Glu
50 55

<210> SEQ ID NO 37
<211> LENGTH: 171
<212> TYPE: DNA
<213> ORGANISM: Artificial Sequence
<220> FEATURE:
<223> OTHER INFORMATION: Human Lm 1 LEa-1 [DNA, 171 bp]

<400> SEQUENCE: 37
atgtgtatct gctatggcca tgctagtagc tgcccatggg atgaaactac aaagaaactg 60
cagtgtcaat gtgagcataa tacttgcggg gagagctgta acaggtgctg tcctgggtac 120
catcagcagc cctggaggcc gggaaccgtg tcctccggca atacatgtga a 171

<210> SEQ ID NO 38
<211> LENGTH: 57
<212> TYPE: PRT
<213> ORGANISM: Artificial Sequence
<220> FEATURE:
<223> OTHER INFORMATION: Human Lm 1 LEa-1

<400> SEQUENCE: 38

Met Cys Ile Cys Tyr Gly His Ala Ser Ser Cys Pro Trp Asp Glu Thr
1 5 10 15

Thr Lys Lys Leu Gln Cys Gln Cys Glu His Asn Thr Cys Gly Glu Ser
20 25 30

Cys Asn Arg Cys Cys Pro Gly Tyr His Gln Gln Pro Trp Arg Pro Gly
35 40 45

Thr Val Ser Ser Gly Asn Thr Cys Glu
50 55

<210> SEQ ID NO 39
<211> LENGTH: 210
<212> TYPE: DNA
<213> ORGANISM: Artificial Sequence
<220> FEATURE:
<223> OTHER INFORMATION: Mouse Lm 1 LEa-2 domain [DNA, 210 bp]

<400> SEQUENCE: 39
gaatgcaact gtcacaacaa agccaaagat tgttactatg acagcagtgt tgcaaaggag 60
aggagaagcc tgaacactgc cgggcagtac agtggaggag gggtttgtgt caactgctcg 120
cagaatacca cagggatcaa ctgtgaaacc tgtatcgacc agtattacag acctcacaag 180
gtatctcctt atgatgacca cccttgccgt 210

<210> SEQ ID NO 40
<211> LENGTH: 70
<212> TYPE: PRT
<213> ORGANISM: Artificial Sequence
<220> FEATURE:
<223> OTHER INFORMATION: Mouse Lm 1 LEa-2 [required for LN folding; spacer domain]

<400> SEQUENCE: 40

```
Glu Cys Asn Cys His Asn Lys Ala Lys Asp Cys Tyr Tyr Asp Ser Ser
1               5                   10                  15

Val Ala Lys Glu Arg Arg Ser Leu Asn Thr Ala Gly Gln Tyr Ser Gly
            20                  25                  30

Gly Gly Val Cys Val Asn Cys Ser Gln Asn Thr Thr Gly Ile Asn Cys
        35                  40                  45

Glu Thr Cys Ile Asp Gln Tyr Tyr Arg Pro His Lys Val Ser Pro Tyr
    50                  55                  60

Asp Asp His Pro Cys Arg
65                  70
```

<210> SEQ ID NO 41
<211> LENGTH: 210
<212> TYPE: DNA
<213> ORGANISM: Artificial Sequence
<220> FEATURE:
<223> OTHER INFORMATION: Human Lm 1 LEa-2 [DNA, 210 bp]

<400> SEQUENCE: 41

```
gcatgtaatt gtcacaataa agccaaagac tgttactatg atgaaagtgt tgcaaagcag     60

aagaaaagtt tgaatactgc tggacagttc agaggaggag ggtttgcat aaattgcttg    120

cagaacacca tgggaatcaa ctgtgaaacc tgtattgatg gatattatag accacacaaa    180

gtgtctcctt atgaggatga gccttgccgc                                      210
```

<210> SEQ ID NO 42
<211> LENGTH: 70
<212> TYPE: PRT
<213> ORGANISM: Artificial Sequence
<220> FEATURE:
<223> OTHER INFORMATION: Human Lm 1 LEa-2

<400> SEQUENCE: 42

```
Ala Cys Asn Cys His Asn Lys Ala Lys Asp Cys Tyr Tyr Asp Glu Ser
1               5                   10                  15

Val Ala Lys Gln Lys Lys Ser Leu Asn Thr Ala Gly Gln Phe Arg Gly
            20                  25                  30

Gly Gly Val Cys Ile Asn Cys Leu Gln Asn Thr Met Gly Ile Asn Cys
        35                  40                  45

Glu Thr Cys Ile Asp Gly Tyr Tyr Arg Pro His Lys Val Ser Pro Tyr
    50                  55                  60

Glu Asp Glu Pro Cys Arg
65                  70
```

<210> SEQ ID NO 43
<211> LENGTH: 171
<212> TYPE: DNA
<213> ORGANISM: Artificial Sequence
<220> FEATURE:
<223> OTHER INFORMATION: Mouse Lm 1 LEa-3 domain [DNA, 171 bp]

<400> SEQUENCE: 43

```
ccctgtaact gtgaccctgt ggggtctctg agttctgtct gtatcaagga tgaccgccat     60

gccgatttag ccaatggaaa gtggccaggt cagtgtccat gtaggaaagg ttatgctgga    120

gataaatgtg accgctgcca gtttggctac cggggtttcc caaattgcat c             171
```

<210> SEQ ID NO 44
<211> LENGTH: 57
<212> TYPE: PRT
<213> ORGANISM: Artificial Sequence
<220> FEATURE:
<223> OTHER INFORMATION: Mouse Lm 1 LEa-3 [domain acting as spacer]

<400> SEQUENCE: 44

```
Pro Cys Asn Cys Asp Pro Val Gly Ser Leu Ser Ser Val Cys Ile Lys
1               5                   10                  15

Asp Asp Arg His Ala Asp Leu Ala Asn Gly Lys Trp Pro Gly Gln Cys
            20                  25                  30

Pro Cys Arg Lys Gly Tyr Ala Gly Asp Lys Cys Asp Arg Cys Gln Phe
        35                  40                  45

Gly Tyr Arg Gly Phe Pro Asn Cys Ile
    50                  55
```

<210> SEQ ID NO 45
<211> LENGTH: 171
<212> TYPE: DNA
<213> ORGANISM: Artificial Sequence
<220> FEATURE:
<223> OTHER INFORMATION: Human Lm 1 LEa-3 [DNA, 171 bp]

<400> SEQUENCE: 45

```
ccctgtaatt gtgaccctgt ggggtccctc agttctgtct gtattaagga tgacctccat     60

tctgacttac acaatgggaa gcagccaggt cagtgcccat gtaaggaagg ttatacagga    120

gaaaaatgtg atcgctgcca acttggctat aaggattacc cgacctgtgt c             171
```

<210> SEQ ID NO 46
<211> LENGTH: 57
<212> TYPE: PRT
<213> ORGANISM: Artificial Sequence
<220> FEATURE:
<223> OTHER INFORMATION: Human Lm 1 LEa-3

<400> SEQUENCE: 46

```
Pro Cys Asn Cys Asp Pro Val Gly Ser Leu Ser Ser Val Cys Ile Lys
1               5                   10                  15

Asp Asp Leu His Ser Asp Leu His Asn Gly Lys Gln Pro Gly Gln Cys
            20                  25                  30

Pro Cys Lys Glu Gly Tyr Thr Gly Glu Lys Cys Asp Arg Cys Gln Leu
        35                  40                  45

Gly Tyr Lys Asp Tyr Pro Thr Cys Val
    50                  55
```

<210> SEQ ID NO 47
<211> LENGTH: 147
<212> TYPE: DNA
<213> ORGANISM: Artificial Sequence
<220> FEATURE:
<223> OTHER INFORMATION: Mouse Lm 1 LEa-4 domain [DNA, 147 bp]

<400> SEQUENCE: 47

```
ccctgtgact gcaggactgt cggcagcctg aatgaggatc catgcataga gccgtgtctt     60
```

tgtaagaaaa atgttgaggg taagaactgt gatcgctgca agccaggatt ctacaacttg 120
aaggaacgaa accccgaggg ctgctcc 147

<210> SEQ ID NO 48
<211> LENGTH: 49
<212> TYPE: PRT
<213> ORGANISM: Artificial Sequence
<220> FEATURE:
<223> OTHER INFORMATION: Mouse Lm 1 LEa-4 [spacer domain]

<400> SEQUENCE: 48

Pro Cys Asp Cys Arg Thr Val Gly Ser Leu Asn Glu Asp Pro Cys Ile
1 5 10 15

Glu Pro Cys Leu Cys Lys Lys Asn Val Glu Gly Lys Asn Cys Asp Arg
20 25 30

Cys Lys Pro Gly Phe Tyr Asn Leu Lys Glu Arg Asn Pro Glu Gly Cys
35 40 45

Ser

<210> SEQ ID NO 49
<211> LENGTH: 147
<212> TYPE: DNA
<213> ORGANISM: Artificial Sequence
<220> FEATURE:
<223> OTHER INFORMATION: Human Lm 1 LEa-4 [DNA, 147 bp]

<400> SEQUENCE: 49
tcctgtgggt gcaacccagt gggcagtgcc agtgatgagc cctgcacagg gccctgtgtt 60
tgtaaggaaa acgttgaggg gaaggcctgt gatcgctgca agccaggatt ctataacttg 120
aaggaaaaaa acccccgggg ctgctcc 147

<210> SEQ ID NO 50
<211> LENGTH: 49
<212> TYPE: PRT
<213> ORGANISM: Artificial Sequence
<220> FEATURE:
<223> OTHER INFORMATION: Human Lm 1 LEa-4

<400> SEQUENCE: 50

Ser Cys Gly Cys Asn Pro Val Gly Ser Ala Ser Asp Glu Pro Cys Thr
1 5 10 15

Gly Pro Cys Val Cys Lys Glu Asn Val Glu Gly Lys Ala Cys Asp Arg
20 25 30

Cys Lys Pro Gly Phe Tyr Asn Leu Lys Glu Lys Asn Pro Arg Gly Cys
35 40 45

Ser

<210> SEQ ID NO 51
<211> LENGTH: 33
<212> TYPE: DNA
<213> ORGANISM: Artificial Sequence
<220> FEATURE:
<223> OTHER INFORMATION: Mouse Lm 1 LF domain LE-type fragment with 3 cys [DNA, 33 bp]

<400> SEQUENCE: 51
gagtgcttct gcttcggtgt ctctggtgtc tgt 33

<210> SEQ ID NO 52
<211> LENGTH: 11

<212> TYPE: PRT
<213> ORGANISM: Artificial Sequence
<220> FEATURE:
<223> OTHER INFORMATION: Mouse Lm 1 LF fragment (with 3 cys) [spacer segment]

<400> SEQUENCE: 52

Glu Cys Phe Cys Phe Gly Val Ser Gly Val Cys
1               5                   10

<210> SEQ ID NO 53
<211> LENGTH: 33
<212> TYPE: DNA
<213> ORGANISM: Artificial Sequence
<220> FEATURE:
<223> OTHER INFORMATION: Human Lm 1 LF fragment (with 3 cys)[DNA, 33 bp]

<400> SEQUENCE: 53
gagtgcttct gctttggcgt ttctgatgtc tgc 33

<210> SEQ ID NO 54
<211> LENGTH: 10
<212> TYPE: PRT
<213> ORGANISM: Artificial Sequence
<220> FEATURE:
<223> OTHER INFORMATION: Human Lm 1 LF fragment (with 3 cys)

<400> SEQUENCE: 54

Cys Phe Cys Phe Gly Val Ser Asp Val Cys
1               5                   10

<210> SEQ ID NO 55
<211> LENGTH: 843
<212> TYPE: DNA
<213> ORGANISM: Artificial Sequence
<220> FEATURE:
<223> OTHER INFORMATION: Mouse Nidogen-1 G2 domain [DNA, 843 bp]

<400> SEQUENCE: 55
cagcagactt gtgccaacaa tagacaccag tgctccgtgc atgcagagtg cagagactat 60
gctactggct tctgctgcag gtgtgtggcc aactacacag gcaatggcag acagtgcgtg 120
gcagaaggct ctccacaacg ggtcaatggc aaggtgaagg gaaggatctt cgtggggagc 180
agccaggtcc ccgtggtgtt tgagaacact gacctgcact cctatgtggt gatgaaccac 240
gggcgctctt acacagccat cagcaccatc cctgaaaccg tcggctactc tctgctcccc 300
ctggcaccca ttggaggcat catcggatgg atgtttgcag tggagcagga tgggttcaag 360
aatgggttta gcatcactgg gggcgagttt acccggcaag ctgaggtgac cttcctgggg 420
cacccaggca agctggtcct gaagcagcag ttcagcggta ttgatgaaca tggacacctg 480
accatcagca cggagctgga gggccgcgtg ccgcagatcc cctatggagc ctcggtgcac 540
attgagccct acaccgaact gtaccactac tccagctcag tgatcacttc ctcctccacc 600
cgggagtaca cggtgatgga gcctgatcag gacggcgctg caccctcaca cacccatatt 660
taccagtggc gtcagaccat caccttccag gagtgtgccc acgatgacgc caggccagcc 720
ctgcccagca cccagcagct ctctgtggac agcgtgtttg tcctgtacaa caaggaggag 780
aggatcttgc gctatgccct cagcaactcc atcgggcctg tgagggatgg ctcccctgat 840
gcc 843

<210> SEQ ID NO 56
<211> LENGTH: 281

<212> TYPE: PRT
<213> ORGANISM: Artificial Sequence
<220> FEATURE:
<223> OTHER INFORMATION: Mouse Nidogen-1 G2 domain [direct collagen-IV, perlecan binding]

<400> SEQUENCE: 56

```
Gln Gln Thr Cys Ala Asn Asn Arg His Gln Cys Ser Val His Ala Glu
1               5                   10                  15

Cys Arg Asp Tyr Ala Thr Gly Phe Cys Cys Arg Cys Val Ala Asn Tyr
            20                  25                  30

Thr Gly Asn Gly Arg Gln Cys Val Ala Glu Gly Ser Pro Gln Arg Val
        35                  40                  45

Asn Gly Lys Val Lys Gly Arg Ile Phe Val Gly Ser Ser Gln Val Pro
    50                  55                  60

Val Val Phe Glu Asn Thr Asp Leu His Ser Tyr Val Val Met Asn His
65                  70                  75                  80

Gly Arg Ser Tyr Thr Ala Ile Ser Thr Ile Pro Glu Thr Val Gly Tyr
                85                  90                  95

Ser Leu Leu Pro Leu Ala Pro Ile Gly Gly Ile Ile Gly Trp Met Phe
            100                 105                 110

Ala Val Glu Gln Asp Gly Phe Lys Asn Gly Phe Ser Ile Thr Gly Gly
        115                 120                 125

Glu Phe Thr Arg Gln Ala Glu Val Thr Phe Leu Gly His Pro Gly Lys
    130                 135                 140

Leu Val Leu Lys Gln Gln Phe Ser Gly Ile Asp Glu His Gly His Leu
145                 150                 155                 160

Thr Ile Ser Thr Glu Leu Glu Gly Arg Val Pro Gln Ile Pro Tyr Gly
                165                 170                 175

Ala Ser Val His Ile Glu Pro Tyr Thr Glu Leu Tyr His Tyr Ser Ser
            180                 185                 190

Ser Val Ile Thr Ser Ser Ser Thr Arg Glu Tyr Thr Val Met Glu Pro
        195                 200                 205

Asp Gln Asp Gly Ala Ala Pro Ser His Thr His Ile Tyr Gln Trp Arg
    210                 215                 220

Gln Thr Ile Thr Phe Gln Glu Cys Ala His Asp Asp Ala Arg Pro Ala
225                 230                 235                 240

Leu Pro Ser Thr Gln Gln Leu Ser Val Asp Ser Val Phe Val Leu Tyr
                245                 250                 255

Asn Lys Glu Glu Arg Ile Leu Arg Tyr Ala Leu Ser Asn Ser Ile Gly
            260                 265                 270

Pro Val Arg Asp Gly Ser Pro Asp Ala
        275                 280
```

<210> SEQ ID NO 57
<211> LENGTH: 843
<212> TYPE: DNA
<213> ORGANISM: Artificial Sequence
<220> FEATURE:
<223> OTHER INFORMATION: Human Nidogen-1 G2 domain (direct collagen-IV, perlecan binding)[DNA, 843 bp]

<400> SEQUENCE: 57

```
cgccagacgt gtgctaacaa cagacaccag tgctcggtgc acgcagagtg cagggactac      60

gccacgggct tctgctgcag ctgtgtcgct ggctatacgg gcaatggcag gcaatgtgtt     120

gcagaaggtt ccccccagcg agtcaatggc aaggtgaaag gaaggatctt tgtggggagc     180
```

```
agccaggtcc ccattgtctt tgagaacact gacctccact cttacgtagt aatgaaccac    240

gggcgctcct acacagccat cagcaccatt cccgagaccg ttggatattc tctgcttcca    300

ctggccccag ttggaggcat cattggatgg atgtttgcag tggagcagga cggattcaag    360

aatgggttca gcatcaccgg gggtgagttc actcgccagg ctgaggtgac cttcgtgggg    420

cacccgggca atctggtcat taagcagcgg ttcagcggca tcgatgagca tgggcacctg    480

accatcgaca cggagctgga gggccgcgtg ccgcagattc cgttcggctc ctccgtgcac    540

attgagccct acacggagct gtaccactac tccacctcag tgatcacttc ctcctccacc    600

cgggagtaca cggtgactga gcccgagcga gatggggcat ctccttcacg catctacact    660

taccagtggc gccagaccat caccttccag gaatgcgtcc acgatgactc ccggccagcc    720

ctgcccagca cccagcagct ctcggtggac agcgtgttcg tcctgtacaa ccaggaggag    780

aagatcttgc gctatgctct cagcaactcc attgggcctg tgagggaagg ctcccctgat    840

gct                                                                  843
```

```
<210> SEQ ID NO 58
<211> LENGTH: 281
<212> TYPE: PRT
<213> ORGANISM: Artificial Sequence
<220> FEATURE:
<223> OTHER INFORMATION: Human Nidogen-1 G2 domain (direct collagen-IV,
      perlecan binding)

<400> SEQUENCE: 58

Arg Gln Thr Cys Ala Asn Asn Arg His Gln Cys Ser Val His Ala Glu
1               5                   10                  15

Cys Arg Asp Tyr Ala Thr Gly Phe Cys Cys Ser Cys Val Ala Gly Tyr
            20                  25                  30

Thr Gly Asn Gly Arg Gln Cys Val Ala Glu Gly Ser Pro Gln Arg Val
        35                  40                  45

Asn Gly Lys Val Lys Gly Arg Ile Phe Val Gly Ser Ser Gln Val Pro
    50                  55                  60

Ile Val Phe Glu Asn Thr Asp Leu His Ser Tyr Val Val Met Asn His
65                  70                  75                  80

Gly Arg Ser Tyr Thr Ala Ile Ser Thr Ile Pro Glu Thr Val Gly Tyr
                85                  90                  95

Ser Leu Leu Pro Leu Ala Pro Val Gly Gly Ile Ile Gly Trp Met Phe
            100                 105                 110

Ala Val Glu Gln Asp Gly Phe Lys Asn Gly Phe Ser Ile Thr Gly Gly
        115                 120                 125

Glu Phe Thr Arg Gln Ala Glu Val Thr Phe Val Gly His Pro Gly Asn
    130                 135                 140

Leu Val Ile Lys Gln Arg Phe Ser Gly Ile Asp Glu His Gly His Leu
145                 150                 155                 160

Thr Ile Asp Thr Glu Leu Glu Gly Arg Val Pro Gln Ile Pro Phe Gly
                165                 170                 175

Ser Ser Val His Ile Glu Pro Tyr Thr Glu Leu Tyr His Tyr Ser Thr
            180                 185                 190

Ser Val Ile Thr Ser Ser Ser Thr Arg Glu Tyr Thr Val Thr Glu Pro
        195                 200                 205

Glu Arg Asp Gly Ala Ser Pro Ser Arg Ile Tyr Thr Tyr Gln Trp Arg
    210                 215                 220

Gln Thr Ile Thr Phe Gln Glu Cys Val His Asp Asp Ser Arg Pro Ala
225                 230                 235                 240
```

-continued

```
Leu Pro Ser Thr Gln Gln Leu Ser Val Asp Ser Val Phe Val Leu Tyr
                245                 250                 255

Asn Gln Glu Glu Lys Ile Leu Arg Tyr Ala Leu Ser Asn Ser Ile Gly
            260                 265                 270

Pro Val Arg Glu Gly Ser Pro Asp Ala
        275                 280


<210> SEQ ID NO 59
<211> LENGTH: 126
<212> TYPE: DNA
<213> ORGANISM: Artificial Sequence
<220> FEATURE:
<223> OTHER INFORMATION: Mouse Nidogen-1 EGF-like 2 domain [126 bp]

<400> SEQUENCE: 59

cttcagaatc catgctacat tggcacccat gggtgtgaca gcaatgctgc ctgtcgccct      60

ggccctggaa cacagttcac ctgcgaatgc tccatcggct tccgaggaga cgggcagact     120

tgctat                                                                126


<210> SEQ ID NO 60
<211> LENGTH: 42
<212> TYPE: PRT
<213> ORGANISM: Artificial Sequence
<220> FEATURE:
<223> OTHER INFORMATION: Mouse Nidogen-1 EGF-like 2 [spacer]

<400> SEQUENCE: 60

Leu Gln Asn Pro Cys Tyr Ile Gly Thr His Gly Cys Asp Ser Asn Ala
1               5                   10                  15

Ala Cys Arg Pro Gly Pro Gly Thr Gln Phe Thr Cys Glu Cys Ser Ile
            20                  25                  30

Gly Phe Arg Gly Asp Gly Gln Thr Cys Tyr
        35                  40


<210> SEQ ID NO 61
<211> LENGTH: 126
<212> TYPE: DNA
<213> ORGANISM: Artificial Sequence
<220> FEATURE:
<223> OTHER INFORMATION: Human Nidogen-1 EGF-like 2 domain [DNA, 126 bp]

<400> SEQUENCE: 61

cttcagaatc cctgctacat cggcactcat gggtgtgaca ccaacgcggc ctgtcgccct      60

ggtcccagga cacagttcac ctgcgagtgc tccatcggct tccgaggaga cgggcgaacc     120

tgctat                                                                126


<210> SEQ ID NO 62
<211> LENGTH: 42
<212> TYPE: PRT
<213> ORGANISM: Artificial Sequence
<220> FEATURE:
<223> OTHER INFORMATION: Human Nidogen-1 EGF-like 2 domain

<400> SEQUENCE: 62

Leu Gln Asn Pro Cys Tyr Ile Gly Thr His Gly Cys Asp Thr Asn Ala
1               5                   10                  15

Ala Cys Arg Pro Gly Pro Arg Thr Gln Phe Thr Cys Glu Cys Ser Ile
            20                  25                  30

Gly Phe Arg Gly Asp Gly Arg Thr Cys Tyr
        35                  40
```

<210> SEQ ID NO 63
<211> LENGTH: 126
<212> TYPE: DNA
<213> ORGANISM: Artificial Sequence
<220> FEATURE:
<223> OTHER INFORMATION: Mouse Niogen-1 EGF-like 3 domain [126 bp]:

<400> SEQUENCE: 63
gatattgatg agtgttcaga gcagccttcc cgctgtggga accatgcggt ctgcaacaac 60
ctcccaggaa ccttccgctg cgagtgtgta gagggctacc acttctcaga caggggaaca 120
tgcgtg 126

<210> SEQ ID NO 64
<211> LENGTH: 42
<212> TYPE: PRT
<213> ORGANISM: Artificial Sequence
<220> FEATURE:
<223> OTHER INFORMATION: Mouse Nidogen-1 EGF-like 3

<400> SEQUENCE: 64

Asp Ile Asp Glu Cys Ser Glu Gln Pro Ser Arg Cys Gly Asn His Ala
1               5                   10                  15

Val Cys Asn Asn Leu Pro Gly Thr Phe Arg Cys Glu Cys Val Glu Gly
            20                  25                  30

Tyr His Phe Ser Asp Arg Gly Thr Cys Val
        35                  40

<210> SEQ ID NO 65
<211> LENGTH: 126
<212> TYPE: DNA
<213> ORGANISM: Artificial Sequence
<220> FEATURE:
<223> OTHER INFORMATION: Human Nidogen 1 EGF like 3 domain DNA 126 bp

<400> SEQUENCE: 65
cttcagaatc cctgctacat cggcactcat gggtgtgaca ccaacgcggc ctgtcgccct 60
ggtcccagga cacagttcac ctgcgagtgc tccatcggct tccgaggaga cgggcgaacc 120
tgctat 126

<210> SEQ ID NO 66
<211> LENGTH: 42
<212> TYPE: PRT
<213> ORGANISM: Artificial Sequence
<220> FEATURE:
<223> OTHER INFORMATION: Human Nidogen-1 EGF-like 3 domain

<400> SEQUENCE: 66

Leu Gln Asn Pro Cys Tyr Ile Gly Thr His Gly Cys Asp Thr Asn Ala
1               5                   10                  15

Ala Cys Arg Pro Gly Pro Arg Thr Gln Phe Thr Cys Glu Cys Ser Ile
            20                  25                  30

Gly Phe Arg Gly Asp Gly Arg Thr Cys Tyr
        35                  40

<210> SEQ ID NO 67
<211> LENGTH: 18
<212> TYPE: DNA
<213> ORGANISM: Artificial Sequence
<220> FEATURE:
<223> OTHER INFORMATION: Mouse Nidogen-1 spacer segment between EGF-3
and -4 [DNA, 18 bp]

<400> SEQUENCE: 67
gctgccgagg accaacgt 18

<210> SEQ ID NO 68
<211> LENGTH: 6
<212> TYPE: PRT
<213> ORGANISM: Artificial Sequence
<220> FEATURE:
<223> OTHER INFORMATION: Mouse Nidogen-1 spacer segment between EGF-3 and -4

<400> SEQUENCE: 68

Ala Ala Glu Asp Gln Arg
1 5

<210> SEQ ID NO 69
<211> LENGTH: 18
<212> TYPE: DNA
<213> ORGANISM: Artificial Sequence
<220> FEATURE:
<223> OTHER INFORMATION: Human Nidogen-1 spacer segment between EGF-3 and -4 [DNA, 18 bp]

<400> SEQUENCE: 69
gctgtcgtgg accagcgc 18

<210> SEQ ID NO 70
<211> LENGTH: 6
<212> TYPE: PRT
<213> ORGANISM: Artificial Sequence
<220> FEATURE:
<223> OTHER INFORMATION: Human Nidogen-1 spacer segment between EGF-3 and -4

<400> SEQUENCE: 70

Ala Val Val Asp Gln Arg
1 5

<210> SEQ ID NO 71
<211> LENGTH: 132
<212> TYPE: DNA
<213> ORGANISM: Artificial Sequence
<220> FEATURE:
<223> OTHER INFORMATION: Mouse Nidogen-1 EGF-like 4 domain [132 bp]

<400> SEQUENCE: 71
cccatcaact actgtgaaac tggtctccac aactgtgata tcccccagcg agcccagtgc 60
atctatatgg gtggttcctc ctacacctgc tcctgtctgc ctggcttctc tggggatggc 120
agagcctgcc ga 132

<210> SEQ ID NO 72
<211> LENGTH: 44
<212> TYPE: PRT
<213> ORGANISM: Artificial Sequence
<220> FEATURE:
<223> OTHER INFORMATION: Mouse Nidogen-1 EGF-like 4

<400> SEQUENCE: 72

Pro Ile Asn Tyr Cys Glu Thr Gly Leu His Asn Cys Asp Ile Pro Gln
1 5 10 15

Arg Ala Gln Cys Ile Tyr Met Gly Gly Ser Ser Tyr Thr Cys Ser Cys
20 25 30

Leu Pro Gly Phe Ser Gly Asp Gly Arg Ala Cys Arg

-continued

```
        35                  40


<210> SEQ ID NO 73
<211> LENGTH: 132
<212> TYPE: DNA
<213> ORGANISM: Artificial Sequence
<220> FEATURE:
<223> OTHER INFORMATION: Human Nidogen-1 EGF-like 4 domain [DNA, 132 bp]

<400> SEQUENCE: 73

cccatcaact actgtgaaac tggccttcat aactgcgaca taccccagcg ggcccagtgt     60

atctacacag gaggctcctc ctacacctgt tcctgcttgc caggcttttc tggggatggc    120

caagcctgcc aa                                                        132


<210> SEQ ID NO 74
<211> LENGTH: 44
<212> TYPE: PRT
<213> ORGANISM: Artificial Sequence
<220> FEATURE:
<223> OTHER INFORMATION: Human Nidogen-1 EGF-like 4 domain

<400> SEQUENCE: 74

Pro Ile Asn Tyr Cys Glu Thr Gly Leu His Asn Cys Asp Ile Pro Gln
1               5                   10                  15

Arg Ala Gln Cys Ile Tyr Thr Gly Gly Ser Ser Tyr Thr Cys Ser Cys
            20                  25                  30

Leu Pro Gly Phe Ser Gly Asp Gly Gln Ala Cys Gln
        35                  40


<210> SEQ ID NO 75
<211> LENGTH: 141
<212> TYPE: DNA
<213> ORGANISM: Artificial Sequence
<220> FEATURE:
<223> OTHER INFORMATION: Mouse Nidogen-1 EGF-like 5 domain [DNA, 141 bp]

<400> SEQUENCE: 75

gacgtggatg aatgccagca cagccgatgt caccccgatg ccttctgcta caacacacca     60

ggctctttca catgtcagtg caagcctggc tatcaggggg atggcttccg atgcatgccc    120

ggagaggtga gcaaaacccg g                                              141


<210> SEQ ID NO 76
<211> LENGTH: 47
<212> TYPE: PRT
<213> ORGANISM: Artificial Sequence
<220> FEATURE:
<223> OTHER INFORMATION: Mouse Nidogen-1 EGF-like 5 [spacer]

<400> SEQUENCE: 76

Asp Val Asp Glu Cys Gln His Ser Arg Cys His Pro Asp Ala Phe Cys
1               5                   10                  15

Tyr Asn Thr Pro Gly Ser Phe Thr Cys Gln Cys Lys Pro Gly Tyr Gln
            20                  25                  30

Gly Asp Gly Phe Arg Cys Met Pro Gly Glu Val Ser Lys Thr Arg
        35                  40                  45


<210> SEQ ID NO 77
<211> LENGTH: 141
<212> TYPE: DNA
<213> ORGANISM: Artificial Sequence
<220> FEATURE:
<223> OTHER INFORMATION: Human Nidogen-1 EGF-like 5 domain [DNA, 141 bp]
```

<400> SEQUENCE: 77

```
gatgtagatg aatgccagcc aagccgatgt caccctgacg ccttctgcta caacactcca      60

ggctctttca cgtgccagtg caaacctggt tatcagggag acggcttccg ttgcgtgccc     120

ggagaggtgg agaaaacccg g                                               141
```

<210> SEQ ID NO 78
<211> LENGTH: 47
<212> TYPE: PRT
<213> ORGANISM: Artificial Sequence
<220> FEATURE:
<223> OTHER INFORMATION: Human Nidogen-1 EGF-like 5 domain

<400> SEQUENCE: 78

```
Asp Val Asp Glu Cys Gln Pro Ser Arg Cys His Pro Asp Ala Phe Cys
1               5                   10                  15

Tyr Asn Thr Pro Gly Ser Phe Thr Cys Gln Cys Lys Pro Gly Tyr Gln
            20                  25                  30

Gly Asp Gly Phe Arg Cys Val Pro Gly Glu Val Glu Lys Thr Arg
        35                  40                  45
```

<210> SEQ ID NO 79
<211> LENGTH: 282
<212> TYPE: DNA
<213> ORGANISM: Artificial Sequence
<220> FEATURE:
<223> OTHER INFORMATION: Mouse Nidogen-1 G3 TY (thyroglobulin-like)
      domain [DNA, 282 bp]

<400> SEQUENCE: 79

```
tgtcaactgg aacgagagca catccttgga gcagccggcg gggcagatgc acagcggccc      60

accctgcagg ggatgtttgt gcctcagtgt gatgaatatg gacactatgt acccacccag     120

tgtcaccaca gcactggcta ctgctggtgt gtggaccgag atggtcggga gctggagggt     180

agccgtaccc cacctgggat gaggcccccg tgtctgagta cagtggctcc tcctattcac     240

cagggaccag tagtacctac agctgtcatc cccctgcctc ca                        282
```

<210> SEQ ID NO 80
<211> LENGTH: 94
<212> TYPE: PRT
<213> ORGANISM: Artificial Sequence
<220> FEATURE:
<223> OTHER INFORMATION: Mouse Nidogen “G3” TY (thyroglobulin-like)
      domain

<400> SEQUENCE: 80

```
Cys Gln Leu Glu Arg Glu His Ile Leu Gly Ala Ala Gly Gly Ala Asp
1               5                   10                  15

Ala Gln Arg Pro Thr Leu Gln Gly Met Phe Val Pro Gln Cys Asp Glu
            20                  25                  30

Tyr Gly His Tyr Val Pro Thr Gln Cys His His Ser Thr Gly Tyr Cys
        35                  40                  45

Trp Cys Val Asp Arg Asp Gly Arg Glu Leu Glu Gly Ser Arg Thr Pro
    50                  55                  60

Pro Gly Met Arg Pro Pro Cys Leu Ser Thr Val Ala Pro Pro Ile His
65                  70                  75                  80

Gln Gly Pro Val Val Pro Thr Ala Val Ile Pro Leu Pro Pro
                85                  90
```

<210> SEQ ID NO 81
<211> LENGTH: 282
<212> TYPE: DNA
<213> ORGANISM: Artificial Sequence
<220> FEATURE:
<223> OTHER INFORMATION: Human Nidogen-1 G3 TY (thyroglobulin-like) domain [DNA, 282 bp]

<400> SEQUENCE: 81

```
tgccagcacg agcgagaaca cattctcggg gcagcggggg cgacagaccc acagcgaccc     60

attcctccgg ggctgttcgt tcctgagtgc gatgcgcacg ggcactacgc gcccacccag    120

tgccacggca gcaccggcta ctgctggtgc gtggatcgcg acggccgcga ggtggagggc    180

accaggacca ggcccgggat gacgcccccg tgtctgagta cagtggctcc cccgattcac    240

caaggacctg cggtgcctac cgccgtgatc cccttgcctc ct                      282
```

<210> SEQ ID NO 82
<211> LENGTH: 94
<212> TYPE: PRT
<213> ORGANISM: Artificial Sequence
<220> FEATURE:
<223> OTHER INFORMATION: Human Nidogen-1 G3 TY (thyroglobulin-like) domain

<400> SEQUENCE: 82

```
Cys Gln His Glu Arg Glu His Ile Leu Gly Ala Ala Gly Ala Thr Asp
1               5                   10                  15

Pro Gln Arg Pro Ile Pro Pro Gly Leu Phe Val Pro Glu Cys Asp Ala
            20                  25                  30

His Gly His Tyr Ala Pro Thr Gln Cys His Gly Ser Thr Gly Tyr Cys
        35                  40                  45

Trp Cys Val Asp Arg Asp Gly Arg Glu Val Glu Gly Thr Arg Thr Arg
    50                  55                  60

Pro Gly Met Thr Pro Pro Cys Leu Ser Thr Val Ala Pro Pro Ile His
65                  70                  75                  80

Gln Gly Pro Ala Val Pro Thr Ala Val Ile Pro Leu Pro Pro
                85                  90
```

<210> SEQ ID NO 83
<211> LENGTH: 744
<212> TYPE: DNA
<213> ORGANISM: Artificial Sequence
<220> FEATURE:
<223> OTHER INFORMATION: Mouse Nidogen-1 G3 -Propeller domain [DNA, 744 bp]

<400> SEQUENCE: 83

```
gggacacact tactctttgc tcagactgga aagattgaac gcctgcccct ggaaagaaac     60

accatgaaga agacagaacg caaggccttt ctccatatcc ctgcaaaagt catcattgga    120

ctggcctttg actgcgtgga caaggtggtt tactggacag acatcagcga gccttccatt    180

gggagagcca gcctccacgg tggagagcca accaccatca ttcgacaaga tcttggaagc    240

cctgaaggca ttgcccttga ccatcttggt cgaaccatct tctggacgga ctctcagttg    300

gatcgaatag aagttgcaaa gatggatggc acccagcgcc gagtgctgtt tgacacgggt    360

ttggtgaatc ccagaggcat tgtgacagac cccgtaagag ggaaccttta ttggacagat    420

tggaacagag ataatcccaa aattgagact tctcacatgg atggcaccaa ccggaggatt    480

ctcgcacagg acaacctggg cttgcccaat ggtctgacct ttgatgcatt ctcatctcag    540

ctttgctggg tggatgcagg cacccatagg gcagaatgcc tgaacccagc tcagcctggc    600
```

agacgcaaag ttctcgaagg gctccagtat cctttcgctg tgactagcta tgggaagaat 660
ttgtactaca cagactggaa gacgaattca gtgattgcca tggaccttgc tatatccaaa 720
gagatggata ccttccaccc acac 744

<210> SEQ ID NO 84
<211> LENGTH: 248
<212> TYPE: PRT
<213> ORGANISM: Artificial Sequence
<220> FEATURE:
<223> OTHER INFORMATION: Mouse Nidogen “G3” -Propeller [laminin-binding domain]

<400> SEQUENCE: 84

Gly Thr His Leu Leu Phe Ala Gln Thr Gly Lys Ile Glu Arg Leu Pro
1 5 10 15

Leu Glu Arg Asn Thr Met Lys Lys Thr Glu Arg Lys Ala Phe Leu His
20 25 30

Ile Pro Ala Lys Val Ile Ile Gly Leu Ala Phe Asp Cys Val Asp Lys
35 40 45

Val Val Tyr Trp Thr Asp Ile Ser Glu Pro Ser Ile Gly Arg Ala Ser
50 55 60

Leu His Gly Gly Glu Pro Thr Thr Ile Ile Arg Gln Asp Leu Gly Ser
65 70 75 80

Pro Glu Gly Ile Ala Leu Asp His Leu Gly Arg Thr Ile Phe Trp Thr
85 90 95

Asp Ser Gln Leu Asp Arg Ile Glu Val Ala Lys Met Asp Gly Thr Gln
100 105 110

Arg Arg Val Leu Phe Asp Thr Gly Leu Val Asn Pro Arg Gly Ile Val
115 120 125

Thr Asp Pro Val Arg Gly Asn Leu Tyr Trp Thr Asp Trp Asn Arg Asp
130 135 140

Asn Pro Lys Ile Glu Thr Ser His Met Asp Gly Thr Asn Arg Arg Ile
145 150 155 160

Leu Ala Gln Asp Asn Leu Gly Leu Pro Asn Gly Leu Thr Phe Asp Ala
165 170 175

Phe Ser Ser Gln Leu Cys Trp Val Asp Ala Gly Thr His Arg Ala Glu
180 185 190

Cys Leu Asn Pro Ala Gln Pro Gly Arg Arg Lys Val Leu Glu Gly Leu
195 200 205

Gln Tyr Pro Phe Ala Val Thr Ser Tyr Gly Lys Asn Leu Tyr Tyr Thr
210 215 220

Asp Trp Lys Thr Asn Ser Val Ile Ala Met Asp Leu Ala Ile Ser Lys
225 230 235 240

Glu Met Asp Thr Phe His Pro His
245

<210> SEQ ID NO 85
<211> LENGTH: 744
<212> TYPE: DNA
<213> ORGANISM: Artificial Sequence
<220> FEATURE:
<223> OTHER INFORMATION: Human Nidogen-1 G3 -Propeller domain [DNA, 744 bp]

<400> SEQUENCE: 85
gggacccatt tactctttgc ccagactggg aagattgagc gcctgcccct ggagggaaat 60

-continued

```
accatgagga agacagaagc aaaggcgttc cttcatgtcc cggctaaagt catcattgga    120

ctggcctttg actgcgtgga caagatggtt tactggacgg acatcactga gccttccatt    180

gggagagcta gtctacatgg tggagagcca accaccatca ttagacaaga tcttggaagt    240

ccagaaggta tcgctgttga tcaccttggc cgcaacatct tctggacaga ctctaacctg    300

gatcgaatag aagtggcgaa gctggacggc acgcagcgcc gggtgctctt tgagactgac    360

ttggtgaatc ccagaggcat tgtaacggat tccgtgagag ggaaccttta ctggacagac    420

tggaacagag ataaccccaa gattgaaact tcctacatgg acggcacgaa ccggaggatc    480

cttgtgcagg atgacctggg cttgcccaat ggactgacct tcgatgcgtt ctcatctcag    540

ctctgctggg tggatgcagg caccaatcgg gcggaatgcc tgaaccccag tcagcccagc    600

agacgcaagg ctctcgaagg gctccagtat ccttttgctg tgacgagcta cgggaagaat    660

ctgtatttca cagactggaa gatgaattcc gtggttgctc tcgatcttgc aatttccaag    720

gagacggatg ctttccaacc ccac                                           744
```

```
<210> SEQ ID NO 86
<211> LENGTH: 248
<212> TYPE: PRT
<213> ORGANISM: Artificial Sequence
<220> FEATURE:
<223> OTHER INFORMATION: Human Nidogen-1 G3 -Propeller domain

<400> SEQUENCE: 86

Gly Thr His Leu Leu Phe Ala Gln Thr Gly Lys Ile Glu Arg Leu Pro
1               5                   10                  15

Leu Glu Gly Asn Thr Met Arg Lys Thr Glu Ala Lys Ala Phe Leu His
            20                  25                  30

Val Pro Ala Lys Val Ile Ile Gly Leu Ala Phe Asp Cys Val Asp Lys
        35                  40                  45

Met Val Tyr Trp Thr Asp Ile Thr Glu Pro Ser Ile Gly Arg Ala Ser
    50                  55                  60

Leu His Gly Gly Glu Pro Thr Thr Ile Ile Arg Gln Asp Leu Gly Ser
65                  70                  75                  80

Pro Glu Gly Ile Ala Val Asp His Leu Gly Arg Asn Ile Phe Trp Thr
                85                  90                  95

Asp Ser Asn Leu Asp Arg Ile Glu Val Ala Lys Leu Asp Gly Thr Gln
            100                 105                 110

Arg Arg Val Leu Phe Glu Thr Asp Leu Val Asn Pro Arg Gly Ile Val
        115                 120                 125

Thr Asp Ser Val Arg Gly Asn Leu Tyr Trp Thr Asp Trp Asn Arg Asp
    130                 135                 140

Asn Pro Lys Ile Glu Thr Ser Tyr Met Asp Gly Thr Asn Arg Arg Ile
145                 150                 155                 160

Leu Val Gln Asp Asp Leu Gly Leu Pro Asn Gly Leu Thr Phe Asp Ala
                165                 170                 175

Phe Ser Ser Gln Leu Cys Trp Val Asp Ala Gly Thr Asn Arg Ala Glu
            180                 185                 190

Cys Leu Asn Pro Ser Gln Pro Ser Arg Arg Lys Ala Leu Glu Gly Leu
        195                 200                 205

Gln Tyr Pro Phe Ala Val Thr Ser Tyr Gly Lys Asn Leu Tyr Phe Thr
    210                 215                 220

Asp Trp Lys Met Asn Ser Val Val Ala Leu Asp Leu Ala Ile Ser Lys
225                 230                 235                 240
```

```
Glu Thr Asp Ala Phe Gln Pro His
                245


<210> SEQ ID NO 87
<211> LENGTH: 171
<212> TYPE: DNA
<213> ORGANISM: Artificial Sequence
<220> FEATURE:
<223> OTHER INFORMATION: Mouse Nidogen-1 G3 EGF-like 6 domain [DNA, 171
      bp]

<400> SEQUENCE: 87

aagcagaccc ggctatatgg catcaccatc gccctgtccc agtgtcccca aggccacaat     60

tactgctcag tgaataatgg tggatgtacc cacctctgct tgcccactcc agggagcagg    120

acctgccgat gtcctgacaa caccctggga gttgactgca ttgaacggaa a             171


<210> SEQ ID NO 88
<211> LENGTH: 57
<212> TYPE: PRT
<213> ORGANISM: Artificial Sequence
<220> FEATURE:
<223> OTHER INFORMATION: Mouse Nidogen "G3" EGF-like 6 [contacts laminin
      LE surface]

<400> SEQUENCE: 88

Lys Gln Thr Arg Leu Tyr Gly Ile Thr Ile Ala Leu Ser Gln Cys Pro
1               5                   10                  15

Gln Gly His Asn Tyr Cys Ser Val Asn Asn Gly Gly Cys Thr His Leu
            20                  25                  30

Cys Leu Pro Thr Pro Gly Ser Arg Thr Cys Arg Cys Pro Asp Asn Thr
        35                  40                  45

Leu Gly Val Asp Cys Ile Glu Arg Lys
    50                  55


<210> SEQ ID NO 89
<211> LENGTH: 162
<212> TYPE: DNA
<213> ORGANISM: Artificial Sequence
<220> FEATURE:
<223> OTHER INFORMATION: Human Nidogen-1 G3 EGF-like 6 domain [DNA, 162
      bp]

<400> SEQUENCE: 89

aagcagaccc ggctgtatgg catcaccacg gccctgtctc agtgtccgca aggccataac     60

tactgctcag tgaacaatgg cggctgcacc cacctatgct tggccacccc agggagcagg    120

acctgccgtt gccctgacaa caccttggga gttgactgta tc                       162


<210> SEQ ID NO 90
<211> LENGTH: 54
<212> TYPE: PRT
<213> ORGANISM: Artificial Sequence
<220> FEATURE:
<223> OTHER INFORMATION: Human Nidogen-1 G3 EGF-like 6 domain

<400> SEQUENCE: 90

Lys Gln Thr Arg Leu Tyr Gly Ile Thr Thr Ala Leu Ser Gln Cys Pro
1               5                   10                  15

Gln Gly His Asn Tyr Cys Ser Val Asn Asn Gly Gly Cys Thr His Leu
            20                  25                  30

Cys Leu Ala Thr Pro Gly Ser Arg Thr Cys Arg Cys Pro Asp Asn Thr
        35                  40                  45
```

```
Leu Gly Val Asp Cys Ile
    50


<210> SEQ ID NO 91
<211> LENGTH: 63
<212> TYPE: DNA
<213> ORGANISM: Artificial Sequence
<220> FEATURE:
<223> OTHER INFORMATION: Mouse Laminin 1 signal peptide [63 bp]:

<400> SEQUENCE: 91

atggggctgc tccaggtgtt cgcctttggt gtcctagccc tatggggcac ccgagtgtgc     60

gct                                                                   63


<210> SEQ ID NO 92
<211> LENGTH: 21
<212> TYPE: PRT
<213> ORGANISM: Artificial Sequence
<220> FEATURE:
<223> OTHER INFORMATION: Mouse Laminin 1 signal peptide

<400> SEQUENCE: 92

Met Gly Leu Leu Gln Val Phe Ala Phe Gly Val Leu Ala Leu Trp Gly
1               5                   10                  15

Thr Arg Val Cys Ala
            20


<210> SEQ ID NO 93
<211> LENGTH: 63
<212> TYPE: DNA
<213> ORGANISM: Artificial Sequence
<220> FEATURE:
<223> OTHER INFORMATION: Human Laminin 1 signal [63 bp]

<400> SEQUENCE: 93

atggggcttc tccagttgct agctttcagt ttcttagccc tgtgcagagc ccgagtgcgc     60

gct                                                                   63


<210> SEQ ID NO 94
<211> LENGTH: 21
<212> TYPE: PRT
<213> ORGANISM: Artificial Sequence
<220> FEATURE:
<223> OTHER INFORMATION: Human Laminin 1 signal peptide

<400> SEQUENCE: 94

Met Gly Leu Leu Gln Leu Leu Ala Phe Ser Phe Leu Ala Leu Cys Arg
1               5                   10                  15

Ala Arg Val Arg Ala
            20


<210> SEQ ID NO 95
<211> LENGTH: 744
<212> TYPE: DNA
<213> ORGANISM: Artificial Sequence
<220> FEATURE:
<223> OTHER INFORMATION: Mouse Laminin 1 LN domain [744 bp]

<400> SEQUENCE: 95

caggaaccgg agttcagcta tggctgcgca gaaggcagct gctaccctgc cactggcgac     60

cttctcatcg gccgagcgca aaagctctcc gtgacttcga catgtggact gcacaaacca    120

gagccctact gtattgttag ccacctgcag gaggacaaga aatgcttcat atgtgactcc    180
```

-continued

```
cgagaccctt atcacgagac cctcaacccc gacagccatc tcattgagaa cgtggtcacc    240

acatttgctc caaaccgcct taagatctgg tggcaatcgg aaaatggtgt ggagaacgtg    300

accatccaac tggacctgga agcagaattc catttcactc atctcatcat gaccttcaag    360

acattccgcc cagccgccat gctgatcgag cggtcttctg actttgggaa gacttggggc    420

gtgtacagat acttcgccta cgactgtgag agctcgttcc caggcatttc aactggaccc    480

atgaagaaag tggatgacat catctgtgac tctcgatatt ctgacattga gccctcgaca    540

gaaggagagg taatatttcg tgctttagat cctgctttca aaattgaaga cccttatagt    600

ccaaggatac agaatctatt aaaaatcacc aacttgagaa tcaagtttgt gaaactgcac    660

accttggggg ataacctttt ggactccaga atggaaatcc gagagaagta ctattacgct    720

gtttatgata tggtggttcg aggg                                           744
```

```
<210> SEQ ID NO 96
<211> LENGTH: 248
<212> TYPE: PRT
<213> ORGANISM: Artificial Sequence
<220> FEATURE:
<223> OTHER INFORMATION: Mouse Laminin 1 LN

<400> SEQUENCE: 96

Gln Glu Pro Glu Phe Ser Tyr Gly Cys Ala Glu Gly Ser Cys Tyr Pro
1               5                   10                  15

Ala Thr Gly Asp Leu Leu Ile Gly Arg Ala Gln Lys Leu Ser Val Thr
            20                  25                  30

Ser Thr Cys Gly Leu His Lys Pro Glu Pro Tyr Cys Ile Val Ser His
        35                  40                  45

Leu Gln Glu Asp Lys Lys Cys Phe Ile Cys Asp Ser Arg Asp Pro Tyr
    50                  55                  60

His Glu Thr Leu Asn Pro Asp Ser His Leu Ile Glu Asn Val Val Thr
65                  70                  75                  80

Thr Phe Ala Pro Asn Arg Leu Lys Ile Trp Trp Gln Ser Glu Asn Gly
                85                  90                  95

Val Glu Asn Val Thr Ile Gln Leu Asp Leu Glu Ala Glu Phe His Phe
            100                 105                 110

Thr His Leu Ile Met Thr Phe Lys Thr Phe Arg Pro Ala Ala Met Leu
        115                 120                 125

Ile Glu Arg Ser Ser Asp Phe Gly Lys Thr Trp Gly Val Tyr Arg Tyr
    130                 135                 140

Phe Ala Tyr Asp Cys Glu Ser Ser Phe Pro Gly Ile Ser Thr Gly Pro
145                 150                 155                 160

Met Lys Lys Val Asp Asp Ile Ile Cys Asp Ser Arg Tyr Ser Asp Ile
                165                 170                 175

Glu Pro Ser Thr Glu Gly Glu Val Ile Phe Arg Ala Leu Asp Pro Ala
            180                 185                 190

Phe Lys Ile Glu Asp Pro Tyr Ser Pro Arg Ile Gln Asn Leu Leu Lys
        195                 200                 205

Ile Thr Asn Leu Arg Ile Lys Phe Val Lys Leu His Thr Leu Gly Asp
    210                 215                 220

Asn Leu Leu Asp Ser Arg Met Glu Ile Arg Glu Lys Tyr Tyr Tyr Ala
225                 230                 235                 240

Val Tyr Asp Met Val Val Arg Gly
                245
```

-continued

<210> SEQ ID NO 97
<211> LENGTH: 744
<212> TYPE: DNA
<213> ORGANISM: Artificial Sequence
<220> FEATURE:
<223> OTHER INFORMATION: Human Laminin 1 LN domain [DNA, 744 bp]

<400> SEQUENCE: 97
caggaacccg agttcagcta cggctgcgca gaaggcagct gctatcccgc cacgggcgac 60
cttctcatcg gccgagcaca gaagctttcg gtgacctcga cgtgcgggct gcacaagccc 120
gaaccctact gtatcgtcag ccacttgcag gaggacaaaa aatgcttcat atgcaattcc 180
caagatcctt atcatgagac cctgaatcct gacagccatc tcattgaaaa tgtggtcact 240
acatttgctc caaaccgcct taagatttgg tggcaatctg aaaatggtgt ggaaaatgta 300
actatccaac tggatttgga agcagaattc cattttactc atctcataat gactttcaag 360
acattccgtc cagctgctat gctgatagaa cgatcgtccg actttgggaa aacctggggt 420
gtgtatagat acttcgccta tgactgtgag gcctcgtttc caggcatttc aactggcccc 480
atgaaaaaag tcgatgacat aatttgtgat tctcgatatt ctgacattga accctcaact 540
gaaggagagg tgatatttcg tgctttagat cctgctttca aaatagaaga tccttatagc 600
ccaaggatac agaatttatt aaaaattacc aacttgagaa tcaagtttgt gaaactgcat 660
actttgggag ataaccttct ggattccagg atggaaatca gagaaaagta ttattatgca 720
gtttatgata tggtggttcg agga 744

<210> SEQ ID NO 98
<211> LENGTH: 248
<212> TYPE: PRT
<213> ORGANISM: Artificial Sequence
<220> FEATURE:
<223> OTHER INFORMATION: Human Laminin 1 LN

<400> SEQUENCE: 98

Gln Glu Pro Glu Phe Ser Tyr Gly Cys Ala Glu Gly Ser Cys Tyr Pro
1               5                   10                  15

Ala Thr Gly Asp Leu Leu Ile Gly Arg Ala Gln Lys Leu Ser Val Thr
            20                  25                  30

Ser Thr Cys Gly Leu His Lys Pro Glu Pro Tyr Cys Ile Val Ser His
        35                  40                  45

Leu Gln Glu Asp Lys Lys Cys Phe Ile Cys Asn Ser Gln Asp Pro Tyr
    50                  55                  60

His Glu Thr Leu Asn Pro Asp Ser His Leu Ile Glu Asn Val Val Thr
65                  70                  75                  80

Thr Phe Ala Pro Asn Arg Leu Lys Ile Trp Trp Gln Ser Glu Asn Gly
                85                  90                  95

Val Glu Asn Val Thr Ile Gln Leu Asp Leu Glu Ala Glu Phe His Phe
            100                 105                 110

Thr His Leu Ile Met Thr Phe Lys Thr Phe Arg Pro Ala Ala Met Leu
        115                 120                 125

Ile Glu Arg Ser Ser Asp Phe Gly Lys Thr Trp Gly Val Tyr Arg Tyr
    130                 135                 140

Phe Ala Tyr Asp Cys Glu Ala Ser Phe Pro Gly Ile Ser Thr Gly Pro
145                 150                 155                 160

Met Lys Lys Val Asp Asp Ile Ile Cys Asp Ser Arg Tyr Ser Asp Ile
                165                 170                 175

Glu Pro Ser Thr Glu Gly Glu Val Ile Phe Arg Ala Leu Asp Pro Ala

-continued

```
        180                 185                 190

Phe Lys Ile Glu Asp Pro Tyr Ser Pro Arg Ile Gln Asn Leu Leu Lys
        195                 200                 205

Ile Thr Asn Leu Arg Ile Lys Phe Val Lys Leu His Thr Leu Gly Asp
    210                 215                 220

Asn Leu Leu Asp Ser Arg Met Glu Ile Arg Glu Lys Tyr Tyr Tyr Ala
225                 230                 235                 240

Val Tyr Asp Met Val Val Arg Gly
                245


<210> SEQ ID NO 99
<211> LENGTH: 192
<212> TYPE: DNA
<213> ORGANISM: Artificial Sequence
<220> FEATURE:
<223> OTHER INFORMATION: Mouse Laminin 1 LEa-1 domain [DNA, 192 bp]

<400> SEQUENCE: 99

aactgcttct gctatggcca cgccagtgaa tgcgcccctg tggatggagt caatgaagaa      60

gtggaaggaa tggttcacgg gcactgcatg tgcagacaca acaccaaagg cctgaactgt     120

gagctgtgca tggatttcta ccacgatttg ccgtggagac ctgctgaagg ccggaacagc     180

aacgcctgca aa                                                         192


<210> SEQ ID NO 100
<211> LENGTH: 64
<212> TYPE: PRT
<213> ORGANISM: Artificial Sequence
<220> FEATURE:
<223> OTHER INFORMATION: Mouse Laminin 1 LEa-1

<400> SEQUENCE: 100

Asn Cys Phe Cys Tyr Gly His Ala Ser Glu Cys Ala Pro Val Asp Gly
1               5                   10                  15

Val Asn Glu Glu Val Glu Gly Met Val His Gly His Cys Met Cys Arg
            20                  25                  30

His Asn Thr Lys Gly Leu Asn Cys Glu Leu Cys Met Asp Phe Tyr His
        35                  40                  45

Asp Leu Pro Trp Arg Pro Ala Glu Gly Arg Asn Ser Asn Ala Cys Lys
    50                  55                  60


<210> SEQ ID NO 101
<211> LENGTH: 192
<212> TYPE: DNA
<213> ORGANISM: Artificial Sequence
<220> FEATURE:
<223> OTHER INFORMATION: Human Laminin 1 LEa-1 [DNA, 192 bp]

<400> SEQUENCE: 101

aattgcttct gctatggtca tgccagcgaa tgtgcccctg tggatggatt caatgaagaa      60

gtggaaggaa tggttcacgg acactgcatg tgcaggcata acaccaaggg cttaaactgt     120

gaactctgca tggatttcta ccatgattta ccttggagac ctgctgaagg ccgaaacagc     180

aacgcctgta aa                                                         192


<210> SEQ ID NO 102
<211> LENGTH: 64
<212> TYPE: PRT
<213> ORGANISM: Artificial Sequence
<220> FEATURE:
<223> OTHER INFORMATION: Human Laminin 1 LEa-1
```

<400> SEQUENCE: 102

Asn Cys Phe Cys Tyr Gly His Ala Ser Glu Cys Ala Pro Val Asp Gly
1 5 10 15

Phe Asn Glu Glu Val Glu Gly Met Val His Gly His Cys Met Cys Arg
20 25 30

His Asn Thr Lys Gly Leu Asn Cys Glu Leu Cys Met Asp Phe Tyr His
35 40 45

Asp Leu Pro Trp Arg Pro Ala Glu Gly Arg Asn Ser Asn Ala Cys Lys
50 55 60

<210> SEQ ID NO 103
<211> LENGTH: 189
<212> TYPE: DNA
<213> ORGANISM: Artificial Sequence
<220> FEATURE:
<223> OTHER INFORMATION: Mouse Laminin 1 LEa-2 domain [DNA, 189 bp]

<400> SEQUENCE: 103
aaatgtaact gcaatgaaca ttccagctcg tgtcactttg acatggcagt cttcctggct 60
actggcaacg tcagcggggg agtgtgtgat aactgtcagc acaacaccat ggggcgcaac 120
tgtgaacagt gcaaaccgtt ctacttccag caccctgaga gggacatccg ggaccccaat 180
ctctgtgaa 189

<210> SEQ ID NO 104
<211> LENGTH: 63
<212> TYPE: PRT
<213> ORGANISM: Artificial Sequence
<220> FEATURE:
<223> OTHER INFORMATION: Mouse Laminin 1 LEa-2

<400> SEQUENCE: 104

Lys Cys Asn Cys Asn Glu His Ser Ser Ser Cys His Phe Asp Met Ala
1 5 10 15

Val Phe Leu Ala Thr Gly Asn Val Ser Gly Gly Val Cys Asp Asn Cys
20 25 30

Gln His Asn Thr Met Gly Arg Asn Cys Glu Gln Cys Lys Pro Phe Tyr
35 40 45

Phe Gln His Pro Glu Arg Asp Ile Arg Asp Pro Asn Leu Cys Glu
50 55 60

<210> SEQ ID NO 105
<211> LENGTH: 189
<212> TYPE: DNA
<213> ORGANISM: Artificial Sequence
<220> FEATURE:
<223> OTHER INFORMATION: Human Laminin 1 LEa-2 [DNA, 189 bp]

<400> SEQUENCE: 105
aaatgtaact gcaatgaaca ttccatctct tgtcactttg acatggctgt ttacctggcc 60
acggggaacg tcagcggagg cgtgtgtgat gactgtcagc acaacaccat ggggcgcaac 120
tgtgagcagt gcaagccgtt ttactaccag cacccagaga gggacatccg agatcctaat 180
ttctgtgaa 189

<210> SEQ ID NO 106
<211> LENGTH: 63
<212> TYPE: PRT
<213> ORGANISM: Artificial Sequence
<220> FEATURE:

-continued

<223> OTHER INFORMATION: Human Laminin 1 LEa-

<400> SEQUENCE: 106

```
Lys Cys Asn Cys Asn Glu His Ser Ile Ser Cys His Phe Asp Met Ala
1               5                   10                  15

Val Tyr Leu Ala Thr Gly Asn Val Ser Gly Gly Val Cys Asp Asp Cys
            20                  25                  30

Gln His Asn Thr Met Gly Arg Asn Cys Glu Gln Cys Lys Pro Phe Tyr
        35                  40                  45

Tyr Gln His Pro Glu Arg Asp Ile Arg Asp Pro Asn Phe Cys Glu
    50                  55                  60
```

<210> SEQ ID NO 107
<211> LENGTH: 180
<212> TYPE: DNA
<213> ORGANISM: Artificial Sequence
<220> FEATURE:
<223> OTHER INFORMATION: Mouse Laminin 1 LEa-3 domain [DNA, 180 bp]

<400> SEQUENCE: 107

```
ccatgtacct gtgacccagc tggttctgag aatggcggga tctgtgatgg gtacactgat     60

ttttctgtgg gtctcattgc tggtcagtgt cggtgcaaat tgcacgtgga gggagagcgc    120

tgtgatgttt gtaaagaagg cttctacgac ttaagtgctg aagacccgta tggttgtaaa    180
```

<210> SEQ ID NO 108
<211> LENGTH: 60
<212> TYPE: PRT
<213> ORGANISM: Artificial Sequence
<220> FEATURE:
<223> OTHER INFORMATION: Mouse Laminin 1 LEa-3

<400> SEQUENCE: 108

```
Pro Cys Thr Cys Asp Pro Ala Gly Ser Glu Asn Gly Gly Ile Cys Asp
1               5                   10                  15

Gly Tyr Thr Asp Phe Ser Val Gly Leu Ile Ala Gly Gln Cys Arg Cys
            20                  25                  30

Lys Leu His Val Glu Gly Glu Arg Cys Asp Val Cys Lys Glu Gly Phe
        35                  40                  45

Tyr Asp Leu Ser Ala Glu Asp Pro Tyr Gly Cys Lys
    50                  55                  60
```

<210> SEQ ID NO 109
<211> LENGTH: 180
<212> TYPE: DNA
<213> ORGANISM: Artificial Sequence
<220> FEATURE:
<223> OTHER INFORMATION: Human Laminin 1 LEa-3 [DNA, 180 bp]

<400> SEQUENCE: 109

```
cgatgtacgt gtgacccagc tggctctcaa aatgagggaa tttgtgacag ctatactgat     60

ttttctactg gtctcattgc tggccagtgt cggtgtaaat taaatgtgga aggagaacat    120

tgtgatgttt gcaaagaagg cttctatgat ttaagcagtg aagatccatt tggttgtaaa    180
```

<210> SEQ ID NO 110
<211> LENGTH: 60
<212> TYPE: PRT
<213> ORGANISM: Artificial Sequence
<220> FEATURE:
<223> OTHER INFORMATION: Human Laminin 1 LEa-3

<400> SEQUENCE: 110

```
Arg Cys Thr Cys Asp Pro Ala Gly Ser Gln Asn Glu Gly Ile Cys Asp
1               5                   10                  15

Ser Tyr Thr Asp Phe Ser Thr Gly Leu Ile Ala Gly Gln Cys Arg Cys
            20                  25                  30

Lys Leu Asn Val Glu Gly Glu His Cys Asp Val Cys Lys Glu Gly Phe
        35                  40                  45

Tyr Asp Leu Ser Ser Glu Asp Pro Phe Gly Cys Lys
    50                  55                  60


<210> SEQ ID NO 111
<211> LENGTH: 156
<212> TYPE: DNA
<213> ORGANISM: Artificial Sequence
<220> FEATURE:
<223> OTHER INFORMATION: Mouse Laminin 1 LEa-4 domain [DNA, 156 bp]

<400> SEQUENCE: 111

tcatgtgctt gcaatcctct gggaacaatt cctggtggga atccttgtga ttctgagact     60

ggctactgct actgtaagcg cctggtgaca ggacagcgct gtgaccagtg cctgccgcag    120

cactggggtt taagcaatga tttggatggg tgtcga                              156


<210> SEQ ID NO 112
<211> LENGTH: 52
<212> TYPE: PRT
<213> ORGANISM: Artificial Sequence
<220> FEATURE:
<223> OTHER INFORMATION: Mouse Laminin 1 LEa-4

<400> SEQUENCE: 112

Ser Cys Ala Cys Asn Pro Leu Gly Thr Ile Pro Gly Gly Asn Pro Cys
1               5                   10                  15

Asp Ser Glu Thr Gly Tyr Cys Tyr Cys Lys Arg Leu Val Thr Gly Gln
            20                  25                  30

Arg Cys Asp Gln Cys Leu Pro Gln His Trp Gly Leu Ser Asn Asp Leu
        35                  40                  45

Asp Gly Cys Arg
    50


<210> SEQ ID NO 113
<211> LENGTH: 156
<212> TYPE: DNA
<213> ORGANISM: Artificial Sequence
<220> FEATURE:
<223> OTHER INFORMATION: Human Laminin 1 LEa-4 [DNA, 156 bp]

<400> SEQUENCE: 113

tcttgtgctt gcaatcctct gggaacaatt cctggaggga atccttgtga ttccgagaca     60

ggtcactgct actgcaagcg tctggtgaca ggacagcatt gtgaccagtg cctgccagag    120

cactggggct taagcaatga tttggatgga tgtcga                              156


<210> SEQ ID NO 114
<211> LENGTH: 52
<212> TYPE: PRT
<213> ORGANISM: Artificial Sequence
<220> FEATURE:
<223> OTHER INFORMATION: Human Laminin 1 LEa-4

<400> SEQUENCE: 114

Ser Cys Ala Cys Asn Pro Leu Gly Thr Ile Pro Gly Gly Asn Pro Cys
1               5                   10                  15
```

-continued

```
Asp Ser Glu Thr Gly His Cys Tyr Cys Lys Arg Leu Val Thr Gly Gln
            20                  25                  30

His Cys Asp Gln Cys Leu Pro Glu His Trp Gly Leu Ser Asn Asp Leu
        35                  40                  45

Asp Gly Cys Arg
    50


<210> SEQ ID NO 115
<211> LENGTH: 99
<212> TYPE: DNA
<213> ORGANISM: Artificial Sequence
<220> FEATURE:
<223> OTHER INFORMATION: Mouse Laminin 1 signal peptide [DNA, 99 bp]

<400> SEQUENCE: 115

atgacgggcg gcgggcgggc cgcgctggcc ctgcagcccc gggggcggct gtggccgctg      60

ttggctgtgc tggcggctgt ggcgggctgt gtccgggcg                             99


<210> SEQ ID NO 116
<211> LENGTH: 33
<212> TYPE: PRT
<213> ORGANISM: Artificial Sequence
<220> FEATURE:
<223> OTHER INFORMATION: Mouse Laminin 1 signal peptide

<400> SEQUENCE: 116

Met Thr Gly Gly Gly Arg Ala Ala Leu Ala Leu Gln Pro Arg Gly Arg
1               5                   10                  15

Leu Trp Pro Leu Leu Ala Val Leu Ala Ala Val Ala Gly Cys Val Arg
            20                  25                  30

Ala


<210> SEQ ID NO 117
<211> LENGTH: 99
<212> TYPE: DNA
<213> ORGANISM: Artificial Sequence
<220> FEATURE:
<223> OTHER INFORMATION: Human Laminin 1 signal peptide [DNA, 99 bp]

<400> SEQUENCE: 117

atgagaggga gccatcgggc cgcgccggcc ctgcggcccc gggggcggct ctggcccgtg      60

ctggccgtgc tggcggcggc cgccgcggcg ggctgtgcc                             99


<210> SEQ ID NO 118
<211> LENGTH: 33
<212> TYPE: PRT
<213> ORGANISM: Artificial Sequence
<220> FEATURE:
<223> OTHER INFORMATION: HUMAN Laminin 1signal peptide:

<400> SEQUENCE: 118

Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Ala Gly Cys
            20                  25                  30

Ala


<210> SEQ ID NO 119
<211> LENGTH: 768
<212> TYPE: DNA
<213> ORGANISM: Artificial Sequence
```

-continued

<220> FEATURE:
<223> OTHER INFORMATION: Mouse Laminin 1 LN domain [DNA, 768 bp]
(note: E/GAG (2) in human 1 vs D/GAC (1) D or E in mouse I,
but E in crystal structure of mouse LN-LEa)

<400> SEQUENCE: 119

```
gccatggact acaaggacga cgatgacaag gagtgcgcgg atgagggcgg gcggccgcag     60

cgctgcatgc cggagtttgt taatgccgcc ttcaatgtga ccgtggtggc taccaacacg    120

tgtgggactc cgcccgagga gtactgcgtg cagactgggg tgaccggagt cactaagtcc    180

tgtcacctgt gcgacgccgg ccagcagcac ctgcaacacg gggcagcctt cctgaccgac    240

tacaacaacc aggccgacac cacctggtgg caaagccaga ctatgctggc cggggtgcag    300

taccccaact ccatcaacct cacgctgcac ctgggaaagg cttttgacat cacttacgtg    360

cgcctcaagt tccacaccag ccgtccagag agcttcgcca tctataagcg cactcgggaa    420

gacgggccct ggattcctta tcagtactac agtgggtcct gtgagaacac gtactcaaag    480

gctaaccgtg gcttcatcag gaccggaggg gacgagcagc aggccttgtg tactgatgaa    540

ttcagtgaca tttcccccct caccggtggc aacgtggcct tttcaaccct ggaaggacgg    600

ccgagtgcct acaactttga caacagccct gtgctccagg aatgggtaac tgccactgac    660

atcagagtga cgctcaatcg cctgaacacc tttggagatg aagtgtttaa cgagcccaaa    720

gttctcaagt cttactatta cgcaatctca gactttgctg tgggcggc                 768
```

<210> SEQ ID NO 120
<211> LENGTH: 249
<212> TYPE: PRT
<213> ORGANISM: Artificial Sequence
<220> FEATURE:
<223> OTHER INFORMATION: Mouse Laminin 1 LN domain

<400> SEQUENCE: 120

```
Ala Met Asp Glu Cys Ala Asp Glu Gly Gly Arg Pro Gln Arg Cys Met
1               5                   10                  15

Pro Glu Phe Val Asn Ala Ala Phe Asn Val Thr Val Val Ala Thr Asn
            20                  25                  30

Thr Cys Gly Thr Pro Pro Glu Glu Tyr Cys Val Gln Thr Gly Val Thr
        35                  40                  45

Gly Val Thr Lys Ser Cys His Leu Cys Asp Ala Gly Gln Gln His Leu
    50                  55                  60

Gln His Gly Ala Ala Phe Leu Thr Asp Tyr Asn Asn Gln Ala Asp Thr
65                  70                  75                  80

Thr Trp Trp Gln Ser Gln Thr Met Leu Ala Gly Val Gln Tyr Pro Asn
                85                  90                  95

Ser Ile Asn Leu Thr Leu His Leu Gly Lys Ala Phe Asp Ile Thr Tyr
            100                 105                 110

Val Arg Leu Lys Phe His Thr Ser Arg Pro Glu Ser Phe Ala Ile Tyr
        115                 120                 125

Lys Arg Thr Arg Glu Asp Gly Pro Trp Ile Pro Tyr Gln Tyr Tyr Ser
    130                 135                 140

Gly Ser Cys Glu Asn Thr Tyr Ser Lys Ala Asn Arg Gly Phe Ile Arg
145                 150                 155                 160

Thr Gly Gly Asp Glu Gln Gln Ala Leu Cys Thr Asp Glu Phe Ser Asp
                165                 170                 175

Ile Ser Pro Leu Thr Gly Gly Asn Val Ala Phe Ser Thr Leu Glu Gly
            180                 185                 190
```

-continued

```
Arg Pro Ser Ala Tyr Asn Phe Asp Asn Ser Pro Val Leu Gln Glu Trp
        195                 200                 205

Val Thr Ala Thr Asp Ile Arg Val Thr Leu Asn Arg Leu Asn Thr Phe
    210                 215                 220

Gly Asp Glu Val Phe Asn Glu Pro Lys Val Leu Lys Ser Tyr Tyr Tyr
225                 230                 235                 240

Ala Ile Ser Asp Phe Ala Val Gly Gly
                245
```

<210> SEQ ID NO 121
<211> LENGTH: 753
<212> TYPE: DNA
<213> ORGANISM: Artificial Sequence
<220> FEATURE:
<223> OTHER INFORMATION: Human Laminin 1 LN domain [DNA, 753 bp]

<400> SEQUENCE: 121

```
caggcagcca tggacgagtg cacggacgag ggcgggcggc cgcaacgctg catgcccgag     60

ttcgtcaacg ccgctttcaa cgtgactgtg gtggccacca acacgtgtgg gactccgccc    120

gaggaatact gtgtgcagac cggggtgacc ggggtcacca agtcctgtca cctgtgcgac    180

gccgggcagc cccacctgca gcacggggca gccttcctga ccgactacaa caaccaggcc    240

gacaccacct ggtggcaaag ccagaccatg ctggccgggg tgcagtaccc cagctccatc    300

aacctcacgc tgcacctggg aaaagctttt gacatcacct atgtgcgtct caagttccac    360

accagccgcc cggagagctt tgccatttac aagcgcacat gggaagacgg gccctggatt    420

ccttaccagt actacagtgg ttcctgcgag aacacctact ccaaggcaaa ccgcggcttc    480

atcaggacag gaggggacga gcagcaggcc ttgtgtactg atgaattcag tgacatttct    540

cccctcactg gggcaacgt ggcctttttct accctggaag gaaggcccag cgcctataac    600

tttgacaata gccctgtgct gcaggaatgg gtaactgcca ctgacatcag tgtaactctt    660

aatcgcctga acacttttgg agatgaagtg tttaacgatc ccaaagttct caagtcctat    720

tattatgcca tctctgattt tgctgtaggt ggc                                 753
```

<210> SEQ ID NO 122
<211> LENGTH: 251
<212> TYPE: PRT
<213> ORGANISM: Artificial Sequence
<220> FEATURE:
<223> OTHER INFORMATION: Human Laminin 1 LN domain

<400> SEQUENCE: 122

```
Gln Ala Ala Met Asp Glu Cys Thr Asp Glu Gly Gly Arg Pro Gln Arg
1               5                   10                  15

Cys Met Pro Glu Phe Val Asn Ala Ala Phe Asn Val Thr Val Val Ala
            20                  25                  30

Thr Asn Thr Cys Gly Thr Pro Pro Glu Glu Tyr Cys Val Gln Thr Gly
        35                  40                  45

Val Thr Gly Val Thr Lys Ser Cys His Leu Cys Asp Ala Gly Gln Pro
    50                  55                  60

His Leu Gln His Gly Ala Ala Phe Leu Thr Asp Tyr Asn Asn Gln Ala
65                  70                  75                  80

Asp Thr Thr Trp Trp Gln Ser Gln Thr Met Leu Ala Gly Val Gln Tyr
                85                  90                  95

Pro Ser Ser Ile Asn Leu Thr Leu His Leu Gly Lys Ala Phe Asp Ile
            100                 105                 110
```

```
Thr Tyr Val Arg Leu Lys Phe His Thr Ser Arg Pro Glu Ser Phe Ala
        115                 120                 125

Ile Tyr Lys Arg Thr Trp Glu Asp Gly Pro Trp Ile Pro Tyr Gln Tyr
    130                 135                 140

Tyr Ser Gly Ser Cys Glu Asn Thr Tyr Ser Lys Ala Asn Arg Gly Phe
145                 150                 155                 160

Ile Arg Thr Gly Gly Asp Glu Gln Gln Ala Leu Cys Thr Asp Glu Phe
                165                 170                 175

Ser Asp Ile Ser Pro Leu Thr Gly Gly Asn Val Ala Phe Ser Thr Leu
            180                 185                 190

Glu Gly Arg Pro Ser Ala Tyr Asn Phe Asp Asn Ser Pro Val Leu Gln
        195                 200                 205

Glu Trp Val Thr Ala Thr Asp Ile Ser Val Thr Leu Asn Arg Leu Asn
    210                 215                 220

Thr Phe Gly Asp Glu Val Phe Asn Asp Pro Lys Val Leu Lys Ser Tyr
225                 230                 235                 240

Tyr Tyr Ala Ile Ser Asp Phe Ala Val Gly Gly
                245                 250
```

<210> SEQ ID NO 123
<211> LENGTH: 168
<212> TYPE: DNA
<213> ORGANISM: Artificial Sequence
<220> FEATURE:
<223> OTHER INFORMATION: Mouse Laminin 1 LEa 1 domain DNA 68 bp
note TGC for cys Durkin et al Biochemistry 27 14

<400> SEQUENCE: 123

```
aggtgtaaat gtaacggaca tgccagcgag tgtgtaaaga acgagtttga caaactcatg     60

tgcaactgca aacataacac atacggagtt gactgtgaaa agtgcctgcc tttcttcaat    120

gaccggccgt ggaggagggc gactgctgag agcgccagcg agtgcctt                 168
```

<210> SEQ ID NO 124
<211> LENGTH: 56
<212> TYPE: PRT
<213> ORGANISM: Artificial Sequence
<220> FEATURE:
<223> OTHER INFORMATION: Mouse Laminin 1 LEa-1

<400> SEQUENCE: 124

```
Arg Cys Lys Cys Asn Gly His Ala Ser Glu Cys Val Lys Asn Glu Phe
1               5                   10                  15

Asp Lys Leu Met Cys Asn Cys Lys His Asn Thr Tyr Gly Val Asp Cys
            20                  25                  30

Glu Lys Cys Leu Pro Phe Phe Asn Asp Arg Pro Trp Arg Arg Ala Thr
        35                  40                  45

Ala Glu Ser Ala Ser Glu Cys Leu
    50                  55
```

<210> SEQ ID NO 125
<211> LENGTH: 168
<212> TYPE: DNA
<213> ORGANISM: Artificial Sequence
<220> FEATURE:
<223> OTHER INFORMATION: Human Laminin 1 LEa-1 [DNA, 168 bp]

<400> SEQUENCE: 125

```
agatgtaaat gtaatggaca cgcaagcgag tgtatgaaga acgaatttga taagctggtg     60

tgtaattgca aacataacac atatggagta gactgtgaaa agtgtcttcc tttcttcaat    120
```

-continued gaccggccgt ggaggagggc aactgcggaa agtgccagtg aatgcctg 168

<210> SEQ ID NO 126
<211> LENGTH: 56
<212> TYPE: PRT
<213> ORGANISM: Artificial Sequence
<220> FEATURE:
<223> OTHER INFORMATION: Human Laminin 1 LEa-1

<400> SEQUENCE: 126

Arg Cys Lys Cys Asn Gly His Ala Ser Glu Cys Met Lys Asn Glu Phe
1 5 10 15

Asp Lys Leu Val Cys Asn Cys Lys His Asn Thr Tyr Gly Val Asp Cys
20 25 30

Glu Lys Cys Leu Pro Phe Phe Asn Asp Arg Pro Trp Arg Arg Ala Thr
35 40 45

Ala Glu Ser Ala Ser Glu Cys Leu
50 55

<210> SEQ ID NO 127
<211> LENGTH: 168
<212> TYPE: DNA
<213> ORGANISM: Artificial Sequence
<220> FEATURE:
<223> OTHER INFORMATION: Mouse Laminin 1 LEa-2 domain [DNA, 168 bp]

<400> SEQUENCE: 127
ccttgtgact gcaatggccg atcccaagag tgctactttg atcctgaact ataccgttcc 60
actggacatg gtggccactg taccaactgc cgggataaca cagatggtgc caagtgcgag 120
aggtgccggg agaatttctt ccgcctgggg aacactgaag cctgctct 168

<210> SEQ ID NO 128
<211> LENGTH: 56
<212> TYPE: PRT
<213> ORGANISM: Artificial Sequence
<220> FEATURE:
<223> OTHER INFORMATION: Mouse Laminin 1 LEa-2

<400> SEQUENCE: 128

Pro Cys Asp Cys Asn Gly Arg Ser Gln Glu Cys Tyr Phe Asp Pro Glu
1 5 10 15

Leu Tyr Arg Ser Thr Gly His Gly Gly His Cys Thr Asn Cys Arg Asp
20 25 30

Asn Thr Asp Gly Ala Lys Cys Glu Arg Cys Arg Glu Asn Phe Phe Arg
35 40 45

Leu Gly Asn Thr Glu Ala Cys Ser
50 55

<210> SEQ ID NO 129
<211> LENGTH: 168
<212> TYPE: DNA
<213> ORGANISM: Artificial Sequence
<220> FEATURE:
<223> OTHER INFORMATION: Human Laminin 1 LEa-2 [DNA, 168 bp]

<400> SEQUENCE: 129
ccctgtgatt gcaatggtcg atcccaggaa tgctacttcg accctgaact ctatcgttcc 60
actggccatg gggccactg taccaactgc caggataaca cagatggcgc ccactgtgag 120
aggtgccgag agaacttctt ccgccttggc aacaatgaag cctgctct 168

<210> SEQ ID NO 130
<211> LENGTH: 56
<212> TYPE: PRT
<213> ORGANISM: Artificial Sequence
<220> FEATURE:
<223> OTHER INFORMATION: Human Laminin 1 LEa-2

<400> SEQUENCE: 130

```
Pro Cys Asp Cys Asn Gly Arg Ser Gln Glu Cys Tyr Phe Asp Pro Glu
1               5                   10                  15

Leu Tyr Arg Ser Thr Gly His Gly Gly His Cys Thr Asn Cys Gln Asp
            20                  25                  30

Asn Thr Asp Gly Ala His Cys Glu Arg Cys Arg Glu Asn Phe Phe Arg
        35                  40                  45

Leu Gly Asn Asn Glu Ala Cys Ser
    50                  55
```

<210> SEQ ID NO 131
<211> LENGTH: 141
<212> TYPE: DNA
<213> ORGANISM: Artificial Sequence
<220> FEATURE:
<223> OTHER INFORMATION: Mouse Laminin 1 LEa-3 domain [DNA, 141 bp]

<400> SEQUENCE: 131

```
ccgtgccact gcagccctgt tggttctctc agcacacagt gtgacagtta cggcagatgc     60

agctgtaagc caggagtgat gggtgacaag tgtgaccgtt gtcagcctgg gttccattcc    120

ctcactgagg caggatgcag g                                              141
```

<210> SEQ ID NO 132
<211> LENGTH: 47
<212> TYPE: PRT
<213> ORGANISM: Artificial Sequence
<220> FEATURE:
<223> OTHER INFORMATION: Mouse Laminin 1 LEa-3

<400> SEQUENCE: 132

```
Pro Cys His Cys Ser Pro Val Gly Ser Leu Ser Thr Gln Cys Asp Ser
1               5                   10                  15

Tyr Gly Arg Cys Ser Cys Lys Pro Gly Val Met Gly Asp Lys Cys Asp
            20                  25                  30

Arg Cys Gln Pro Gly Phe His Ser Leu Thr Glu Ala Gly Cys Arg
        35                  40                  45
```

<210> SEQ ID NO 133
<211> LENGTH: 141
<212> TYPE: DNA
<213> ORGANISM: Artificial Sequence
<220> FEATURE:
<223> OTHER INFORMATION: Human Laminin 1 LEa-3 [DNA, 141 bp]

<400> SEQUENCE: 133

```
tcatgccact gtagtcctgt gggctctcta agcacacagt gtgatagtta cggcagatgc     60

agctgtaagc caggagtgat gggggacaaa tgtgaccgtt gccagcctgg attccattct    120

ctcactgaag caggatgcag g                                              141
```

<210> SEQ ID NO 134
<211> LENGTH: 47
<212> TYPE: PRT
<213> ORGANISM: Artificial Sequence
<220> FEATURE:

<223> OTHER INFORMATION: Human Laminin 1 LEa-3

<400> SEQUENCE: 134

Ser Cys His Cys Ser Pro Val Gly Ser Leu Ser Thr Gln Cys Asp Ser
1 5 10 15

Tyr Gly Arg Cys Ser Cys Lys Pro Gly Val Met Gly Asp Lys Cys Asp
20 25 30

Arg Cys Gln Pro Gly Phe His Ser Leu Thr Glu Ala Gly Cys Arg
35 40 45

<210> SEQ ID NO 135
<211> LENGTH: 150
<212> TYPE: DNA
<213> ORGANISM: Artificial Sequence
<220> FEATURE:
<223> OTHER INFORMATION: Mouse Laminin 1 LEa-4 [DNA, 150 bp]

<400> SEQUENCE: 135
ccatgctcct gcgatcttcg gggcagcaca gacgagtgta atgttgaaac aggaagatgc 60
gtttgcaaag acaatgttga aggcttcaac tgtgagagat gcaaacctgg attttttaat 120
ctggagtcat ctaatcctaa gggctgcaca 150

<210> SEQ ID NO 136
<211> LENGTH: 50
<212> TYPE: PRT
<213> ORGANISM: Artificial Sequence
<220> FEATURE:
<223> OTHER INFORMATION: Mouse Laminin 1 LEa-4

<400> SEQUENCE: 136

Pro Cys Ser Cys Asp Leu Arg Gly Ser Thr Asp Glu Cys Asn Val Glu
1 5 10 15

Thr Gly Arg Cys Val Cys Lys Asp Asn Val Glu Gly Phe Asn Cys Glu
20 25 30

Arg Cys Lys Pro Gly Phe Phe Asn Leu Glu Ser Ser Asn Pro Lys Gly
35 40 45

Cys Thr
50

<210> SEQ ID NO 137
<211> LENGTH: 150
<212> TYPE: DNA
<213> ORGANISM: Artificial Sequence
<220> FEATURE:
<223> OTHER INFORMATION: Human Laminin 1 LEa-4 [DNA, 150 bp]

<400> SEQUENCE: 137
ccatgctctt gtgatccctc tggcagcata gatgaatgta atgttgaaac aggaagatgt 60
gtttgcaaag acaatgtcga aggcttcaat tgtgaaagat gcaaacctgg attttttaat 120
ctggaatcat ctaatcctcg ggggttgcaca 150

<210> SEQ ID NO 138
<211> LENGTH: 50
<212> TYPE: PRT
<213> ORGANISM: Artificial Sequence
<220> FEATURE:
<223> OTHER INFORMATION: Human Laminin 1 LEa-4

<400> SEQUENCE: 138

Pro Cys Ser Cys Asp Pro Ser Gly Ser Ile Asp Glu Cys Asn Val Glu
1 5 10 15

```
Thr Gly Arg Cys Val Cys Lys Asp Asn Val Glu Gly Phe Asn Cys Glu
            20                  25                  30

Arg Cys Lys Pro Gly Phe Phe Asn Leu Glu Ser Ser Asn Pro Arg Gly
        35                  40                  45

Cys Thr
    50


<210> SEQ ID NO 139
<211> LENGTH: 531
<212> TYPE: DNA
<213> ORGANISM: Artificial Sequence
<220> FEATURE:
<223> OTHER INFORMATION: Mouse agrin LG1 domain [DNA, 531 bp]

<400> SEQUENCE: 139

ccctctgtgc cagcttttaa gggccactcc ttcttggcct tccccaccct ccgagcctac      60

cacacgctgc gtctggcact agaattccgg gcgctggaga cagagggact gctgctctac     120

aatggcaatg cacgtggcaa agatttcctg gctctggctc tgttggatgg tcatgtacag     180

ttcaggttcg acacgggctc agggccggcg gtgctaacaa gcttagtgcc agtggaaccg     240

ggacggtggc accgcctcga gttgtcacgg cattggcggc agggcacact ttctgtggat     300

ggcgaggctc ctgttgtagg tgaaagtccg agtggcactg atggcctcaa cttggacacg     360

aagctctatg tgggtggtct cccagaagaa caagttgcca cggtgcttga tcggacctct     420

gtgggcatcg gcctgaaagg atgcattcgt atgttggaca tcaacaacca gcagctggag     480

ctgagcgatt ggcagagggc tgtggttcaa agctctggtg tgggggaatg c              531


<210> SEQ ID NO 140
<211> LENGTH: 177
<212> TYPE: PRT
<213> ORGANISM: Artificial Sequence
<220> FEATURE:
<223> OTHER INFORMATION: Mouse agrin LG1 domain

<400> SEQUENCE: 140

Pro Ser Val Pro Ala Phe Lys Gly His Ser Phe Leu Ala Phe Pro Thr
1               5                   10                  15

Leu Arg Ala Tyr His Thr Leu Arg Leu Ala Leu Glu Phe Arg Ala Leu
            20                  25                  30

Glu Thr Glu Gly Leu Leu Leu Tyr Asn Gly Asn Ala Arg Gly Lys Asp
        35                  40                  45

Phe Leu Ala Leu Ala Leu Leu Asp Gly His Val Gln Phe Arg Phe Asp
    50                  55                  60

Thr Gly Ser Gly Pro Ala Val Leu Thr Ser Leu Val Pro Val Glu Pro
65                  70                  75                  80

Gly Arg Trp His Arg Leu Glu Leu Ser Arg His Trp Arg Gln Gly Thr
                85                  90                  95

Leu Ser Val Asp Gly Glu Ala Pro Val Val Gly Glu Ser Pro Ser Gly
            100                 105                 110

Thr Asp Gly Leu Asn Leu Asp Thr Lys Leu Tyr Val Gly Gly Leu Pro
        115                 120                 125

Glu Glu Gln Val Ala Thr Val Leu Asp Arg Thr Ser Val Gly Ile Gly
    130                 135                 140

Leu Lys Gly Cys Ile Arg Met Leu Asp Ile Asn Asn Gln Gln Leu Glu
145                 150                 155                 160

Leu Ser Asp Trp Gln Arg Ala Val Val Gln Ser Ser Gly Val Gly Glu
```

```
                165                 170                 175

Cys


<210> SEQ ID NO 141
<211> LENGTH: 531
<212> TYPE: DNA
<213> ORGANISM: Artificial Sequence
<220> FEATURE:
<223> OTHER INFORMATION: Human Agrin LG1 [DNA, 531 bp]

<400> SEQUENCE: 141

gcccctgtgc cggccttcga gggccgctcc ttcctggcct tccccactct ccgcgcctac      60

cacacgctgc gcctggcact ggaattccgg gcgctggagc ctcaggggct gctgctgtac     120

aatggcaacg cccggggcaa ggacttcctg gcattggcgc tgctagatgg ccgcgtgcag     180

ctcaggtttg acacaggttc ggggccggcg gtgctgacca gtgccgtgcc ggtagagccg     240

ggccagtggc accgcctgga gctgtcccgg cactggcgcc ggggcaccct ctcggtggat     300

ggtgagaccc ctgttctggg cgagagtccc agtggcaccg acggcctcaa cctggacaca     360

gacctctttg tgggcggcgt acccgaggac caggctgccg tggcgctgga gcggaccttc     420

gtgggcgccg gcctgagggg gtgcatccgt ttgctggacg tcaacaacca gcgcctggag     480

cttggcattg ggccgggggc tgccacccga ggctctggcg tgggcgagtg c              531


<210> SEQ ID NO 142
<211> LENGTH: 177
<212> TYPE: PRT
<213> ORGANISM: Artificial Sequence
<220> FEATURE:
<223> OTHER INFORMATION: Human Agrin LG1

<400> SEQUENCE: 142

Ala Pro Val Pro Ala Phe Glu Gly Arg Ser Phe Leu Ala Phe Pro Thr
1               5                   10                  15

Leu Arg Ala Tyr His Thr Leu Arg Leu Ala Leu Glu Phe Arg Ala Leu
            20                  25                  30

Glu Pro Gln Gly Leu Leu Leu Tyr Asn Gly Asn Ala Arg Gly Lys Asp
        35                  40                  45

Phe Leu Ala Leu Ala Leu Leu Asp Gly Arg Val Gln Leu Arg Phe Asp
    50                  55                  60

Thr Gly Ser Gly Pro Ala Val Leu Thr Ser Ala Val Pro Val Glu Pro
65                  70                  75                  80

Gly Gln Trp His Arg Leu Glu Leu Ser Arg His Trp Arg Arg Gly Thr
                85                  90                  95

Leu Ser Val Asp Gly Glu Thr Pro Val Leu Gly Glu Ser Pro Ser Gly
            100                 105                 110

Thr Asp Gly Leu Asn Leu Asp Thr Asp Leu Phe Val Gly Gly Val Pro
        115                 120                 125

Glu Asp Gln Ala Ala Val Ala Leu Glu Arg Thr Phe Val Gly Ala Gly
    130                 135                 140

Leu Arg Gly Cys Ile Arg Leu Leu Asp Val Asn Asn Gln Arg Leu Glu
145                 150                 155                 160

Leu Gly Ile Gly Pro Gly Ala Ala Thr Arg Gly Ser Gly Val Gly Glu
                165                 170                 175

Cys


<210> SEQ ID NO 143
```

<211> LENGTH: 114
<212> TYPE: DNA
<213> ORGANISM: Artificial Sequence
<220> FEATURE:
<223> OTHER INFORMATION: Mouse agrin EGF-like domain 2 [DNA, 114 bp]

<400> SEQUENCE: 143
ggagaccatc cctgctcacc taacccctgc catggcgggg ccctctgcca ggccctggag 60
gctggcgtgt tcctctgtca gtgcccacct ggccgctttg gcccaacttg tgca 114

<210> SEQ ID NO 144
<211> LENGTH: 38
<212> TYPE: PRT
<213> ORGANISM: Artificial Sequence
<220> FEATURE:
<223> OTHER INFORMATION: Mouse agrin EGF-like domain 2

<400> SEQUENCE: 144

Gly Asp His Pro Cys Ser Pro Asn Pro Cys His Gly Gly Ala Leu Cys
1 5 10 15

Gln Ala Leu Glu Ala Gly Val Phe Leu Cys Gln Cys Pro Pro Gly Arg
20 25 30

Phe Gly Pro Thr Cys Ala
35

<210> SEQ ID NO 145
<211> LENGTH: 114
<212> TYPE: DNA
<213> ORGANISM: Artificial Sequence
<220> FEATURE:
<223> OTHER INFORMATION: Human agrin EGF-like domain 2 [DNA, 114 bp]

<400> SEQUENCE: 145
ggggaccacc cctgcctgcc caacccctgc catggcgggg ccccatgcca gaacctggag 60
gctggaaggt tccattgcca gtgcccgccc ggccgcgtcg gaccaacctg tgcc 114

<210> SEQ ID NO 146
<211> LENGTH: 38
<212> TYPE: PRT
<213> ORGANISM: Artificial Sequence
<220> FEATURE:
<223> OTHER INFORMATION: Human Agrin EGF-like 2

<400> SEQUENCE: 146

Gly Asp His Pro Cys Leu Pro Asn Pro Cys His Gly Gly Ala Pro Cys
1 5 10 15

Gln Asn Leu Glu Ala Gly Arg Phe His Cys Gln Cys Pro Pro Gly Arg
20 25 30

Val Gly Pro Thr Cys Ala
35

<210> SEQ ID NO 147
<211> LENGTH: 117
<212> TYPE: DNA
<213> ORGANISM: Artificial Sequence
<220> FEATURE:
<223> OTHER INFORMATION: Mouse agrin EGF-like domain 3 [DNA, 117 bp]

<400> SEQUENCE: 147
gatgaaaaga acccctgcca accgaacccc tgccacgggt cagccccctg ccatgtgctt 60
tccaggggtg gggccaagtg tgcgtgcccc ctgggacgca gtggttcctt ctgtgag 117

<210> SEQ ID NO 148
<211> LENGTH: 39
<212> TYPE: PRT
<213> ORGANISM: Artificial Sequence
<220> FEATURE:
<223> OTHER INFORMATION: Mouse agrin EGF-like domain 3

<400> SEQUENCE: 148

Asp Glu Lys Asn Pro Cys Gln Pro Asn Pro Cys His Gly Ser Ala Pro
1 5 10 15

Cys His Val Leu Ser Arg Gly Gly Ala Lys Cys Ala Cys Pro Leu Gly
20 25 30

Arg Ser Gly Ser Phe Cys Glu
35

<210> SEQ ID NO 149
<211> LENGTH: 117
<212> TYPE: DNA
<213> ORGANISM: Artificial Sequence
<220> FEATURE:
<223> OTHER INFORMATION: Human Agrin EGF-like 3 [DNA, 117 bp]

<400> SEQUENCE: 149
gatgagaaga gcccctgcca gcccaacccc tgccatgggg cggcgccctg ccgtgtgctg 60
cccgagggtg gtgctcagtg cgagtgcccc ctggggcgtg agggcacctt ctgccag 117

<210> SEQ ID NO 150
<211> LENGTH: 39
<212> TYPE: PRT
<213> ORGANISM: Artificial Sequence
<220> FEATURE:
<223> OTHER INFORMATION: Human Agrin EGF-like 3

<400> SEQUENCE: 150

Asp Glu Lys Ser Pro Cys Gln Pro Asn Pro Cys His Gly Ala Ala Pro
1 5 10 15

Cys Arg Val Leu Pro Glu Gly Gly Ala Gln Cys Glu Cys Pro Leu Gly
20 25 30

Arg Glu Gly Thr Phe Cys Gln
35

<210> SEQ ID NO 151
<211> LENGTH: 27
<212> TYPE: DNA
<213> ORGANISM: Artificial Sequence
<220> FEATURE:
<223> OTHER INFORMATION: Mouse agrin LG Spacer-1 [DNA, 27 bp]

<400> SEQUENCE: 151
acagtcctgg agaatgctgg ctcccgg 27

<210> SEQ ID NO 152
<211> LENGTH: 9
<212> TYPE: PRT
<213> ORGANISM: Artificial Sequence
<220> FEATURE:
<223> OTHER INFORMATION: Mouse agrin spacer domain-1

<400> SEQUENCE: 152

Thr Val Leu Glu Asn Ala Gly Ser Arg
1 5

<210> SEQ ID NO 153
<211> LENGTH: 27

<212> TYPE: DNA
<213> ORGANISM: Artificial Sequence
<220> FEATURE:
<223> OTHER INFORMATION: Human spacer [DNA, 27 bp]

<400> SEQUENCE: 153
acagcctcgg ggcaggacgg ctctggg 27

<210> SEQ ID NO 154
<211> LENGTH: 9
<212> TYPE: PRT
<213> ORGANISM: Artificial Sequence
<220> FEATURE:
<223> OTHER INFORMATION: Human spacer

<400> SEQUENCE: 154

Thr Ala Ser Gly Gln Asp Gly Ser Gly
1 5

<210> SEQ ID NO 155
<211> LENGTH: 537
<212> TYPE: DNA
<213> ORGANISM: Artificial Sequence
<220> FEATURE:
<223> OTHER INFORMATION: Mouse agrin LG2 domain [DNA, 537 bp]

<400> SEQUENCE: 155
cccttcctgg ctgactttaa tggcttctcc tacctggaac tgaaaggctt gcacaccttc 60
gagagagacc taggggagaa gatggcgctg gagatggtgt tcttggctcg tgggcccagt 120
ggcttactcc tctacaatgg gcagaagacg gatggcaagg gggactttgt atccctggcc 180
ctgcataacc ggcacctaga gttccgctat gaccttggca agggggctgc aatcatcagg 240
agcaaagagc ccatagccct gggcacctgg gttagggtat tcctggaacg aaatggccgc 300
aagggtgccc ttcaagtggg tgatgggccc cgtgtgctag gggaatctcc ggtcccgcac 360
accatgctca acctcaagga gcccctctat gtggggggag ctcctgactt cagcaagctg 420
gctcggggcg ctgcagtggc ctccggcttt gatggtgcca tccagctggt gtctctaaga 480
ggccatcagc tgctgactca ggagcatgtg ttgcgggcag tagatgtagc gcctttt 537

<210> SEQ ID NO 156
<211> LENGTH: 179
<212> TYPE: PRT
<213> ORGANISM: Artificial Sequence
<220> FEATURE:
<223> OTHER INFORMATION: Mouse agrin LG2 domain

<400> SEQUENCE: 156

Pro Phe Leu Ala Asp Phe Asn Gly Phe Ser Tyr Leu Glu Leu Lys Gly
1 5 10 15

Leu His Thr Phe Glu Arg Asp Leu Gly Glu Lys Met Ala Leu Glu Met
20 25 30

Val Phe Leu Ala Arg Gly Pro Ser Gly Leu Leu Leu Tyr Asn Gly Gln
35 40 45

Lys Thr Asp Gly Lys Gly Asp Phe Val Ser Leu Ala Leu His Asn Arg
50 55 60

His Leu Glu Phe Arg Tyr Asp Leu Gly Lys Gly Ala Ala Ile Ile Arg
65 70 75 80

Ser Lys Glu Pro Ile Ala Leu Gly Thr Trp Val Arg Val Phe Leu Glu
85 90 95

Arg Asn Gly Arg Lys Gly Ala Leu Gln Val Gly Asp Gly Pro Arg Val

```
            100                 105                 110

Leu Gly Glu Ser Pro Val Pro His Thr Met Leu Asn Leu Lys Glu Pro
        115                 120                 125

Leu Tyr Val Gly Gly Ala Pro Asp Phe Ser Lys Leu Ala Arg Gly Ala
    130                 135                 140

Ala Val Ala Ser Gly Phe Asp Gly Ala Ile Gln Leu Val Ser Leu Arg
145                 150                 155                 160

Gly His Gln Leu Leu Thr Gln Glu His Val Leu Arg Ala Val Asp Val
                165                 170                 175

Ala Pro Phe


<210> SEQ ID NO 157
<211> LENGTH: 537
<212> TYPE: DNA
<213> ORGANISM: Artificial Sequence
<220> FEATURE:
<223> OTHER INFORMATION: Human Agrin G2 [DNA, 537 bp]

<400> SEQUENCE: 157

cccttcctgg ctgacttcaa cggcttctcc cacctggagc tgagaggcct gcacaccttt     60

gcacgggacc tgggggagaa gatggcgctg gaggtcgtgt tcctggcacg aggccccagc    120

ggcctcctgc tctacaacgg gcagaagacg gacggcaagg gggacttcgt gtcgctggca    180

ctgcgggacc gccgcctgga gttccgctac gacctgggca agggggcagc ggtcatcagg    240

agcagggagc cagtcaccct gggagcctgg accagggtct cactggagcg aaacggccgc    300

aagggtgccc tgcgtgtggg cgacggcccc cgtgtgttgg gggagtcccc ggttccgcac    360

accgtcctca acctgaagga gccgctctac gtagggggcg ctcccgactt cagcaagctg    420

gcccgtgctg ctgccgtgtc ctctggcttc gacggtgcca tccagctggt ctccctcgga    480

ggccgccagc tgctgacccc ggagcacgtg ctgcggcagg tggacgtcac gtccttt       537


<210> SEQ ID NO 158
<211> LENGTH: 179
<212> TYPE: PRT
<213> ORGANISM: Artificial Sequence
<220> FEATURE:
<223> OTHER INFORMATION: Human Agrin LG2

<400> SEQUENCE: 158

Pro Phe Leu Ala Asp Phe Asn Gly Phe Ser His Leu Glu Leu Arg Gly
1               5                   10                  15

Leu His Thr Phe Ala Arg Asp Leu Gly Glu Lys Met Ala Leu Glu Val
            20                  25                  30

Val Phe Leu Ala Arg Gly Pro Ser Gly Leu Leu Leu Tyr Asn Gly Gln
        35                  40                  45

Lys Thr Asp Gly Lys Gly Asp Phe Val Ser Leu Ala Leu Arg Asp Arg
    50                  55                  60

Arg Leu Glu Phe Arg Tyr Asp Leu Gly Lys Gly Ala Ala Val Ile Arg
65                  70                  75                  80

Ser Arg Glu Pro Val Thr Leu Gly Ala Trp Thr Arg Val Ser Leu Glu
                85                  90                  95

Arg Asn Gly Arg Lys Gly Ala Leu Arg Val Gly Asp Gly Pro Arg Val
            100                 105                 110

Leu Gly Glu Ser Pro Val Pro His Thr Val Leu Asn Leu Lys Glu Pro
        115                 120                 125

Leu Tyr Val Gly Gly Ala Pro Asp Phe Ser Lys Leu Ala Arg Ala Ala
```

```
    130                 135                 140

Ala Val Ser Ser Gly Phe Asp Gly Ala Ile Gln Leu Val Ser Leu Gly
145                 150                 155                 160

Gly Arg Gln Leu Leu Thr Pro Glu His Val Leu Arg Gln Val Asp Val
                165                 170                 175

Thr Ser Phe


<210> SEQ ID NO 159
<211> LENGTH: 120
<212> TYPE: DNA
<213> ORGANISM: Artificial Sequence
<220> FEATURE:
<223> OTHER INFORMATION: Mouse agrin EGF-like domain 4 [DNA, 120 bp]

<400> SEQUENCE: 159

gcaggccacc cttgtaccca ggccgtggac aacccctgcc ttaatggggg ctcctgtatc     60

ccgagggaag ccacttatga gtgcctgtgt cctgggggct tctctgggct gcactgcgag    120


<210> SEQ ID NO 160
<211> LENGTH: 40
<212> TYPE: PRT
<213> ORGANISM: Artificial Sequence
<220> FEATURE:
<223> OTHER INFORMATION: Mouse agrin EGF-like domain 4

<400> SEQUENCE: 160

Ala Gly His Pro Cys Thr Gln Ala Val Asp Asn Pro Cys Leu Asn Gly
1               5                   10                  15

Gly Ser Cys Ile Pro Arg Glu Ala Thr Tyr Glu Cys Leu Cys Pro Gly
            20                  25                  30

Gly Phe Ser Gly Leu His Cys Glu
        35                  40


<210> SEQ ID NO 161
<211> LENGTH: 120
<212> TYPE: DNA
<213> ORGANISM: Artificial Sequence
<220> FEATURE:
<223> OTHER INFORMATION: Human Agrin Egf-like 4 [DNA, 120 bp]

<400> SEQUENCE: 161

gcaggtcacc cctgcacccg ggcctcaggc cacccctgcc tcaatggggc ctcctgcgtc     60

ccgagggagg ctgcctatgt gtgcctgtgt cccgggggat tctcaggacc gcactgcgag    120


<210> SEQ ID NO 162
<211> LENGTH: 40
<212> TYPE: PRT
<213> ORGANISM: Artificial Sequence
<220> FEATURE:
<223> OTHER INFORMATION: Human Agrin EGF-like 4

<400> SEQUENCE: 162

Ala Gly His Pro Cys Thr Arg Ala Ser Gly His Pro Cys Leu Asn Gly
1               5                   10                  15

Ala Ser Cys Val Pro Arg Glu Ala Ala Tyr Val Cys Leu Cys Pro Gly
            20                  25                  30

Gly Phe Ser Gly Pro His Cys Glu
        35                  40


<210> SEQ ID NO 163
<211> LENGTH: 30
```

<212> TYPE: DNA
<213> ORGANISM: Artificial Sequence
<220> FEATURE:
<223> OTHER INFORMATION: Mouse agrin LG Spacer-2 [DNA, 30 bp]

<400> SEQUENCE: 163
aaggggatag ttgagaagtc agtgggggac 30

<210> SEQ ID NO 164
<211> LENGTH: 10
<212> TYPE: PRT
<213> ORGANISM: Artificial Sequence
<220> FEATURE:
<223> OTHER INFORMATION: Mouse agrin LG Spacer-2

<400> SEQUENCE: 164

Lys Gly Ile Val Glu Lys Ser Val Gly Asp
1 5 10

<210> SEQ ID NO 165
<211> LENGTH: 30
<212> TYPE: DNA
<213> ORGANISM: Artificial Sequence
<220> FEATURE:
<223> OTHER INFORMATION: Human Spacer [30 bp]

<400> SEQUENCE: 165
aaggggctgg tggagaagtc agcgggggac 30

<210> SEQ ID NO 166
<211> LENGTH: 10
<212> TYPE: PRT
<213> ORGANISM: Artificial Sequence
<220> FEATURE:
<223> OTHER INFORMATION: Human Spacer

<400> SEQUENCE: 166

Lys Gly Leu Val Glu Lys Ser Ala Gly Asp
1 5 10

<210> SEQ ID NO 167
<211> LENGTH: 537
<212> TYPE: DNA
<213> ORGANISM: Artificial Sequence
<220> FEATURE:
<223> OTHER INFORMATION: Mouse agrin LG3 domain [DNA, 537 bp]

<400> SEQUENCE: 167
ctagaaacac tggcctttga tgggcggacc tacatcgagt acctcaatgc tgtgactgag 60
agtgagaaag cgctgcagag caaccacttt gagctgagct tacgcactga ggccacgcag 120
gggctggtgc tgtggattgg aaaggttgga gaacgtgcag actacatggc tctggccatt 180
gtggatgggc acctacaact gagctatgac ctaggctccc agccagttgt gctgcgctcc 240
actgtgaagg tcaacaccaa ccgctggctt cgagtcaggg ctcacaggga gcacagggaa 300
ggttcccttc aggtgggcaa tgaagcccct gtgactggct cttccccgct gggtgccaca 360
caattggaca cagatggagc cctgtggctt ggaggcctac agaagcttcc tgtggggcag 420
gctctcccca aggcctatgg cacgggtttt gtgggctgtc tgcgggacgt ggtagtgggc 480
catcgccagc tgcatctgct ggaggacgct gtcaccaaac cagagctaag accctgc 537

<210> SEQ ID NO 168
<211> LENGTH: 179
<212> TYPE: PRT

<213> ORGANISM: Artificial Sequence
<220> FEATURE:
<223> OTHER INFORMATION: Mouse agrin LG3 domain

<400> SEQUENCE: 168

```
Leu Glu Thr Leu Ala Phe Asp Gly Arg Thr Tyr Ile Glu Tyr Leu Asn
1               5                   10                  15

Ala Val Thr Glu Ser Glu Lys Ala Leu Gln Ser Asn His Phe Glu Leu
            20                  25                  30

Ser Leu Arg Thr Glu Ala Thr Gln Gly Leu Val Leu Trp Ile Gly Lys
        35                  40                  45

Val Gly Glu Arg Ala Asp Tyr Met Ala Leu Ala Ile Val Asp Gly His
    50                  55                  60

Leu Gln Leu Ser Tyr Asp Leu Gly Ser Gln Pro Val Val Leu Arg Ser
65                  70                  75                  80

Thr Val Lys Val Asn Thr Asn Arg Trp Leu Arg Val Arg Ala His Arg
                85                  90                  95

Glu His Arg Glu Gly Ser Leu Gln Val Gly Asn Glu Ala Pro Val Thr
            100                 105                 110

Gly Ser Ser Pro Leu Gly Ala Thr Gln Leu Asp Thr Asp Gly Ala Leu
        115                 120                 125

Trp Leu Gly Gly Leu Gln Lys Leu Pro Val Gly Gln Ala Leu Pro Lys
    130                 135                 140

Ala Tyr Gly Thr Gly Phe Val Gly Cys Leu Arg Asp Val Val Val Gly
145                 150                 155                 160

His Arg Gln Leu His Leu Leu Glu Asp Ala Val Thr Lys Pro Glu Leu
                165                 170                 175

Arg Pro Cys
```

<210> SEQ ID NO 169
<211> LENGTH: 537
<212> TYPE: DNA
<213> ORGANISM: Artificial Sequence
<220> FEATURE:
<223> OTHER INFORMATION: Human Agrin LG3 [DNA, 537 bp]

<400> SEQUENCE: 169

```
gtggatacct tggcctttga cgggcggacc tttgtcgagt acctcaacgc tgtgaccgag     60

agcgagaagg cactgcagag caaccacttt gaactgagcc tgcgcactga ggccacgcag    120

gggctggtgc tctggagtgg caaggccacg gagcgggcag actatgtggc actggccatt    180

gtggacgggc acctgcaact gagctacaac ctgggctccc agcccgtggt gctgcgttcc    240

accgtgcccg tcaacaccaa ccgctggttg cgggtcgtgg cacataggga gcagagggaa    300

ggttccctgc aggtgggcaa tgaggcccct gtgaccggct cctccccgct gggcgccacg    360

cagctggaca ctgatggagc cctgtggctt gggggcctgc cggagctgcc cgtgggccca    420

gcactgccca aggcctacgg cacaggcttt gtgggctgct tgcgggacgt ggtggtgggc    480

cggcacccgc tgcacctgct ggaggacgcc gtcaccaagc cagagctgcg gccctgc       537
```

<210> SEQ ID NO 170
<211> LENGTH: 179
<212> TYPE: PRT
<213> ORGANISM: Artificial Sequence
<220> FEATURE:
<223> OTHER INFORMATION: Human Agrin LG3

<400> SEQUENCE: 170

-continued

```
Val Asp Thr Leu Ala Phe Asp Gly Arg Thr Phe Val Glu Tyr Leu Asn
1               5                   10                  15

Ala Val Thr Glu Ser Glu Lys Ala Leu Gln Ser Asn His Phe Glu Leu
            20                  25                  30

Ser Leu Arg Thr Glu Ala Thr Gln Gly Leu Val Leu Trp Ser Gly Lys
        35                  40                  45

Ala Thr Glu Arg Ala Asp Tyr Val Ala Leu Ala Ile Val Asp Gly His
    50                  55                  60

Leu Gln Leu Ser Tyr Asn Leu Gly Ser Gln Pro Val Val Leu Arg Ser
65                  70                  75                  80

Thr Val Pro Val Asn Thr Asn Arg Trp Leu Arg Val Val Ala His Arg
                85                  90                  95

Glu Gln Arg Glu Gly Ser Leu Gln Val Gly Asn Glu Ala Pro Val Thr
            100                 105                 110

Gly Ser Ser Pro Leu Gly Ala Thr Gln Leu Asp Thr Asp Gly Ala Leu
        115                 120                 125

Trp Leu Gly Gly Leu Pro Glu Leu Pro Val Gly Pro Ala Leu Pro Lys
    130                 135                 140

Ala Tyr Gly Thr Gly Phe Val Gly Cys Leu Arg Asp Val Val Val Gly
145                 150                 155                 160

Arg His Pro Leu His Leu Leu Glu Asp Ala Val Thr Lys Pro Glu Leu
                165                 170                 175

Arg Pro Cys
```